US009758829B2

(12) United States Patent
Wang et al.

(10) Patent No.: US 9,758,829 B2
(45) Date of Patent: Sep. 12, 2017

(54) MOLECULAR MALIGNANCY IN MELANOCYTIC LESIONS

(71) Applicants: HTG Molecular Diagnostics, Inc., Tucson, AZ (US); John Wayne Cancer Institute, Santa Monica, CA (US)

(72) Inventors: Hui Wang, San Bruno, CA (US); Christopher Roberts, Tucson, AZ (US); Krishna Maddula, Tucson, AZ (US); Zhenquiang Lu, Tucson, AZ (US); Tom Vasicek, Minneapolis, MN (US); B J Kerns, Madison, WI (US); Bruce E. Seligmann, Tucson, AZ (US); Dave S. B. Hoon, Los Angeles, CA (US)

(73) Assignees: HTG Molecular Diagnostics, Inc., Tucson, AZ (US); John Wayne Cancer Institute, Santa Monica, CA (US)

( * ) Notice: Subject to any disclaimer, the term of this patent is extended or adjusted under 35 U.S.C. 154(b) by 6 days.

(21) Appl. No.: 14/405,739

(22) PCT Filed: Jun. 24, 2013

(86) PCT No.: PCT/US2013/047354
§ 371 (c)(1),
(2) Date: Dec. 4, 2014

(87) PCT Pub. No.: WO2013/192616
PCT Pub. Date: Dec. 27, 2013

(65) Prior Publication Data

US 2015/0176072 A1 Jun. 25, 2015

Related U.S. Application Data

(66) Substitute for application No. 61/663,428, filed on Jun. 22, 2012.

(51) Int. Cl.
*C12Q 1/68* (2006.01)

(52) U.S. Cl.
CPC ......... *C12Q 1/6883* (2013.01); *C12Q 1/6886* (2013.01); *C12Q 2600/158* (2013.01); *C12Q 2600/16* (2013.01); *C12Q 2600/166* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2012/0041274 | A1 | 2/2012 | Stone et al. |
| 2012/0053253 | A1 | 3/2012 | Stone et al. |

FOREIGN PATENT DOCUMENTS

| | | | |
|---|---|---|---|
| JP | 2008-504034 | | 2/2008 |
| JP | 2010-522748 | | 7/2010 |
| JP | 2011-520451 | | 7/2011 |
| WO | WO 02/103320 | A2 | 12/2002 |
| WO | WO 2006/002433 | A2 | 1/2006 |
| WO | WO 2008/118017 | A2 | 10/2008 |
| WO | WO 2009/062199 | A1 | 5/2009 |
| WO | WO 2009/099905 | A2 | 8/2009 |
| WO | WO 2009/140550 | A9 | 11/2009 |
| WO | WO 2012/031008 | A2 | 3/2012 |
| WO | WO 2012/040500 | A2 | 3/2012 |

OTHER PUBLICATIONS

Gamper et al (BMC Genomics, 2009, 10(199): 1-17).*
Koh et al (Modern Pathology, 2012, 25: 828-837).*
Riker et al (BMC Med Genomics, 2008, 1(13): 1-16).*
Rakosy et al (Int J Cancer, 2007, 121, 1729-1737).*
Yang et al (Appl Immunohistochem Mol Morphol, 2011, 19(1): 62-69).*
Talantov et al (Clinical Cancer Research, 2005, 11(20): 7234-7242).*
Mauerer et al (Exp Dermatol, 2011, 20(6): Abstract).*
Affymetrix Datasheet, "GeneChip® Human Genome Arrays," downloaded from the internet on Dec. 1, 2014, http://media.affymetrix.com/support/technical/datasheets/human_datasheet.pdf, Fig. 1, GeneChip Human Genome U133 Plus 2.0 Array.
Fountain et al., "Homozygous Deletions Within Human Chromosome Band 9p21 in Melanoma", *Proc Natl Acad Sci U S A 89*:10557-10561, 1992.
Herzog et al., "Chapter 5—Malignant Melanoma," in *Cancer Epidemiology in Older Adolescents and Young Adults 15 to 29 Years of Age—Including SEER Incidence and Survival*: 1975-2000, Bleyer et al. (eds), National Cancer Institute, NIH Pub. No. 06-5767, Bethesda, MD, 2006.
Kashani-Sabet et al., "A Multi-Marker Assay to Distinguish Malignant Melanomas from Benign Nevi," Proc Natl Acad Sci. 106:6268-6272, 2009.
Martinez and Hoon, "Molecular Markers in Malignant Cutaneous Melanoma: Gift Horse or One-Trick Pony?" *J Cell Biochem* 96:473-483, 2005.
Meier et al., "Molecular Events in Melanoma Development and Progression," *Front Biosci* 3:D1005-D1010, 1998.
Melanoma Research Alliance, "Transformative Advances in Melanoma Research—Accelerating Scientific Discovery and Translation to Eliminate Death and Suffering Due to Melanoma," Highlights of the Melanoma Research Alliance, Second Annual Scientific Retreat, Feb. 24-26, 2010.
Pacheco et al., "Towards New Therapeutic Approaches for Malignant Melanoma," *Expert Rev Mol Med.* 13:e33, 2011.
Tokita et al., "Methylation Status of the SOCS3 Gene in Human Malignant Melanomas," *Int J Oncol.* 30:689-694, 2007.
Troxel, "Pitfalls in the Diagnosis of Malignant Melanoma: Findings of a Risk Management Panel Study," downloaded from the Internet on Apr. 12, 2012, 6 pages, http://www.thedoctors.com/TDC/PressRoom/IntheMedia/CON_ID_001327.

(Continued)

*Primary Examiner* — Sean Aeder
(74) *Attorney, Agent, or Firm* — Klarquist Sparkman, LLP

(57) ABSTRACT

Disclosed are methods for determining whether a melanocyte-containing sample (such as a nevus or other pigmented lesion) is benign or a primary melanoma. These methods can include detecting (at the molecular level, e.g., mRNA, miRNA, or protein) the expression of at least two disclosed genes in a biological sample obtained from a subject. Also provided are arrays and kits that can be used with the methods.

13 Claims, 14 Drawing Sheets

(56) References Cited

OTHER PUBLICATIONS

Yu et al., "Nuclear Orphan Receptor TR3/Nur77 Mediates Melanoma Cell Apoptosis," *Cancer Biol Ther.* 6:405-412, 2007.

Basarab et al., "Melanoma antigen-encoding gene expression in melanocytic naevi and cutaneous malignant melanomas," *Br J Dermatol.* 140:106-108, 1998.

Fratta et al., "The biology of cancer testis antigens: Putative function, regulation and therapeutic potential," *Mol Oncol.* 5:164-182, 2011.

Lüftl et al., "*Dermatopathology*—Melanoma or not? Cancer testis antigens may help," *Br J Dermatol.* 151:1213-1218, 2004.

DeSmet et al., "Sequence and expression pattern of the human MAGE2 gene," *Immunogenetics* 39:121-129, 1994.

European Patent Office, Partial Supplementary European Search Report dated Feb. 26, 2016 for European Patent Application No. 13806645.1 (9 pages).

Lesinski et al., "Modulation of SOCS Protein Expression Influences the Interferon Responsiveness of Human Melanoma Cells," *BMC Cancer* 10:1-10, 2010.

Perry, "Complex Regulation of Acetylcholinesterase Gene Expression in Human Brain Tumors," *Oncogene* 21:8428-8441, 2002.

Smith et al., "Regulation of NR4A Nuclear Receptor Expression by Oncogenic BRAF in Melanoma Cells," *Pigment Cell Melanoma Res.* 24:551-563, 2011.

CN 201380045664.3, Office-Action dated 14, 2017 (with English translation) (8 pages).

JP 2015-518637, Office-Action dated Jun. 7, 2017 (with English translation) (10 pages).

* cited by examiner

FIG. 2A
MFI2
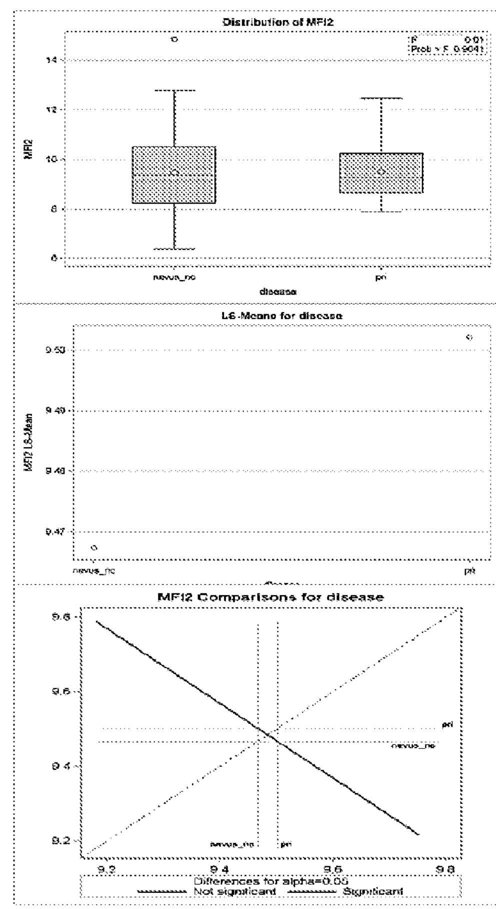
RAP2B
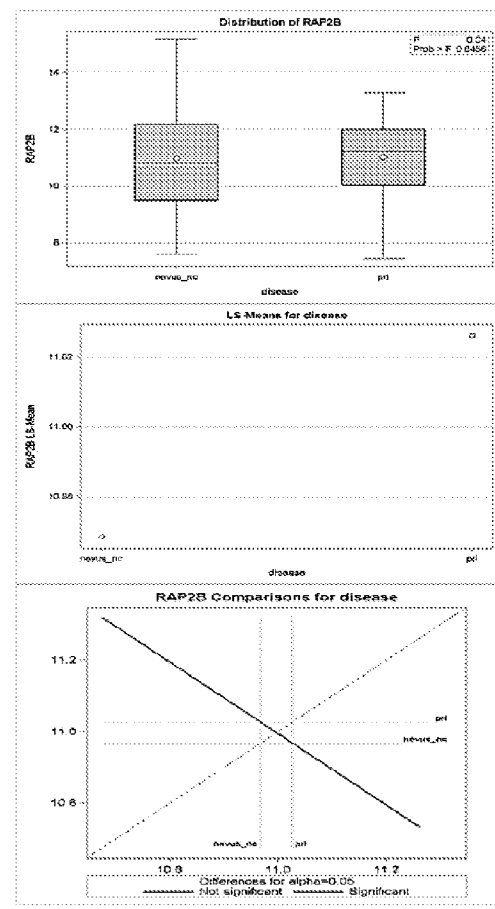

FIG. 3

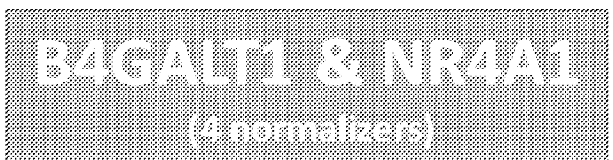

- Logistic Regression estimated using SAS Proc Logistic
  - Binary Logit and iteratively reweighted least squares (Fisher Scoring) optimization
- Very good overall model fit statistics
- No lack of fit indicated by Hosmer and Lemeshow test
- Cross Validation Method:
  - SAS One step approximation based on the full model maximum likelihood estimate versus the maximum likelihood estimate with the $j^{th}$ observation omitted

| Model Convergence Status |
|---|
| Convergence criterion (GCONV=1E-8) satisfied. |

| Model Fit Statistics | | |
|---|---|---|
| Criterion | Intercept Only | Intercept and Covariates |
| AIC | 133.851 | 31.908 |
| SC | 136.446 | 39.694 |
| -2 Log L | 131.851 | 25.908 |

| Testing Global Null Hypothesis: BETA=0 | | | |
|---|---|---|---|
| Test | Chi-Square | DF | Pr > ChiSq |
| Likelihood Ratio | 105.9423 | 2 | <.0001 |
| Score | 73.2725 | 2 | <.0001 |
| Wald | 15.8564 | 2 | 0.0004 |

| Hosmer and Lemeshow Goodness-of-Fit Test | | |
|---|---|---|
| Chi-Square | DF | Pr > ChiSq |
| 2.4164 | 8 | 0.9655 |

- Can use the model to obtain high specificity with relatively little impact on sensitivity Classification Table

| Prob Level | Correct Event | Correct Non-Event | Incorrect Event | Incorrect Non-Event | Percentages Correct | Sensi-tivity | Speci-ficity | False POS | False NEG |
|---|---|---|---|---|---|---|---|---|---|
| 0.640 | 57 | 36 | 2 | 4 | 93.9 | 93.4 | 94.7 | 3.4 | 10.0 |
| 0.660 | 56 | 36 | 2 | 5 | 92.9 | 91.8 | 94.7 | 3.4 | 12.2 |
| 0.680 | 56 | 36 | 2 | 5 | 92.9 | 91.8 | 94.7 | 3.4 | 12.2 |
| 0.700 | 56 | 37 | 1 | 5 | 93.9 | 91.8 | 97.4 | 1.8 | 11.9 |
| 0.720 | 56 | 37 | 1 | 5 | 93.9 | 91.8 | 97.4 | 1.8 | 11.9 |
| 0.740 | 56 | 37 | 1 | 5 | 93.9 | 91.8 | 97.4 | 1.8 | 11.9 |
| 0.760 | 56 | 37 | 1 | 5 | 93.9 | 91.8 | 97.4 | 1.8 | 11.9 |
| 0.780 | 56 | 37 | 1 | 5 | 93.9 | 91.8 | 97.4 | 1.8 | 11.9 |
| 0.800 | 55 | 37 | 1 | 6 | 92.9 | 90.2 | 97.4 | 1.8 | 14.0 |
| 0.820 | 53 | 37 | 1 | 8 | 90.9 | 86.9 | 97.4 | 1.9 | 17.8 |
| 0.840 | 53 | 38 | 0 | 8 | 91.9 | 86.9 | 100.0 | 0.0 | 17.4 |
| 0.860 | 53 | 38 | 0 | 8 | 91.9 | 86.9 | 100.0 | 0.0 | 17.4 |
| 0.880 | 53 | 38 | 0 | 8 | 91.9 | 86.9 | 100.0 | 0.0 | 17.4 |
| 0.900 | 53 | 38 | 0 | 8 | 91.9 | 86.9 | 100.0 | 0.0 | 17.4 |
| 0.920 | 53 | 38 | 0 | 8 | 91.9 | 86.9 | 100.0 | 0.0 | 17.4 |
| 0.940 | 53 | 38 | 0 | 8 | 91.9 | 86.9 | 100.0 | 0.0 | 17.4 |
| 0.960 | 52 | 38 | 0 | 9 | 90.9 | 85.2 | 100.0 | 0.0 | 19.1 |
| 0.980 | 48 | 38 | 0 | 13 | 86.9 | 78.7 | 100.0 | 0.0 | 25.5 |
| 1.000 | 0 | 38 | 0 | 61 | 38.4 | 0.0 | 100.0 | . | 61.6 |

FIG. 6

B4GALT1 & NR4A1
(4 normalizers)

Classification Table

| Prob Level | Correct | | Incorrect | | Percentages | | | | |
|---|---|---|---|---|---|---|---|---|---|
| | Event | Non-Event | Event | Non-Event | Correct | Sensi-tivity | Speci-ficity | False POS | False NEG |
| 0.000 | 61 | 0 | 38 | 0 | 61.6 | 100.0 | 0.0 | 38.4 | |
| 0.020 | 61 | 22 | 16 | 0 | 83.8 | 100.0 | 57.9 | 20.8 | 0.0 |
| 0.040 | 61 | 26 | 12 | 0 | 87.9 | 100.0 | 68.4 | 16.4 | 0.0 |
| 0.060 | 60 | 29 | 9 | 1 | 89.9 | 98.4 | 76.3 | 13.0 | 3.3 |
| 0.080 | 60 | 29 | 9 | 1 | 89.9 | 98.4 | 76.3 | 13.0 | 3.3 |
| 0.100 | 60 | 29 | 9 | 1 | 89.9 | 98.4 | 76.3 | 13.0 | 3.3 |
| 0.120 | 60 | 29 | 9 | 1 | 89.9 | 98.4 | 76.3 | 13.0 | 3.3 |
| 0.140 | 58 | 29 | 9 | 3 | 87.9 | 95.1 | 76.3 | 13.4 | 9.4 |
| 0.160 | 58 | 30 | 8 | 3 | 88.9 | 95.1 | 78.9 | 12.1 | 9.1 |
| 0.180 | 58 | 30 | 8 | 3 | 88.9 | 95.1 | 78.9 | 12.1 | 9.1 |
| 0.200 | 58 | 30 | 8 | 3 | 88.9 | 95.1 | 78.9 | 12.1 | 9.1 |
| 0.220 | 58 | 30 | 8 | 3 | 88.9 | 95.1 | 78.9 | 12.1 | 9.1 |
| 0.240 | 58 | 31 | 7 | 3 | 89.9 | 95.1 | 81.6 | 10.8 | 8.8 |
| 0.260 | 58 | 31 | 7 | 3 | 89.9 | 95.1 | 81.6 | 10.8 | 8.8 |
| 0.280 | 58 | 32 | 6 | 3 | 90.9 | 95.1 | 84.2 | 9.4 | 8.6 |
| 0.300 | 58 | 32 | 6 | 3 | 90.9 | 95.1 | 84.2 | 9.4 | 8.6 |
| 0.320 | 58 | 32 | 6 | 3 | 90.9 | 95.1 | 84.2 | 9.4 | 8.6 |
| 0.340 | 58 | 32 | 6 | 3 | 90.9 | 95.1 | 84.2 | 9.4 | 8.6 |
| 0.360 | 58 | 32 | 6 | 3 | 90.9 | 95.1 | 84.2 | 9.4 | 8.6 |
| 0.380 | 58 | 33 | 5 | 3 | 91.9 | 95.1 | 86.8 | 7.9 | 8.3 |
| 0.400 | 58 | 33 | 5 | 3 | 91.9 | 95.1 | 86.8 | 7.9 | 8.3 |
| 0.420 | 58 | 33 | 5 | 3 | 91.9 | 95.1 | 86.8 | 7.9 | 8.3 |
| 0.440 | 58 | 34 | 4 | 3 | 92.9 | 95.1 | 89.5 | 6.5 | 8.1 |
| 0.460 | 58 | 34 | 4 | 3 | 92.9 | 95.1 | 89.5 | 6.5 | 8.1 |
| 0.480 | 58 | 34 | 4 | 3 | 92.9 | 95.1 | 89.5 | 6.5 | 8.1 |
| 0.500 | 58 | 34 | 4 | 3 | 92.9 | 95.1 | 89.5 | 6.5 | 8.1 |
| 0.520 | 58 | 35 | 3 | 3 | 93.9 | 95.1 | 92.1 | 4.9 | 7.9 |
| 0.540 | 58 | 35 | 3 | 3 | 93.9 | 95.1 | 92.1 | 4.9 | 7.9 |
| 0.560 | 58 | 35 | 3 | 3 | 93.9 | 95.1 | 92.1 | 4.9 | 7.9 |
| 0.580 | 58 | 35 | 3 | 3 | 93.9 | 95.1 | 92.1 | 4.9 | 7.9 |
| 0.600 | 58 | 36 | 2 | 3 | 94.9 | 95.1 | 94.7 | 3.3 | 7.7 |
| 0.620 | 58 | 36 | 2 | 3 | 94.9 | 95.1 | 94.7 | 3.3 | 7.7 |

- Can obtain higher sensitivity with relatively little impact on specificity
- Very large range of possible threshold values for calling a sample primary melanoma that maintain high sensitivity with specificity >80%
  - Robust model

FIG. 7

Other methods validate the B4GALT1 & NR4A1 (4 normalizer) model:

- Model testing with Empirical Covariance "Sandwich" Estimators
  - Estimated using proc GLIMMIX in SAS
  - Sandwich estimators are:
    - Less sensitive to choice of covariance model
    - Minimize bias due to heteroskedastic variances

| Fit Statistics | |
|---|---|
| -2 Log Likelihood | 25.91 |
| AIC (smaller is better) | 31.91 |
| AICC (smaller is better) | 32.16 |
| BIC (smaller is better) | 39.69 |
| CAIC (smaller is better) | 42.69 |
| HQIC (smaller is better) | 35.06 |
| Pearson Chi-Square | 31.16 |
| Pearson Chi-Square / DF | 0.32 |

Type III Tests of Fixed Effects

| Effect | Num DF | Den DF | F Value | Pr > F |
|---|---|---|---|---|
| B4GALT1 | 1 | 96 | 10.87 | 0.0014 |
| NR4A1 | 1 | 96 | 14.73 | 0.0002 |

Firth Bias Reduction Penalized Likelihood

| Model Convergence Status |
|---|
| Convergence criterion (GCONV=1E-8) satisfied. |

Model Fit Statistics

| Criterion | Intercept Only | Intercept and Covariates |
|---|---|---|
| AIC | 124.760 | 29.552 |
| SC | 127.355 | 37.338 |
| -2 Log L | 122.760 | 23.552 |

Testing Global Null Hypothesis: BETA=0

| Test | Chi-Square | DF | Pr > ChiSq |
|---|---|---|---|
| Likelihood Ratio | 99.2081 | 2 | <.0001 |
| Score | 73.1213 | 2 | <.0001 |
| Wald | 20.1588 | 2 | <.0001 |

FIG. 8
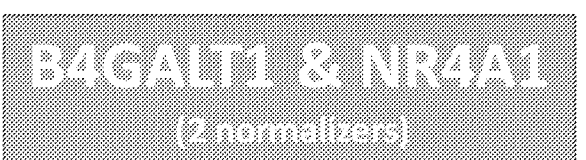
| Model Information | |
|---|---|
| Data Set | WORK.MYR_HK |
| Response Variable | disease |
| Number of Response Levels | 2 |
| Model | binary logit |
| Optimization Technique | Fisher's scoring |
| Model Convergence Status |
|---|
| Convergence criterion (GCONV=1E-8) satisfied. |
| Testing Global Null Hypothesis: BETA=0 | | | |
|---|---|---|---|
| Test | Chi-Square | DF | Pr > ChiSq |
| Likelihood Ratio | 93.6780 | 2 | <.0001 |
| Score | 67.4852 | 2 | <.0001 |
| Wald | 22.0216 | 2 | <.0001 |
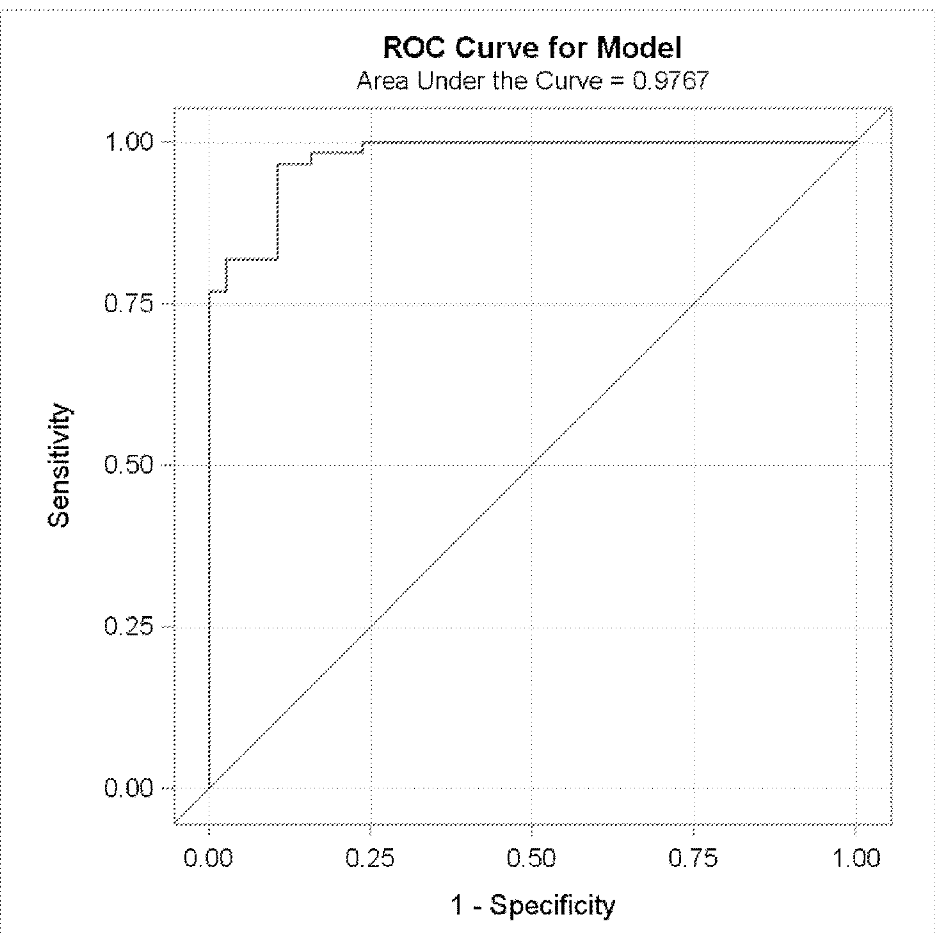

Classification Table

| Prob Level | Correct Event | Correct Non-Event | Incorrect Event | Incorrect Non-Event | Percentages Correct | Sensi-tivity | Speci-ficity | False POS | False NEG |
|---|---|---|---|---|---|---|---|---|---|
| 0.000 | 61 | 0 | 38 | 0 | 61.6 | 100.0 | 0.0 | 38.4 | . |
| 0.020 | 61 | 20 | 18 | 0 | 81.8 | 100.0 | 52.6 | 22.8 | 0.0 |
| 0.040 | 61 | 23 | 15 | 0 | 84.8 | 100.0 | 60.5 | 19.7 | 0.0 |
| 0.060 | 61 | 24 | 14 | 0 | 85.9 | 100.0 | 63.2 | 18.7 | 0.0 |
| 0.080 | 61 | 26 | 12 | 0 | 87.9 | 100.0 | 68.4 | 16.4 | 0.0 |
| 0.100 | 60 | 27 | 11 | 1 | 87.9 | 98.4 | 71.1 | 15.5 | 3.6 |
| 0.120 | 60 | 28 | 10 | 1 | 88.9 | 98.4 | 73.7 | 14.3 | 3.4 |
| 0.140 | 60 | 29 | 9 | 1 | 89.9 | 98.4 | 76.3 | 13.0 | 3.3 |
| 0.160 | 60 | 29 | 9 | 1 | 89.9 | 98.4 | 76.3 | 13.0 | 3.3 |
| 0.180 | 60 | 29 | 9 | 1 | 89.9 | 98.4 | 76.3 | 13.0 | 3.3 |
| 0.200 | 60 | 29 | 9 | 1 | 89.9 | 98.4 | 76.3 | 13.0 | 3.3 |
| 0.220 | 60 | 31 | 7 | 1 | 91.9 | 98.4 | 81.6 | 10.4 | 3.1 |
| 0.240 | 60 | 31 | 7 | 1 | 91.9 | 98.4 | 81.6 | 10.4 | 3.1 |
| 0.260 | 60 | 31 | 7 | 1 | 91.9 | 98.4 | 81.6 | 10.4 | 3.1 |
| 0.280 | 60 | 31 | 7 | 1 | 91.9 | 98.4 | 81.6 | 10.4 | 3.1 |
| 0.300 | 59 | 31 | 7 | 2 | 90.9 | 96.7 | 81.6 | 10.6 | 6.1 |
| 0.320 | 59 | 31 | 7 | 2 | 90.9 | 96.7 | 81.6 | 10.6 | 6.1 |
| 0.340 | 59 | 31 | 7 | 2 | 90.9 | 96.7 | 81.6 | 10.6 | 6.1 |
| 0.360 | 58 | 31 | 7 | 3 | 89.9 | 95.1 | 81.6 | 10.8 | 8.8 |
| 0.380 | 58 | 32 | 6 | 3 | 90.9 | 95.1 | 84.2 | 9.4 | 8.6 |
| 0.400 | 58 | 32 | 6 | 3 | 90.9 | 95.1 | 84.2 | 9.4 | 8.6 |
| 0.420 | 58 | 32 | 6 | 3 | 90.9 | 95.1 | 84.2 | 9.4 | 8.6 |
| 0.440 | 58 | 33 | 5 | 3 | 91.9 | 95.1 | 86.8 | 7.9 | 8.3 |
| 0.460 | 58 | 34 | 4 | 3 | 92.9 | 95.1 | 89.5 | 6.5 | 8.1 |
| 0.480 | 58 | 34 | 4 | 3 | 92.9 | 95.1 | 89.5 | 6.5 | 8.1 |
| 0.500 | 57 | 34 | 4 | 4 | 91.9 | 93.4 | 89.5 | 6.6 | 10.5 |

Classification Table

| Prob Level | Correct Event | Correct Non-Event | Incorrect Event | Incorrect Non-Event | Percentages Correct | Sensi-tivity | Speci-ficity | False POS | False NEG |
|---|---|---|---|---|---|---|---|---|---|
| 0.500 | 57 | 34 | 4 | 4 | 91.9 | 93.4 | 89.5 | 6.6 | 10.5 |
| 0.520 | 57 | 34 | 4 | 4 | 91.9 | 93.4 | 89.5 | 6.6 | 10.5 |
| 0.540 | 57 | 34 | 4 | 4 | 91.9 | 93.4 | 89.5 | 6.6 | 10.5 |
| 0.560 | 57 | 34 | 4 | 4 | 91.9 | 93.4 | 89.5 | 6.6 | 10.5 |
| 0.580 | 57 | 34 | 4 | 4 | 91.9 | 93.4 | 89.5 | 6.6 | 10.5 |
| 0.600 | 57 | 34 | 4 | 4 | 91.9 | 93.4 | 89.5 | 6.6 | 10.5 |
| 0.620 | 57 | 34 | 4 | 4 | 91.9 | 93.4 | 89.5 | 6.6 | 10.5 |
| 0.640 | 56 | 34 | 4 | 5 | 90.9 | 91.8 | 89.5 | 6.7 | 12.8 |
| 0.660 | 55 | 34 | 4 | 6 | 89.9 | 90.2 | 89.5 | 6.8 | 15.0 |
| 0.680 | 54 | 34 | 4 | 7 | 88.9 | 88.5 | 89.5 | 6.9 | 17.1 |
| 0.700 | 54 | 34 | 4 | 7 | 88.9 | 88.5 | 89.5 | 6.9 | 17.1 |
| 0.720 | 53 | 34 | 4 | 8 | 87.9 | 86.9 | 89.5 | 7.0 | 19.0 |
| 0.740 | 53 | 34 | 4 | 8 | 87.9 | 86.9 | 89.5 | 7.0 | 19.0 |
| 0.760 | 53 | 34 | 4 | 8 | 87.9 | 86.9 | 89.5 | 7.0 | 19.0 |
| 0.780 | 51 | 34 | 4 | 10 | 85.9 | 83.6 | 89.5 | 7.3 | 22.7 |
| 0.800 | 51 | 34 | 4 | 10 | 85.9 | 83.6 | 89.5 | 7.3 | 22.7 |
| 0.820 | 50 | 34 | 4 | 11 | 84.8 | 82.0 | 89.5 | 7.4 | 24.4 |
| 0.840 | 50 | 34 | 4 | 11 | 84.8 | 82.0 | 89.5 | 7.4 | 24.4 |
| 0.860 | 50 | 34 | 4 | 11 | 84.8 | 82.0 | 89.5 | 7.4 | 24.4 |
| 0.880 | 50 | 35 | 3 | 11 | 85.9 | 82.0 | 92.1 | 5.7 | 23.9 |
| 0.900 | 49 | 35 | 3 | 12 | 84.8 | 80.3 | 92.1 | 5.8 | 25.5 |
| 0.920 | 47 | 36 | 2 | 14 | 83.8 | 77.0 | 94.7 | 4.1 | 28.0 |
| 0.940 | 40 | 37 | 1 | 21 | 77.8 | 65.6 | 97.4 | 2.4 | 36.2 |
| 0.960 | 34 | 37 | 1 | 27 | 71.7 | 55.7 | 97.4 | 2.9 | 42.2 |
| 0.980 | 30 | 38 | 0 | 31 | 68.7 | 49.2 | 100.0 | 0.0 | 44.9 |
| 1.000 | 0 | 38 | 0 | 61 | 38.4 | 0.0 | 100.0 | . | 61.6 |

SEQUENCE LISTING

```
<160> NUMBER OF SEQ ID NOS: 164

<210> SEQ ID NO 1
<211> LENGTH: 50
<212> TYPE: DNA
<213> ORGANISM: Artificial
<220> FEATURE:
<223> OTHER INFORMATION: Oligonucleotide probe

<400> SEQUENCE: 1

ctgctggatg acgtgagtaa acctgaatct ttggagtacg ctggatagcc              50


<210> SEQ ID NO 2
<211> LENGTH: 50
```

<212> TYPE: DNA
<213> ORGANISM: Artificial
<220> FEATURE:
<223> OTHER INFORMATION: Oligonucleotide probe

<400> SEQUENCE: 2
gtcttggaac ctgagcccag gctggacctg gcaaaggcgc tcagtggtag 50

<210> SEQ ID NO 3
<211> LENGTH: 50
<212> TYPE: DNA
<213> ORGANISM: Artificial
<220> FEATURE:
<223> OTHER INFORMATION: Oligonucleotide probe

<400> SEQUENCE: 3
ccgcaaggtc gataggtgaa cacaatatag ctgtcctcgt cagtgcgctc 50

<210> SEQ ID NO 4
<211> LENGTH: 50
<212> TYPE: DNA
<213> ORGANISM: Artificial
<220> FEATURE:
<223> OTHER INFORMATION: Oligonucleotide probe

<400> SEQUENCE: 4
gtaagtggaa cattctccaa cacttccaca tgcaattctt ctccagtaag 50

<210> SEQ ID NO 5
<211> LENGTH: 50
<212> TYPE: DNA
<213> ORGANISM: Artificial
<220> FEATURE:
<223> OTHER INFORMATION: Oligonucleotide probe

<400> SEQUENCE: 5
caagttcaga gggcccacct gagtccaaat agcccaaggc caagcctggt 50

<210> SEQ ID NO 6
<211> LENGTH: 50
<212> TYPE: DNA
<213> ORGANISM: Artificial
<220> FEATURE:
<223> OTHER INFORMATION: Oligonucleotide probe

<400> SEQUENCE: 6
cctgggttga tactagagcc gctgcctcct cgtagaagct ccgacagttg 50

<210> SEQ ID NO 7
<211> LENGTH: 50
<212> TYPE: DNA
<213> ORGANISM: Artificial
<220> FEATURE:
<223> OTHER INFORMATION: Oligonucleotide probe

<400> SEQUENCE: 7
cagcatctgt gatggttcag ccaaacgctg gacattagtg ggatgagcag 50

<210> SEQ ID NO 8
<211> LENGTH: 50
<212> TYPE: DNA
<213> ORGANISM: Artificial
<220> FEATURE:
<223> OTHER INFORMATION: Oligonucleotide probe

<400> SEQUENCE: 8
gggctcagct tgtcactctc cagctggttg aaggcgtgct gtctgtaggg 50

<210> SEQ ID NO 9
<211> LENGTH: 50
<212> TYPE: DNA
<213> ORGANISM: Artificial
<220> FEATURE:
<223> OTHER INFORMATION: Oligonucleotide probe

<400> SEQUENCE: 9
ctcgctgagt cttagattcc gcagcctaag actcgagaga ggtgcctccg 50

<210> SEQ ID NO 10
<211> LENGTH: 50
<212> TYPE: DNA
<213> ORGANISM: Artificial
<220> FEATURE:
<223> OTHER INFORMATION: Oligonucleotide probe

<400> SEQUENCE: 10
ctcaggctct ccacctggat gcttggcaga tcctagaacc actgcatctg 50

<210> SEQ ID NO 11
<211> LENGTH: 50
<212> TYPE: DNA
<213> ORGANISM: Artificial
<220> FEATURE:
<223> OTHER INFORMATION: Oligonucleotide probe

<400> SEQUENCE: 11
cttcaccttt cgggctttct tggctttgac cttgggccga gtatcctgat 50

<210> SEQ ID NO 12
<211> LENGTH: 50
<212> TYPE: DNA
<213> ORGANISM: Artificial
<220> FEATURE:
<223> OTHER INFORMATION: Oligonucleotide probe

<400> SEQUENCE: 12
tcctggtgtg ctaagcttgg agacgtcagg cacaacaatc agtgtccctg 50

<210> SEQ ID NO 13
<211> LENGTH: 50
<212> TYPE: DNA
<213> ORGANISM: Artificial
<220> FEATURE:
<223> OTHER INFORMATION: Oligonucleotide probe

<400> SEQUENCE: 13
gctggcattg aagaactcgc tcactgctgt gaggacgtca cagtccttgg 50

<210> SEQ ID NO 14
<211> LENGTH: 50
<212> TYPE: DNA
<213> ORGANISM: Artificial
<220> FEATURE:
<223> OTHER INFORMATION: Oligonucleotide probe

<400> SEQUENCE: 14
cccggtacag cagcgggtac acagcactcc gggagtgccc tggctccgtc 50

<210> SEQ ID NO 15
<211> LENGTH: 50
<212> TYPE: DNA
<213> ORGANISM: Artificial

<220> FEATURE:
<223> OTHER INFORMATION: Oligonucleotide probe

<400> SEQUENCE: 15
cgccacagct gccacgtgct ccttcaggca gctggcgatg cggttctgca 50

<210> SEQ ID NO 16
<211> LENGTH: 50
<212> TYPE: DNA
<213> ORGANISM: Artificial
<220> FEATURE:
<223> OTHER INFORMATION: Oligonucleotide probe

<400> SEQUENCE: 16
cacatcaaac ctgctggcca gcacagacgc tgaggttgca tcgatcttgg 50

<210> SEQ ID NO 17
<211> LENGTH: 50
<212> TYPE: DNA
<213> ORGANISM: Artificial
<220> FEATURE:
<223> OTHER INFORMATION: Oligonucleotide probe

<400> SEQUENCE: 17
cttcgatgtg tgtgaggcta cccgcattct cgccatcgat gctcagcacc 50

<210> SEQ ID NO 18
<211> LENGTH: 50
<212> TYPE: DNA
<213> ORGANISM: Artificial
<220> FEATURE:
<223> OTHER INFORMATION: Oligonucleotide probe

<400> SEQUENCE: 18
attcactcac tcactcactc actcattcat tcggccatag ctggaatcaa 50

<210> SEQ ID NO 19
<211> LENGTH: 50
<212> TYPE: DNA
<213> ORGANISM: Artificial
<220> FEATURE:
<223> OTHER INFORMATION: Oligonucleotide probe

<400> SEQUENCE: 19
tggtatcacc cagggaatac gtaaccagac aacacacaag actgagatgc 50

<210> SEQ ID NO 20
<211> LENGTH: 50
<212> TYPE: DNA
<213> ORGANISM: Artificial
<220> FEATURE:
<223> OTHER INFORMATION: Oligonucleotide probe

<400> SEQUENCE: 20
gtctggctgt gtctcccgtc aaaggctgcc atgaagagtg gcgggaagag 50

<210> SEQ ID NO 21
<211> LENGTH: 50
<212> TYPE: DNA
<213> ORGANISM: Artificial
<220> FEATURE:
<223> OTHER INFORMATION: Oligonucleotide probe

<400> SEQUENCE: 21
cttcaccttt agctggcaga ccacaaactg aggattgcaa gttccgccac 50

<210> SEQ ID NO 22
<211> LENGTH: 50
<212> TYPE: DNA
<213> ORGANISM: Artificial
<220> FEATURE:
<223> OTHER INFORMATION: Oligonucleotide probe

<400> SEQUENCE: 22
cctctcctcc tgctccttca tatggttctc ccggacttcc ttccatgtat 50

<210> SEQ ID NO 23
<211> LENGTH: 50
<212> TYPE: DNA
<213> ORGANISM: Artificial
<220> FEATURE:
<223> OTHER INFORMATION: Oligonucleotide probe

<400> SEQUENCE: 23
ctgatggcgg actttaccgt gacagcggaa gtggtattgt acgtccaggc 50

<210> SEQ ID NO 24
<211> LENGTH: 50
<212> TYPE: DNA
<213> ORGANISM: Artificial
<220> FEATURE:
<223> OTHER INFORMATION: Oligonucleotide probe

<400> SEQUENCE: 24
gcagagtcac acacatgcaa acacgcactc ttcggaaggc agccactgtc 50

<210> SEQ ID NO 25
<211> LENGTH: 50
<212> TYPE: DNA
<213> ORGANISM: Artificial
<220> FEATURE:
<223> OTHER INFORMATION: Oligonucleotide probe

<400> SEQUENCE: 25
atttcaaaca tgcaacaacg ccactggtaa taaagctttg gaatgggtgc 50

<210> SEQ ID NO 26
<211> LENGTH: 50
<212> TYPE: DNA
<213> ORGANISM: Artificial
<220> FEATURE:
<223> OTHER INFORMATION: Oligonucleotide probe

<400> SEQUENCE: 26
gtcttctcta ccaggagcct gaggtgaaag atgtcccgtc tcctccatcc 50

<210> SEQ ID NO 27
<211> LENGTH: 50
<212> TYPE: DNA
<213> ORGANISM: Artificial
<220> FEATURE:
<223> OTHER INFORMATION: Oligonucleotide probe

<400> SEQUENCE: 27
ctccgcctct cgaatgaaag ggatcttgtc gctgtctttg agcagcttcc 50

<210> SEQ ID NO 28
<211> LENGTH: 50
<212> TYPE: DNA
<213> ORGANISM: Artificial
<220> FEATURE:
<223> OTHER INFORMATION: Oligonucleotide probe

<400> SEQUENCE: 28
ccatggttgt gtagctctgc ctctgggctt tcttcatcac agggcaacgg 50

<210> SEQ ID NO 29
<211> LENGTH: 50
<212> TYPE: DNA
<213> ORGANISM: Artificial
<220> FEATURE:
<223> OTHER INFORMATION: Oligonucleotide probe

<400> SEQUENCE: 29
cccaggaaac atcagcacac acacacacag ggaccctccc ttcatgtcac 50

<210> SEQ ID NO 30
<211> LENGTH: 50
<212> TYPE: DNA
<213> ORGANISM: Artificial
<220> FEATURE:
<223> OTHER INFORMATION: Oligonucleotide probe

<400> SEQUENCE: 30
cgggattcaa tctcatgttg ctggctctcc acaggtgttt cgagaactgg 50

<210> SEQ ID NO 31
<211> LENGTH: 50
<212> TYPE: DNA
<213> ORGANISM: Artificial
<220> FEATURE:
<223> OTHER INFORMATION: Oligonucleotide probe

<400> SEQUENCE: 31
ctacccatcc agcagcttca ggatgctctc acgctccttc agagtcttcc 50

<210> SEQ ID NO 32
<211> LENGTH: 50
<212> TYPE: DNA
<213> ORGANISM: Artificial
<220> FEATURE:
<223> OTHER INFORMATION: Oligonucleotide probe

<400> SEQUENCE: 32
agtatgagta tgaggcaggg agctggacag gaagaggttc tgatgaggct 50

<210> SEQ ID NO 33
<211> LENGTH: 50
<212> TYPE: DNA
<213> ORGANISM: Artificial
<220> FEATURE:
<223> OTHER INFORMATION: Oligonucleotide probe

<400> SEQUENCE: 33
gacgtgctgc agggaagtcc tctcctggct cctccctcac tggagactcg 50

<210> SEQ ID NO 34
<211> LENGTH: 50
<212> TYPE: DNA
<213> ORGANISM: Artificial
<220> FEATURE:
<223> OTHER INFORMATION: Oligonucleotide probe

<400> SEQUENCE: 34
ggtagtgaac ccgttgatgt ccacttgcag tgtgttatcc ctgctgtcac 50

<210> SEQ ID NO 35

<211> LENGTH: 50
<212> TYPE: DNA
<213> ORGANISM: Artificial
<220> FEATURE:
<223> OTHER INFORMATION: Oligonucleotide probe

<400> SEQUENCE: 35
cccgggacaa agcaaatgga agtcctgggt gcttctgacg cacacctatt 50

<210> SEQ ID NO 36
<211> LENGTH: 50
<212> TYPE: DNA
<213> ORGANISM: Artificial
<220> FEATURE:
<223> OTHER INFORMATION: Oligonucleotide probe

<400> SEQUENCE: 36
cgccagcagc agcagattca gcatcctggc cgctccctgt tccttctacc 50

<210> SEQ ID NO 37
<211> LENGTH: 3963
<212> TYPE: DNA
<213> ORGANISM: Homo sapiens

<400> SEQUENCE: 37
cacttaagga gctcgggcca gcgcgagggg gagcagggag gaagcccggc tgctgcggac 60
ctcctcggac ccggacccag ccccagcccg gccccagcca gccccgacgg cgccatgcgg 120
ggtccgagcg gggctctgtg gctgctcctg gctctgcgca ccgtgctcgg tggcatggag 180
gtgcggtggt gcgccacctc ggacccagag cagcacaagt gcggcaacat gagcgaggcc 240
ttccgggaag cgggcatcca gccctccctc ctctgcgtcc ggggcacctc cgccgaccac 300
tgcgtccagc tcatcgcggc ccaggaggct gacgccatca ctctggatgg aggagccatc 360
tatgaggcgg gaaaggagca cggcctgaag ccggtggtgg gcgaagtgta cgatcaagag 420
gtcggtacct cctattacgc cgtggctgtg gtcaggagga gctcccatgt gaccattgac 480
accctgaaag gcgtgaagtc ctgccacacg ggcatcaatc gcacagtggg ctggaacgtg 540
cccgtgggct acctggtgga gagcggccgc ctctcggtga tgggctgcga tgtactcaaa 600
gctgtcagcg actattttgg gggcagctgc gtcccggggg caggagagac cagttactct 660
gagtccctct gtcgcctctg caggggtgac agctctgggg aaggggtgtg tgacaagagc 720
cccctggaga gatactacga ctacagcggg gccttccggt gcctggcgga aggggcaggg 780
gacgtggctt ttgtgaagca cagcacggta ctggagaaca cggatgggaa gacgcttccc 840
tcctggggcc aggccctgct gtcacaggac ttcgagctgc tgtgccggga tggtagccgg 900
gccgatgtca ccgagtggag gcagtgccat ctggcccggg tgcctgctca cgccgtggtg 960
gtccgggccg acacagatgg gggcctcatc ttccggctgc tcaacgaagg ccagcgtctg 1020
ttcagccacg agggcagcag cttccagatg ttcagctctg aggcctatgg ccagaaggat 1080
ctactcttca aagactctac ctcggagctt gtgcccatcg ccacacagac ctatgaggcg 1140
tggctgggcc atgagtacct gcacgccatg aagggtctgc tctgtgaccc caaccggctg 1200 ccccccctacc tgcgctggtg tgtgctctcc actcccgaga tccagaagtg tggagacatg 1260
gccgtggcct tccgccggca gcggctcaag ccagagatcc agtgcgtgtc agccaagtcc 1320
ccccaacact gcatggagcg gatccaggct gagcaggtcg acgctgtgac cctgagtggc 1380
gaggacattt acacggcggg gaagacgtac ggcctggttc ccgcagccgg ggagcactat 1440
gccccggaag acagcagcaa ctcgtactac gtggtggccg tggtgagacg ggacagctcc 1500

```
cacgccttca ccttggatga gcttcggggc aagcgctcct gccacgccgg tttcggcagc   1560
cctgcaggct gggatgtccc cgtgggtgcc cttattcaga gaggcttcat ccggcccaag   1620
gactgtgacg tcctcacagc agtgagcgag ttcttcaatg ccagctgcgt gcccgtgaac   1680
aaccccaaga actacccctc ctcgctgtgt gcactgtgcg tgggggacga gcagggccgc   1740
aacaagtgtg tgggcaacag ccaggagcgg tattacggct accgcggcgc cttcaggtgc   1800
ctggtggaga atgcgggtga cgttgccttc gtcaggcaca caaccgtctt tgacaacaca   1860
aacggccaca attccgagcc ctgggctgct gagctcaggt cagaggacta tgaactgctg   1920
tgccccaacg ggcccgagc cgaggtgtcc cagtttgcag cctgcaacct ggcacagata   1980
ccaccccacg ccgtgatggt ccggcccgac accaacatct tcaccgtgta tggactgctg   2040
gacaaggccc aggacctgtt tggagacgac cacaataaga acgggttcaa aatgttcgac   2100
tcctccaact atcatggcca agacctgctt ttcaaggatg ccaccgtccg ggcggtgcct   2160
gtcggagaga aaaccaccta ccgcggctgg ctggggctgg actacgtggc ggcgctggaa   2220
gggatgtcgt ctcagcagtg ctcgggcgca gcggccccgg cgcccggggc gcccctgctc   2280
ccgctgctgc tgcccgccct cgccgcccgc ctgctcccgc ccgccctctg agcccggccg   2340
ccccgcccca gagctccgat gcccgcccgg ggagtttccg cggcggcttc gcgctggaat   2400
ccagaaggaa gctcgcgaag gccgggcccg gcgtgggcgg gagcaggcgc ctccccggga   2460
gccccgccgc ccacgggcgc cacctggcgc tgctacctga ggcgccgccc ccgggcccgc   2520
gcggcccttc ccgccaaccg ccgcctcccg ccacctggag ccgcgcgggc cgcgccggag   2580
gaggccggtt gcccaggaaa ccgctgagtc cgggcttccc gccgcccgcc ccgcggtgtc   2640
gcccgagggg cccgcccgcc tcctccccgc agccccgcgc ccccgtccgc gaggccccct   2700
ggggacgcgg tggccgccga ggcgcctaca cccgcaggcc gcggccaggc cgtcccagga   2760
ggccccggcg ccaacgggac ccggcgcgtg ggacagcggc ctctgctggc ggcggcggga   2820
gggaggccgg accggggcga cggggagaag ccttcgcccg cgggaccgtg tccggggtgg   2880
gggctccagt tcctccgacc gcccgtgcgc tgggagggag gccgagcccg gggaacgccg   2940
cgtgccctgc ctcgtccccc actgtggccg cgccagctcc atcccgggcc agccgcgtcc   3000
acgggccccc tcccgagtct cctcaggctc tcgcctcccc tacccccgtg ggatgcccac   3060
cgcccgcacc cacgcccgag cctggcggca gcagccgccc cccgcctgaa gggagccgga   3120
ggtgacccag gccgcgggct cccgaggccc ctgaagggct gcgcgtgggg acccgccatg   3180
cttctgggtt ccgaacgggg gtgagctccg tctcctcacc cggccccgca cccgctgggc   3240
ctggggaccc ctcactcccc gtgcccgccc ctccgcgagg cagcagaaag cgcccggccg   3300
gggcctctct ctactccatc ttgccacagt tgtctgagaa gccagaaaaa gtttccagaa   3360
ctggcagccc ttaaaaaaaa tgaagaggaa gagaagaaat gggagcaggc agccctcgtc   3420
agcagaccgg gagccgcgtg ggcgcggagc catttgcatt ccggtctgcg ggggctcggg   3480
gatgctggtg acaggcccgg ttcccggtgg ctcgccccca cctgcgggcg tcgggaagga   3540
tcccttccat ctctcagccg cagaggaggc cctggcagcg ccccggctgt agccatgcaa   3600
ccccgaggag tcccgggcac cttcacccca ccgggagggg ccacaaggac ctgggcctcg   3660
gccaccaagc tttgtcccct ctcgctgtgg ggggctagtg attctcctcc gacctgacga   3720
ttgcttggtt ttttcaaaag ggagttttgt gcggtgagaa gtgtgtttct gtgtggctaa   3780
ctctgggcta gcgtgccgtg gccattgaag gtgtggcctg cgtgggtgca gtgtaagtga   3840
```

```
cgctggattg tcaggtggca gcaggggacc cctgctgtgt cagtgctaat gaaacatgtt   3900

ggttggtttc taaaataaag ccaaacaagc cagcacatgc agaggcttgg accctgatag   3960

aaa                                                                 3963
```

<210> SEQ ID NO 38
<211> LENGTH: 1696
<212> TYPE: DNA
<213> ORGANISM: Homo sapiens

<400> SEQUENCE: 38

```
acttaaggag ctcgggccag cgcgaggggg agcagggagg aagcccggct gctgcggacc     60

tcctcggacc cggacccagc cccagcccgg ccccagccag ccccgacggc gccatgcggg    120

gtccgagcgg ggctctgtgg ctgctcctgg ctctgcgcac cgtgctcggt ggcatggagg    180

tgcggtggtg cgccacctcg gacccagagc agcacaagtg cggcaacatg agcgaggcct    240

tccgggaagc gggcatccag ccctccctcc tctgcgtccg gggcacctcc gccgaccact    300

gcgtccagct catcgcggcc caggaggctg acgccatcac tctggatgga ggagccatct    360

atgaggcggg aaaggagcac ggcctgaagc cggtggtggg cgaagtgtac gatcaagagg    420

tcggtacctc ctattacgcc gtggctgtgg tcaggaggag ctcccatgtg accattgaca    480

ccctgaaagg cgtgaagtcc tgccacacgg gcatcaatcg cacagtgggc tggaacgtgc    540

ccgtgggcta cctggtggag agcggccgcc tctcggtgat gggctgcgat gtactcaaag    600

ctgtcagcga ctattttggg ggcagctgcg tcccgggggc aggagagacc agttactctg    660

agtccctctg tcgcctctgc aggggtgaca gctctgggga aggggtgtgt gacaagagcc    720

ccctggagag atactacgac tacagcgggg ccttccggtg cctggcggaa ggggcagggg    780

acgtggcttt tgtgaagcac agcacggtac tggagaacac ggatgaaagt ccatcacgaa    840

ggcaaacatg gaccagatct gaggaggaag aaggcgagtg ccctgcacac gaggaagcac    900

gtaggacgat gcgctctagt gctgggcaag cctggaaatg ggctcccgtt cacaggcccc    960

aggacgagtc tgacaaagga gaatttggaa aacgggcaaa gagtagggat atgttgggtt   1020

aagaatcagc tctttcaaac ttggggtttt ttttgagatg ggggtctcac catgttgccc   1080

aggctggtct caaacccccca gcctcaactg atcctcgcat ctcagcctcc tgagtagctg   1140

ggatgacagg cgtgcacctg gcagcttttt caaagtgttg atggtaatct gaggcaatct   1200

aagggagtca ttttttaagt gactttatac agaaagattg gtaagagcca aggggtagaa   1260

gtggcataaa tgtctaaagc agggaagtga caggactttc attgttcttg gctgaggaga   1320

agcgggagtg gctgatggaa gcacctaaat gatgcctttg tctgtgggaa ggcaaatgat   1380

gccccagagc tctaaccaaa ggttttgcag ccgccgaaaa acaggaaagt tgggaagcgg   1440

gggtaggact acactgaatc attaacagtg ctgtaaacta ccatgtggcc attaacaatg   1500

acctttaggg agttttccta aacgatcact ctggtgcggg tgtttggttt tgttttaaaa   1560

tagctttgca gtgaaagctt tcatgaccat acaaattatc ttttttcttc ctatttcctt   1620

gtagaggttt ttttcctcct tgtcttaagg tcataaaaat attgttatgt gggaaaaaaa   1680

aaaaaaaaaa aaaaaa                                                   1696
```

<210> SEQ ID NO 39
<211> LENGTH: 6237
<212> TYPE: DNA
<213> ORGANISM: Homo sapiens

<400> SEQUENCE: 39

-continued

```
gagagagcgc gatgggccgc ggcggtgggc gcacgttccg cggggactca tgccacgcgc     60
gtcccggccc gacgcgcaat tagcagccac ctccgcagcc cgccgccacc gcctccctgc    120
cctcccgggc tgccgcagct aggagctcca gccgtcgcct cgcgcaggct gcgggcattg    180
tcctctcggt tcgccgcccg ggctgctgct gccgccgcgg actgctgcgg ggcccggacc    240
cgcaccccag ggatacgctg ccgccgccgc cggccggccc ggcgcccggc ctccgttcgg    300
tggtttccgc cctgcgttct ctgggttgct ctctcctggg tttttcctgc gtagctgagg    360
aaggggaaga gaagtccagc cgccaagccc agccttcccc ggcgcgcagc cccgacgggg    420
ccgcggcagg cgcggcgaga gcgctgacgg agccatgaga gagtacaaag tggtggtgct    480
gggctcgggc ggcgtgggca agtccgcgct caccgtgcag ttcgtgacgg gctccttcat    540
cgagaagtac gacccgacca tcgaagactt ttaccgcaag gagattgagg tggactcgtc    600
gccgtcggtg ctggagatcc tggatacggc gggcaccgag cagttcgcgt ccatgcggga    660
cctgtacatc aagaacggcc agggcttcat cctggtctac agcctcgtca accagcagag    720
cttccaggac atcaagccca tgcgggacca gatcatccgc gtgaagcggt acgagcgcgt    780
gcccatgatc ctggtgggca acaaggtgga cctggagggt gagcgcgagg tctcgtacgg    840
ggagggcaag gccctggctg aggagtggag ctgccccttc atggagacgt cggccaaaaa    900
caaagcctcg gtagacgagc tatttgccga gatcgtgcgg cagatgaact acgcggcgca    960
gcccaacggc gatgagggct gctgctcggc ctgcgtgatc ctctgaggcg gccaccgcgc   1020
gccggccgcg ctctgcgcac aaaagccaaa cgcatccgac tctctaaatg tgatttattt   1080
cttgctttga gattggagac cactttgcat tggccagggt gtcttgggag cccggctggc   1140
ctccgcggcc ggcgtcccct gcctccaccc tgtgcccgag gggtgtccg gtcctgccca    1200
tccgatactc tggtggaaat gtggctcttt gcagcatgta cgtttctccc tgattttggt   1260
tgatgcatat ttccccgttt aagtagccgt tagggcgcag tatcggcagc ttgacaccca   1320
ccaagcaaaa gtttcagcct ggaaaaaaaa tggggggga gggtggatga aaaggaggga    1380
gagaaggtgg aaatggtttt tttttttttt tttctatttt ctttcttttt tttttttttt   1440
ttttttggtc aacagccgtt tttctagttc caagttttaa atacatggaa ggaagtccgg   1500
gagaaccata tgaaggagca ggaggagagg aagaaacttt ttttccttct tttccaggag   1560
tagctggaaa ttaagatcgg gttccttttc tgccagcttg gaagggcaac cccatgactg   1620
attgcgattc tgaggatgtc tatgcaaagt tggattcttg ttacagtgta tccaatctga   1680
agtattgcac atctgaactg ggactgttaa cactgatgcc aatacagtgt ggggtgccag   1740
aaagtgtctg ctgatatttg tggaaaaaaa atctattttg tttacctact gtatcaaagg   1800
ggagtctggg ggagaatggt agtatttttt tttttttatca gctgtgaaaa aaatgttaca   1860
gatctgcaca ttttcgtgtg tactatggtg tgtgtgtgta tgtgtgtggt gtgtgtgtgt   1920
tttaagttta gccttttgtt tttgtttttt ggttggcagt aaccgatttt aatgactagc   1980
ttttaaaaat acagtacaaa gactttgtaa atgtgattca gggcccccag cacccctgtg   2040
tctgcagagt gccttcaaaa ctcagctgtt ccagccggtg ccaacctgtg aacttcccac   2100
catatcccag aatctgctat tccccaaacc acttcccagt ttcctttcag taatctttct   2160
gaaggagcca ggacaatagg gcctgttgtt tagtgaattt ctttattatt ttcagccttt   2220
aaaatgtaat ttccatctct tgcaatgaat ttgtttccct tttttttgct tcattttgtt   2280
taaattttca ggtatttagc tccccttca tattattttt aaatttttta attacctgtt    2340
```

```
gtagggtgtt cctccagaag caaagagcaa aattttactg ttgtgatgta ccaattctaa   2400
ctaattgtaa tttttaattt catgcgttta atcattgtct cttcatttta agacttttaa   2460
tacaaatgtc atttttaaag aaacaaaccc aaaactattg tttgtgtttc tgtgtttcat   2520
attcagtgat ttaatacagt atcatggctg aggtggatgg ggcaggtgca tgatactctt   2580
cagagctatt tgtgaaattt taaagacaga agtgtctcag tgacaagttg gatgacacta   2640
ctcccaactt tttaaatttg gagaaaacca tcaaggtcga ggaagccctg ggtatggcca   2700
ttaccatctg attagaagat gaacaggtat tttgaatctg atctgacatg gaacagttta   2760
cctcattgta ggtagggaac aagagaaccc atctattaaa attgccttag atctgggaaa   2820
gtaaccatcc ttctggcaaa gtaggatggc acttttaagt tttcttcct tttttccctc   2880
tgtttatatt gcacatcaag tcaaaaacat gtttgggaaa gatggttttc aattctgaag   2940
ttatacctag tgatgttttt tgcagtacat ttgaatggat tgtagacact gcctcaaccc   3000
ttttgaggtt ttgatttgga aatagattta aaagaaaaca ggctaagata atatccttgt   3060
tctcatttac accctgcagt ttggaccaca tttgacctca taagtttttc cttttaacag   3120
taggaggcag tgtgagcttt ttattttta tttttcttaa ggtggtctta gtaatataac   3180
atgttcatac atatcaagag agtacttggt ataccttagg tctatgaagt gtagctgaaa   3240
tctgaagagt cttgacaaag ggatttacac ccttgacaaa accaaaagaa attaacaggc   3300
cacaggtttc tttaaagctg tgttaacata tcttgcctta aaatgtgtgt gtgtgttttt   3360
gctttgcttt tttttttttg cccaagaggc atctcagtac tccagcaatg gaggaagaat   3420
agagaatttt gcctggcaat ggtcctactg ccattttttt tttcccactc tgatctcact   3480
taagtttgat atcaaacaca attgggaggc aatagtatca atatcctaaa tgtagaaatt   3540
aaaagatact gtataatttt atgcctttgc aaagattcgt tcttgtattt gaataaattc   3600
agttgctaaa gtagatccaa agtgttaaaa atgctgaagt catgtcaagt actgtctgga   3660
gggttttttt aagaaaaggc atttggcatt taactgtctc ttgttttatt tttaagtttt   3720
tggaaacctt ttgacataaa atgctgccaa gtatctaaga aatgtatata ctgacagaag   3780
atatttgaaa gtggaaaatt ggaaatgaaa tatgttgctg ggtgcgttaa tcacctccgc   3840
ccaggattta gtcacttgca ggacctcttt atagtctagg atggcagagc agaagatttt   3900
aatatgcttt tattaagtga tgtaaaataa atgcttttttg gattatcaat gaaagcaatt   3960
ttatgtgtgc ctgaagcaag aaaatagcgt ttttggtttt atctcatatt ttcttggcaa   4020
aattgagaga aattaggaac actgctattt ttttcttaaa aatgttttta agaatatgtt   4080
cgtttctttg actattaaga accccttgtg gtattagtgt gtgaagagat aagggcattt   4140
gtttcaatga aaaagttagt gttaaaggaa gtgagtcagg gagggcggag tttgttgtaa   4200
ggcaatcacc tgtcaaaaca gaaattgggt gggaaaggag tctttatctt ggggagcaaa   4260
agctgacttt taaacttgac ccctgctgtt tttaaacagc ttttcctttt ggtctctgac   4320
agtcaatcca ggttttatgt tatttcaaaa gggttatttt tgtcctcctt ttttaatagc   4380
ttcaggaaag ttaaaggtat catcttaggt ctaacactct agtctttgag agttacggtt   4440
ctttcgtaga acaatttcca tgttgttaac tgttgtagac ttaattgaat cacattttgg   4500
gaccagatgt atttggggat agaattcttt aaatgtatgg gacttcatgc ttcctgatta   4560
tgtaatattt cctgtggttg ggaatcctag aatgcctgat ctattttatc tgttcaggta   4620
gttttgttat tgtaccctct tttgggtcat attctagtat ttctcacagg gggtatgaga   4680
aacagaaagc tatatgtagc agctggtctt gagaagtaga agcatcttaa ctgtcataag   4740
```

agcatagatt ttttgttttt cacaacagct ggaataagtt cctgcattat aagtataaag 4800
ggaaccgaga tttaatttgg agatcatcac tgttaaaacg ataccagaca tttgtcacag 4860
tgtcttattt ggggaaagtt tgctaatata cattttgtct gtgaaaatat agtaaatttt 4920
aaaatactaa tataatgtgg tattcttgat tacagtattt tatgcagact attaggaatg 4980
attcagtgca tttaactgaa cacagagcta gttctaggtg agtgagatct ttatctatta 5040
actggatttt gaaggtttga gaaggctatg gggatcatct ggttgaaagg ttctcaaact 5100
tgaccatata tcaaaatcac ctggagctta aaacatgtac tgctgggacc ctcctccagt 5160
ttcttaccca gtgggtctcg ggtagggtct caattttcat ttctaacaag tttccaagtg 5220
attgtgttat tgctgttcca gggaccacac tttgaaaacc agtgatctag actgaactcc 5280
aaatgagtac tatactgaca gccacctaga tattgagaga cacagacttc agactcatgt 5340
cacacatttt ggagtgctgt ctactacagt tagagaataa tctctattga aatctaagct 5400
aaagaggaca tataccattt atactaagac taactgttgt gtgtgaaata gaataaacat 5460
tgcaggtagt ttttgatcat tttcacatta ttacaggaac attttgacta tggttttcaa 5520
tgttaattca gaagttgact ttaaatgaaa atgtggttag aatagaggca aagcctaagt 5580
gatcagaatc aacattcccc ttctccccaa cctaggggaa aaaaaatttg aaaagtatgt 5640
cttcaataaa aggggacact ttatttgtct tctcttcaac attaaaaaac aaagatttta 5700
agttttcatg gcaagggttc taaaaatcat tgtgccagag aatttaaatc ttcatatcat 5760
ggtaagcaca tgcgtatgtc tgtgactcag tttcttagcc agacttccag gtgttagtta 5820
attccttctc atttagttct actgtaatcc attctgggaa aatgcatacc acaaaactgt 5880
gtatcttgca gcttctttcg ttatgcatct taattccctc agaaggtccc agaactttat 5940
gttaaagatc tgggttttta aagacaattt gggggccttc taaagaaaca atagtagatc 6000
taattacaag tagtggattg cttacttcaa atttctcttt tacaatttag aaagtttagt 6060
accagtttat agactgaggg agtagtagct actatttaga tgctgagaat aatattatca 6120
tgcttgggtg gggaagaaag gcccttactc aaatctccat tttcattttt aatgcttcct 6180
ggacttcagt tattttcttg cttttgcctc aagaataata aatatttttg gttaaaa 6237

<210> SEQ ID NO 40
<211> LENGTH: 2747
<212> TYPE: DNA
<213> ORGANISM: Homo sapiens

<400> SEQUENCE: 40
gtcggaggga gggagggagg gagagaaaga aagagagaaa aagaaggaaa gggagaggga 60
gacggctgga gcccgaggac gagcgcggag ccgcggaccg agcggggggc gggagacagg 120
aaggagggag gcgagcagag ggaaggggaa gaggtcgggg agcgagggcg ggagcggtcg 180
cggtcgcgat cgagcaagca agcgggcgag aggacgccct cccctggcct ccagtgcgcc 240
gcttccctcg ccgccgcccc gccagcatgc ccggcgtggc ccgcctgccg ctgctgctcg 300
ggctgctgct gctcccgcgt cccggccggc cgctggactt ggccgactac acctatgacc 360
tggcggagga ggacgactcg gagcccctca actacaaaga cccctgcaag gcggctgcct 420
ttcttgggga cattgccctg gacgaagagg acctgagggc cttccaggta cagcaggctg 480
tggatctcag acggcacaca gctcgtaagt cctccatcaa agctgcagtt ccaggaaaca 540
cttctacccc cagctgccag agcaccaacg ggcagcctca gaggggagcc tgtgggagat 600

```
ggagaggtag atcccgtagc cggcgggcgg cgacgtcccg accagagcgt gtgtggcccg    660
atggggtcat cccctttgtc attgggggaa acttcactgg tagccagagg gcagtcttcc    720
ggcaggccat gaggcactgg gagaagcaca cctgtgtcac cttcctggag cgcactgacg    780
aggacagcta tattgtgttc acctatcgac cttgcgggtg ctgctcctac gtgggtcgcc    840
gcggcggggg cccccaggcc atctccatcg gcaagaactg tgacaagttc ggcattgtgg    900
tccacgagct gggccacgtc gtcggcttct ggcacgaaca cactcggcca gaccgggacc    960
gccacgtttc catcgttcgt gagaacatcc agccagggca ggagtataac ttcctgaaga   1020
tggagcctca ggaggtggag tccctggggg agacctatga cttcgacagc atcatgcatt   1080
acgctcggaa cacattctcc aggggcatct tcctggatac cattgtcccc aagtatgagg   1140
tgaacggggt gaaacctccc attggccaaa ggacacggct cagcaagggg gacattgccc   1200
aagcccgcaa gctttacaag tgcccagcct gtggagagac cctgcaagac agcacaggca   1260
acttctcctc ccctgaatac cccaatggct actctgctca catgcactgc gtgtggcgca   1320
tctctgtcac acccggggag aagatcatcc tgaacttcac gtccctggac ctgtaccgca   1380
gccgcctgtg ctggtacgac tatgtggagg tccgagatgg cttctggagg aaggcgcccc   1440
tccgaggccg cttctgcggg tccaaactcc ctgagcctat cgtctccact gacagccgcc   1500
tctgggttga attccgcagc agcagcaatt gggttggaaa gggcttcttt gcagtctacg   1560
aagccatctg cgggggtgat gtgaaaaagg actatggcca cattcaatcg cccaactacc   1620
cagacgatta ccggcccagc aaagtctgca tctggcggat ccaggtgtct gagggcttcc   1680
acgtgggcct cacattccag tcctttgaga ttgagcgcca cgacagctgt gcctacgact   1740
atctggaggt gcgcgacggg cacagtgaga gcagcaccct catcgggcgc tactgtggct   1800
atgagaagcc tgatgacatc aagagcacgt ccagccgcct ctggctcaag ttcgtctctg   1860
acgggtccat taacaaagcg ggctttgccg tcaacttttt caaagaggtg gacgagtgct   1920
ctcggcccaa ccgcgggggc tgtgagcagc ggtgcctcaa caccctgggc agctacaagt   1980
gcagctgtga ccccgggtac gagctggccc cagacaagcg ccgctgtgag gctgcttgtg   2040
gcggattcct caccaagctc aacggctcca tcaccagccc gggctggccc aaggagtacc   2100
cccccaacaa gaactgcatc tggcagctgg tggcccccac ccagtaccgc atctccctgc   2160
agtttgactt ctttgagaca gagggcaatg atgtgtgcaa gtacgacttc gtggaggtgc   2220
gcagtggact cacagctgac tccaagctgc atggcaagtt ctgtggttct gagaagcccg   2280
aggtcatcac ctcccagtac aacaacatgc gcgtggagtt caagtccgac aacaccgtgt   2340
ccaaaaaggg cttcaaggcc cacttcttct cagaaaagag gccagctctg cagccccctc   2400
ggggacgccc ccaccagctc aaattccgag tgcagaaaag aaaccggacc ccccagtgag   2460
gcctgccagg cctcccggac cccttgttac tcaggaacct caccttggac ggaatgggat   2520
gggggcttcg gtgcccacca accccccacc tccactctgc cattccggcc cacctccctc   2580
tggccggaca gaactggtgc tctcttctcc ccactgtgcc cgtccgcgga ccggggaccc   2640
ttccccgtgc cctaccccct cccattttga tggtgtctgt gacatttcct gttgtgaagt   2700
aaaagaggga cccctgcgtc ctgctccttt ctcttgcaga aaaaaaa                 2747
```

<210> SEQ ID NO 41
<211> LENGTH: 3835
<212> TYPE: DNA
<213> ORGANISM: Homo sapiens

<400> SEQUENCE: 41

-continued

```
gtcggaggga gggagggagg gagagaaaga aagagagaaa aagaaggaaa gggagaggga      60
gacggctgga gcccgaggac gagcgcggag ccgcggaccg agcggggggc gggagacagg     120
aaggagggag gcgagcagag ggaaggggaa gaggtcgggg agcgagggcg ggagcggtcg     180
cggtcgcgat cgagcaagca agcgggcgag aggacgccct cccctggcct ccagtgcgcc     240
gcttccctcg ccgccgcccc gccagcatgc ccggcgtggc ccgcctgccg ctgctgctcg     300
ggctgctgct gctcccgcgt cccggccggc cgctggactt ggccgactac acctatgacc     360
tggcggagga ggacgactcg gagcccctca actacaaaga cccctgcaag gcggctgcct     420
ttcttgggga cattgccctg gacgaagagg acctgagggc cttccaggta cagcaggctg     480
tggatctcag acggcacaca gctcgtaagt cctccatcaa agctgcagtt ccaggaaaca     540
cttctacccc cagctgccag agcaccaacg ggcagcctca gaggggagcc tgtgggagat     600
ggagaggtag atcccgtagc cggcgggcgg cgacgtcccg accagagcgt gtgtggcccg     660
atggggtcat cccctttgtc attgggggaa acttcactgg tagccagagg gcagtcttcc     720
ggcaggccat gaggcactgg gagaagcaca cctgtgtcac cttcctggag cgcactgacg     780
aggacagcta tattgtgttc acctatcgac cttgcgggtg ctgctcctac gtgggtcgcc     840
gcggcggggg cccccaggcc atctccatcg gcaagaactg tgacaagttc ggcattgtgg     900
tccacgagct gggccacgtc gtcggcttct ggcacgaaca cactcggcca gaccgggacc     960
gccacgtttc catcgttcgt gagaacatcc agccagggca ggagtataac ttcctgaaga    1020
tggagcctca ggaggtggag tccctggggg agacctatga cttcgacagc atcatgcatt    1080
acgctcggaa cacattctcc aggggcatct tcctggatac cattgtcccc aagtatgagg    1140
tgaacggggt gaaacctccc attggccaaa ggacacggct cagcaagggg gacattgccc    1200
aagcccgcaa gctttacaag tgcccagcct gtggagagac cctgcaagac agcacaggca    1260
acttctcctc ccctgaatac cccaatggct actctgctca catgcactgc gtgtggcgca    1320
tctctgtcac acccggggag aagatcatcc tgaacttcac gtccctggac ctgtaccgca    1380
gccgcctgtg ctggtacgac tatgtggagg tccgagatgg cttctggagg aaggcgcccc    1440
tccgaggccg cttctgcggg tccaaactcc ctgagcctat cgtctccact gacagccgcc    1500
tctgggttga attccgcagc agcagcaatt gggttggaaa gggcttcttt gcagtctacg    1560
aagccatctg cgggggtgat gtgaaaaagg actatggcca cattcaatcg cccaactacc    1620
cagacgatta ccggcccagc aaagtctgca tctggcggat ccaggtgtct gagggcttcc    1680
acgtgggcct cacattccag tcctttgaga ttgagcgcca cgacagctgt gcctacgact    1740
atctggaggt gcgcgacggg cacagtgaga gcagcaccct catcgggcgc tactgtggct    1800
atgagaagcc tgatgacatc aagagcacgt ccagccgcct ctggctcaag ttcgtctctg    1860
acgggtccat taacaaagcg ggctttgccg tcaacttttt caaagaggtg gacgagtgct    1920
ctcggcccaa ccgcgggggc tgtgagcagc ggtgcctcaa caccctgggc agctacaagt    1980
gcagctgtga ccccgggtac gagctggccc cagacaagcg ccgctgtgag gctgcttgtg    2040
gcggattcct caccaagctc aacggctcca tcaccagccc gggctggccc aaggagtacc    2100
cccccaacaa gaactgcatc tggcagctgg tggcccccac ccagtaccgc atctccctgc    2160
agtttgactt ctttgagaca gagggcaatg atgtgtgcaa gtacgacttc gtggaggtgc    2220
gcagtggact cacagctgac tccaagctgc atggcaagtt ctgtggttct gagaagcccg    2280
aggtcatcac ctcccagtac aacaacatgc gcgtggagtt caagtccgac aacaccgtgt    2340
```

```
ccaaaaaggg cttcaaggcc cacttcttct cagacaagga cgagtgctcc aaggataacg   2400

gcggctgcca gcaggactgc gtcaacacgt tcggcagtta tgagtgccaa tgccgcagtg   2460

gcttcgtcct ccatgacaac aagcacgact gcaaagaagc cggctgtgac cacaaggtga   2520

catccaccag tggtaccatc accagcccca actggcctga caagtatccc agcaagaagg   2580

agtgcacgtg ggccatctcc agcacccccg ggcaccgggt caagctgacc ttcatggaga   2640

tggacatcga gtcccagcct gagtgtgcct acgaccacct agaggtgttc gacgggcgag   2700

acgccaaggc cccgtcctc ggccgcttct gtgggagcaa gaagcccgag cccgtcctgg   2760

ccacaggcag ccgcatgttc ctgcgcttct actcagataa ctcggtccag cgaaagggct   2820

tccaggcctc ccacgccaca gagtgcgggg gccaggtacg ggcagacgtg aagaccaagg   2880

acctttactc ccacgcccag tttggcgaca acaactaccc tgggggtgtg gactgtgagt   2940

gggtcattgt ggccgaggaa ggctacggcg tggagctcgt gttccagacc tttgaggtgg   3000

aggaggagac cgactgcggc tatgactaca tggagctctt cgacggctac gacagcacag   3060

cccccaggct ggggcgctac tgtggctcag ggcctcctga ggaggtgtac tcggcgggag   3120

attctgtcct ggtgaagttc cactcggatg acaccatcac caaaaaaggt ttccacctgc   3180

gatacaccag caccaagttc caggacacac tccacagcag gaagtgacca ctgcctgagc   3240

aggggcgggg actggagcct gctgcccttg gtcgcctaga ctggatagtg ggggtgggcg   3300

gaaggcaacg caccatccct ctcccccagg ccccaggacc tgcagggcca atggcctggt   3360

gagactgtcc ataggaggtg gggaactgg actccggcat aagccacttc cccacaaacc   3420

cccaccagca aggggctggg gccagggagc agagcttcca caagacattt cgaagtcatc   3480

attcctctct tagggggccc tgcctggtgg caagagggaa tgtcagcagg accccatcgc   3540

catccctgtg tctctacacg ctgtattgtg tatcaccggg ggcattattt tcattgtaat   3600

gttcatttcc cacccctgct ccagcctcga tttggtttta ttttgagccc ccattccacc   3660

accccagttt cctggggcac aagtgtctgt gcatgtcccc caggagccac cgtggggagc   3720

cgatggggag gggatggaga aacaagacag ggcttctctc aggcccagtg gccggtcagc   3780

cacaccaggg caccgcagcc aataaaccga aagtgttaca gccaaaaaaa aaaaa        3835
```

<210> SEQ ID NO 42
<211> LENGTH: 3872
<212> TYPE: DNA
<213> ORGANISM: Homo sapiens

<400> SEQUENCE: 42

```
gtcggaggga gggagggagg gagagaaaga aagagagaaa aagaaggaaa gggagaggga     60

gacggctgga gcccgaggac gagcgcggag ccgcggaccg agcgggggc gggagacagg    120

aaggagggag gcgagcagag ggaaggggaa gaggtcgggg agcgagggcg ggagcggtcg    180

cggtcgcgat cgagcaagca agcgggcgag aggacgccct cccctggcct ccagtgcgcc    240

gcttccctcg ccgccgcccc gccagcatgc ccggcgtggc ccgcctgccg ctgctgctcg    300

ggctgctgct gctcccgcgt cccggccggc cgctggactt ggccgactac acctatgacc    360

tggcggagga ggacgactcg gagcccctca actacaaaga cccctgcaag gcggctgcct    420

ttcttgggga cattgccctg gacgaagagg acctgagggc cttccaggta cagcaggctg    480

tggatctcag acggcacaca gctcgtaagt cctccatcaa agctgcagtt ccaggaaaca    540

cttctacccc cagctgccag agcaccaacg ggcagcctca gaggggagcc tgtgggagat    600

ggagaggtag atcccgtagc cggcgggcgg cgacgtcccg accagagcgt gtgtggcccg    660
```

```
atggggtcat cccctttgtc attgggggaa acttcactgg tagccagagg gcagtcttcc    720
ggcaggccat gaggcactgg gagaagcaca cctgtgtcac cttcctggag cgcactgacg    780
aggacagcta tattgtgttc acctatcgac cttgcggctc gggaccgccc ccctgagctg    840
gccccgccct ccaggtgctg ctcctacgtg ggtcgccgcg gcgggggccc ccaggccatc    900
tccatcggca agaactgtga caagttcggc attgtggtcc acgagctggg ccacgtcgtc    960
ggcttctggc acgaacacac tcggccagac cgggaccgcc acgtttccat cgttcgtgag   1020
aacatccagc cagggcagga gtataacttc ctgaagatgg agcctcagga ggtggagtcc   1080
ctgggggaga cctatgactt cgacagcatc atgcattacg ctcggaacac attctccagg   1140
ggcatcttcc tggataccat tgtccccaag tatgaggtga acggggtgaa acctcccatt   1200
ggccaaagga cacggctcag caaggggggac attgcccaag cccgcaagct ttacaagtgc   1260
ccagcctgtg gagagaccct gcaagacagc acaggcaact tctcctcccc tgaataccccc   1320
aatggctact ctgctcacat gcactgcgtg tggcgcatct ctgtcacacc cggggagaag   1380
atcatcctga acttcacgtc cctggacctg taccgcagcc gcctgtgctg gtacgactat   1440
gtggaggtcc gagatggctt ctggaggaag gcgcccctcc gaggccgctt ctgcgggtcc   1500
aaactccctg agcctatcgt ctccactgac agccgcctct gggttgaatt ccgcagcagc   1560
agcaattggg ttggaaaggg cttctttgca gtctacgaag ccatctgcgg gggtgatgtg   1620
aaaaaggact atggccacat tcaatcgccc aactacccag acgattaccg gcccagcaaa   1680
gtctgcatct ggcggatcca ggtgtctgag ggcttccacg tgggcctcac attccagtcc   1740
tttgagattg agcgccacga cagctgtgcc tacgactatc tggaggtgcg cgacgggcac   1800
agtgagagca gcaccctcat cgggcgctac tgtggctatg agaagcctga tgacatcaag   1860
agcacgtcca gccgcctctg gctcaagttc gtctctgacg ggtccattaa caaagcgggc   1920
tttgccgtca actttttcaa agaggtggac gagtgctctc ggcccaaccg cgggggctgt   1980
gagcagcggt gcctcaacac cctgggcagc tacaagtgca gctgtgaccc cgggtacgag   2040
ctggccccag acaagcgccg ctgtgaggct gcttgtggcg gattcctcac caagctcaac   2100
ggctccatca ccagcccggg ctggcccaag gagtaccccc ccaacaagaa ctgcatctgg   2160
cagctggtgg cccccaccca gtaccgcatc tccctgcagt ttgacttctt tgagacagag   2220
ggcaatgatg tgtgcaagta cgacttcgtg gaggtgcgca gtggactcac agctgactcc   2280
aagctgcatg gcaagttctg tggttctgag aagcccgagg tcatcacctc ccagtacaac   2340
aacatgcgcg tggagttcaa gtccgacaac accgtgtcca aaaagggctt caaggcccac   2400
ttcttctcag acaaggacga gtgctccaag gataacggcg gctgccagca ggactgcgtc   2460
aacacgttcg gcagttatga gtgccaatgc cgcagtggct tcgtcctcca tgacaacaag   2520
cacgactgca aagaagccgg ctgtgaccac aaggtgacat ccaccagtgg taccatcacc   2580
agccccaact ggcctgacaa gtatcccagc aagaaggagt gcacgtgggc catctccagc   2640
acccccgggc accgggtcaa gctgaccttc atggagatgg acatcgagtc ccagcctgag   2700
tgtgcctacg accacctaga ggtgttcgac gggcgagacg ccaaggcccc cgtcctcggc   2760
cgcttctgtg ggagcaagaa gcccgagccc gtcctggcca caggcagccg catgttcctg   2820
cgcttctact cagataactc ggtccagcga aagggcttcc aggcctccca cgccacagag   2880
tgcgggggcc aggtacgggc agacgtgaag accaaggacc tttactccca cgcccagttt   2940
ggcgacaaca actaccctgg gggtgtggac tgtgagtggg tcattgtggc cgaggaaggc   3000
```

```
tacggcgtgg agctcgtgtt ccagaccttt gaggtggagg aggagaccga ctgcggctat   3060

gactacatgg agctcttcga cggctacgac agcacagccc ccaggctggg gcgctactgt   3120

ggctcagggc ctcctgagga ggtgtactcg gcgggagatt ctgtcctggt gaagttccac   3180

tcggatgaca ccatcaccaa aaaaggtttc cacctgcgat acaccagcac caagttccag   3240

gacacactcc acagcaggaa gtgaccactg cctgagcagg ggcggggact ggagcctgct   3300

gcccttggtc gcctagactg gatagtgggg gtgggcggaa ggcaacgcac catccctctc   3360

ccccaggccc caggacctgc agggccaatg gcctggtgag actgtccata ggaggtgggg   3420

gaactggact ccggcataag ccacttcccc acaaaccccc accagcaagg ggctggggcc   3480

agggagcaga gcttccacaa gacatttcga agtcatcatt cctctcttag gggccctgc    3540

ctggtggcaa gagggaatgt cagcaggacc ccatcgccat ccctgtgtct ctacacgctg   3600

tattgtgtat caccgggggc attattttca ttgtaatgtt catttcccac ccctgctcca   3660

gcctcgattt ggttttattt tgagccccca ttccaccacc ccagtttcct ggggcacaag   3720

tgtctgtgca tgtcccccag gagccaccgt ggggagccga tggggagggg atggagaaac   3780

aagacagggc ttctctcagg cccagtggcc ggtcagccac accagggcac cgcagccaat   3840

aaaccgaaag tgttacagcc aaaaaaaaaa aa                                 3872


<210> SEQ ID NO 43
<211> LENGTH: 2784
<212> TYPE: DNA
<213> ORGANISM: Homo sapiens

<400> SEQUENCE: 43

gtcggaggga gggagggagg gagagaaaga aagagagaaa aagaaggaaa gggagaggga     60

gacggctgga gcccgaggac gagcgcggag ccgcggaccg agcggggggc gggagacagg    120

aaggagggag gcgagcagag ggaaggggaa gaggtcgggg agcgagggcg ggagcggtcg    180

cggtcgcgat cgagcaagca agcgggcgag aggacgccct cccctggcct ccagtgcgcc    240

gcttccctcg ccgccgcccc gccagcatgc ccggcgtggc ccgcctgccg ctgctgctcg    300

ggctgctgct gctcccgcgt cccggccggc cgctggactt ggccgactac acctatgacc    360

tggcggagga ggacgactcg gagcccctca actacaaaga cccctgcaag gcggctgcct    420

ttcttgggga cattgccctg gacgaagagg acctgagggc cttccaggta cagcaggctg    480

tggatctcag acggcacaca gctcgtaagt cctccatcaa agctgcagtt ccaggaaaca    540

cttctacccc cagctgccag agcaccaacg ggcagcctca gaggggagcc tgtgggagat    600

ggagaggtag atcccgtagc cggcgggcgg cgacgtcccg accagagcgt gtgtggcccg    660

atggggtcat cccctttgtc attgggggaa acttcactgg tagccagagg gcagtcttcc    720

ggcaggccat gaggcactgg gagaagcaca cctgtgtcac cttcctggag cgcactgacg    780

aggacagcta tattgtgttc acctatcgac cttgcggctc gggaccgccc ccctgagctg    840

gccccgccct ccaggtgctg ctcctacgtg ggtcgccgcg gcgggggccc ccaggccatc    900

tccatcggca agaactgtga caagttcggc attgtggtcc acgagctggg ccacgtcgtc    960

ggcttctggc acgaacacac tcggccagac cgggaccgcc acgtttccat cgttcgtgag   1020

aacatccagc cagggcagga gtataacttc ctgaagatgg agcctcagga ggtggagtcc   1080

ctgggggaga cctatgactt cgacagcatc atgcattacg ctcggaacac attctccagg   1140

ggcatcttcc tggataccat tgtccccaag tatgaggtga acggggtgaa acctcccatt   1200

ggccaaagga cacggctcag caagggggac attgcccaag cccgcaagct ttacaagtgc   1260
```

```
ccagcctgtg gagagaccct gcaagacagc acaggcaact tctcctcccc tgaatacccc   1320

aatggctact ctgctcacat gcactgcgtg tggcgcatct ctgtcacacc cggggagaag   1380

atcatcctga acttcacgtc cctggacctg taccgcagcc gcctgtgctg gtacgactat   1440

gtggaggtcc gagatggctt ctggaggaag gcgcccctcc gaggccgctt ctgcgggtcc   1500

aaactccctg agcctatcgt ctccactgac agccgcctct gggttgaatt ccgcagcagc   1560

agcaattggg ttggaaaggg cttctttgca gtctacgaag ccatctgcgg gggtgatgtg   1620

aaaaaggact atggccacat tcaatcgccc aactacccag acgattaccg gcccagcaaa   1680

gtctgcatct ggcggatcca ggtgtctgag ggcttccacg tggcctcac attccagtcc   1740

tttgagattg agcgccacga cagctgtgcc tacgactatc tggaggtgcg cgacgggcac   1800

agtgagagca gcaccctcat cgggcgctac tgtggctatg agaagcctga tgacatcaag   1860

agcacgtcca gccgcctctg gctcaagttc gtctctgacg ggtccattaa caaagcgggc   1920

tttgccgtca actttttcaa agaggtggac gagtgctctc ggcccaaccg cgggggctgt   1980

gagcagcggt gcctcaacac cctgggcagc tacaagtgca gctgtgaccc cgggtacgag   2040

ctggccccag acaagcgccg ctgtgaggct gcttgtggcg gattcctcac caagctcaac   2100

ggctccatca ccagcccggg ctggcccaag gagtaccccc ccaacaagaa ctgcatctgg   2160

cagctggtgg cccccaccca gtaccgcatc tccctgcagt ttgacttctt tgagacagag   2220

ggcaatgatg tgtgcaagta cgacttcgtg gaggtgcgca gtggactcac agctgactcc   2280

aagctgcatg gcaagttctg tggttctgag aagcccgagg tcatcacctc ccagtacaac   2340

aacatgcgcg tggagttcaa gtccgacaac accgtgtcca aaaagggctt caaggcccac   2400

ttcttctcag aaaagaggcc agctctgcag ccccctcggg gacgccccca ccagctcaaa   2460

ttccgagtgc agaaaagaaa ccggaccccc cagtgaggcc tgccaggcct cccggacccc   2520

ttgttactca ggaacctcac cttggacgga atgggatggg ggcttcggtg cccaccaacc   2580

ccccacctcc actctgccat tccggcccac ctccctctgg ccggacagaa ctggtgctct   2640

cttctcccca ctgtgcccgt ccgcggaccg gggacccttc cccgtgccct accccctccc   2700

attttgatgg tgtctgtgac atttcctgtt gtgaagtaaa agagggaccc ctgcgtcctg   2760

ctcctttctc ttgcagaaaa aaaa                                          2784
```

<210> SEQ ID NO 44
<211> LENGTH: 8857
<212> TYPE: DNA
<213> ORGANISM: Homo sapiens

<400> SEQUENCE: 44

```
gccggcgccc taggaggcgg cggcgggagg atcgcgtccc gacccgaggc cgggcctgct     60

gcgcgccccc agcccgatcg gcaccgccac ttgcctgagc gccccggcgg cccgagcgcg    120

ccccaagccc gggcgccacc gctgccacct ccgcgaggtc tccctgagtc tttgaggaca    180

cagcctcgct ggaggcagtt tctggtgcca gtgacggggt ggcccgtgag ctgatgacga    240

ggactggctt ttaatccttg gtggtgatta agagaaagct tattggggcc tgggagcagc    300

tccccgccga cccccaccac catgtcggga tccacacagc ctgtggcaca gacgtggagg    360

gccactgagc cccgctaccc gccccacagc ctttcctacc cagtgcagat cgcccggacg    420

cacacggacg tcgggctcct ggagtaccag caccactccc gcgactatgc ctcccacctg    480

tcgcccggct ccatcatcca gccccagcgg cggaggccct ccctgctgtc tgagttccag    540
```

```
cccgggaatg aacggtccca ggagctccac ctgcggccag agtcccactc atacctgccc    600
gagctgggga agtcagagat ggagttcatt gaaagcaagc gccctcggct agagctgctg    660
cctgaccccc tgctgcgacc gtcacccctg ctggccacgg gccagcctgc gggatctgaa    720
gacctcacca aggaccgtag cctgacgggc aagctggaac cggtgtctcc ccccagcccc    780
ccgcacactg accctgagct ggagctggtg ccgccacggc tgtccaagga ggagctgatc    840
cagaacatgg accgcgtgga ccgagagatc accatggtag agcagcagat ctctaagctg    900
aagaagaagc agcaacagct ggaggaggag gctgccaagc cgcccgagcc tgagaagccc    960
gtgtcaccgc cgcccatcga gtcgaagcac cgcagcctgg tgcagatcat ctacgacgag   1020
aaccggaaga aggctgaagc tgcacatcgg attctggaag gcctggggcc ccaggtggag   1080
ctgccgctgt acaaccagcc ctccgacacc cggcagtatc atgagaacat caaaataaac   1140
caggcgatgc ggaagaagct aatcttgtac ttcaagagga ggaatcacgc tcggaaacaa   1200
tgggagcaga agttctgcca gcgctatgac cagctcatgg aggcctggga gaagaaggtg   1260
gagcgcatcg agaacaaccc ccggcggcgg gccaaggaga gcaaggtgcg cgagtactac   1320
gagaagcagt tccctgagat ccgcaagcag cgcgagctgc aggagcgcat gcagagcagg   1380
gtgggccagc ggggcagtgg gctgtccatg tcggccgccc gcagcgagca cgaggtgtca   1440
gagatcatcg atggcctctc agagcaggag aacctggaga agcagatgcg ccagctggcc   1500
gtgatcccgc ccatgctgta cgacgctgac cagcagcgca tcaagttcat caacatgaac   1560
gggcttatgg ccgaccccat gaaggtgtac aaagaccgcc aggtcatgaa catgtggagt   1620
gagcaggaga aggagacctt ccgggagaag ttcatgcagc atcccaagaa ctttggcctg   1680
atcgcatcat tcctggagag gaagacagtg gctgagtgcg tcctctatta ctacctgact   1740
aagaagaatg agaactataa gagcctggtg agacggagct atcggcgccg cggcaagagc   1800
cagcagcagc aacaacagca gcagcagcag cagcagcagc agcagcagca gcccatgccc   1860
cgcagcagcc aggaggagaa agatgagaag gagaaggaaa aggaggcgga gaaggaggag   1920
gagaagccgg aggtggagaa cgacaaggaa gacctcctca aggagaagac agacgacacc   1980
tcaggggagg acaacgacga gaaggaggct gtggcctcca aaggccgcaa aactgccaac   2040
agccagggaa gacgcaaagg ccgcatcacc cgctcaatgg ctaatgaggc caacagcgag   2100
gaggccatca ccccccagca gagcgccgag ctggcctcca tggagctgaa tgagagttct   2160
cgctggacag aagaagaaat ggaaacagcc aagaaaggtc tcctggaaca cggccgcaac   2220
tggtcggcca tcgcccggat ggtgggctcc aagactgtgt cgcagtgtaa gaacttctac   2280
ttcaactaca agaagaggca gaacctcgat gagatcttgc agcagcacaa gctgaagatg   2340
gagaaggaga ggaacgcgcg gaggaagaag aagaaagcgc cggcggcggc cagcgaggag   2400
gctgcattcc cgcccgtggt ggaggatgag gagatggagg cgtcgggcgt gagcggaaat   2460
gaggaggaga tggtggagga ggctgaagcc ttacatgcct ctgggaatga ggtgcccaga   2520
ggggaatgca gtggcccagc cactgtcaac aacagctcag acaccgagag catcccctct   2580
cctcacactg aggccgccaa ggacacaggg cagaatgggc ccaagccccc agccaccctg   2640
ggcgccgacg ggccaccccc agggccaccc accccaccac cggaggacat cccggccccc   2700
actgagccca ccccggcctc tgaagccacc ggagccccta cgccccccac agcaccccca   2760
tcgccctctg cacctcctcc tgtggtcccc aaggaggaga aggaggagga gaccgcagca   2820
gcgcccccag tggaggaggg ggaggagcag aagccccccg cggctgagga gctggcagtg   2880
gacacaggga aggccgagga gcccgtcaag agcgagtgca cggaggaagc cgaggagggg   2940
```

```
ccggccaagg gcaaggacgc ggaggccgct gaggccacgg ccgagggggc gctcaaggca   3000
gagaagaagg agggcgggag cggcagggcc accacagcca agagctcggg cgccccccag   3060
gacagcgact ccagtgctac ctgcagtgca gacgaggtgg atgaggccga gggcggcgac   3120
aagaaccggc tgctgtcccc aaggcccagc ctcctcaccc cgactggcga cccccgggcc   3180
aatgcctcac cccagaagcc actggacctg aagcagctga agcagcgagc ggctgccatc   3240
ccccccatcc aggtcaccaa agtccatgag cccccccggg aggacgcagc tcccaccaag   3300
ccagctcccc cagccccacc gccaccgcaa aacctgcagc cggagagcga cgcccctcag   3360
cagcctggca gcagcccccg gggcaagagc aggagcccgg caccccccgc cgacaaggag   3420
gccttcgcag ccgaggccca gaagctgcct ggggaccccc cttgctggac ttccggcctg   3480
cccttccccg tgcccccccg tgaggtgatc aaggcctccc cgcatgcccc ggacccctca   3540
gccttctcct acgctccacc tggtcaccca ctgcccctgg gcctccatga cactgcccgg   3600
cccgtcctgc cgcgcccacc caccatctcc aacccgcctc ccctcatctc ctctgccaag   3660
caccccagcg tcctcgagag gcaaataggt gccatctccc aaggaatgtc ggtccagctc   3720
cacgtcccgt actcagagca tgccaaggcc ccggtgggcc ctgtcaccat ggggctgccc   3780
ctgcccatgg accccaaaaa gctggcaccc ttcagcggag tgaagcagga gcagctgtcc   3840
ccacggggcc aggctgggcc accggagagc ctgggggtgc ccacagccca ggaggcgtcc   3900
gtgctgagag ggacagctct gggctcagtt ccgggcggaa gcatcaccaa aggcattccc   3960
agcacacggg tgccctcgga cagcgccatc acataccgcg gctccatcac ccacggcacg   4020
ccagctgacg tcctgtacaa gggcaccatc accaggatca tcggcgagga cagcccgagt   4080
cgcttggacc gcggccggga ggacagcctg cccaagggcc acgtcatcta cgaaggcaag   4140
aagggccacg tcttgtccta tgagggtggc atgtctgtga cccagtgctc caaggaggac   4200
ggcagaagca gctcaggacc cccccatgag acggccgccc ccaagcgcac ctatgacatg   4260
atggagggcc gcgtgggcag agccatctcc tcagccagca tcgaaggtct catgggccgt   4320
gccatcccgc cggagcgaca cagcccccac cacctcaaag agcagcacca catccgcggg   4380
tccatcacac aagggatccc tcggtcctac gtggaggcac aggaggacta cctgcgtcgg   4440
gaggccaagc tcctaaagcg ggagggcacg cctccgcccc caccgccctc acgggacctg   4500
accgaggcct acaagacgca ggccctgggc cccctgaagc tgaagccggc ccatgagggc   4560
ctggtggcca cggtgaagga ggcgggccgc tccatccatg agatcccgcg cgaggagctg   4620
cggcacacgc ccgagctgcc cctggccccg cggccgctca aggagggctc catcacgcag   4680
ggcaccccgc tcaagtacga caccggcgcg tccaccactg gctccaaaaa gcacgacgta   4740
cgctccctca tcggcagccc cggccggacg ttcccacccg tgcacccgct ggatgtgatg   4800
gccgacgccc gggcactgga acgtgcctgc tacgaggaga gcctgaagag ccggccaggg   4860
accgccagca gctcgggggg ctccattgcg cgcggcgccc cggtcattgt gcctgagctg   4920
ggtaagccgc ggcagagccc cctgacctat gaggaccacg gggcaccctt tgccggccac   4980
ctcccacgag gttcgcccgt gaccacgcgg gagcccacgc cgcgcctgca ggagggcagc   5040
ctttcgtcca gcaaggcatc ccaggaccga aagctgacgt cgacgcctcg tgagatcgcc   5100
aagtccccgc acagcaccgt gcccgagcac cacccacacc ccatctcgcc ctatgagcac   5160
ctgcttcggg gcgtgagtgg cgtggacctg tatcgcagcc acatccccct ggccttcgac   5220
cccacctcca taccccgcgg catccctctg gacgcagccg ctgcctacta cctgccccga   5280
```

```
cacctggccc ccaaccccac ctacccgcac ctgtacccac cctacctcat ccgcggctac   5340
cccgacacgg cggcgctgga gaaccggcag accatcatca atgactacat cacctcgcag   5400
cagatgcacc acaacgcggc caccgccatg gcccagcgag ctgatatgct gaggggcctc   5460
tcgccccgcg agtcctcgct ggcactcaac tacgctgcgg gtccccgagg catcatcgac   5520
ctgtcccaag tgccacacct gcctgtgctc gtgcccccga caccaggcac cccagccacc   5580
gccatggacc gccttgccta cctccccacc gcgccccagc ccttcagcag ccgccacagc   5640
agctccccac tctccccagg aggtccaaca cacttgacaa aaccaaccac cacgtcctcg   5700
tccgagcggg agcgagaccg ggatcgagag cgggaccggg atcgggagcg ggaaaagtcc   5760
atcctcacgt ccaccacgac ggtggagcac gcacccatct ggagacctgg tacagagcag   5820
agcagcggca gcagcggcgg gggtgggggc agcagcagcc gccccgcctc ccactcccat   5880
gcccaccagc actcgcccat ctcccctcgg acccaggatg ccctccagca gagacccagt   5940
gtgcttcaca acacaggcat gaagggtatc atcaccgctg tggagcccag cacgcccacg   6000
gtcctgaggt ccacctccac ctcctcaccc gttcgcccgg ctgccacatt cccacctgcc   6060
acccactgcc cactgggcgg caccctcgat ggggtctacc ctaccctcat ggagcccgtc   6120
ttgctgccca aggaggcccc ccgggtcgcc cggccagagc ggccccgagc agacaccggc   6180
catgccttcc tcgccaagcc cccagcccgc tccgggctgg agcccgcctc ctcccccagc   6240
aagggctcgg agccccggcc cctagtgcct cctgtctctg gccacgccac catcgcccgc   6300
accccctgcga agaacctcgc acctcaccac gccagcccgg acccgccggc gccacctgcc   6360
tcggcctcgg acccgcaccg ggaaaagact caaagtaaac ccttttccat ccaggaactg   6420
gaactccgtt ctctgggtta ccacggcagc agctacagcc ccgaaggggt ggagcccgtc   6480
agccctgtga gctcacccag tctgacccac gacaaggggc tccccaagca cctggaagag   6540
ctcgacaaga gccacctgga gggggagctg cggcccaagc agccaggccc cgtgaagctt   6600
ggcggggagg ccgcccacct cccacacctg cggccgctgc ctgagagcca gccctcgtcc   6660
agcccgctgc tccagaccgc cccaggggtc aaaggtcacc agcgggtggt caccctggcc   6720
cagcacatca gtgaggtcat cacacaggac tacacccggc accacccaca gcagctcagc   6780
gcaccccctgc ccgccccccct ctactccttc cctggggcca gctgccccgt cctggacctc   6840
cgccgcccac ccagtgacct ctacctcccg cccccggacc atggtgcccc ggcccgtggc   6900
tccccccaca gcgaaggggg caagaggtct ccagagccaa acaagacgtc ggtcttgggt   6960
ggtggtgagg acggtattga acctgtgtcc ccaccggagg gcatgacgga gccagggcac   7020
tcccggagtg ctgtgtaccc gctgctgtac cgggatgggg aacagacgga gcccagcagg   7080
atgggctcca agtctccagg caacaccagc cagccgccag ccttcttcag caagctgacc   7140
gagagcaact ccgccatggt caagtccaag aagcaagaga tcaacaagaa gctgaacacc   7200
cacaaccgga atgagcctga atacaatatc agccagcctg ggacggagat cttcaatatg   7260
cccgccatca ccggaacagg ccttatgacc tatagaagcc aggcggtgca ggaacatgcc   7320
agcaccaaca tggggctgga ggccataatt agaaaggcac tcatgggtaa atatgaccag   7380
tgggaagagt ccccgccgct cagcgccaat gcttttaacc ctctgaatgc cagtgccagc   7440
ctgcccgctg ctatgcccat aaccgctgct gacggacgga gtgaccacac actcacctcg   7500
ccaggtggcg gcgggaaggc caaggtctct ggcagaccca gcagccgaaa agccaagtcc   7560
ccggccccgg gcctggcatc tggggaccgg ccaccctctg tctcctcagt gcactcggag   7620
ggagactgca accgccggac gccgctcacc aaccgcgtgt gggaggacag gccctcgtcc   7680
```

```
gcaggttcca cgccattccc ctacaacccc ctgatcatgc ggctgcaggc gggtgtcatg   7740

gcttccccac ccccaccggg cctccccgcg ggcagcgggc ccctcgctgg cccccaccac   7800

gcctgggacg aggagcccaa gccactgctc tgctcgcagt acgagacact ctccgacagc   7860

gagtgactca gaacagggcg gggggggggg cggtgtcagg tcccagcgag ccacaggaac   7920

ggccctgcag gagcagggcg gctgccgact cccccaacca aggaaggagc ccctgagtcc   7980

gcctgcgcct ccatccatct gtccgtccag agccggcatc cttgcctgtc taaagcctta   8040

actaagactc ccgccccggg ctggccctgt gcagacctta ctcaggggat gtttacctgg   8100

tgctcgggaa gggaggggaa ggggccgggg agggggcacg gcaggcgtgt ggcagccaca   8160

cgcaggcggc cagggcggcc agggacccaa agcaggatga ccacgcacct ccacgccact   8220

gcctcccccg aatgcatttg gaaccaaagt ctaaactgag ctcgcagccc ccgcgccctc   8280

cctccgcctc ccatcccgct tagcgctctg gacagatgga cgcaggccct gtccagcccc   8340

cagtgcgctc gttccggtcc ccacagactg ccccagccaa cgagattgct ggaaaccaag   8400

tcaggccagg tgggcggaca aaagggccag gtgcggcctg gggggaacgg atgctccgag   8460

gactggactg tttttttcac acatcgttgc cgcagcggtg ggaaggaaag gcagatgtaa   8520

atgatgtgtt ggtttacagg gtatattttt gataccttca atgaattaat tcagatgttt   8580

tacgcaagga aggacttacc cagtattact gctgctgtgc ttttgatctc tgcttaccgt   8640

tcaagaggcg tgtgcaggcc gacagtcggt gaccccatca ctcgcaggac caagggggcg   8700

gggactgctg gctcacgccc cgctgtgtcc tccctccctc ccttccttgg gcagaatgaa   8760

ttcgatgcgt attctgtggc cgccatctgc gcagggtggt ggtattctgt catttacaca   8820

cgtcgttcta attaaaaagc gaattatact ccagtta                            8857
```

<210> SEQ ID NO 45
<211> LENGTH: 8689
<212> TYPE: DNA
<213> ORGANISM: Homo sapiens

<400> SEQUENCE: 45

```
gccggcgccc taggaggcgg cggcgggagg atcgcgtccc gacccgaggc cgggcctgct     60

gcgcgccccc agcccgatcg gcaccgccac ttgcctgagc gccccggcgg cccgagcgcg    120

ccccaagccc gggcgccacc gctgccacct ccgcgaggtc tccctgagtc tttgaggaca    180

cagcctcgct ggaggcagtt tctggtgcca gtgacggggt ggcccgtgag ctgatgacga    240

ggactggctt ttaatccttg gtggtgatta agagaaagct tattggggcc tgggagcagc    300

tccccgccga cccccaccac catgtcggga tccacacagc ctgtggcaca gacgtggagg    360

gccactgagc cccgctaccc gccccacagc ctttcctacc cagtgcagat cgcccggacg    420

cacacggacg tcgggctcct ggagtaccag caccactccc gcgactatgc ctcccacctg    480

tcgcccggct ccatcatcca gccccagcgg cggaggccct ccctgctgtc tgagttccag    540

cccgggaatg aacggtccca ggagctccac ctgcggccag agtcccactc atacctgccc    600

gagctgggga agtcagagat ggagttcatt gaaagcaagc gccctcggct agagctgctg    660

cctgaccccc tgctgcgacc gtcacccctg ctggccacgg gccagcctgc gggatctgaa    720

gacctcacca aggaccgtag cctgacgggc aagctggaac cggtgtctcc ccccagcccc    780

ccgcacactg accctgagct ggagctggtg ccgccacggc tgtccaagga ggagctgatc    840

cagaacatgg accgcgtgga ccgagagatc accatggtag agcagcagat ctctaagctg    900
```

```
aagaagaagc agcaacagct ggaggaggag gctgccaagc cgcccgagcc tgagaagccc    960

gtgtcaccgc cgcccatcga gtcgaagcac cgcagcctgg tgcagatcat ctacgacgag   1020

aaccggaaga aggctgaagc tgcacatcgg attctggaag gcctggggcc ccaggtggag   1080

ctgccgctgt acaaccagcc ctccgacacc cggcagtatc atgagaacat caaaataaac   1140

caggcgatgc ggaagaagct aatcttgtac ttcaagagga ggaatcacgc tcggaaacaa   1200

tgggagcaga agttctgcca gcgctatgac cagctcatgg aggcctggga gaagaaggtg   1260

gagcgcatcg agaacaaccc ccggcggcgg gccaaggaga gcaaggtgcg cgagtactac   1320

gagaagcagt tccctgagat ccgcaagcag cgcgagctgc aggagcgcat gcagagggtg   1380

ggccagcggg gcagtgggct gtccatgtcg gccgcccgca gcgagcacga ggtgtcagag   1440

atcatcgatg gcctctcaga gcaggagaac ctggagaagc agatgcgcca gctggccgtg   1500

atcccgccca tgctgtacga cgctgaccag cagcgcatca agttcatcaa catgaacggg   1560

cttatggccg accccatgaa ggtgtacaaa gaccgccagg tcatgaacat gtggagtgag   1620

caggagaagg agaccttccg ggagaagttc atgcagcatc ccaagaactt tggcctgatc   1680

gcatcattcc tggagaggaa gacagtggct gagtgcgtcc tctattacta cctgactaag   1740

aagaatgaga actataagag cctggtgaga cggagctatc ggcgccgcgg caagagccag   1800

cagcagcaac aacagcagca gcagcagcag cagcagcagc agcagcagcc catgccccgc   1860

agcagccagg aggagaaaga tgagaaggag aaggaaaagg aggcggagaa ggaggaggag   1920

aagccggagg tggagaacga caaggaagac ctcctcaagg agaagacaga cgacacctca   1980

ggggaggaca acgacgagaa ggaggctgtg gcctccaaag gccgcaaaac tgccaacagc   2040

cagggaagac gcaaaggccg catcacccgc tcaatggcta atgaggccaa cagcgaggag   2100

gccatcaccc cccagcagag cgccgagctg gcctccatgg agctgaatga gagttctcgc   2160

tggacagaag aagaaatgga aacagccaag aaaggtctcc tggaacacgg ccgcaactgg   2220

tcggccatcg cccggatggt gggctccaag actgtgtcgc agtgtaagaa cttctacttc   2280

aactacaaga agaggcagaa cctcgatgag atcttgcagc agcacaagct gaagatggag   2340

aaggagagga acgcgcggag gaagaagaag aaagcgccgg cggcggccag cgaggaggct   2400

gcattcccgc ccgtggtgga ggatgaggag atggaggcgt cgggcgtgag cggaaatgag   2460

gaggagatgg tggaggaggc tgaagccact gtcaacaaca gctcagacac cgagagcatc   2520

ccctctcctc acactgaggc cgccaaggac acagggcaga atgggcccaa gcccccagcc   2580

accctgggcg ccgacgggcc acccccaggg ccacccaccc caccaccgga ggacatcccg   2640

gcccccactg agcccacccc ggcctctgaa gccaccggag cccctacgcc cccaccagca   2700

cccccatcgc cctctgcacc tcctcctgtg gtccccaagg aggagaagga ggaggagacc   2760

gcagcagcgc cccccagtgga ggagggggag gagcagaagc cccccgcggc tgaggagctg   2820

gcagtggaca cagggaaggc cgaggagccc gtcaagagcg agtgcacgga ggaagccgag   2880

gaggggccgg ccaagggcaa ggacgcggag gccgctgagg ccacggccga gggggcgctc   2940

aaggcagaga agaaggaggg cgggagcggc agggccacca cagccaagag ctcgggcgcc   3000

ccccaggaca gcgactccag tgctacctgc agtgcagacg aggtggatga ggccgagggc   3060

ggcgacaaga accggctgct gtccccaagg cccagcctcc tcaccccgac tggcgacccc   3120

cgggccaatg cctcacccca gaagccactg gacctgaagc agctgaagca gcgagcggct   3180

gccatccccc ccatccaggt caccaaagtc catgagcccc cccgggagga cgcagctccc   3240

accaagccag ctcccccagc ccccaccgcca ccgcaaaacc tgcagccgga gagcgacgcc   3300
```

```
cctcagcagc ctggcagcag cccccggggc aagagcagga gcccggcacc ccccgccgac   3360
aaggaggcag agaagcctgt gttcttccca gccttcgcag ccgaggccca gaagctgcct   3420
ggggaccccc cttgctggac ttccggcctg cccttccccg tgcccccccg tgaggtgatc   3480
aaggcctccc cgcatgcccc ggacccctca gccttctcct acgctccacc tggtcaccca   3540
ctgcccctgg gcctccatga cactgcccgg cccgtcctgc cgcgcccacc caccatctcc   3600
aacccgcctc ccctcatctc ctctgccaag caccccagcg tcctcgagag gcaaataggt   3660
gccatctccc aaggaatgtc ggtccagctc cacgtcccgt actcagagca tgccaaggcc   3720
ccggtgggcc ctgtcaccat ggggctgccc ctgcccatgg accccaaaaa gctggcaccc   3780
ttcagcggag tgaagcagga gcagctgtcc ccacggggcc aggctgggcc accggagagc   3840
ctgggggtgc ccacagccca ggaggcgtcc gtgctgagag ggacagctct gggctcagtt   3900
ccgggcggaa gcatcaccaa aggcattccc agcacacggg tgccctcgga cagcgccatc   3960
acataccgcg gctccatcac ccacggcacg ccagctgacg tcctgtacaa gggcaccatc   4020
accaggatca tcggcgagga cagcccgagt cgcttggacc gcggccggga ggacagcctg   4080
cccaagggcc acgtcatcta cgaaggcaag aagggccacg tcttgtccta tgagggtggc   4140
atgtctgtga cccagtgctc caaggaggac ggcagaagca gctcaggacc cccccatgag   4200
acggccgccc ccaagcgcac ctatgacatg atggagggcc gcgtgggcag agccatctcc   4260
tcagccagca tcgaaggtct catgggccgt gccatcccgc cggagcgaca cagcccccac   4320
cacctcaaag agcagcacca catccgcggg tccatcacac aagggatccc tcggtcctac   4380
gtggaggcac aggaggacta cctgcgtcgg gaggccaagc tcctaaagcg ggagggcacg   4440
cctccgcccc caccgccctc acgggacctg accgaggcct acaagacgca ggccctgggc   4500
cccctgaagc tgaagccggc ccatgagggc ctggtggcca cggtgaagga ggcgggccgc   4560
tccatccatg agatcccgcg cgaggagctg cggcacacgc ccgagctgcc cctggccccg   4620
cggccgctca aggagggctc catcacgcag ggcaccccgc tcaagtacga caccggcgcg   4680
tccaccactg gctccaaaaa gcacgacgta cgctccctca tcggcagccc cggccggacg   4740
ttcccacccg tgcacccgct ggatgtgatg gccgacgccc gggcactgga acgtgcctgc   4800
tacgaggaga gcctgaagag ccggccaggg accgccagca gctcgggggg ctccattgcg   4860
cgcggcgccc cggtcattgt gcctgagctg ggtaagccgc ggcagagccc cctgacctat   4920
gaggaccacg gggcaccctt tgccggccac ctcccacgag gttcgcccgt gaccacgcgg   4980
gagcccacgc cgcgcctgca ggagggcagc ctttcgtcca gcaaggcatc ccaggaccga   5040
aagctgacgt cgacgcctcg tgagatcgcc aagtccccgc acagcaccgt gcccgagcac   5100
cacccacacc ccatctcgcc ctatgagcac ctgcttcggg gcgtgagtgg cgtggacctg   5160
tatcgcagcc acatcccct ggccttcgac cccacctcca taccccgcgg catccctctg   5220
gacgcagccg ctgcctacta cctgccccga cacctggccc ccaaccccac ctacccgcac   5280
ctgtacccac cctacctcat ccgcggctac cccgacacgg cggcgctgga gaaccggcag   5340
accatcatca atgactacat cacctcgcag cagatgcacc acaacgcggc caccgccatg   5400
gcccagcgag ctgatatgct gaggggcctc tcgccccgcg agtcctcgct ggcactcaac   5460
tacgctgcgg gtccccgagg catcatcgac ctgtcccaag tgccacacct gcctgtgctc   5520
gtgcccccga caccaggcac cccagccacc gccatggacc gccttgccta cctccccacc   5580
gcgccccagc ccttcagcag ccgccacagc agctccccac tctccccagg aggtccaaca   5640
```

```
cacttgacaa aaccaaccac cacgtcctcg tccgagcggg agcgagaccg ggatcgagag   5700
cgggaccggg atcgggagcg ggaaaagtcc atcctcacgt ccaccacgac ggtggagcac   5760
gcacccatct ggagacctgg tacagagcag agcagcggca gcagcggcgg gggtgggggc   5820
agcagcagcc gccccgcctc ccactcccat gcccaccagc actcgcccat ctcccctcgg   5880
acccaggatg ccctccagca gagacccagt gtgcttcaca acacaggcat gaagggtatc   5940
atcaccgctg tggagcccag cacgcccacg gtcctgaggt ccacctccac ctcctcaccc   6000
gttcgcccgg ctgccacatt cccacctgcc acccactgcc cactgggcgg caccctcgat   6060
ggggtctacc ctaccctcat ggagcccgtc ttgctgccca aggaggcccc ccgggtcgcc   6120
cggccagagc ggccccgagc agacaccggc catgccttcc tcgccaagcc cccagcccgc   6180
tccgggctgg agcccgcctc ctcccccagc aagggctcgg agccccggcc cctagtgcct   6240
cctgtctctg gccacgccac catcgcccgc acccctgcga agaacctcgc acctcaccac   6300
gccagcccgg acccgccggc gccacctgcc tcggcctcgg acccgcaccg ggaaaagact   6360
caaagtaaac ccttttccat ccaggaactg gaactccgtt ctctgggtta ccacggcagc   6420
agctacagcc ccgaaggggt ggagcccgtc agccctgtga gctcacccag tctgacccac   6480
gacaaggggc tccccaagca cctggaagag ctcgacaaga gccacctgga gggggagctg   6540
cggcccaagc agccaggccc cgtgaagctt ggcggggagg ccgcccacct cccacacctg   6600
cggccgctgc ctgagagcca gccctcgtcc agcccgctgc tccagaccgc cccaggggtc   6660
aaaggtcacc agcgggtggt caccctggcc cagcacatca gtgaggtcat cacacaggac   6720
tacacccggc accacccaca gcagctcagc gcacccctgc ccgccccct ctactccttc   6780
cctggggcca gctgccccgt cctggacctc cgccgcccac ccagtgacct ctacctcccg   6840
cccccggacc atggtgcccc ggcccgtggc tccccccaca gcgaaggggg caagaggtct   6900
ccagagccaa acaagacgtc ggtcttgggt ggtggtgagg acggtattga acctgtgtcc   6960
ccaccggagg gcatgacgga gccagggcac tcccggagtg ctgtgtaccc gctgctgtac   7020
cgggatgggg aacagacgga gcccagcagg atgggctcca agtctccagg caacaccagc   7080
cagccgccag ccttcttcag caagctgacc gagagcaact ccgccatggt caagtccaag   7140
aagcaagaga tcaacaagaa gctgaacacc cacaaccgga atgagcctga atacaatatc   7200
agccagcctg ggacggagat cttcaatatg cccgccatca ccggaacagg ccttatgacc   7260
tatagaagcc aggcggtgca ggaacatgcc agcaccaaca tggggctgga ggccataatt   7320
agaaaggcac tcatgggtgg cggcgggaag gccaaggtct ctggcagacc cagcagccga   7380
aaagccaagt ccccggcccc gggcctggca tctggggacc ggccaccctc tgtctcctca   7440
gtgcactcgg agggagactg caaccgccgg acgccgctca ccaaccgcgt gtgggaggac   7500
aggccctcgt ccgcaggttc cacgccattc ccctacaacc ccctgatcat gcggctgcag   7560
gcgggtgtca tggcttcccc acccccaccg ggcctccccg cgggcagcgg gcccctcgct   7620
ggcccccacc acgcctggga cgaggagccc aagccactgc tctgctcgca gtacgagaca   7680
ctctccgaca gcgagtgact cagaacaggg cggggggggg ggcggtgtca ggtcccagcg   7740
agccacagga acggccctgc aggagcaggg cggctgccga ctcccccaac caaggaagga   7800
gcccctgagt ccgcctgcgc ctccatccat ctgtccgtcc agagccggca tccttgcctg   7860
tctaaagcct taactaagac tcccgccccg ggctggccct gtgcagacct tactcagggg   7920
atgtttacct ggtgctcggg aagggagggg aaggggccgg ggagggggca cggcaggcgt   7980
gtggcagcca cacgcaggcg gccagggcgg ccagggaccc aaagcaggat gaccacgcac   8040
```

```
ctccacgcca ctgcctcccc cgaatgcatt tggaaccaaa gtctaaactg agctcgcagc   8100
ccccgcgccc tccctccgcc tcccatcccg cttagcgctc tggacagatg gacgcaggcc   8160
ctgtccagcc cccagtgcgc tcgttccggt ccccacagac tgccccagcc aacgagattg   8220
ctggaaacca agtcaggcca ggtgggcgga caaaagggcc aggtgcggcc tggggggaac   8280
ggatgctccg aggactggac tgtttttttc acacatcgtt gccgcagcgg tgggaaggaa   8340
aggcagatgt aaatgatgtg ttggtttaca gggtatattt ttgatacctt caatgaatta   8400
attcagatgt tttacgcaag gaaggactta cccagtatta ctgctgctgt gcttttgatc   8460
tctgcttacc gttcaagagg cgtgtgcagg ccgacagtcg gtgaccccat cactcgcagg   8520
accaaggggg cggggactgc tggctcacgc cccgctgtgt cctccctccc tcccttcctt   8580
gggcagaatg aattcgatgc gtattctgtg gccgccatct gcgcagggtg gtggtattct   8640
gtcatttaca cacgtcgttc taattaaaaa gcgaattata ctccagtta              8689
```

<210> SEQ ID NO 46
<211> LENGTH: 8827
<212> TYPE: DNA
<213> ORGANISM: Homo sapiens

<400> SEQUENCE: 46

```
gccggcgccc taggaggcgg cggcgggagg atcgcgtccc gacccgaggc cgggcctgct     60
gcgcgccccc agcccgatcg gcaccgccac ttgcctgagc gccccggcgg cccgagcgcg    120
ccccaagccc gggcgccacc gctgccacct ccgcgaggtc tccctgagtc tttgaggaca    180
cagcctcgct ggaggcagtt tctggtgcca gtgacggggt ggcccgtgag ctgatgacga    240
ggactggctt ttaatccttg gtggtgatta agagaaagct tattggggcc tgggagcagc    300
tccccgccga cccccaccac catgtcggga tccacacagc ctgtggcaca gacgtggagg    360
gccactgagc cccgctaccc gccccacagc ctttcctacc cagtgcagat cgcccggacg    420
cacacggacg tcgggctcct ggagtaccag caccactccc gcgactatgc ctcccacctg    480
tcgcccggct ccatcatcca gccccagcgg cggaggccct ccctgctgtc tgagttccag    540
cccgggaatg aacggtccca ggagctccac ctgcggccag agtcccactc atacctgccc    600
gagctgggga agtcagagat ggagttcatt gaaagcaagc gccctcggct agagctgctg    660
cctgaccccc tgctgcgacc gtcacccctg ctggccacgg gccagcctgc gggatctgaa    720
gacctcacca aggaccgtag cctgacgggc aagctggaac cggtgtctcc ccccagcccc    780
ccgcacactg accctgagct ggagctggtg ccgccacggc tgtccaagga ggagctgatc    840
cagaacatgg accgcgtgga ccgagagatc accatggtag agcagcagat ctctaagctg    900
aagaagaagc agcaacagct ggaggaggag gctgccaagc cgcccgagcc tgagaagccc    960
gtgtcaccgc cgcccatcga gtcgaagcac cgcagcctgg tgcagatcat ctacgacgag   1020
aaccggaaga aggctgaagc tgcacatcgg attctggaag gcctggggcc ccaggtggag   1080
ctgccgctgt acaaccagcc ctccgacacc cggcagtatc atgagaacat caaaataaac   1140
caggcgatgc ggaagaagct aatcttgtac ttcaagagga ggaatcacgc tcggaaacaa   1200
tgggagcaga agttctgcca gcgctatgac cagctcatgg aggcctggga gaagaaggtg   1260
gagcgcatcg agaacaaccc ccggcggcgg gccaaggaga gcaaggtgcg cgagtactac   1320
gagaagcagt tccctgagat ccgcaagcag cgcgagctgc aggagcgcat gcagagggtg   1380
ggccagcggg gcagtgggct gtccatgtcg gccgcccgca gcgagcacga ggtgtcagag   1440
```

```
atcatcgatg gcctctcaga gcaggagaac ctggagaagc agatgcgcca gctggccgtg   1500
atcccgccca tgctgtacga cgctgaccag cagcgcatca agttcatcaa catgaacggg   1560
cttatggccg accccatgaa ggtgtacaaa gaccgccagg tcatgaacat gtggagtgag   1620
caggagaagg agaccttccg ggagaagttc atgcagcatc ccaagaactt tggcctgatc   1680
gcatcattcc tggagaggaa gacagtggct gagtgcgtcc tctattacta cctgactaag   1740
aagaatgaga actataagag cctggtgaga cggagctatc ggcgccgcgg caagagccag   1800
cagcagcaac aacagcagca gcagcagcag cagcagcagc agcagcagcc catgccccgc   1860
agcagccagg aggagaaaga tgagaaggag aaggaaaagg aggcggagaa ggaggaggag   1920
aagccggagg tggagaacga caaggaagac ctcctcaagg agaagacaga cgacacctca   1980
ggggaggaca acgacgagaa ggaggctgtg gcctccaaag gccgcaaaac tgccaacagc   2040
cagggaagac gcaaaggccg catcacccgc tcaatggcta atgaggccaa cagcgaggag   2100
gccatcaccc cccagcagag cgccgagctg gcctccatgg agctgaatga gagttctcgc   2160
tggacagaag aagaaatgga aacagccaag aaaggtctcc tggaacacgg ccgcaactgg   2220
tcggccatcg cccggatggt gggctccaag actgtgtcgc agtgtaagaa cttctacttc   2280
aactacaaga agaggcagaa cctcgatgag atcttgcagc agcacaagct gaagatggag   2340
aaggagagga acgcgcggag gaagaagaag aaagcgccgg cggcggccag cgaggaggct   2400
gcattcccgc ccgtggtgga ggatgaggag atggaggcgt cgggcgtgag cggaaatgag   2460
gaggagatgg tggaggaggc tgaagccact gtcaacaaca gctcagacac cgagagcatc   2520
ccctctcctc acactgaggc cgccaaggac acagggcaga atgggcccaa gcccccagcc   2580
accctgggcg ccgacgggcc acccccaggg ccacccaccc caccaccgga ggacatcccg   2640
gcccccactg agcccacccc ggcctctgaa gccaccggag cccctacgcc cccaccagca   2700
cccccatcgc cctctgcacc tcctcctgtg gtccccaagg aggagaagga ggaggagacc   2760
gcagcagcgc ccccagtgga ggagggggag gagcagaagc cccccgcggc tgaggagctg   2820
gcagtggaca cagggaaggc cgaggagccc gtcaagagcg agtgcacgga ggaagccgag   2880
gaggggccgg ccaagggcaa ggacgcggag gccgctgagg ccacggccga gggggcgctc   2940
aaggcagaga agaaggaggg cgggagcggc agggccacca cagccaagag ctcgggcgcc   3000
ccccaggaca gcgactccag tgctacctgc agtgcagacg aggtggatga ggccgagggc   3060
ggcgacaaga accggctgct gtccccaagg cccagcctcc tcaccccgac tggcgacccc   3120
cgggccaatg cctcacccca gaagccactg gacctgaagc agctgaagca gcgagcggct   3180
gccatccccc ccatccaggt caccaaagtc catgagcccc cccgggagga cgcagctccc   3240
accaagccag ctcccccagc ccccaccgcca ccgcaaaacc tgcagccgga gagcgacgcc   3300
cctcagcagc ctggcagcag cccccggggc aagagcagga gcccggcacc ccccgccgac   3360
aaggaggcag agaagcctgt gttcttccca gccttcgcag ccgaggccca gaagctgcct   3420
ggggaccccc cttgctggac ttccggcctg cccttccccg tgcccccccg tgaggtgatc   3480
aaggcctccc cgcatgcccc ggacccctca gccttctcct acgctccacc tggtcaccca   3540
ctgcccctgg gcctccatga cactgcccgg cccgtcctgc cgcgcccacc caccatctcc   3600
aacccgcctc ccctcatctc ctctgccaag caccccagcg tcctcgagag gcaaataggt   3660
gccatctccc aaggaatgtc ggtccagctc cacgtcccgt actcagagca tgccaaggcc   3720
ccggtgggcc ctgtcaccat ggggctgccc ctgcccatgg accccaaaaa gctggcaccc   3780
ttcagcggag tgaagcagga gcagctgtcc ccacggggcc aggctgggcc accggagagc   3840
```

```
ctgggggtgc ccacagccca ggaggcgtcc gtgctgagag ggacagctct gggctcagtt   3900
ccgggcggaa gcatcaccaa aggcattccc agcacacggg tgccctcgga cagcgccatc   3960
acataccgcg gctccatcac ccacggcacg ccagctgacg tcctgtacaa gggcaccatc   4020
accaggatca tcggcgagga cagcccgagt cgcttggacc gcggccggga ggacagcctg   4080
cccaagggcc acgtcatcta cgaaggcaag aagggccacg tcttgtccta tgagggtggc   4140
atgtctgtga cccagtgctc caaggaggac ggcagaagca gctcaggacc cccccatgag   4200
acggccgccc ccaagcgcac ctatgacatg atggagggcc gcgtgggcag agccatctcc   4260
tcagccagca tcgaaggtct catgggccgt gccatcccgc cggagcgaca cagcccccac   4320
cacctcaaag agcagcacca catccgcggg tccatcacac aagggatccc tcggtcctac   4380
gtggaggcac aggaggacta cctgcgtcgg gaggccaagc tcctaaagcg ggagggcacg   4440
cctccgcccc caccgccctc acgggacctg accgaggcct acaagacgca ggccctgggc   4500
cccctgaagc tgaagccggc ccatgagggc ctggtggcca cggtgaagga ggcgggccgc   4560
tccatccatg agatcccgcg cgaggagctg cggcacacgc ccgagctgcc cctggccccg   4620
cggccgctca aggagggctc catcacgcag ggcaccccgc tcaagtacga caccggcgcg   4680
tccaccactg gctccaaaaa gcacgacgta cgctccctca tcggcagccc cggccggacg   4740
ttcccacccg tgcacccgct ggatgtgatg gccgacgccc gggcactgga acgtgcctgc   4800
tacgaggaga gcctgaagag ccggccaggg accgccagca gctcgggggg ctccattgcg   4860
cgcggcgccc cggtcattgt gcctgagctg ggtaagccgc ggcagagccc cctgacctat   4920
gaggaccacg gggcaccctt tgccggccac ctcccacgag gttcgcccgt gaccacgcgg   4980
gagcccacgc cgcgcctgca ggagggcagc ctttcgtcca gcaaggcatc ccaggaccga   5040
aagctgacgt cgacgcctcg tgagatcgcc aagtccccgc acagcaccgt gcccgagcac   5100
cacccacacc ccatctcgcc ctatgagcac ctgcttcggg gcgtgagtgg cgtggacctg   5160
tatcgcagcc acatccccct ggccttcgac cccacctcca taccccgcgg catccctctg   5220
gacgcagccg ctgcctacta cctgccccga cacctggccc ccaaccccac ctacccgcac   5280
ctgtacccac cctacctcat ccgcggctac cccgacacgg cggcgctgga gaaccggcag   5340
accatcatca atgactacat cacctcgcag cagatgcacc acaacgcggc caccgccatg   5400
gcccagcgag ctgatatgct gaggggcctc tcgccccgcg agtcctcgct ggcactcaac   5460
tacgctgcgg gtccccgagg catcatcgac ctgtcccaag tgccacacct gcctgtgctc   5520
gtgcccccga caccaggcac cccagccacc gccatggacc gccttgccta cctccccacc   5580
gcgccccagc ccttcagcag ccgccacagc agctccccac tctccccagg aggtccaaca   5640
cacttgacaa aaccaaccac cacgtcctcg tccgagcggg agcgagaccg ggatcgagag   5700
cgggaccggg atcgggagcg ggaaaagtcc atcctcacgt ccaccacgac ggtggagcac   5760
gcacccatct ggagacctgg tacagagcag agcagcggca gcagcggcgg gggtgggggc   5820
agcagcagcc gccccgcctc ccactcccat gcccaccagc actcgcccat ctcccctcgg   5880
acccaggatg ccctccagca gagacccagt gtgcttcaca acacaggcat gaagggtatc   5940
atcaccgctg tggagcccag cacgcccacg gtcctgaggt ccacctccac ctcctcaccc   6000
gttcgcccgg ctgccacatt cccacctgcc acccactgcc cactgggcgg caccctcgat   6060
ggggtctacc ctaccctcat ggagcccgtc ttgctgccca aggaggcccc ccgggtcgcc   6120
cggccagagc ggccccgagc agacaccggc catgccttcc tcgccaagcc cccagcccgc   6180
```

```
tccgggctgg agcccgcctc ctcccccagc aagggctcgg agccccggcc cctagtgcct   6240
cctgtctctg gccacgccac catcgcccgc acccctgcga agaacctcgc acctcaccac   6300
gccagcccgg acccgccggc gccacctgcc tcggcctcgg acccgcaccg ggaaaagact   6360
caaagtaaac ccttttccat ccaggaactg gaactccgtt ctctgggtta ccacggcagc   6420
agctacagcc ccgaaggggt ggagcccgtc agccctgtga gctcacccag tctgacccac   6480
gacaaggggc tccccaagca cctggaagag ctcgacaaga gccacctgga gggggagctg   6540
cggcccaagc agccaggccc cgtgaagctt ggcggggagg ccgcccacct cccacacctg   6600
cggccgctgc ctgagagcca gccctcgtcc agcccgctgc tccagaccgc cccaggggtc   6660
aaaggtcacc agcgggtggt caccctggcc cagcacatca gtgaggtcat cacacaggac   6720
tacacccggc accacccaca gcagctcagc gcacccctgc ccgccccccct ctactccttc   6780
cctggggcca gctgccccgt cctggacctc cgccgcccac ccagtgacct ctacctcccg   6840
cccccggacc atggtgcccc ggcccgtggc tccccccaca gcgaaggggg caagaggtct   6900
ccagagccaa acaagacgtc ggtcttgggt ggtggtgagg acggtattga acctgtgtcc   6960
ccaccggagg gcatgacgga gccagggcac tcccggagtg ctgtgtaccc gctgctgtac   7020
cgggatgggg aacagacgga gcccagcagg atgggctcca agtctccagg caacaccagc   7080
cagccgccag ccttcttcag caagctgacc gagagcaact ccgccatggt caagtccaag   7140
aagcaagaga tcaacaagaa gctgaacacc cacaaccgga atgagcctga atacaatatc   7200
agccagcctg ggacggagat cttcaatatg cccgccatca ccggaacagg ccttatgacc   7260
tatagaagcc aggcggtgca ggaacatgcc agcaccaaca tggggctgga ggccataatt   7320
agaaaggcac tcatgggtaa atatgaccag tgggaagagt ccccgccgct cagcgccaat   7380
gcttttaacc ctctgaatgc cagtgccagc ctgcccgctg ctatgcccat aaccgctgct   7440
gacggacgga gtgaccacac actcacctcg ccaggtggcg gcgggaaggc caaggtctct   7500
ggcagaccca gcagccgaaa agccaagtcc ccggccccgg gcctggcatc tggggaccgg   7560
ccacccctctg tctcctcagt gcactcggag ggagactgca accgccggac gccgctcacc   7620
aaccgcgtgt gggaggacag gccctcgtcc gcaggttcca cgccattccc ctacaacccc   7680
ctgatcatgc ggctgcaggc gggtgtcatg gcttccccac ccccaccggg cctccccgcg   7740
ggcagcgggc ccctcgctgg cccccaccac gcctgggacg aggagcccaa gccactgctc   7800
tgctcgcagt acgagacact ctccgacagc gagtgactca gaacagggcg gggggggggg   7860
cggtgtcagg tcccagcgag ccacaggaac ggccctgcag gagcagggcg gctgccgact   7920
cccccaacca aggaaggagc ccctgagtcc gcctgcgcct ccatccatct gtccgtccag   7980
agccggcatc cttgcctgtc taaagcctta actaagactc ccgcccccggg ctggccctgt   8040
gcagacctta ctcaggggat gtttacctgg tgctcgggaa gggaggggaa ggggccgggg   8100
agggggcacg gcaggcgtgt ggcagccaca cgcaggcggc cagggcggcc agggacccaa   8160
agcaggatga ccacgcacct ccacgccact gcctcccccg aatgcatttg gaaccaaagt   8220
ctaaactgag ctcgcagccc ccgcgccctc cctccgcctc ccatcccgct tagcgctctg   8280
gacagatgga cgcaggccct gtccagcccc cagtgcgctc gttccggtcc ccacagactg   8340
ccccagccaa cgagattgct ggaaaccaag tcaggccagg tgggcggaca aaagggccag   8400
gtgcggcctg gggggaacgg atgctccgag gactggactg tttttttcac acatcgttgc   8460
cgcagcggtg ggaaggaaag gcagatgtaa atgatgtgtt ggtttacagg gtatattttt   8520
gataccttca atgaattaat tcagatgttt tacgcaagga aggacttacc cagtattact   8580
```

```
gctgctgtgc ttttgatctc tgcttaccgt tcaagaggcg tgtgcaggcc gacagtcggt   8640

gaccccatca ctcgcaggac caagggggcg gggactgctg gctcacgccc cgctgtgtcc   8700

tccctccctc ccttccttgg gcagaatgaa ttcgatgcgt attctgtggc cgccatctgc   8760

gcagggtggt ggtattctgt catttacaca cgtcgttcta attaaaaagc gaattatact   8820

ccagtta                                                               8827
```

<210> SEQ ID NO 47
<211> LENGTH: 2692
<212> TYPE: DNA
<213> ORGANISM: Homo sapiens

<400> SEQUENCE: 47

```
gtcacggagc gcttaagagg agggtcgggc tcggccgggg agtcccagtg gcggaggcta     60

cgaaacttgg gggagtgcac agaagaactt cgggagcgca cgcgggacca gggaccaggc    120

tgagactcgg ggcgccagtc cgggcagggg cagcgggagc cggccgggta gggtgcagcc    180

tgaggcttgt tcagcagaac aggtgcaagc cacattgttg ccaagacctg cctgaagccg    240

gattctcccc actgcctcct tcaaccccgc ctcttcctcc tcctgtggga ctgctccccc    300

ctcctgtgag gctagataga tgccctgtat ccaagcccaa tatgggacac cagcaccgag    360

tccgggaccc cgtgaccacc tggcaagcga cccccctgacc cctgagttca tcaagcccac   420

catggacctg gccagccccg aggcagcccc cgctgccccc actgccctgc ccagcttcag    480

caccttcatg gacggctaca caggagagtt tgacaccttc ctctaccagc tgccaggaac    540

agtccagcca tgctcctcag cctcctcctc ggcctcctcc acatcctcgt cctcagccac    600

ctcccctgcc tctgcctcct tcaagttcga ggacttccag gtgtacggct gctaccccgg    660

cccccctgagc ggcccagtgg atgaggccct gtcctccagt ggctctgact actatggcag   720

cccctgctcg gccccgtcgc cctccacgcc cagcttccag ccgcccccagc tctctccctg   780

ggatggctcc ttcggccact tctcgcccag ccagacttac gaaggcctgc gggcatggac    840

agagcagctg cccaaagcct ctgggccccc acagcctcca gccttctttt ccttcagtcc    900

tcccaccggc cccagcccca gcctggccca gagcccccctg aagttgttcc cctcacaggc   960

cacccaccag ctgggggagg gagagagcta ttccatgcct acggccttcc caggtttggc   1020

acccacttct ccacaccttg agggctcggg gatactggat acacccgtga cctcaaccaa   1080

ggcccggagc ggggccccag gtggaagtga aggccgctgt gctgtgtgtg gggacaacgc   1140

ttcatgccag cattatggtg tccgcacatg tgagggctgc aagggcttct tcaagcgcac   1200

agtgcagaaa aacgccaagt acatctgcct ggctaacaag gactgccctg tggacaagag   1260

gcggcgaaac cgctgccagt tctgccgctt ccagaagtgc ctggcggtgg gcatggtgaa   1320

ggaagttgtc cgaacagaca gcctgaaggg gcggcggggc cggctacctt caaaacccaa   1380

gcagcccccca gatgcctccc ctgccaatct cctcacttcc ctggtccgtg cacacctgga  1440

ctcagggccc agcactgcca aactggacta ctccaagttc caggagctgg tgctgcccca   1500

ctttgggaag gaagatgctg gggatgtaca gcagttctac gacctgctct ccggttctct   1560

ggaggtcatc cgcaagtggg cggagaagat ccctggcttt gctgagctgt caccggctga   1620

ccaggacctg ttgctggagt cggccttcct ggagctcttc atcctccgcc tggcgtacag   1680

gtctaagcca ggcgagggca agctcatctt ctgctcaggc ctggtgctac accggctgca   1740

gtgtgcccgt ggcttcgggg actggattga cagtatcctg gccttctcaa ggtccctgca   1800
```

```
cagcttgctt gtcgatgtcc ctgccttcgc ctgcctctct gcccttgtcc tcatcaccga   1860

ccggcatggg ctgcaggagc cgcggcgggt ggaggagctg cagaaccgca tcgccagctg   1920

cctgaaggag cacgtggcag ctgtggcggg cgagccccag ccagccagct gcctgtcacg   1980

tctgttgggc aaactgcccg agctgcggac cctgtgcacc cagggcctgc agcgcatctt   2040

ctacctcaag ctggaggact tggtgccccc tccacccatc attgacaaga tcttcatgga   2100

cacgctgccc ttctgacccc tgcctgggaa cacgtgtgca catgcgcact ctcatatgcc   2160

accccatgtg cctttagtcc acggaccccc agagcacccc caagcctggg cttgagctgc   2220

agaatgactc caccttctca cctgctccag gaggtttgca gggagctcaa gcccttgggg   2280

agggggatgc cttcatgggg gtgaccccac gatttgtctt atcccccca gcctggcccc   2340

ggcctttatg ttttttgtaa gataaaccgt tttaacaca tagcgccgtg ctgtaaataa   2400

gcccagtgct gctgtaaata caggaagaaa gagcttgagg tgggagcggg gctgggagga   2460

agggatgggc cccgccttcc tgggcagcct ttccagcctc ctgctggctc tctcttccta   2520

ccctccttcc acatgtacat aaactgtcac tctaggaaga agacaaatga cagattctga   2580

catttatatt tgtgtatttt cctggattta tagtatgtga cttttctgat taatatattt   2640

aatatattga ataaaaaata gacatgtagt tggaactgaa aaaaaaaaaa aa           2692
```

<210> SEQ ID NO 48
<211> LENGTH: 2542
<212> TYPE: DNA
<213> ORGANISM: Homo sapiens

<400> SEQUENCE: 48

```
gtcacggagc gcttaagagg agggtcgggc tcggccgggg agtcccagtg gcggaggcta     60

cgaaacttgg gggagtgcac agaagaactt cgggagcgca cgcgggacca gggaccaggc    120

tgagactcgg ggcgccagtc cgggcagggg cagcgggagc cggccggaga tgccctgtat    180

ccaagcccaa tatgggacac cagcaccgag tccgggaccc cgtgaccacc tggcaagcga    240

ccccctgacc cctgagttca tcaagcccac catggacctg gccagccccg aggcagcccc    300

cgctgccccc actgccctgc ccagcttcag caccttcatg gacggctaca caggagagtt    360

tgacaccttc ctctaccagc tgccaggaac agtccagcca tgctcctcag cctcctcctc    420

ggcctcctcc acatcctcgt cctcagccac ctcccctgcc tctgcctcct tcaagttcga    480

ggacttccag gtgtacggct gctaccccgg cccctgagc ggcccagtgg atgaggccct    540

gtcctccagt ggctctgact actatggcag cccctgctcg gccccgtcgc cctccacgcc    600

cagcttccag ccgccccagc tctctccctg ggatggctcc ttcggccact tctcgcccag    660

ccagacttac gaaggcctgc gggcatggac agagcagctg cccaaagcct ctgggccccc    720

acagcctcca gccttctttt ccttcagtcc tcccaccggc cccagcccca gcctggccca    780

gagcccccctg aagttgttcc cctcacaggc cacccaccag ctgggggagg gagagagcta    840

ttccatgcct acggccttcc caggtttggc acccacttct ccacaccttg agggctcggg    900

gatactggat acacccgtga cctcaaccaa ggcccggagc ggggccccag gtggaagtga    960

aggccgctgt gctgtgtgtg gggacaacgc ttcatgccag cattatggtg tccgcacatg   1020

tgagggctgc aagggcttct tcaagcgcac agtgcagaaa aacgccaagt acatctgcct   1080

ggctaacaag gactgccctg tggacaagag gcggcgaaac cgctgccagt tctgccgctt   1140

ccagaagtgc ctggcggtgg gcatggtgaa ggaagttgtc cgaacagaca gcctgaaggg   1200

gcggcggggc cggctacctt caaaacccaa gcagccccca gatgcctccc ctgccaatct   1260
```

```
cctcacttcc ctggtccgtg cacacctgga ctcagggccc agcactgcca aactggacta   1320
ctccaagttc caggagctgg tgctgcccca ctttgggaag gaagatgctg ggatgtaca    1380
gcagttctac gacctgctct ccggttctct ggaggtcatc cgcaagtggg cggagaagat   1440
ccctggcttt gctgagctgt caccggctga ccaggacctg ttgctggagt cggccttcct   1500
ggagctcttc atcctccgcc tggcgtacag gtctaagcca ggcgagggca agctcatctt   1560
ctgctcaggc ctggtgctac accggctgca gtgtgcccgt ggcttcgggg actggattga   1620
cagtatcctg gccttctcaa ggtccctgca cagcttgctt gtcgatgtcc ctgccttcgc   1680
ctgcctctct gcccttgtcc tcatcaccga ccggcatggg ctgcaggagc cgcggcgggt   1740
ggaggagctg cagaaccgca tcgccagctg cctgaaggag cacgtggcag ctgtggcggg   1800
cgagccccag ccagccagct gcctgtcacg tctgttgggc aaactgcccg agctgcggac   1860
cctgtgcacc cagggcctgc agcgcatctt ctacctcaag ctggaggact tggtgccccc   1920
tccacccatc attgacaaga tcttcatgga cacgctgccc ttctgacccc tgcctgggaa   1980
cacgtgtgca catgcgcact ctcatatgcc accccatgtg cctttagtcc acggaccccc   2040
agagcacccc caagcctggg cttgagctgc agaatgactc caccttctca cctgctccag   2100
gaggtttgca gggagctcaa gcccttgggg agggggatgc cttcatgggg gtgaccccac   2160
gatttgtctt atccccccca gcctggcccc ggcctttatg ttttttgtaa gataaaccgt   2220
ttttaacaca tagcgccgtg ctgtaaataa gcccagtgct gctgtaaata caggaagaaa   2280
gagcttgagg tgggagcggg gctgggagga agggatgggc cccgccttcc tgggcagcct   2340
ttccagcctc ctgctggctc tctcttccta ccctccttcc acatgtacat aaactgtcac   2400
tctaggaaga agacaaatga cagattctga catttatatt tgtgtatttt cctggattta   2460
tagtatgtga cttttctgat taatatattt aatatattga ataaaaaata gacatgtagt   2520
tggaactgaa aaaaaaaaaa aa                                            2542
```

<210> SEQ ID NO 49
<211> LENGTH: 2603
<212> TYPE: DNA
<213> ORGANISM: Homo sapiens

<400> SEQUENCE: 49

```
ttcctggtgt aagctttggt atggatggtg gccgtctccc tacagactgg gagctgttag     60
agggcaggga tcctagctga cacatctatg tcctcgcctt ggttggaggc ctccaccatg    120
gacagaggcc aggccctgcc cctcccaggc agcctggctc cttctgctgg gccctgaagg    180
cagacgggat aatgtggttg gccaaggcct gttggtccat ccagagtgag atgccctgta    240
tccaagccca atatgggaca ccagcaccga gtccgggacc ccgtgaccac ctggcaagcg    300
accccctgac ccctgagttc atcaagccca ccatggacct ggccagcccc gaggcagccc    360
ccgctgcccc cactgccctg cccagcttca gcaccttcat ggacggctac acaggagagt    420
ttgacacctt cctctaccag ctgccaggaa cagtccagcc atgctcctca gcctcctcct    480
cggcctcctc cacatcctcg tcctcagcca cctcccctgc ctctgcctcc ttcaagttcg    540
aggacttcca ggtgtacggc tgctaccccg gcccccctgag cggcccagtg gatgaggccc    600
tgtcctccag tggctctgac tactatggca gcccctgctc ggccccgtcg ccctccacgc    660
ccagcttcca gccgccccag ctctctccct gggatggctc cttcggccac ttctcgccca    720
gccagactta cgaaggcctg cgggcatgga cagagcagct gcccaaagcc tctgggcccc    780
```

```
cacagcctcc agccttcttt tccttcagtc ctcccaccgg ccccagcccc agcctggccc     840

agagccccct gaagttgttc ccctcacagg ccacccacca gctgggggag ggagagagct     900

attccatgcc tacggccttc ccaggtttgg cacccacttc tccacacctt gagggctcgg     960

ggatactgga tacacccgtg acctcaacca aggcccggag cggggcccca ggtggaagtg    1020

aaggccgctg tgctgtgtgt ggggacaacg cttcatgcca gcattatggt gtccgcacat    1080

gtgagggctg caagggcttc ttcaagcgca cagtgcagaa aaacgccaag tacatctgcc    1140

tggctaacaa ggactgccct gtggacaaga ggcggcgaaa ccgctgccag ttctgccgct    1200

tccagaagtg cctggcggtg ggcatggtga aggaagttgt ccgaacagac agcctgaagg    1260

ggcggcgggg ccggctacct tcaaaaccca agcagccccc agatgcctcc cctgccaatc    1320

tcctcacttc cctggtccgt gcacacctgg actcagggcc cagcactgcc aaactggact    1380

actccaagtt ccaggagctg gtgctgcccc actttgggaa ggaagatgct ggggatgtac    1440

agcagttcta cgacctgctc tccggttctc tggaggtcat ccgcaagtgg gcggagaaga    1500

tccctggctt tgctgagctg tcaccggctg accaggacct gttgctggag tcggccttcc    1560

tggagctctt catcctccgc ctggcgtaca ggtctaagcc aggcgagggc aagctcatct    1620

tctgctcagg cctggtgcta caccggctgc agtgtgcccg tggcttcggg gactggattg    1680

acagtatcct ggccttctca aggtccctgc acagcttgct tgtcgatgtc cctgccttcg    1740

cctgcctctc tgcccttgtc ctcatcaccg accggcatgg gctgcaggag ccgcggcggg    1800

tggaggagct gcagaaccgc atcgccagct gcctgaagga gcacgtggca gctgtggcgg    1860

gcgagcccca gccagccagc tgcctgtcac gtctgttggg caaactgccc gagctgcgga    1920

ccctgtgcac ccagggcctg cagcgcatct tctacctcaa gctggaggac ttggtgcccc    1980

ctccacccat cattgacaag atcttcatgg acacgctgcc cttctgaccc ctgcctggga    2040

acacgtgtgc acatgcgcac tctcatatgc caccccatgt gcctttagtc cacggacccc    2100

cagagcaccc ccaagcctgg gcttgagctg cagaatgact ccaccttctc acctgctcca    2160

ggaggtttgc agggagctca agcccttggg gagggggatg ccttcatggg ggtgacccca    2220

cgatttgtct tatccccccc agcctggccc cggcctttat gttttttgta agataaaccg    2280

tttttaacac atagcgccgt gctgtaaata agcccagtgc tgctgtaaat acaggaagaa    2340

agagcttgag gtgggagcgg ggctgggagg aagggatggg ccccgccttc ctgggcagcc    2400

tttccagcct cctgctggct ctctcttcct accctccttc cacatgtaca taaactgtca    2460

ctctaggaag aagacaaatg acagattctg acatttatat ttgtgtattt tcctggattt    2520

atagtatgtg acttttctga ttaatatatt taatatattg aataaaaaat agacatgtag    2580

ttggaactga aaaaaaaaaa aaa                                             2603
```

<210> SEQ ID NO 50
<211> LENGTH: 4214
<212> TYPE: DNA
<213> ORGANISM: Homo sapiens

<400> SEQUENCE: 50

```
gcgcctcggg cggcttctcg ccgctcccag gtctggctgg ctggaggagt ctcagctctc      60

agccgctcgc ccgcccccgc tccgggccct cccctagtcg ccgctgtggg gcagcgcctg     120

gcgggcggcc cgcgggcggg tcgcctcccc tcctgtagcc cacacccttc ttaaagcggc     180

ggcgggaaga tgaggcttcg ggagccgctc ctgagcggca gcgccgcgat gccaggcgcg     240

tccctacagc gggcctgccg cctgctcgtg gccgtctgcg ctctgcacct tggcgtcacc     300
```

```
ctcgtttact acctggctgg ccgcgacctg agccgcctgc cccaactggt cggagtctcc    360
acaccgctgc agggcggctc gaacagtgcc gccgccatcg ggcagtcctc cggggagctc    420
cggaccggag gggcccggcc gccgcctcct ctaggcgcct cctcccagcc gcgcccgggt    480
ggcgactcca gcccagtcgt ggattctggc cctggccccg ctagcaactt gacctcggtc    540
ccagtgcccc acaccaccgc actgtcgctg cccgcctgcc ctgaggagtc cccgctgctt    600
gtgggcccca tgctgattga gtttaacatg cctgtggacc tggagctcgt ggcaaagcag    660
aacccaaatg tgaagatggg cggccgctat gcccccaggg actgcgtctc tcctcacaag    720
gtggccatca tcattccatt ccgcaaccgg caggagcacc tcaagtactg gctatattat    780
ttgcacccag tcctgcagcg ccagcagctg gactatggca tctatgttat caaccaggcg    840
ggagacacta tattcaatcg tgctaagctc ctcaatgttg gctttcaaga agccttgaag    900
gactatgact acacctgctt tgtgtttagt gacgtggacc tcattccaat gaatgaccat    960
aatgcgtaca ggtgtttttc acagccacgg cacatttccg ttgcaatgga taagtttgga   1020
ttcagcctac cttatgttca gtattttgga ggtgtctctg ctctaagtaa acaacagttt   1080
ctaaccatca atggatttcc taataattat tggggctggg gaggagaaga tgatgacatt   1140
tttaacagat tagtttttag aggcatgtct atatctcgcc caaatgctgt ggtcgggagg   1200
tgtcgcatga tccgccactc aagagacaag aaaaatgaac ccaatcctca gaggtttgac   1260
cgaattgcac acacaaagga gacaatgctc tctgatggtt tgaactcact cacctaccag   1320
gtgctggatg tacagagata cccattgtat acccaaatca cagtggacat cgggacaccg   1380
agctagcgtt ttggtacacg gataagagac ctgaaattag ccagggacct ctgctgtgtg   1440
tctctgccaa tctgctgggc tggtccctct catttttacc agtctgagtg acaggtcccc   1500
ttcgctcatc attcagatgg ctttccagat gaccaggacg agtgggatat tttgccccca   1560
acttggctcg gcatgtgaat tcttagctct gcaaggtgtt tatgcctttg cgggtttctt   1620
gatgtgttcg cagtgtcacc ccagagtcag aactgtacac atcccaaaat ttggtggccg   1680
tggaacacat tcccggtgat agaattgcta aattgtcgtg aaataggtta gaatttttct   1740
ttaaattatg gttttcttat tcgtgaaaat tcggagagtg ctgctaaaat tggattggtg   1800
tgatcttttt ggtagttgta atttaacaga aaaacacaaa atttcaacca ttcttaatgt   1860
tacgtcctcc ccccaccccc ttctttcagt ggtatgcaac cactgcaatc actgtgcata   1920
tgtcttttct tagcaaaagg attttaaaac ttgagccctg gacctttgt  cctatgtgtg   1980
tggattccag ggcaactcta gcatcagagc aaaagccttg ggtttctcgc attcagtggc   2040
ctatctccag attgtctgat ttctgaatgt aaagttgttg tgtttttttt taaatagtag   2100
tttgtagtat tttaaagaaa gaacagatcg agttctaatt atgatctagc ttgattttgt   2160
gttgatccaa atttgcatag ctgtttaatg ttaagtcatg acaatttatt tttcttggca   2220
tgctatgtaa acttgaattt cctatgtatt tttattgtgg tgttttaaat atggggaggg   2280
gtattgagca ttttttaggg agaaaaataa atatatgctg tagtggccac aaataggcct   2340
atgatttagc tggcaggcca ggttttctca agagcaaaat caccctctgg ccccttggca   2400
ggtaaggcct cccggtcagc attatcctgc cagacctcgg ggaggatacc tgggagacag   2460
aagcctctgc acctactgtg cagaactctc cacttcccca accctcccca ggtgggcagg   2520
gcggagggag cctcagcctc cttagactga cccctcaggc ccctaggctg gggggttgta   2580
aataacagca gtcaggttgt ttaccagccc tttgcacctc cccaggcaga gggagcctct   2640
```

```
gttctggtgg gggccacctc cctcagaggc tctgctagcc acactccgtg gcccacccctt   2700
tgttaccagt tcttcctcct tcctcttttc ccctgccttt ctcattcctt ccttcgtctc   2760
cctttttgtt cctttgcctc ttgcctgtcc cctaaaactt gactgtggca ctcagggtca   2820
aacagactat ccattcccca gcatgaatgt gccttttaat tagtgatcta gaaagaagtt   2880
cagccgaacc cacaccccaa ctccctccca agaacttcgg tgcctaaagc ctcctgttcc   2940
acctcaggtt ttcacaggtg ctcccacccc agttgaggct cccacccaca gggctgtctg   3000
tcacaaaccc acctctgttg ggagctattg agccacctgg gatgagatga cacaaggcac   3060
tcctaccact gagcgccttt gccaggtcca gcctgggctc aggttccaag actcagctgc   3120
ctaatcccag ggttgagcct tgtgctcgtg gcggacccca aaccactgcc ctcctgggta   3180
ccagccctca gtgtggaggc tgagctggtg cctggcccca gtcttatctg tgcctttact   3240
gctttgcgca tctcagatgc taacttggtt ctttttccag aagcctttgt attggttaaa   3300
aattattttc cattgcagaa gcagctggac tatgcaaaaa gtatttctct gtcagttccc   3360
cactctatac caaggatatt attaaaacta gaaatgactg cattgagagg gagttgtggg   3420
aaataagaag aatgaaagcc tctctttctg tccgcagatc ctgacttttc caaagtgcct   3480
taaaagaaat cagacaaatg ccctgagtgg taacttctgt gttattttac tcttaaaacc   3540
aaactctacc ttttcttgtt gttttttttt tttttttttt ttttttttg gttaccttct   3600
cattcatgtc aagtatgtgg ttcattctta gaaccaaggg aaatactgct ccccccattt   3660
gctgacgtag tgctctcatg ggctcacctg ggcccaaggc acagccaggg cacagttagg   3720
cctggatgtt tgcctggtcc gtgagatgcc gcgggtcctg tttccttact ggggatttca   3780
gggctggggg ttcagggagc atttcctttt cctgggagtt atgaccgcga agttgtcatg   3840
tgccgtgccc ttttctgttt ctgtgtatcc tattgctggt gactctgtgt gaactggcct   3900
ttgggaaaga tcagagaggg cagaggtggc acaggacagt aaaggagatg ctgtgctggc   3960
cttcagcctg gacagggtct ctgctgactg ccaggggcgg gggctctgca tagccaggat   4020
gacggctttc atgtcccaga gacctgttgt gctgtgtatt ttgatttcct gtgtatgcaa   4080
atgtgtgtat ttaccattgt gtagggggct gtgtctgatc ttggtgttca aaacagaact   4140
gtatttttgc ctttaaaatt aaataatata acgtgaataa atgaccctat ctttgtaaca   4200
aaaaaaaaaa aaaa                                                     4214
```

<210> SEQ ID NO 51
<211> LENGTH: 1089
<212> TYPE: DNA
<213> ORGANISM: Homo sapiens

<400> SEQUENCE: 51

```
ggccaatgtt caaatgcgca gctcttagtc gcgggccgac tggtgtttat ccgtcactcg     60
ccgaggttcc ttgggtcatg gtgccagcct gactgagaag aggacgctcc cgggagacga    120
atgaggaacc acctcctcct actgttcaag tacaggggcc tggtccgcaa agggaagaaa    180
agcaaaagac gaaaatggct aaattcgtga tccgcccagc cactgccgcc gactgcagtg    240
acatactgcg gctgatcaag gagctggcta aatatgaata catggaagaa caagtaatct    300
taactgaaaa agatctgcta gaagatggtt ttggagagca cccctttttac cactgcctgg    360
ttgcagaagt gccgaaagag cactggactc cggaaggaca cagcattgtt ggttttgcca    420
tgtactattt tacctatgac ccgtggattg gcaagttatt gtatcttgag gacttcttcg    480
tgatgagtga ttatagaggc tttggcatag gatcagaaat tctgaagaat ctaagccagg    540
```

```
ttgcaatgag gtgtcgctgc agcagcatgc acttcttggt agcagaatgg aatgaaccat    600

ccatcaactt ctataaaaga agaggtgctt ctgatctgtc cagtgaagag ggttggagac    660

tgttcaagat cgacaaggag tacttgctaa aaatggcaac agaggagtga ggagtgctgc    720

tgtagatgac aacctccatt ctattttaga ataaattccc aacttctctt gctttctatg    780

ctgtttgtag tgaaataata gaatgagcac ccattccaaa gctttattac cagtggcgtt    840

gttgcatgtt tgaaatgagg tctgtttaaa gtggcaatct cagatgcagt ttggagagtc    900

agatctttct ccttgaatat ctttcgataa acaacaaggt ggtgtgatct taatatattt    960

gaaaaaaact tcattctcgt gagtcattta aatgtgtaca atgtacacac tggtacttag   1020

agtttctgtt tgattctttt ttaataaact actctttgat ttaaaaaaaa aaaaaaaaaa   1080

aaaaaaaaa                                                           1089
```

<210> SEQ ID NO 52
<211> LENGTH: 1199
<212> TYPE: DNA
<213> ORGANISM: Homo sapiens

<400> SEQUENCE: 52

```
ggccaatgtt caaatgcgca gctcttagtc gcgggccgac tggtgtttat ccgtcactcg     60

ccgaggttcc ttgggtcatg gtgccagcct gactgagaag aggacgctcc cgggagacga    120

atgaggaacc acctcctcct actgttcaag tacaggggcc tggtccgcaa agggaagaaa    180

agcaaaagac gaaaatggct aaattcgtga tccgcccagc cactgccgcc gactgcagtg    240

acatactgcg gctgatcaag gagctggcta aatatgaata catggaagaa caagtaatct    300

taactgaaaa agatctgcta gaagatggtt ttggagagca ccccttttac cactgcctgg    360

ttgcagaagt gccgaaagag cactggactc cggaaggtta cagtctctag cttcgccatg    420

tacatggccc ttccgtgtac atggatgggc ggggaggtaa ctaaaagatc ctttacacaa    480

taaagtagat gatcatgata aatgaggaca cagcattgtt ggttttgcca tgtactattt    540

tacctatgac ccgtggattg gcaagttatt gtatcttgag gacttcttcg tgatgagtga    600

ttatagaggc tttggcatag gatcagaaat tctgaagaat ctaagccagg ttgcaatgag    660

gtgtcgctgc agcagcatgc acttcttggt agcagaatgg aatgaaccat ccatcaactt    720

ctataaaaga agaggtgctt ctgatctgtc cagtgaagag ggttggagac tgttcaagat    780

cgacaaggag tacttgctaa aaatggcaac agaggagtga ggagtgctgc tgtagatgac    840

aacctccatt ctattttaga ataaattccc aacttctctt gctttctatg ctgtttgtag    900

tgaaataata gaatgagcac ccattccaaa gctttattac cagtggcgtt gttgcatgtt    960

tgaaatgagg tctgtttaaa gtggcaatct cagatgcagt ttggagagtc agatctttct   1020

ccttgaatat ctttcgataa acaacaaggt ggtgtgatct taatatattt gaaaaaaact   1080

tcattctcgt gagtcattta aatgtgtaca atgtacacac tggtacttag agtttctgtt   1140

tgattctttt ttaataaact actctttgat ttaaaaaaaa aaaaaaaaaa aaaaaaaaa    1199
```

<210> SEQ ID NO 53
<211> LENGTH: 2591
<212> TYPE: DNA
<213> ORGANISM: Homo sapiens

<400> SEQUENCE: 53

```
gatgggattg gggttttccc ctcccatgtg ctcaagactg gcgctaaaag ttttgagctt     60
```

```
ctcaaaagtc tagagccacc gtccagggag caggtagctg ctgggctccg gggacacttt    120
gcgttcgggc tgggagcgtg ctttccacga cggtgacacg cttccctgga ttggcagcca    180
gactgccttc cgggtcactg ccatggagga gccgcagtca gatcctagcg tcgagccccc    240
tctgagtcag gaaacatttt cagacctatg gaaactactt cctgaaaaca acgttctgtc    300
cccttgccg tcccaagcaa tggatgattt gatgctgtcc ccggacgata ttgaacaatg     360
gttcactgaa gacccaggtc cagatgaagc tcccagaatg ccagaggctg ctccccccgt    420
ggcccctgca ccagcagctc ctacaccggc ggcccctgca ccagcccct cctggcccct     480
gtcatcttct gtcccttccc agaaaaccta ccagggcagc tacggtttcc gtctgggctt    540
cttgcattct gggacagcca agtctgtgac ttgcacgtac tcccctgccc tcaacaagat    600
gttttgccaa ctggccaaga cctgccctgt gcagctgtgg gttgattcca cacccccgcc    660
cggcacccgc gtccgcgcca tggccatcta caagcagtca cagcacatga cggaggttgt    720
gaggcgctgc ccccaccatg agcgctgctc agatagcgat ggtctggccc ctcctcagca    780
tcttatccga gtggaaggaa atttgcgtgt ggagtatttg gatgacagaa acacttttcg    840
acatagtgtg gtggtgccct atgagccgcc tgaggttggc tctgactgta ccaccatcca    900
ctacaactac atgtgtaaca gttcctgcat gggcggcatg aaccggaggc ccatcctcac    960
catcatcaca ctggaagact ccagtggtaa tctactggga cggaacagct ttgaggtgcg   1020
tgtttgtgcc tgtcctggga gagaccggcg cacagaggaa gagaatctcc gcaagaaagg   1080
ggagcctcac cacgagctgc ccccagggag cactaagcga gcactgccca acaacaccag   1140
ctcctctccc cagccaaaga agaaaccact ggatggagaa tatttcaccc ttcagatccg   1200
tgggcgtgag cgcttcgaga tgttccgaga gctgaatgag gccttggaac tcaaggatgc   1260
ccaggctggg aaggagccag gggggagcag ggctcactcc agccacctga agtccaaaaa   1320
gggtcagtct acctcccgcc ataaaaaact catgttcaag acagaagggc ctgactcaga   1380
ctgacattct ccacttcttg ttccccactg acagcctccc acccccatct ctccctcccc   1440
tgccattttg ggttttgggt ctttgaaccc ttgcttgcaa taggtgtgcg tcagaagcac   1500
ccaggacttc catttgcttt gtcccggggc tccactgaac aagttggcct gcactggtgt   1560
tttgttgtgg ggaggaggat ggggagtagg acataccagc ttagatttta aggtttttac   1620
tgtgagggat gtttgggaga tgtaagaaat gttcttgcag ttaagggtta gtttacaatc   1680
agccacattc taggtagggg cccacttcac cgtactaacc agggaagctg tccctcactg   1740
ttgaattttc tctaacttca aggcccatat ctgtgaaatg ctggcatttg cacctacctc   1800
acagagtgca ttgtgagggt taatgaaata atgtacatct ggccttgaaa ccacctttta   1860
ttacatgggg tctagaactt gaccccttg agggtgcttg ttccctctcc ctgttggtcg    1920
gtgggttggt agtttctaca gttgggcagc tggttaggta gagggagttg tcaagtctct   1980
gctggcccag ccaaaccctg tctgacaacc tcttggtgaa ccttagtacc taaaaggaaa   2040
tctcacccca tcccacaccc tggaggattt catctcttgt atatgatgat ctggatccac   2100
caagacttgt tttatgctca gggtcaattt ctttttcttt ttttttttt tttttctttt    2160
ttctttgaga ctgggtctcg ctttgttgcc caggctggag tggagtggcg tgatcttggc   2220
ttactgcagc ctttgcctcc ccggctcgag cagtcctgcc tcagcctccg gagtagctgg   2280
gaccacaggt tcatgccacc atggccagcc aacttttgca tgttttgtag agatggggtc   2340
tcacagtgtt gcccaggctg gtctcaaact cctgggctca ggcgatccac ctgtctcagc   2400
ctcccagagt gctgggatta caattgtgag ccaccacgtc cagctggaag ggtcaacatc   2460
```

```
ttttacattc tgcaagcaca tctgcatttt caccccaccc ttcccctcct tctccctttt   2520

tatatcccat ttttatatcg atctcttatt ttacaataaa actttgctgc cacctgtgtg   2580

tctgaggggt g                                                        2591


<210> SEQ ID NO 54
<211> LENGTH: 2588
<212> TYPE: DNA
<213> ORGANISM: Homo sapiens

<400> SEQUENCE: 54

gatgggattg gggttttccc ctcccatgtg ctcaagactg gcgctaaaag ttttgagctt     60

ctcaaaagtc tagagccacc gtccagggag caggtagctg ctgggctccg gggacacttt    120

gcgttcgggc tgggagcgtg ctttccacga cggtgacacg cttccctgga ttggccagac    180

tgccttccgg gtcactgcca tggaggagcc gcagtcagat cctagcgtcg agcccccctct   240

gagtcaggaa acattttcag acctatggaa actacttcct gaaaacaacg ttctgtcccc    300

cttgccgtcc caagcaatgg atgatttgat gctgtccccg gacgatattg aacaatggtt    360

cactgaagac ccaggtccag atgaagctcc cagaatgcca gaggctgctc cccccgtggc    420

ccctgcacca gcagctccta caccggcggc ccctgcacca gcccccctcct ggcccctgtc   480

atcttctgtc ccttcccaga aaacctacca gggcagctac ggtttccgtc tgggcttctt    540

gcattctggg acagccaagt ctgtgacttg cacgtactcc cctgccctca acaagatgtt    600

ttgccaactg gccaagacct gccctgtgca gctgtgggtt gattccacac ccccgcccgg    660

cacccgcgtc cgcgccatgg ccatctacaa gcagtcacag cacatgacgg aggttgtgag    720

gcgctgcccc caccatgagc gctgctcaga tagcgatggt ctggcccctc ctcagcatct    780

tatccgagtg gaaggaaatt tgcgtgtgga gtatttggat gacagaaaca cttttcgaca    840

tagtgtggtg gtgccctatg agccgcctga ggttggctct gactgtacca ccatccacta    900

caactacatg tgtaacagtt cctgcatggg cggcatgaac cggaggccca tcctcaccat    960

catcacactg gaagactcca gtggtaatct actgggacgg aacagctttg aggtgcgtgt   1020

ttgtgcctgt cctgggagag accggcgcac agaggaagag aatctccgca agaaagggga   1080

gcctcaccac gagctgcccc cagggagcac taagcgagca ctgcccaaca acaccagctc   1140

ctctccccag ccaaagaaga aaccactgga tggagaatat ttcacccttc agatccgtgg   1200

gcgtgagcgc ttcgagatgt tccgagagct gaatgaggcc ttggaactca aggatgccca   1260

ggctgggaag gagccagggg ggagcagggc tcactccagc cacctgaagt ccaaaaaggg   1320

tcagtctacc tcccgccata aaaaactcat gttcaagaca gaagggcctg actcagactg   1380

acattctcca cttcttgttc cccactgaca gcctcccacc cccatctctc cctcccctgc   1440

cattttgggt tttgggtctt tgaacccttg cttgcaatag gtgtgcgtca gaagcaccca   1500

ggacttccat ttgctttgtc ccggggctcc actgaacaag ttggcctgca ctggtgtttt   1560

gttgtgggga ggaggatggg gagtaggaca taccagctta gattttaagg tttttactgt   1620

gagggatgtt tgggagatgt aagaaatgtt cttgcagtta agggttagtt tacaatcagc   1680

cacattctag gtaggggccc acttcaccgt actaaccagg gaagctgtcc ctcactgttg   1740

aattttctct aacttcaagg cccatatctg tgaaatgctg gcatttgcac ctacctcaca   1800

gagtgcattg tgagggttaa tgaaataatg tacatctggc cttgaaacca ccttttatta   1860

catggggtct agaacttgac ccccttgagg gtgcttgttc cctctccctg ttggtcggtg   1920
```

```
ggttggtagt ttctacagtt gggcagctgg ttaggtagag ggagttgtca agtctctgct   1980
ggcccagcca aaccctgtct gacaacctct tggtgaacct tagtacctaa aaggaaatct   2040
caccccatcc cacaccctgg aggatttcat ctcttgtata tgatgatctg gatccaccaa   2100
gacttgtttt atgctcaggg tcaatttctt ttttcttttt tttttttttt tttctttttc   2160
tttgagactg ggtctcgctt tgttgcccag gctggagtgg agtggcgtga tcttggctta   2220
ctgcagcctt tgcctccccg gctcgagcag tcctgcctca gcctccggag tagctgggac   2280
cacaggttca tgccaccatg gccagccaac ttttgcatgt tttgtagaga tggggtctca   2340
cagtgttgcc caggctggtc tcaaactcct gggctcaggc gatccacctg tctcagcctc   2400
ccagagtgct gggattacaa ttgtgagcca ccacgtccag ctggaagggt caacatcttt   2460
tacattctgc aagcacatct gcattttcac cccacccttc ccctccttct cccttttat    2520
atcccatttt tatatcgatc tcttatttta caataaaact ttgctgccac ctgtgtgtct   2580
gaggggtg                                                            2588
```

<210> SEQ ID NO 55
<211> LENGTH: 2724
<212> TYPE: DNA
<213> ORGANISM: Homo sapiens

<400> SEQUENCE: 55

```
gatgggattg gggttttccc ctcccatgtg ctcaagactg gcgctaaaag ttttgagctt     60
ctcaaaagtc tagagccacc gtccagggag caggtagctg ctgggctccg gggacacttt    120
gcgttcgggc tgggagcgtg ctttccacga cggtgacacg cttccctgga ttggcagcca    180
gactgccttc cgggtcactg ccatggagga gccgcagtca gatcctagcg tcgagccccc    240
tctgagtcag gaaacatttt cagacctatg gaaactactt cctgaaaaca acgttctgtc    300
ccccttgccg tcccaagcaa tggatgattt gatgctgtcc ccggacgata ttgaacaatg    360
gttcactgaa gacccaggtc cagatgaagc tcccagaatg ccagaggctg ctccccccgt    420
ggcccctgca ccagcagctc ctacaccggc ggcccctgca ccagcccct  cctggcccct    480
gtcatcttct gtcccttccc agaaaaccta ccagggcagc tacggtttcc gtctgggctt    540
cttgcattct gggacagcca agtctgtgac ttgcacgtac tcccctgccc tcaacaagat    600
gttttgccaa ctggccaaga cctgccctgt gcagctgtgg gttgattcca cacccccgcc    660
cggcacccgc gtccgcgcca tggccatcta caagcagtca cagcacatga cggaggttgt    720
gaggcgctgc ccccaccatg agcgctgctc agatagcgat ggtctggccc ctcctcagca    780
tcttatccga gtggaaggaa atttgcgtgt ggagtatttg gatgacagaa acacttttcg    840
acatagtgtg gtggtgccct atgagccgcc tgaggttggc tctgactgta ccaccatcca    900
ctacaactac atgtgtaaca gttcctgcat gggcggcatg aaccggaggc ccatcctcac    960
catcatcaca ctggaagact ccagtggtaa tctactggga cggaacagct ttgaggtgcg   1020
tgtttgtgcc tgtcctggga gagaccggcg cacagaggaa gagaatctcc gcaagaaagg   1080
ggagcctcac cacgagctgc ccccagggag cactaagcga gcactgccca acaacaccag   1140
ctcctctccc cagccaaaga agaaaccact ggatggagaa tatttcaccc ttcaggacca   1200
gaccagcttt caaaaagaaa attgttaaag agagcatgaa aatggttcta tgactttgcc   1260
tgatacagat gctacttgac ttacgatggt gttacttcct gataaactcg tcgtaagttg   1320
aaaatattat ccgtgggcgt gagcgcttcg agatgttccg agagctgaat gaggccttgg   1380
aactcaagga tgcccaggct gggaaggagc cagggggggag cagggctcac tccagccacc   1440
```

```
tgaagtccaa aaagggtcag tctacctccc gccataaaaa actcatgttc aagacagaag   1500
ggcctgactc agactgacat tctccacttc ttgttcccca ctgacagcct cccacccccca  1560
tctctccctc ccctgccatt ttgggttttg ggtctttgaa cccttgcttg caataggtgt   1620
gcgtcagaag cacccaggac ttccatttgc tttgtcccgg ggctccactg aacaagttgg   1680
cctgcactgg tgttttgttg tggggaggag gatggggagt aggacatacc agcttagatt   1740
ttaaggtttt tactgtgagg gatgtttggg agatgtaaga aatgttcttg cagttaaggg   1800
ttagtttaca atcagccaca ttctaggtag gggcccactt caccgtacta accagggaag   1860
ctgtccctca ctgttgaatt ttctctaact tcaaggccca tatctgtgaa atgctggcat   1920
ttgcacctac ctcacagagt gcattgtgag ggttaatgaa ataatgtaca tctggccttg   1980
aaaccacctt ttattacatg gggtctagaa cttgaccccc ttgagggtgc ttgttccctc   2040
tccctgttgg tcggtgggtt ggtagtttct acagttgggc agctggttag gtagagggag   2100
ttgtcaagtc tctgctggcc cagccaaacc ctgtctgaca acctcttggt gaaccttagt   2160
acctaaaagg aaatctcacc ccatcccaca ccctggagga tttcatctct tgtatatgat   2220
gatctggatc caccaagact tgttttatgc tcagggtcaa tttctttttt ctttttttttt  2280
ttttttttc tttttctttg agactgggtc tcgctttgtt gcccaggctg gagtggagtg   2340
gcgtgatctt ggcttactgc agcctttgcc tccccggctc gagcagtcct gcctcagcct   2400
ccggagtagc tgggaccaca ggttcatgcc accatggcca gccaactttt gcatgttttg   2460
tagagatggg gtctcacagt gttgcccagg ctggtctcaa actcctgggc tcaggcgatc   2520
cacctgtctc agcctcccag agtgctggga ttacaattgt gagccaccac gtccagctgg   2580
aagggtcaac atcttttaca ttctgcaagc acatctgcat tttcacccca cccttcccct   2640
ccttctccct ttttatatcc cattttata tcgatctctt attttacaat aaaactttgc    2700
tgccacctgt gtgtctgagg ggtg                                          2724
```

<210> SEQ ID NO 56
<211> LENGTH: 2651
<212> TYPE: DNA
<213> ORGANISM: Homo sapiens

<400> SEQUENCE: 56

```
gatgggattg ggttttccc ctcccatgtg ctcaagactg gcgctaaaag ttttgagctt     60
ctcaaaagtc tagagccacc gtccagggag caggtagctg ctgggctccg gggacacttt   120
gcgttcgggc tgggagcgtg ctttccacga cggtgacacg cttccctgga ttggcagcca   180
gactgccttc cgggtcactg ccatggagga gccgcagtca gatcctagcg tcgagccccc   240
tctgagtcag gaaacatttt cagacctatg gaaactactt cctgaaaaca acgttctgtc   300
ccccttgccg tcccaagcaa tggatgattt gatgctgtcc ccggacgata ttgaacaatg   360
gttcactgaa gacccaggtc cagatgaagc tcccagaatg ccagaggctg ctccccccgt   420
ggcccctgca ccagcagctc ctacaccggc ggcccctgca ccagcccct cctggcccct    480
gtcatcttct gtcccttccc agaaaaccta ccagggcagc tacggtttcc gtctgggctt   540
cttgcattct gggacagcca agtctgtgac ttgcacgtac tcccctgccc tcaacaagat   600
gttttgccaa ctggccaaga cctgccctgt gcagctgtgg gttgattcca cacccccgcc   660
cggcacccgc gtccgcgcca tggccatcta caagcagtca cagcacatga cggaggttgt   720
gaggcgctgc ccccaccatg agcgctgctc agatagcgat ggtctggccc ctcctcagca   780
```

```
tcttatccga gtggaaggaa atttgcgtgt ggagtatttg gatgacagaa acacttttcg    840

acatagtgtg gtggtgccct atgagccgcc tgaggttggc tctgactgta ccaccatcca    900

ctacaactac atgtgtaaca gttcctgcat gggcggcatg aaccggaggc ccatcctcac    960

catcatcaca ctggaagact ccagtggtaa tctactggga cggaacagct ttgaggtgcg   1020

tgtttgtgcc tgtcctggga gagaccggcg cacagaggaa gagaatctcc gcaagaaagg   1080

ggagcctcac cacgagctgc ccccagggag cactaagcga gcactgccca acaacaccag   1140

ctcctctccc cagccaaaga agaaaccact ggatggagaa tatttcaccc ttcagatgct   1200

acttgactta cgatggtgtt acttcctgat aaactcgtcg taagttgaaa atattatccg   1260

tgggcgtgag cgcttcgaga tgttccgaga gctgaatgag gccttggaac tcaaggatgc   1320

ccaggctggg aaggagccag gggggagcag ggctcactcc agccacctga agtccaaaaa   1380

gggtcagtct acctcccgcc ataaaaaact catgttcaag acagaagggc ctgactcaga   1440

ctgacattct ccacttcttg ttccccactg acagcctccc acccccatct ctccctcccc   1500

tgccattttg ggttttgggt ctttgaaccc ttgcttgcaa taggtgtgcg tcagaagcac   1560

ccaggacttc catttgcttt gtcccggggc tccactgaac aagttggcct gcactggtgt   1620

tttgttgtgg ggaggaggat ggggagtagg acataccagc ttagatttta aggtttttac   1680

tgtgagggat gtttgggaga tgtaagaaat gttcttgcag ttaagggtta gtttacaatc   1740

agccacattc taggtagggg cccacttcac cgtactaacc agggaagctg tccctcactg   1800

ttgaattttc tctaacttca aggcccatat ctgtgaaatg ctggcatttg cacctacctc   1860

acagagtgca ttgtgagggt taatgaaata atgtacatct ggccttgaaa ccacctttta   1920

ttacatgggg tctagaactt gaccccettg agggtgcttg ttccctctcc ctgttggtcg   1980

gtgggttggt agtttctaca gttgggcagc tggttaggta gagggagttg tcaagtctct   2040

gctggcccag ccaaaccctg tctgacaacc tcttggtgaa ccttagtacc taaaaggaaa   2100

tctcacccca tcccacaccc tggaggattt catctcttgt atatgatgat ctggatccac   2160

caagacttgt tttatgctca gggtcaattt ctttttttctt tttttttttt tttttttcttt   2220

ttctttgaga ctgggtctcg ctttgttgcc caggctggag tggagtggcg tgatcttggc   2280

ttactgcagc ctttgcctcc ccggctcgag cagtcctgcc tcagcctccg gagtagctgg   2340

gaccacaggt tcatgccacc atggccagcc aacttttgca tgttttgtag agatggggtc   2400

tcacagtgtt gcccaggctg gtctcaaact cctgggctca ggcgatccac ctgtctcagc   2460

ctcccagagt gctgggatta caattgtgag ccaccacgtc cagctggaag ggtcaacatc   2520

ttttacattc tgcaagcaca tctgcatttt caccccaccc ttcccctcct tctccctttt   2580

tatatcccat ttttatatcg atctcttatt ttacaataaa actttgctgc cacctgtgtg   2640

tctgaggggt g                                                        2651
```

<210> SEQ ID NO 57
<211> LENGTH: 2271
<212> TYPE: DNA
<213> ORGANISM: Homo sapiens

<400> SEQUENCE: 57

```
tgaggccagg agatggaggc tgcagtgagc tgtgatcaca ccactgtgct ccagcctgag     60

tgacagagca agaccctatc tcaaaaaaaa aaaaaaaaaa gaaaagctcc tgaggtgtag    120

acgccaactc tctctagctc gctagtgggt tgcaggaggt gcttacgcat gtttgtttct    180

ttgctgccgt cttccagttg ctttatctgt tcacttgtgc cctgactttc aactctgtct    240
```

```
ccttcctctt cctacagtac tcccctgccc tcaacaagat gttttgccaa ctggccaaga    300

cctgccctgt gcagctgtgg gttgattcca cacccccgcc cggcacccgc gtccgcgcca    360

tggccatcta caagcagtca cagcacatga cggaggttgt gaggcgctgc ccccaccatg    420

agcgctgctc agatagcgat ggtctggccc ctcctcagca tcttatccga gtggaaggaa    480

atttgcgtgt ggagtatttg gatgacagaa acacttttcg acatagtgtg gtggtgccct    540

atgagccgcc tgaggttggc tctgactgta ccaccatcca ctacaactac atgtgtaaca    600

gttcctgcat gggcggcatg aaccggaggc ccatcctcac catcatcaca ctggaagact    660

ccagtggtaa tctactggga cggaacagct ttgaggtgcg tgtttgtgcc tgtcctggga    720

gagaccggcg cacagaggaa gagaatctcc gcaagaaagg ggagcctcac cacgagctgc    780

ccccagggag cactaagcga gcactgccca acaacaccag ctcctctccc cagccaaaga    840

agaaaccact ggatggagaa tatttcaccc ttcagatccg tgggcgtgag cgcttcgaga    900

tgttccgaga gctgaatgag gccttggaac tcaaggatgc ccaggctggg aaggagccag    960

gggggagcag ggctcactcc agccacctga agtccaaaaa gggtcagtct acctcccgcc   1020

ataaaaaact catgttcaag acagaagggc ctgactcaga ctgacattct ccacttcttg   1080

ttccccactg acagcctccc acccccatct ctccctcccc tgccattttg ggttttgggt   1140

ctttgaaccc ttgcttgcaa taggtgtgcg tcagaagcac ccaggacttc catttgcttt   1200

gtcccggggc tccactgaac aagttggcct gcactggtgt tttgttgtgg ggaggaggat   1260

ggggagtagg acataccagc ttagatttta aggtttttac tgtgagggat gtttgggaga   1320

tgtaagaaat gttcttgcag ttaagggtta gtttacaatc agccacattc taggtagggg   1380

cccacttcac cgtactaacc agggaagctg tccctcactg ttgaattttc tctaacttca   1440

aggcccatat ctgtgaaatg ctggcatttg cacctacctc acagagtgca ttgtgagggt   1500

taatgaaata atgtacatct ggccttgaaa ccacctttta ttacatgggg tctagaactt   1560

gaccccccttg agggtgcttg ttccctctcc ctgttggtcg gtgggttggt agtttctaca   1620

gttgggcagc tggttaggta gagggagttg tcaagtctct gctggcccag ccaaaccctg   1680

tctgacaacc tcttggtgaa ccttagtacc taaaaggaaa tctcacccca tcccacaccc   1740

tggaggattt catctcttgt atatgatgat ctggatccac caagacttgt tttatgctca   1800

gggtcaattt cttttttctt ttttttttt ttttttcttt ttctttgaga ctgggtctcg   1860

ctttgttgcc caggctggag tggagtggcg tgatcttggc ttactgcagc ctttgcctcc   1920

ccggctcgag cagtcctgcc tcagcctccg gagtagctgg gaccacaggt tcatgccacc   1980

atggccagcc aacttttgca tgttttgtag agatggggtc tcacagtgtt gcccaggctg   2040

gtctcaaact cctgggctca ggcgatccac ctgtctcagc ctcccagagt gctgggatta   2100

caattgtgag ccaccacgtc cagctggaag ggtcaacatc ttttacattc tgcaagcaca   2160

tctgcatttt caccccaccc ttcccctcct tctccctttt tatatcccat ttttatatcg   2220

atctcttatt ttacaataaa actttgctgc cacctgtgtg tctgaggggt g            2271
```

<210> SEQ ID NO 58
<211> LENGTH: 2404
<212> TYPE: DNA
<213> ORGANISM: Homo sapiens

<400> SEQUENCE: 58

```
tgaggccagg agatggaggc tgcagtgagc tgtgatcaca ccactgtgct ccagcctgag     60
```

```
tgacagagca agaccctatc tcaaaaaaaa aaaaaaaaaa gaaaagctcc tgaggtgtag    120
acgccaactc tctctagctc gctagtgggt tgcaggaggt gcttacgcat gtttgtttct    180
ttgctgccgt cttccagttg ctttatctgt tcacttgtgc cctgactttc aactctgtct    240
ccttcctctt cctacagtac tcccctgccc tcaacaagat gttttgccaa ctggccaaga    300
cctgccctgt gcagctgtgg gttgattcca cacccccgcc cggcacccgc gtccgcgcca    360
tggccatcta caagcagtca cagcacatga cggaggttgt gaggcgctgc ccccaccatg    420
agcgctgctc agatagcgat ggtctggccc ctcctcagca tcttatccga gtggaaggaa    480
atttgcgtgt ggagtatttg gatgacagaa acacttttcg acatagtgtg gtggtgccct    540
atgagccgcc tgaggttggc tctgactgta ccaccatcca ctacaactac atgtgtaaca    600
gttcctgcat gggcggcatg aaccggaggc ccatcctcac catcatcaca ctggaagact    660
ccagtggtaa tctactggga cggaacagct ttgaggtgcg tgtttgtgcc tgtcctggga    720
gagaccggcg cacagaggaa gagaatctcc gcaagaaagg ggagcctcac cacgagctgc    780
ccccagggag cactaagcga gcactgccca acaacaccag ctcctctccc cagccaaaga    840
agaaaccact ggatggagaa tatttcaccc ttcaggacca gaccagcttt caaaaagaaa    900
attgttaaag agagcatgaa aatggttcta tgactttgcc tgatacagat gctacttgac    960
ttacgatggt gttacttcct gataaactcg tcgtaagttg aaaatattat ccgtgggcgt   1020
gagcgcttcg agatgttccg agagctgaat gaggccttgg aactcaagga tgcccaggct   1080
gggaaggagc caggggggag cagggctcac tccagccacc tgaagtccaa aaagggtcag   1140
tctacctccc gccataaaaa actcatgttc aagacagaag ggcctgactc agactgacat   1200
tctccacttc ttgttcccca ctgacagcct cccaccccca tctctccctc ccctgccatt   1260
ttgggttttg ggtctttgaa cccttgcttg caataggtgt gcgtcagaag cacccaggac   1320
ttccatttgc tttgtcccgg ggctccactg aacaagttgg cctgcactgg tgttttgttg   1380
tggggaggag gatggggagt aggacatacc agcttagatt ttaaggtttt tactgtgagg   1440
gatgtttggg agatgtaaga aatgttcttg cagttaaggg ttagtttaca atcagccaca   1500
ttctaggtag ggcccactt caccgtacta accagggaag ctgtccctca ctgttgaatt   1560
ttctctaact tcaaggccca tatctgtgaa atgctggcat ttgcacctac ctcacagagt   1620
gcattgtgag ggttaatgaa ataatgtaca tctggccttg aaaccacctt ttattacatg   1680
gggtctagaa cttgaccccc ttgagggtgc ttgttccctc tccctgttgg tcggtgggtt   1740
ggtagtttct acagttgggc agctggttag gtagagggag ttgtcaagtc tctgctggcc   1800
cagccaaacc ctgtctgaca acctcttggt gaaccttagt acctaaaagg aaatctcacc   1860
ccatcccaca ccctggagga tttcatctct tgtatatgat gatctggatc caccaagact   1920
tgttttatgc tcagggtcaa tttctttttt cttttttttt tttttttttc tttttctttg   1980
agactgggtc tcgctttgtt gcccaggctg gagtggagtg gcgtgatctt ggcttactgc   2040
agcctttgcc tccccggctc gagcagtcct gcctcagcct ccggagtagc tgggaccaca   2100
ggttcatgcc accatggcca gccaactttt gcatgttttg tagagatggg gtctcacagt   2160
gttgcccagg ctggtctcaa actcctgggc tcaggcgatc cacctgtctc agcctcccag   2220
agtgctggga ttacaattgt gagccaccac gtccagctgg aagggtcaac atcttttaca   2280
ttctgcaagc acatctgcat tttcacccca cccttcccct ccttctccct ttttatatcc   2340
catttttata tcgatctctt attttacaat aaaactttgc tgccacctgt gtgtctgagg   2400
ggtg                                                                2404
```

<210> SEQ ID NO 59
<211> LENGTH: 2331
<212> TYPE: DNA
<213> ORGANISM: Homo sapiens

<400> SEQUENCE: 59

```
tgaggccagg agatggaggc tgcagtgagc tgtgatcaca ccactgtgct ccagcctgag     60
tgacagagca agaccctatc tcaaaaaaaa aaaaaaaaaa gaaaagctcc tgaggtgtag    120
acgccaactc tctctagctc gctagtgggt tgcaggaggt gcttacgcat gtttgtttct    180
ttgctgccgt cttccagttg ctttatctgt tcacttgtgc cctgactttc aactctgtct    240
ccttcctctt cctacagtac tcccctgccc tcaacaagat gttttgccaa ctggccaaga    300
cctgccctgt gcagctgtgg gttgattcca cacccccgcc cggcacccgc gtccgcgcca    360
tggccatcta caagcagtca cagcacatga cggaggttgt gaggcgctgc ccccaccatg    420
agcgctgctc agatagcgat ggtctggccc ctcctcagca tcttatccga gtggaaggaa    480
atttgcgtgt ggagtatttg gatgacagaa acacttttcg acatagtgtg gtggtgccct    540
atgagccgcc tgaggttggc tctgactgta ccaccatcca ctacaactac atgtgtaaca    600
gttcctgcat gggcggcatg aaccggaggc ccatcctcac catcatcaca ctggaagact    660
ccagtggtaa tctactggga cggaacagct ttgaggtgcg tgtttgtgcc tgtcctggga    720
gagaccggcg cacagaggaa gagaatctcc gcaagaaagg ggagcctcac cacgagctgc    780
ccccagggag cactaagcga gcactgccca acaacaccag ctcctctccc cagccaaaga    840
agaaaccact ggatggagaa tatttcaccc ttcagatgct acttgactta cgatggtgtt    900
acttcctgat aaactcgtcg taagttgaaa atattatccg tgggcgtgag cgcttcgaga    960
tgttccgaga gctgaatgag gccttggaac tcaaggatgc ccaggctggg aaggagccag   1020
gggggagcag ggctcactcc agccacctga agtccaaaaa gggtcagtct acctcccgcc   1080
ataaaaaact catgttcaag acagaagggc ctgactcaga ctgacattct ccacttcttg   1140
ttccccactg acagcctccc acccccatct ctccctcccc tgccattttg ggttttgggt   1200
ctttgaaccc ttgcttgcaa taggtgtgcg tcagaagcac ccaggacttc catttgcttt   1260
gtcccggggc tccactgaac aagttggcct gcactggtgt tttgttgtgg ggaggaggat   1320
ggggagtagg acataccagc ttagatttta aggtttttac tgtgagggat gtttgggaga   1380
tgtaagaaat gttcttgcag ttaagggtta gtttacaatc agccacattc taggtagggg   1440
cccacttcac cgtactaacc agggaagctg tccctcactg ttgaattttc tctaacttca   1500
aggcccatat ctgtgaaatg ctggcatttg cacctacctc acagagtgca ttgtgagggt   1560
taatgaaata atgtacatct ggccttgaaa ccacctttta ttacatgggg tctagaactt   1620
gaccccccttg agggtgcttg ttccctctcc ctgttggtcg gtgggttggt agtttctaca   1680
gttgggcagc tggttaggta gagggagttg tcaagtctct gctggcccag ccaaaccctg   1740
tctgacaacc tcttggtgaa ccttagtacc taaaaggaaa tctcacccca tcccacaccc   1800
tggaggattt catctcttgt atatgatgat ctggatccac caagacttgt tttatgctca   1860
gggtcaattt ctttttttctt tttttttttt ttttttcttt ttctttgaga ctgggtctcg   1920
ctttgttgcc caggctggag tggagtggcg tgatcttggc ttactgcagc ctttgcctcc   1980
ccggctcgag cagtcctgcc tcagcctccg gagtagctgg gaccacaggt tcatgccacc   2040
atggccagcc aacttttgca tgttttgtag agatggggtc tcacagtgtt gcccaggctg   2100
```

```
gtctcaaact cctgggctca ggcgatccac ctgtctcagc ctcccagagt gctgggatta   2160

caattgtgag ccaccacgtc cagctggaag ggtcaacatc ttttacattc tgcaagcaca   2220

tctgcatttt caccccaccc ttcccctcct tctccctttt tatatcccat ttttatatcg   2280

atctcttatt ttacaataaa actttgctgc cacctgtgtg tctgaggggt g            2331
```

<210> SEQ ID NO 60
<211> LENGTH: 2708
<212> TYPE: DNA
<213> ORGANISM: Homo sapiens

<400> SEQUENCE: 60

```
gatgggattg ggttttccc ctcccatgtg ctcaagactg gcgctaaaag ttttgagctt      60

ctcaaaagtc tagagccacc gtccagggag caggtagctg ctgggctccg gggacacttt    120

gcgttcgggc tgggagcgtg ctttccacga cggtgacacg cttccctgga ttggcagcca    180

gactgccttc cgggtcactg ccatggagga gccgcagtca gatcctagcg tcgagccccc    240

tctgagtcag gaaacatttt cagacctatg gaaactgtga gtggatccat tggaagggca    300

ggcccaccac ccccacccca accccagccc cctagcagag acctgtggga agcgaaaatt    360

ccatgggact gactttctgc tcttgtcttt cagacttcct gaaaacaacg ttctgtcccc    420

cttgccgtcc caagcaatgg atgatttgat gctgtccccg gacgatattg aacaatggtt    480

cactgaagac ccaggtccag atgaagctcc cagaatgcca gaggctgctc cccccgtggc    540

ccctgcacca gcagctccta caccggcggc ccctgcacca gccccctcct ggcccctgtc    600

atcttctgtc ccttcccaga aaacctacca gggcagctac ggtttccgtc tgggcttctt    660

gcattctggg acagccaagt ctgtgacttg cacgtactcc cctgccctca acaagatgtt    720

ttgccaactg gccaagacct gccctgtgca gctgtgggtt gattccacac ccccgcccgg    780

cacccgcgtc cgcgccatgg ccatctacaa gcagtcacag cacatgacgg aggttgtgag    840

gcgctgcccc caccatgagc gctgctcaga tagcgatggt ctggcccctc ctcagcatct    900

tatccgagtg gaaggaaatt tgcgtgtgga gtatttggat gacagaaaca cttttcgaca    960

tagtgtggtg gtgccctatg agccgcctga ggttggctct gactgtacca ccatccacta   1020

caactacatg tgtaacagtt cctgcatggg cggcatgaac cggaggccca tcctcaccat   1080

catcacactg gaagactcca gtggtaatct actgggacgg aacagctttg aggtgcgtgt   1140

ttgtgcctgt cctgggagag accggcgcac agaggaagag aatctccgca agaaagggga   1200

gcctcaccac gagctgcccc cagggagcac taagcgagca ctgcccaaca acaccagctc   1260

ctctccccag ccaaagaaga aaccactgga tggagaatat ttcacccttc agatccgtgg   1320

gcgtgagcgc ttcgagatgt tccgagagct gaatgaggcc ttggaactca aggatgccca   1380

ggctgggaag gagccagggg ggagcagggc tcactccagc cacctgaagt ccaaaaaggg   1440

tcagtctacc tcccgccata aaaaactcat gttcaagaca gaagggcctg actcagactg   1500

acattctcca cttcttgttc cccactgaca gcctcccacc cccatctctc cctcccctgc   1560

cattttgggt tttgggtctt tgaacccttg cttgcaatag gtgtgcgtca gaagcaccca   1620

ggacttccat ttgctttgtc ccggggctcc actgaacaag ttggcctgca ctggtgtttt   1680

gttgtgggga ggaggatggg gagtaggaca taccagctta gattttaagg tttttactgt   1740

gagggatgtt tgggagatgt aagaaatgtt cttgcagtta agggttagtt tacaatcagc   1800

cacattctag gtaggggccc acttcaccgt actaaccagg gaagctgtcc ctcactgttg   1860

aattttctct aacttcaagg cccatatctg tgaaatgctg gcatttgcac ctacctcaca   1920
```

```
gagtgcattg tgagggttaa tgaaataatg tacatctggc cttgaaacca ccttttatta   1980
catggggtct agaacttgac cccettgagg gtgcttgttc cctctccctg ttggtcggtg   2040
ggttggtagt ttctacagtt gggcagctgg ttaggtagag ggagttgtca agtctctgct   2100
ggcccagcca aaccctgtct gacaacctct tggtgaacct tagtacctaa aaggaaatct   2160
caccccatcc cacaccctgg aggatttcat ctcttgtata tgatgatctg gatccaccaa   2220
gacttgtttt atgctcaggg tcaatttctt ttttcttttt tttttttttt tttctttttc   2280
tttgagactg ggtctcgctt tgttgcccag gctggagtgg agtggcgtga tcttggctta   2340
ctgcagcctt tgcctccccg gctcgagcag tcctgcctca gcctccggag tagctgggac   2400
cacaggttca tgccaccatg gccagccaac ttttgcatgt tttgtagaga tggggtctca   2460
cagtgttgcc caggctggtc tcaaactcct gggctcaggc gatccacctg tctcagcctc   2520
ccagagtgct gggattacaa ttgtgagcca ccacgtccag ctggaagggt caacatcttt   2580
tacattctgc aagcacatct gcattttcac ccccaccttc ccctccttct ccctttttat   2640
atcccatttt tatatcgatc tcttatttta caataaaact ttgctgccac ctgtgtgtct   2700
gaggggtg                                                             2708
```

<210> SEQ ID NO 61
<211> LENGTH: 2245
<212> TYPE: DNA
<213> ORGANISM: Homo sapiens

<400> SEQUENCE: 61

```
gtacccccat cctttctctc gcccctccta cccgcagctc ctggcgctcg gcggggctaa     60
ctgcagcgcg gagatctcgg ccgccaagct ccgcctcccg ccccgggctg tgccccgggg    120
ctcgcctgag gccgaccacc cgcaccccac ctctagcggc tttgctcgag gcccaccttc    180
ttcccacccc cggcaaactc cagtaggctc gccctcgctg actccccgcc cccgcgtcaa    240
ctgcaagggg cccgcccata gccagttccg gggcggttgc tcacatcgac cggaactccc    300
cgccccctcc cgcggcccct ggggccgtag gaggccgcag cgaggaggta gagggggcgg    360
gggtcgcact agggtgtccc tagagaacga ggactctgaa ggcgggacat ttgggcgacc    420
cccgggcggg gccagccatt aaacagtccc acttctgtgc cagacactga actgggctct    480
tgacgggcat catctcttaa tcctcagaac atcccaggga gctccacagg atccccatat    540
cctgggccat gagtgagttg aaagactgcc ccttgcagtt ccacgacttc aagtctgtgg    600
atcacctgaa ggtctgtccc cgctacacgg cagtgctggc acgctctgag gatgatggca    660
tcggcatcga ggagctggac accctgcagc tggagctgga gaccctgctg tcttctgcca    720
gccggcgcct gcgtgtgctt gaggccgaaa cccagatcct caccgactgg caggataaga    780
aaggtgacag acgattcctg aagctgggtc gagaccatga acttggagct ccccccaaac    840
atgggaagcc caagaagcag aaactggaag ggaaggcagg acatgggccg ggccctggcc    900
caggacggcc caaatccaaa aaccttcagc ccaagatcca ggaatatgaa ttcactgatg    960
accctatcga cgtgccacgg atccccaaaa atgatgcccc caacaggttc tgggcttcag   1020
tggagcccta ctgtgctgac atcaccagcg aggaggtccg cacacttgag gagttactga   1080
agcccccaga agatgaggct gagcattaca agatcccacc cctggggaag cactactccc   1140
agcgctgggc ccaggaggac ctgctggagg agcagaagga tggggcccgg gcagcggctg   1200
tggctgacaa gaagaaaggc ctcatggggc cactgaccga actggacact aaagatgtgg   1260
```

```
atgccctgct gaagaagtct gaggcccagc atgaacagcc ggaagatgga tgcccctttg   1320

gtgccctgac gcagcgcctc ctgcaggccc tggtggagga aaatattatt tcccctatgg   1380

aggattctcc tattcctgac atgtctggga aagaatcagg ggctgacggg gcaagcacct   1440

cccctcgcaa tcagaacaag cccttcagtg tgccgcatac taagtccctg gagagccgca   1500

tcaaggagga gctaattgcc cagggccttt tggagtctga ggaccgcccc gcagaggact   1560

ccgaggatga ggtccttgct gagcttcgca aacggcaggc tgagctgaag gcacttagtg   1620

cccacaaccg caccaagaag cacgacctgc tgaggctggc aaaggaggag gtgagccggc   1680

aggagctgag gcagcgggtg cgcatggctg acaacgaggt catggacgcc tttcgcaaga   1740

tcatggctgc ccggcagaag aagcggactc ccaccaagaa agaaaaggac caggcctgga   1800

agactctgaa ggagcgtgag agcatcctga agctgctgga tgggtagccc tcacccctgc   1860

ctcaggctga ttatctggcc taggggaggg gaagggaggc ccacttcctt ctttgggcac   1920

aggaaacatt ggcctgtggc tgtccctcaa atggcggcag tctctagagg gccgtggccc   1980

ttcccctgag gtcttttggc ctagctctgt acaaccagga cacaggaagc cctgctgggc   2040

tagcctgagg cctagtctct gcttggtccc cgagatgggg ttggagggga cttcgtttct   2100

gggtcttcct cttcccctct ttaccatccc ccactcccta atcccctacc cctgtctccc   2160

cttcaaggac ttctcccttg tggttttgta aagtgcaaac ttaagaataa agtgactgct   2220

gtggttttc aaaaaaaaaa aaaaa                                          2245
```

```
<210> SEQ ID NO 62
<211> LENGTH: 2571
<212> TYPE: DNA
<213> ORGANISM: Homo sapiens

<400> SEQUENCE: 62

gtacccccat cctttctctc gcccctccta cccgcagctc ctggcgctcg gcggggctaa     60

ctgcagcgcg gagatctcgg ccgccaagct ccgcctcccg ccccgggctg tgccccgggg    120

ctcgcctgag gccgaccacc cgcaccccac ctctagcggc tttgctcgag gcccaccttc    180

ttcccacccc cggcaaactc cagtaggctc gccctcgctg actccccgcc cccgcgtcaa    240

ctgcaagggg cccgcccata gccagttccg gggcggttgc tcacatcgac cggaactccc    300

cgccccctcc cgcggcccct ggggccgtag gaggccgcag cgaggaggta gagggggcgg    360

gggtcgcact agggtgtccc tagagaacga ggactctgaa ggcgggacat ttgggcgacc    420

cccgggcggg gccagccatt aaacagtccc acttctgtgc cagacactga actgggctct    480

tgacgggcat catctcttaa tcctcagaac atcccaggga gctccacagg atccccatat    540

cctgggccat gagtgagttg aaagactgcc ccttgcagtt ccacgacttc aagtctgtgg    600

atcacctgaa ggtctgtccc cgctacacgg cagtgctggc acgctctgag gatgatggca    660

tcggcatcga ggagctggac accctgcagc tggagctgga gaccctgctg tcttctgcca    720

gccggcgcct gcgtgtgctt gaggccgaaa cccagatcct caccgactgg caggataaga    780

aaggtgacag acgattcctg aagctgggtc gagaccatga acttggagct ccccccaaac    840

atgggaagcc caagaagcag aaactggaag ggaaggcagg acatgggccg ggccctggcc    900

caggacggcc caaatccaaa aaccttcagc ccaagatcca ggaatatgaa ttcactgatg    960

accctatcga cgtgccacgg atccccaaaa atgatgcccc caacaggttc tgggcttcag   1020

tggagcccta ctgtgctgac atcaccagcg aggaggtccg cacacttgag gagttactga   1080

agcccccaga agatgaggct gagcattaca agatcccacc cctggggaag cactactccc   1140
```

```
agcgctgggc ccaggaggac ctgctggagg agcagaagga tggggcccgg gcagcggctg   1200
tggctgacaa gaagaaaggc ctcatggggc cactgaccga actggacact aaagatgtgg   1260
atgccctgct gaagaagtct gaggcccagc atgaacagcc ggaagatgga tgcccctttg   1320
gtgccctgac gcagcgcctc ctgcaggccc tggtggagga aaatattatt tcccctatgg   1380
aggattctcc tattcctgac atgtctggga aagaatcagg ggctgacggg gcaagcacct   1440
cccctcgcaa tcagaacaag cccttcagtg tgccgcatac taagtccctg gagagccgca   1500
tcaaggagga gctaattgcc cagggccttt tggagtctga ggaccgcccc gcagaggact   1560
ccgaggatga ggtccttgct gagcttcgca aacggcaggc tgagctgaag gcacttagtg   1620
cccacaaccg caccaagaag cacgacctgc tgaggtgagc gttagcagga tgcacagtcc   1680
cgggggtggc cttggaggct gtggccacgg ctagtcacct ttcaggggtt ttacaacagg   1740
ctttccaatc ctggctggcc tctaaatcac ctggagagcc tcgaaaaaaa cagcagtggc   1800
cagtccaccg ggtatgtccc aaacaaattc tgattccaca gagtggggct caggcatctg   1860
tgactgaccg attgatttga tttgtttttg ttttgttttt ttttgagagg gagtctcgca   1920
ctgtcaccca ggctggagtg cagtggcatg atctcggctc actgcaagct ccgcctccca   1980
ggttcatgcc attctcctgc ctcagcctcc tgagtagctg atactacagg cacccaccac   2040
cacgcccagc taattttttt gtatttttag tagagacggg gtttcaccgt gttagccagg   2100
atggtctcga tctcctgacc tcgtgatcca cccgcctcgg cctcccaaag tgccgggatt   2160
acaggcgtga gccactgcgc ctggcctagt ttggtttttt aattatggta aaggcataat   2220
ataaaatgta tctccatggg aggctgaggc aggagaatca gttgaacctg ggaggcggag   2280
gttgcagtga gctgagactg caccattgca ttccagcctg ggcaacaaga gtgaaactgc   2340
atctcaaaaa aaaaaagaaa aaaaatttac gcttcttaac catttttaag tgtacagttt   2400
agtagtgtta cccatattca cattgttgtg tgatttattt tttgtctttt catgcttctt   2460
ttctttttat ccccaaagtt ttgttattaa aaatttgata cacacagaaa atctgaaaga   2520
atcatacaat aaacatcagt atattctcca cctaaaaaaa aaaaaaaaaa a            2571
```

<210> SEQ ID NO 63
<211> LENGTH: 2949
<212> TYPE: DNA
<213> ORGANISM: Homo sapiens

<400> SEQUENCE: 63

```
cgcctccctt cccccctccc gcccgacagc ggccgctcgg gccccggctc tcggttataa     60
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccggaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
ggaatctctg gggaacggaa ctgatttttc tgtttctagc tctgcatcaa tggataccgt    420
tacatcttct tcctcttcta gcctttcagt gctaccttca tctctttcag tttttcaaaa    480
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
```

-continued

```
tcaggatgga gagaagaaac caattggttg ggacactgat atttcctggc ttactggaga    720
agaattgcat gtggaagtgt tggagaatgt tccacttaca acacacaact ttgtacgaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat ccccttccgc   1020
acccgcctcg gactctattg ggccccaaat tctcaccagt ccgtctcctt caaaatccat   1080
tccaattcca cagcccttcc gaccagcaga tgaagatcat cgaaatcaat ttgggcaacg   1140
agaccgatcc tcatcagctc ccaatgtgca tataaacaca atagaacctg tcaatattga   1200
tgacttgatt agagaccaag gatttcgtgg tgatggagga tcaaccacag gtttgtctgc   1260
tacccccct gcctcattac ctggctcact aactaacgtg aaagccttac agaaatctcc   1320
aggacctcag cgagaaagga agtcatcttc atcctcagaa gacaggaatc gaatgaaaac   1380
acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta ttgttaccca gtggtgtgag ggctccagct tgtatcacca   1680
tctccatatc attgagacca aatttgagat gatcaaactt atagatattg cacgacagac   1740
tgcacagggc atggattact tacacgccaa gtcaatcatc cacagagacc tcaagagtaa   1800
taatatattt cttcatgaag acctcacagt aaaaataggt gattttggtc tagctacagt   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg cagggggata   2340
tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaagaa cacttgtgtg gttaaagact agatataatt tttccccaaa   2520
ctaaaattta tacttaacat tggattttta acatccaagg gttaaaatac atagacattg   2580
ctaaaaattg gcagagcctc ttctagaggc tttactttct gttccgggtt tgtatcattc   2640
acttggttat tttaagtagt aaacttcagt ttctcatgca acttttgttg ccagctatca   2700
catgtccact agggactcca gaagaagacc ctacctatgc ctgtgtttgc aggtgagaag   2760
ttggcagtcg gttagcctgg gttagataag gcaaactgaa cagatctaat ttaggaagtc   2820
agtagaattt aataattcta ttattattct taataatttt tctataacta tttcttttta   2880
taacaatttg gaaaatgtgg atgtctttta tttccttgaa gcaataaact aagtttcttt   2940
ttataaaaa                                                           2949
```

<210> SEQ ID NO 64
<211> LENGTH: 5241
<212> TYPE: DNA
<213> ORGANISM: Homo sapiens

<400> SEQUENCE: 64
agagcgtcgg gatatcgggt ggcggctcgg gacggaggac gcgctagtgt gagtgcgggc 60
ttctagaact acaccgaccc tcgtgtcctc ccttcatcct gcggggctgg ctggagcggc 120
cgctccggtg ctgtccagca gccataggga gccgcacggg gagcgggaaa gcggtcgcgg 180
ccccaggcgg ggcggccggg atggagcggg gccgcgagcc tgtggggaag ggggctgtggc 240 ggcgcctcga gcggctgcag gttcttctgt gtggcagttc agaatgatgg atcaagctag 300
atcagcattc tctaacttgt ttggtggaga accattgtca tatacccggt tcagcctggc 360
tcggcaagta gatggcgata acagtcatgt ggagatgaaa cttgctgtag atgaagaaga 420
aaatgctgac aataacacaa aggccaatgt cacaaaacca aaaaggtgta gtggaagtat 480
ctgctatggg actattgctg tgatcgtctt tttcttgatt ggatttatga ttggctactt 540
gggctattgt aaaggggtag aaccaaaaac tgagtgtgag agactggcag gaaccgagtc 600
tccagtgagg gaggagccag gagaggactt ccctgcagca cgtcgcttat attgggatga 660
cctgaagaga aagttgtcgg agaaactgga cagcacagac ttcaccggca ccatcaagct 720
gctgaatgaa aattcatatg tccctcgtga ggctggatct caaaaagatg aaaatcttgc 780
gttgtatgtt gaaaatcaat ttcgtgaatt taaactcagc aaagtctggc gtgatcaaca 840
ttttgttaag attcaggtca aagacagcgc tcaaaactcg gtgatcatag ttgataagaa 900
cggtagactt gtttacctgg tggagaatcc tgggggttat gtggcgtata gtaaggctgc 960
aacagttact ggtaaactgg tccatgctaa ttttggtact aaaaaagatt ttgaggattt 1020
atacactcct gtgaatggat ctatagtgat tgtcagagca gggaaaatca cctttgcaga 1080
aaaggttgca aatgctgaaa gcttaaatgc aattggtgtg ttgatataca tggaccagac 1140
taaatttccc attgttaacg cagaactttc attctttgga catgctcatc tggggacagg 1200
tgacccttac acacctggat tcccttcctt caatcacact cagtttccac catctcggtc 1260
atcaggattg cctaatatac ctgtccagac aatctccaga gctgctgcag aaaagctgtt 1320
tgggaatatg gaaggagact gtccctctga ctggaaaaca gactctacat gtaggatggt 1380
aacctcagaa agcaagaatg tgaagctcac tgtgagcaat gtgctgaaag agataaaaat 1440
tcttaacatc tttggagtta ttaaaggctt tgtagaacca gatcactatg ttgtagttgg 1500
ggcccagaga gatgcatggg gccctggagc tgcaaaatcc ggtgtaggca cagctctcct 1560
attgaaactt gcccagatgt tctcagatat ggtcttaaaa gatgggtttc agcccagcag 1620
aagcattatc tttgccagtt ggagtgctgg agactttgga tcggttggtg ccactgaatg 1680
gctagaggga tacctttcgt ccctgcattt aaaggctttc acttatatta atctggataa 1740
agcggttctt ggtaccagca acttcaaggt ttctgccagc ccactgttgt atacgcttat 1800
tgagaaaaca atgcaaaatg tgaagcatcc ggttactggg caatttctat atcaggacag 1860
caactgggcc agcaaagttg agaaactcac tttagacaat gctgctttcc ctttccttgc 1920
atattctgga atcccagcag tttctttctg tttttgcgag gacacagatt atccttattt 1980
gggtaccacc atggacacct ataaggaact gattgagagg attcctgagt tgaacaaagt 2040
ggcacgagca gctgcagagg tcgctggtca gttcgtgatt aaactaaccc atgatgttga 2100
attgaacctg gactatgaga ggtacaacag ccaactgctt tcatttgtga gggatctgaa 2160

```
ccaatacaga gcagacataa aggaaatggg cctgagttta cagtggctgt attctgctcg   2220
tggagacttc ttccgtgcta cttccagact aacaacagat ttcgggaatg ctgagaaaac   2280
agacagattt gtcatgaaga aactcaatga tcgtgtcatg agagtggagt atcacttcct   2340
ctctccctac gtatctccaa aagagtctcc tttccgacat gtcttctggg gctccggctc   2400
tcacacgctg ccagctttac tggagaactt gaaactgcgt aaacaaaata acggtgcttt   2460
taatgaaacg ctgttcagaa accagttggc tctagctact tggactattc agggagctgc   2520
aaatgccctc tctggtgacg tttgggacat tgacaatgag ttttaaatgt gatacccata   2580
gcttccatga gaacagcagg gtagtctggt ttctagactt gtgctgatcg tgctaaattt   2640
tcagtagggc tacaaaacct gatgttaaaa ttccatccca tcatcttggt actactagat   2700
gtctttaggc agcagctttt aatacagggt agataacctg tacttcaagt taaagtgaat   2760
aaccacttaa aaaatgtcca tgatggaata ttcccctatc tctagaattt taagtgcttt   2820
gtaatgggaa ctgcctcttt cctgttgttg ttaatgaaaa tgtcagaaac cagttatgtg   2880
aatgatctct ctgaatccta agggctggtc tctgctgaag gttgtaagtg gtcgcttact   2940
ttgagtgatc ctccaacttc atttgatgct aaataggaga taccaggttg aaagaccttc   3000
tccaaatgag atctaagcct ttccataagg aatgtagctg gtttcctcat tcctgaaaga   3060
aacagttaac tttcagaaga gatgggcttg ttttcttgcc aatgaggtct gaaatggagg   3120
tccttctgct ggataaaatg aggttcaact gttgattgca ggaataaggc cttaatatgt   3180
taacctcagt gtcatttatg aaaagagggg accagaagcc aaagacttag tatattttct   3240
tttcctctgt cccttccccc ataagcctcc atttagttct ttgttatttt tgtttcttcc   3300
aaagcacatt gaaagagaac cagtttcagg tgtttagttg cagactcagt ttgtcagact   3360
ttaaagaata atatgctgcc aaattttggc caaagtgtta atcttagggg agagctttct   3420
gtccttttgg cactgagata tttattgttt atttatcagt gacagagttc actataaatg   3480
gtgttttttt aatagaatat aattatcgga agcagtgcct tccataatta tgacagttat   3540
actgtcggtt tttttaaat aaaagcagca tctgctaata aaacccaaca gatactggaa   3600
gttttgcatt tatggtcaac acttaagggt tttagaaaac agccgtcagc caaatgtaat   3660
tgaataaagt tgaagctaag atttagagat gaattaaatt taattagggg ttgctaagaa   3720
gcgagcactg accagataag aatgctggtt ttcctaaatg cagtgaattg tgaccaagtt   3780
ataaatcaat gtcacttaaa ggctgtggta gtactcctgc aaaattttat agctcagttt   3840
atccaaggtg taactctaat tcccattttg caaaatttcc agtacctttg tcacaatcct   3900
aacacattat cgggagcagt gtcttccata atgtataaag aacaaggtag tttttaccta   3960
ccacagtgtc tgtatcggag acagtgatct ccatatgtta cactaagggt gtaagtaatt   4020
atcgggaaca gtgtttccca taattttctt catgcaatga catcttcaaa gcttgaagat   4080
cgttagtatc taacatgtat cccaactcct ataattccct atcttttagt tttagttgca   4140
gaaacatttt gtggtcatta agcattgggt gggtaaattc aaccactgta aaatgaaatt   4200
actacaaaat ttgaaattta gcttgggttt ttgttacctt tatggtttct ccaggtcctc   4260
tacttaatga gatagtagca tacatttata atgtttgcta ttgacaagtc attttaactt   4320
tatcacatta tttgcatgtt acctcctata aacttagtgc ggacaagttt taatccagaa   4380
ttgacctttt gacttaaagc agagggactt tgtatagaag gtttgggggc tgtggggaag   4440
gagagtcccc tgaaggtctg acacgtctgc ctacccattc gtggtgatca attaaatgta   4500
ggtatgaata agttcgaagc tccgtgagtg aaccatcatt ataaacgtga tgatcagctg   4560
```

```
tttgtcatag ggcagttgga aacggcctcc tagggaaaag ttcatagggt ctcttcaggt   4620

tcttagtgtc acttacctag atttacagcc tcacttgaat gtgtcactac tcacagtctc   4680

tttaatcttc agttttatct ttaatctcct cttttatctt ggactgacat ttagcgtagc   4740

taagtgaaaa ggtcatagct gagattcctg gttcgggtgt tacgcacacg tacttaaatg   4800

aaagcatgtg gcatgttcat cgtataacac aatatgaata cagggcatgc attttgcagc   4860

agtgagtctc ttcagaaaac ccttttctac agttagggtt gagttacttc ctatcaagcc   4920

agtacgtgct aacaggctca atattcctga atgaaatatc agactagtga caagctcctg   4980

gtcttgagat gtcttctcgt taaggagatg ggccttttgg aggtaaagga taaaatgaat   5040

gagttctgtc atgattcact attctagaac ttgcatgacc tttactgtgt tagctctttg   5100

aatgttcttg aaattttaga ctttctttgt aaacaaatga tatgtcctta tcattgtata   5160

aaagctgtta tgtgcaacag tgtggagatt ccttgtctga tttaataaaa tacttaaaca   5220

ctgaaaaaaa aaaaaaaaaa a                                             5241
```

<210> SEQ ID NO 65
<211> LENGTH: 5100
<212> TYPE: DNA
<213> ORGANISM: Homo sapiens

<400> SEQUENCE: 65

```
acgcacagcc cccctggggg ccgggggcgg ggccaggcta taaaccgccg gttaggggcc     60

gccatcccct cagagcgtcg ggatatcggg tggcggctcg ggacggagga cgcgctagtg    120

ttcttctgtg tggcagttca gaatgatgga tcaagctaga tcagcattct ctaacttgtt    180

tggtggagaa ccattgtcat atacccggtt cagcctggct cggcaagtag atggcgataa    240

cagtcatgtg gagatgaaac ttgctgtaga tgaagaagaa aatgctgaca ataacacaaa    300

ggccaatgtc acaaaaccaa aaaggtgtag tggaagtatc tgctatggga ctattgctgt    360

gatcgtcttt ttcttgattg gatttatgat tggctacttg ggctattgta aaggggtaga    420

accaaaaact gagtgtgaga gactggcagg aaccgagtct ccagtgaggg aggagccagg    480

agaggacttc cctgcagcac gtcgcttata ttgggatgac ctgaagagaa agttgtcgga    540

gaaactggac agcacagact tcaccggcac catcaagctg ctgaatgaaa attcatatgt    600

ccctcgtgag gctggatctc aaaaagatga aaatcttgcg ttgtatgttg aaaatcaatt    660

tcgtgaattt aaactcagca aagtctggcg tgatcaacat tttgttaaga ttcaggtcaa    720

agacagcgct caaaactcgg tgatcatagt tgataagaac ggtagacttg tttacctggt    780

ggagaatcct gggggttatg tggcgtatag taaggctgca acagttactg gtaaactggt    840

ccatgctaat tttggtacta aaaaagattt tgaggattta tacactcctg tgaatggatc    900

tatagtgatt gtcagagcag ggaaaatcac ctttgcagaa aaggttgcaa atgctgaaag    960

cttaaatgca attggtgtgt tgatatacat ggaccagact aaatttccca ttgttaacgc   1020

agaactttca ttctttggac atgctcatct ggggacaggt gacccttaca cacctggatt   1080

cccttccttc aatcacactc agtttccacc atctcggtca tcaggattgc ctaatatacc   1140

tgtccagaca atctccagag ctgctgcaga aaagctgttt gggaatatgg aaggagactg   1200

tccctctgac tggaaaacag actctacatg taggatggta acctcagaaa gcaagaatgt   1260

gaagctcact gtgagcaatg tgctgaaaga gataaaaatt cttaacatct ttggagttat   1320

taaaggcttt gtagaaccag atcactatgt tgtagttggg gcccagagag atgcatgggg   1380
```

```
ccctggagct gcaaaatccg gtgtaggcac agctctccta ttgaaacttg cccagatgtt   1440
ctcagatatg gtcttaaaag atgggtttca gcccagcaga agcattatct ttgccagttg   1500
gagtgctgga gactttggat cggttggtgc cactgaatgg ctagagggat acctttcgtc   1560
cctgcattta aaggctttca cttatattaa tctggataaa gcggttcttg gtaccagcaa   1620
cttcaaggtt tctgccagcc cactgttgta tacgcttatt gagaaaacaa tgcaaaatgt   1680
gaagcatccg gttactgggc aatttctata tcaggacagc aactgggcca gcaaagttga   1740
gaaactcact ttagacaatg ctgctttccc tttccttgca tattctggaa tcccagcagt   1800
ttctttctgt ttttgcgagg acacagatta tccttatttg ggtaccacca tggacaccta   1860
taaggaactg attgagagga ttcctgagtt gaacaaagtg gcacgagcag ctgcagaggt   1920
cgctggtcag ttcgtgatta aactaaccca tgatgttgaa ttgaacctgg actatgagag   1980
gtacaacagc caactgcttt catttgtgag ggatctgaac caatacagag cagacataaa   2040
ggaaatgggc ctgagtttac agtggctgta ttctgctcgt ggagacttct tccgtgctac   2100
ttccagacta acaacagatt tcgggaatgc tgagaaaaca gacagatttg tcatgaagaa   2160
actcaatgat cgtgtcatga gagtggagta tcacttcctc tctccctacg tatctccaaa   2220
agagtctcct ttccgacatg tcttctgggg ctccggctct cacacgctgc cagctttact   2280
ggagaacttg aaactgcgta aacaaaataa cggtgctttt aatgaaacgc tgttcagaaa   2340
ccagttggct ctagctactt ggactattca gggagctgca aatgccctct ctggtgacgt   2400
ttgggacatt gacaatgagt tttaaatgtg atacccatag cttccatgag aacagcaggg   2460
tagtctggtt tctagacttg tgctgatcgt gctaaatttt cagtagggct acaaaacctg   2520
atgttaaaat tccatcccat catcttggta ctactagatg tctttaggca gcagctttta   2580
atacagggta gataacctgt acttcaagtt aaagtgaata accacttaaa aaatgtccat   2640
gatggaatat tcccctatct ctagaatttt aagtgctttg taatgggaac tgcctctttc   2700
ctgttgttgt taatgaaaat gtcagaaacc agttatgtga atgatctctc tgaatcctaa   2760
gggctggtct ctgctgaagg ttgtaagtgg tcgcttactt tgagtgatcc tccaacttca   2820
tttgatgcta aataggagat accaggttga aagaccttct ccaaatgaga tctaagcctt   2880
tccataagga atgtagctgg tttcctcatt cctgaaagaa acagttaact ttcagaagag   2940
atgggcttgt tttcttgcca atgaggtctg aaatggaggt ccttctgctg gataaaatga   3000
ggttcaactg ttgattgcag gaataaggcc ttaatatgtt aacctcagtg tcatttatga   3060
aaagagggga ccagaagcca aagacttagt atattttctt ttcctctgtc ccttccccca   3120
taagcctcca tttagttctt tgttattttt gtttcttcca aagcacattg aaagagaacc   3180
agtttcaggt gtttagttgc agactcagtt tgtcagactt taaagaataa tatgctgcca   3240
aattttggcc aaagtgttaa tcttagggga gagctttctg tccttttggc actgagatat   3300
ttattgttta tttatcagtg acagagttca ctataaatgg tgttttttta atagaatata   3360
attatcggaa gcagtgcctt ccataattat gacagttata ctgtcggttt tttttaaata   3420
aaagcagcat ctgctaataa aacccaacag atactggaag ttttgcattt atggtcaaca   3480
cttaagggtt ttagaaaaca gccgtcagcc aaatgtaatt gaataaagtt gaagctaaga   3540
tttagagatg aattaaattt aattaggggt tgctaagaag cgagcactga ccagataaga   3600
atgctggttt tcctaaatgc agtgaattgt gaccaagtta taaatcaatg tcacttaaag   3660
gctgtggtag tactcctgca aaattttata gctcagttta tccaaggtgt aactctaatt   3720
cccattttgc aaaatttcca gtacctttgt cacaatccta acacattatc gggagcagtg   3780
```

```
tcttccataa tgtataaaga acaaggtagt ttttacctac cacagtgtct gtatcggaga   3840

cagtgatctc catatgttac actaagggtg taagtaatta tcgggaacag tgtttcccat   3900

aattttcttc atgcaatgac atcttcaaag cttgaagatc gttagtatct aacatgtatc   3960

ccaactccta taattcccta tcttttagtt ttagttgcag aaacattttg tggtcattaa   4020

gcattgggtg ggtaaattca accactgtaa aatgaaatta ctacaaaatt tgaaatttag   4080

cttgggtttt tgttaccttt atggtttctc caggtcctct acttaatgag atagtagcat   4140

acatttataa tgtttgctat tgacaagtca ttttaacttt atcacattat ttgcatgtta   4200

cctcctataa acttagtgcg gacaagtttt aatccagaat tgaccttttg acttaaagca   4260

gagggacttt gtatagaagg tttgggggct gtggggaagg agagtcccct gaaggtctga   4320

cacgtctgcc tacccattcg tggtgatcaa ttaaatgtag gtatgaataa gttcgaagct   4380

ccgtgagtga accatcatta taaacgtgat gatcagctgt ttgtcatagg gcagttggaa   4440

acggcctcct agggaaaagt tcatagggtc tcttcaggtt cttagtgtca cttacctaga   4500

tttacagcct cacttgaatg tgtcactact cacagtctct ttaatcttca gttttatctt   4560

taatctcctc ttttatcttg gactgacatt tagcgtagct aagtgaaaag gtcatagctg   4620

agattcctgg ttcgggtgtt acgcacacgt acttaaatga aagcatgtgg catgttcatc   4680

gtataacaca atatgaatac agggcatgca ttttgcagca gtgagtctct tcagaaaacc   4740

cttttctaca gttagggttg agttacttcc tatcaagcca gtacgtgcta acaggctcaa   4800

tattcctgaa tgaaatatca gactagtgac aagctcctgg tcttgagatg tcttctcgtt   4860

aaggagatgg gccttttgga ggtaaaggat aaaatgaatg agttctgtca tgattcacta   4920

ttctagaact tgcatgacct ttactgtgtt agctctttga atgttcttga aattttagac   4980

tttctttgta aacaaatgat atgtccttat cattgtataa aagctgttat gtgcaacagt   5040

gtggagattc cttgtctgat ttaataaaat acttaaacac tgaaaaaaaa aaaaaaaaaa   5100
```

<210> SEQ ID NO 66
<211> LENGTH: 5967
<212> TYPE: DNA
<213> ORGANISM: Homo sapiens

<400> SEQUENCE: 66

```
ctttgggcct cataaacaac cacagaacca caagttgggt agcctggcag tgtcagaagt     60

ctgaacccag catagtggtc agcaggcagg acgaatcaca ctgaatgcaa accacagggt    120

ttcgcagcgt ggtaaaagaa atcattgagt cccccgcctt cagaagaggg tgcattttca    180

ggaggaagcg atggcttcag acagcatatt tgagtcattt ccttcgtacc cacagtgctt    240

catgagagaa tgcatacttg gaatgaatcc ttctagagac gtccacgatg ccagcacgag    300

ccgccgcttc acgccgcctt ccaccgcgct gagcccaggc aagatgagcg aggcgttgcc    360

gctgggcgcc ccggacgccg gcgctgccct ggccggcaag ctgaggagcg gcgaccgcag    420

catggtggag gtgctggccg accacccggg cgagctggtg cgcaccgaca gccccaactt    480

cctctgctcc gtgctgccta cgcactggcg ctgcaacaag accctgccca tcgctttcaa    540

ggtggtggcc ctaggggatg ttccagatgg cactctggtc actgtgatgg ctggcaatga    600

tgaaaactac tcggctgagc tgagaaatgc taccgcagcc atgaagaacc aggttgcaag    660

atttaatgac ctcaggtttg tcggtcgaag tggaagaggg aaaagcttca ctctgaccat    720

cactgtcttc acaaacccac cgcaagtcgc cacctaccac agagccatca aaatcacagt    780
```

```
ggatgggccc cgagaacctc gaagacatcg gcagaaacta gatgatcaga ccaagcccgg    840
gagcttgtcc ttttccgagc ggctcagtga actggagcag ctgcggcgca cagccatgag    900
ggtcagccca caccacccag cccccacgcc caaccctcgt gcctccctga accactccac    960
tgcctttaac cctcagcctc agagtcagat gcaggataca aggcagatcc aaccatcccc   1020
accgtggtcc tacgatcagt cctaccaata cctgggatcc attgcctctc cttctgtgca   1080
cccagcaacg cccatttcac ctggacgtgc cagcggcatg acaaccctct ctgcagaact   1140
ttccagtcga ctctcaacgg cacccgacct gacagcgttc agcgacccgc gccagttccc   1200
cgcgctgccc tccatctccg acccccgcat gcactatcca ggcgccttca cctactcccc   1260
gacgccggtc acctcgggca tcggcatcgg catgtcggcc atgggctcgg ccacgcgcta   1320
ccacacctac ctgccgccgc cctaccccgg ctcgtcgcaa gcgcagggag gcccgttcca   1380
agccagctcg ccctcctacc acctgtacta cggcgcctcg gccggctcct accagttctc   1440
catggtgggc ggcgagcgct cgccgccgcg catcctgccg ccctgcacca acgcctccac   1500
cggctccgcg ctgctcaacc ccagcctccc gaaccagagc gacgtggtgg aggccgaggg   1560
cagccacagc aactccccca ccaacatggc gccctccgcg cgcctggagg aggccgtgtg   1620
gaggccctac tgaggcgcca ggcctggccc ggctgggccc cgcgggccgc cgccttcgcc   1680
tccgggcgcg cgggcctcct gttcgcgaca agcccgccgg gatcccgggc cctgggcccg   1740
gccaccgtcc tggggccgag ggcgcccgac ggccaggatc tcgctgtagg tcaggcccgc   1800
gcagcctcct gcgcccagaa gcccacgccg ccgccgtctg ctggcgcccc ggccctcgcg   1860
gaggtgtccg aggcgacgca cctcgagggt gtccgccggc cccagcaccc aggggacgcg   1920
ctggaaagca aacaggaaga ttcccggagg gaaactgtga atgcttctga tttagcaatg   1980
ctgtgaataa aaagaaagat tttataccct tgacttaact ttttaaccaa gttgtttatt   2040
ccaaagagtg tggaattttg gttggggtgg ggggagagga gggatgcaac tcgccctgtt   2100
tggcatctaa ttcttatttt taatttttcc gcaccttatc aattgcaaaa tgcgtatttg   2160
catttgggtg gtttttattt ttatatacgt ttatataaat atatataaat tgagcttgct   2220
tctttcttgc tttgaccatg gaaagaaata tgattccctt ttctttaagt tttatttaac   2280
ttttcttttg gacttttggg tagttgtttt tttttgtttt gttttgtttt tttgagaaac   2340
agctacagct ttgggtcatt tttaactact gtattcccac aaggaatccc cagatattta   2400
tgtatcttga tgttcagaca tttatgtgtt gataattttt taattattta aatgtactta   2460
tattaagaaa aatatcaagt actacatttt cttttgttct tgatagtagc caaagttaaa   2520
tgtatcacat tgaagaaggc tagaaaaaaa gaatgagtaa tgtgatcgct tggttatcca   2580
gaagtattgt ttacattaaa ctccctttca tgttaatcaa acaagtgagt agctcacgca   2640
gcaacgtttt taataggatt tttagacact gagggtcact ccaaggatca gaagtatgga   2700
attttctgcc aggctcaaca agggtctcat atctaacttc ctccttaaaa cagagaaggt   2760
caatctagtt ccagagggtt gaggcaggtg ccaataatta catctttgga gaggatttga   2820
tttctgccca gggatttgct caccccaagg tcatctgata atttcacaga tgctgtgtaa   2880
cagaacacag ccaaagtaaa ctgtgtaggg gagccacatt tacataggaa ccaaatcaat   2940
gaatttaggg gttacgatta tagcaattta agggcccacc agaagcaggc ctcgaggagt   3000
caatttgcct ctgtgtgcct cagtggagac aagtgggaaa acatggtccc acctgtgcga   3060
gaccccctgt cctgtgctgc tcactcaaca acatctttgt gttgctttca ccaggctgag   3120
accctaccct atggggtata tgggctttta cctgtgcacc agtgtgacag gaaagattca   3180
```

```
tgtcactact gtccgtggct acaattcaaa ggtatccaat gtcgctgtaa attttatggc   3240
actattttta ttggaggatt tggtcagaat gcagttgttg tacaactcat aaatactaac   3300
tgctgatttt gacacatgtg tgctccaaat gatctggtgg ttatttaacg tacctcttaa   3360
aattcgttga aacgatttca ggtcaactct gaagagtatt tgaaagcagg acttcagaac   3420
agtgtttgat ttttatttta taaatttaag cattcaaatt aggcaaatct ttggctgcag   3480
gcagcaaaaa cagctggact tatttaaaac aacttgtttt tgagttttct tatatatata   3540
ttgattattt gttttacaca catgcagtag cactttggta agagttaaag agtaaagcag   3600
cttatgttgt caggtcgttc ttatctagag aagagctata gcagatctcg gacaaactca   3660
gaatatattc actttcattt ttgacaggat tccctccaca actcagtttc atatattatt   3720
ccgtattaca tttttgcagc taaattacca taaaatgtca gcaaatgtaa aaatttaatt   3780
tctgaaaagc accattagcc catttccccc aaattaaacg taaatgtttt ttttcagcac   3840
atgttaccat gtctgacctg caaaaatgct ggagaaaaat gaaggaaaaa attatgtttt   3900
tcagtttaat tctgttaact gaagatattc caactcaaaa ccagcctcat gctctgatta   3960
gataatcttt tacattgaac ctttactctc aaagccatgt gtggaggggg cttgtcacta   4020
ttgtaggctc actggattgg tcatttagag tttcacagac tcttaccagc atatatagta   4080
tttaattgtt tcaaaaaaaa tcaaactgta gttgttttgg cgataggtct cacgcaacac   4140
atttttgtat gtgtgtgtgt gtgcgtgtgt gtgtgtgtgt gtgaaaaatt gcattcattg   4200
acttcaggta gattaaggta tctttttatt cattgccctc aggaaagtta aggtatcaat   4260
gagaccctta agccaatcat gtaataactg catgtgtctg gtccaggaga agtattgaat   4320
aagccatttc tactgcttac tcatgtccct atttatgatt tcaacatgga tacatatttc   4380
agttctttct ttttctcact atctgaaaat acatttccct ccctctcttc cccccaatat   4440
ctcccttttt ttctctcttc ctctatcttc caaaccccac tttctccctc ctccttttcc   4500
tgtgttctct taagcagata gcacataccc ccacccagta ccaaatttca gaacacaaga   4560
aggtccagtt cttccccctt cacataaagg aacatggttt gtcagccttt ctcctgttta   4620
tgggtttctt ccagcagaac agagacattg ccaaccatat tggatctgct tgctgtccaa   4680
accagcaaac tttcctgggc aaatcacaat cagtgagtaa atagacagcc tttctgctgc   4740
cttgggtttc tgtgcagata aacagaaatg ctctgattag aaaggaaatg aatggttcca   4800
ctcaaatgtc ctgcaattta ggattgcaga tttctgcctt gaaatacctg tttctttggg   4860
acattccgtc ctgatgattt ttatttttgt tggtttttat ttttgggggg aatgacatgt   4920
ttgggtcttt tatacatgaa aatttgtttg acaataatct cacaaaacat attttacatc   4980
tgaacaaaat gccttttttgt ttaccgtagc gtatacattt gttttgggat ttttgtgtgt   5040
ttgttgggaa ttttgttttt agccaggtca gtattgatga ggctgatcat ttggctcttt   5100
ttttccttcc agaagagttg catcaacaaa gttaattgta tttatgtatg taaatagatt   5160
ttaagcttca ttataaaata ttgttaatgc ctataacttt ttttcaattt ttttgtgtgt   5220
gtttctaagg actttttctt aggtttgcta aatactgtag ggaaaaaaat gcttctttct   5280
actttgttta ttttagactt taaaatgagc tacttcttat tcacttttgt aaacagctaa   5340
tagcatggtt ccaatttttt ttaagttcac ttttttttgtt ctaggggaaa tgaatgtgca   5400
aaaaaagaaa aagaactgtt ggttatttgt gttattctgg atgtataaaa atcaatggaa   5460
aaaaataaac tttcaaattg aaatgacggt ataacacatc tactgaaaaa gcaacgggaa   5520
```

```
atgtggtcct atttaagcca gcccccacct agggtctatt tgtgtggcag ttattgggtt   5580
tggtcacaaa acatcctgaa aattcgtgcg tgggcttctt tctccctggt acaaacgtat   5640
ggaatgcttc ttaaagggga actgtcaagc tggtgtcttc agccagatga catgagagaa   5700
tatcccagaa ccctctctcc aaggtgtttc tagatagcac aggagagcag gcactgcact   5760
gtccacagtc cacggtacac agtcgggtgg gccgcctccc ctctcctggg agcattcgtc   5820
gtgcccagcc tgagcagggc agctggactg ctgctgttca ggagccacca gagccttcct   5880
ctctttgtac cacagtttct tctgtaaatc cagtgttaca atcagtgtga atggcaaata   5940
aacagtttga caagtacata caccata                                       5967
```

<210> SEQ ID NO 67
<211> LENGTH: 7274
<212> TYPE: DNA
<213> ORGANISM: Homo sapiens

<400> SEQUENCE: 67

```
catagagcca gcgggcgcgg gcgggacggg cgccccgcgg ccggacccag ccagggcacc     60
acgctgcccg gccctgcgcc gccaggcact tctttccggg gctcctaggg acgccagaag    120
gaagtcaacc tctgctgctt ctccttggcc tgcgttggac cttccttttt ttgttgtttt    180
tttttgtttt tccccttttct tccttttgaa ttaactggct tcttggctgg atgttttcaa    240
cttctttcct ggctgcgaac ttttccccaa ttgttttcct tttacaacag ggggagaaag    300
tgctctgtgg tccgaggcga gccgtgaagt tgcgtgtgcg tggcagtgtg cgtggcagga    360
tgtgcgtgcg tgtgtaaccc gagccgcccg atctgtttcg atctgcgccg cggagccctc    420
cctcaaggcc cgctccacct gctgcggtta cgcggcgctc gtgggtgttc gtgcctcgga    480
gcagctaacc ggcgggtgct gggcgacggt ggaggagtat cgtctcgctg ctgcccgagt    540
cagggctgag tcacccagct gatgtagaca gtggctgcct tccgaagagt gcgtgtttgc    600
atgtgtgtga ctctgcggct gctcaactcc caacaaacca gaggaccagc cacaaactta    660
accaacatcc ccaaacccga gttcacagat gtgggagagc tgtagaaccc tgagtgtcat    720
cgactgggcc ttcttatgat tgttgtttta agattagctg aagatctctg aaacgctgaa    780
ttttctgcac tgagcgtttt gacagaattc attgagagaa cagagaacat gacaagtact    840
tctagctcag cactgctcca actactgaag ctgattttca aggctactta aaaaaatctg    900
cagcgtacat taatggattt ctgttgtgtt taaattctcc acagattgta ttgtaaatat    960
tttatgaagt agagcatatg tatatattta tatatacgtg cacatacatt agtagcacta   1020
cctttggaag tctcagctct tgcttttcgg gactgaagcc agttttgcat gataaaagtg   1080
gccttgttac gggagataat tgtgttctgt tgggacttta gacaaaactc acctgcaaaa   1140
aactgacagg cattaactac tggaacttcc aaataatgtg tttgctgatc gttttactct   1200
tcgcataaat attttaggaa gtgtatgaga attttgcctt caggaacttt tctaacagcc   1260
aaagacagaa cttaacctct gcaagcaaga ttcgtggaag atagtctcca ctttttaatg   1320
cactaagcaa tcggttgcta ggagcccatc ctgggtcaga ggccgatccg cagaaccaga   1380
acgttttccc ctcctggact gttagtaact tagtctccct cctcccctaa ccacccccgc   1440
cccccccac cccccgcagt aataaaggcc cctgaacgtg tatgttggtc tcccgggagc   1500
tgcttgctga agatccgcgc ccctgtcgcc gtctggtagg agctgtttgc agggtcctaa   1560
ctcaatcggc ttgttgtgat gcgtatcccc gtagatgcca gcacgagccg ccgcttcacg   1620
ccgccttcca ccgcgctgag cccaggcaag atgagcgagg cgttgccgct gggcgccccg   1680
```

```
gacgccggcg ctgccctggc cggcaagctg aggagcggcg accgcagcat ggtggaggtg   1740
ctggccgacc acccgggcga gctggtgcgc accgacagcc ccaacttcct ctgctccgtg   1800
ctgcctacgc actggcgctg caacaagacc ctgcccatcg ctttcaaggt ggtggcccta   1860
ggggatgttc cagatggcac tctggtcact gtgatggctg gcaatgatga aaactactcg   1920
gctgagctga gaaatgctac cgcagccatg aagaaccagg ttgcaagatt taatgacctc   1980
aggtttgtcg gtcgaagtgg aagagggaaa agcttcactc tgaccatcac tgtcttcaca   2040
aacccaccgc aagtcgccac ctaccacaga gccatcaaaa tcacagtgga tgggccccga   2100
gaacctcgaa gacatcggca gaaactagat gatcagacca agcccgggag cttgtccttt   2160
tccgagcggc tcagtgaact ggagcagctg cggcgcacag ccatgagggt cagcccacac   2220
cacccagccc ccacgcccaa ccctcgtgcc tccctgaacc actccactgc ctttaaccct   2280
cagcctcaga gtcagatgca ggatacaagg cagatccaac catccccacc gtggtcctac   2340
gatcagtcct accaatacct gggatccatt gcctctcctt ctgtgcaccc agcaacgccc   2400
atttcacctg gacgtgccag cggcatgaca accctctctg cagaactttc cagtcgactc   2460
tcaacggcac ccgacctgac agcgttcagc gacccgcgcc agttccccgc gctgccctcc   2520
atctccgacc cccgcatgca ctatccaggc gccttcacct actccccgac gccggtcacc   2580
tcgggcatcg gcatcggcat gtcggccatg ggctcggcca cgcgctacca cacctacctg   2640
ccgccgccct accccggctc gtcgcaagcg cagggaggcc cgttccaagc cagctcgccc   2700
tcctaccacc tgtactacgg cgcctcggcc ggctcctacc agttctccat ggtgggcggc   2760
gagcgctcgc cgccgcgcat cctgccgccc tgcaccaacg cctccaccgg ctccgcgctg   2820
ctcaacccca gcctcccgaa ccagagcgac gtggtggagg ccgagggcag ccacagcaac   2880
tcccccacca acatggcgcc ctccgcgcgc ctggaggagg ccgtgtggag gccctactga   2940
ggcgccaggc ctggcccggc tgggccccgc gggccgccgc cttcgcctcc gggcgcgcgg   3000
gcctcctgtt cgcgacaagc ccgccgggat cccgggccct gggcccggcc accgtcctgg   3060
ggccgagggc gcccgacggc caggatctcg ctgtaggtca ggcccgcgca gcctcctgcg   3120
cccagaagcc cacgccgccg ccgtctgctg gcgccccggc cctcgcggag gtgtccgagg   3180
cgacgcacct cgagggtgtc cgccggcccc agcacccagg ggacgcgctg gaaagcaaac   3240
aggaagattc ccggagggaa actgtgaatg cttctgattt agcaatgctg tgaataaaaa   3300
gaaagatttt ataccttga cttaactttt taaccaagtt gtttattcca aagagtgtgg    3360
aattttggtt ggggtggggg gagaggaggg atgcaactcg ccctgtttgg catctaattc   3420
ttatttttaa tttttccgca ccttatcaat tgcaaaatgc gtatttgcat ttgggtggtt   3480
tttattttta tatacgttta tataaatata tataaattga gcttgcttct ttcttgcttt   3540
gaccatggaa agaaatatga ttccctttc tttaagtttt atttaacttt tcttttggac    3600
ttttgggtag ttgtttttt ttgttttgtt ttgttttttt gagaaacagc tacagctttg    3660
ggtcattttt aactactgta ttcccacaag gaatccccag atatttatgt atcttgatgt   3720
tcagacattt atgtgttgat aattttttaa ttatttaaat gtacttatat taagaaaaat   3780
atcaagtact acattttctt ttgttcttga tagtagccaa agttaaatgt atcacattga   3840
agaaggctag aaaaaaagaa tgagtaatgt gatcgcttgg ttatccagaa gtattgttta   3900
cattaaactc cctttcatgt taatcaaaca agtgagtagc tcacgcagca acgtttttaa   3960
taggattttt agacactgag ggtcactcca aggatcagaa gtatggaatt ttctgccagg   4020
```

-continued

```
ctcaacaagg gtctcatatc taacttcctc cttaaaacag agaaggtcaa tctagttcca   4080
gagggttgag gcaggtgcca ataattacat ctttggagag gatttgattt ctgcccaggg   4140
atttgctcac cccaaggtca tctgataatt tcacagatgc tgtgtaacag aacacagcca   4200
aagtaaactg tgtaggggag ccacatttac ataggaacca aatcaatgaa tttaggggtt   4260
acgattatag caatttaagg gcccaccaga agcaggcctc gaggagtcaa tttgcctctg   4320
tgtgcctcag tggagacaag tgggaaaaca tggtcccacc tgtgcgagac cccctgtcct   4380
gtgctgctca ctcaacaaca tctttgtgtt gctttcacca ggctgagacc ctaccctatg   4440
gggtatatgg gcttttacct gtgcaccagt gtgacaggaa agattcatgt cactactgtc   4500
cgtggctaca attcaaaggt atccaatgtc gctgtaaatt ttatggcact atttttattg   4560
gaggatttgg tcagaatgca gttgttgtac aactcataaa tactaactgc tgattttgac   4620
acatgtgtgc tccaaatgat ctggtggtta tttaacgtac ctcttaaaat tcgttgaaac   4680
gatttcaggt caactctgaa gagtatttga aagcaggact tcagaacagt gtttgatttt   4740
tattttataa atttaagcat tcaaattagg caaatctttg gctgcaggca gcaaaaacag   4800
ctggacttat ttaaaacaac ttgtttttga gttttcttat atatatattg attatttgtt   4860
ttacacacat gcagtagcac tttggtaaga gttaaagagt aaagcagctt atgttgtcag   4920
gtcgttctta tctagagaag agctatagca gatctcggac aaactcagaa tatattcact   4980
ttcatttttg acaggattcc ctccacaact cagtttcata tattattccg tattacattt   5040
ttgcagctaa attaccataa aatgtcagca aatgtaaaaa tttaatttct gaaaagcacc   5100
attagcccat ttcccccaaa ttaaacgtaa atgttttttt tcagcacatg ttaccatgtc   5160
tgacctgcaa aaatgctgga gaaaaatgaa ggaaaaaatt atgtttttca gtttaattct   5220
gttaactgaa gatattccaa ctcaaaacca gcctcatgct ctgattagat aatcttttac   5280
attgaacctt tactctcaaa gccatgtgtg gagggggctt gtcactattg taggctcact   5340
ggattggtca tttagagttt cacagactct taccagcata tatagtattt aattgtttca   5400
aaaaaaatca aactgtagtt gttttggcga taggtctcac gcaacacatt tttgtatgtg   5460
tgtgtgtgtg cgtgtgtgtg tgtgtgtgtg aaaaattgca ttcattgact tcaggtagat   5520
taaggtatct ttttattcat tgccctcagg aaagttaagg tatcaatgag acccttaagc   5580
caatcatgta ataactgcat gtgtctggtc caggagaagt attgaataag ccatttctac   5640
tgcttactca tgtccctatt tatgatttca acatggatac atatttcagt tctttctttt   5700
tctcactatc tgaaaataca tttccctccc tctcttcccc ccaatatctc cctttttttc   5760
tctcttcctc tatcttccaa accccacttt ctccctcctc cttttcctgt gttctcttaa   5820
gcagatagca catacccccca cccagtacca aatttcagaa cacaagaagg tccagttctt   5880
ccccccttcac ataaaggaac atggtttgtc agcctttctc ctgtttatgg gtttcttcca   5940
gcagaacaga gacattgcca accatattgg atctgcttgc tgtccaaacc agcaaacttt   6000
cctgggcaaa tcacaatcag tgagtaaata gacagccttt ctgctgcctt gggtttctgt   6060
gcagataaac agaaatgctc tgattagaaa ggaaatgaat ggttccactc aaatgtcctg   6120
caatttagga ttgcagattt ctgccttgaa atacctgttt ctttgggaca ttccgtcctg   6180
atgattttta tttttgttgg tttttatttt tggggggaat gacatgtttg ggtcttttat   6240
acatgaaaat ttgtttgaca ataatctcac aaaacatatt ttacatctga acaaaatgcc   6300
tttttgttta ccgtagcgta tacatttgtt ttgggatttt tgtgtgtttg ttgggaattt   6360
tgtttttagc caggtcagta ttgatgaggc tgatcatttg gctctttttt tccttccaga   6420
```

```
agagttgcat caacaaagtt aattgtattt atgtatgtaa atagatttta agcttcatta   6480
taaaatattg ttaatgccta taactttttt tcaatttttt tgtgtgtgtt tctaaggact   6540
ttttcttagg tttgctaaat actgtaggga aaaaaatgct tctttctact ttgtttattt   6600
tagactttaa aatgagctac ttcttattca cttttgtaaa cagctaatag catggttcca   6660
attttttta agttcacttt ttttgttcta ggggaaatga atgtgcaaaa aaagaaaaag   6720
aactgttggt tatttgtgtt attctggatg tataaaaatc aatggaaaaa aataaacttt   6780
caaattgaaa tgacggtata acacatctac tgaaaaagca acgggaaatg tggtcctatt   6840
taagccagcc cccacctagg gtctatttgt gtggcagtta ttgggtttgg tcacaaaaca   6900
tcctgaaaat tcgtgcgtgg gcttctttct ccctggtaca aacgtatgga atgcttctta   6960
aaggggaact gtcaagctgg tgtcttcagc cagatgacat gagagaatat cccagaaccc   7020
tctctccaag gtgtttctag atagcacagg agagcaggca ctgcactgtc cacagtccac   7080
ggtacacagt cgggtgggcc gcctcccctc tcctgggagc attcgtcgtg cccagcctga   7140
gcagggcagc tggactgctg ctgttcagga gccaccagag ccttcctctc tttgtaccac   7200
agtttcttct gtaaatccag tgttacaatc agtgtgaatg gcaaataaac agtttgacaa   7260
gtacatacac cata                                                     7274
```

<210> SEQ ID NO 68
<211> LENGTH: 2722
<212> TYPE: DNA
<213> ORGANISM: Homo sapiens

<400> SEQUENCE: 68

```
catagagcca gcgggcgcgg gcgggacggg cgccccgcgg ccggacccag ccagggcacc     60
acgctgcccg gccctgcgcc gccaggcact tctttccggg gctcctaggg acgccagaag    120
gaagtcaacc tctgctgctt ctccttggcc tgcgttggac cttccttttt ttgttgtttt    180
tttttgtttt tccccttctc tccttttgaa ttaactggct tcttggctgg atgttttcaa    240
cttctttcct ggctgcgaac ttttccccaa ttgttttcct tttacaacag ggggagaaag    300
tgctctgtgg tccgaggcga gccgtgaagt tgcgtgtgcg tggcagtgtg cgtggcagga    360
tgtgcgtgcg tgtgtaaccc gagccgcccg atctgtttcg atctgcgccg cggagccctc    420
cctcaaggcc cgctccacct gctgcggtta cgcggcgctc gtgggtgttc gtgcctcgga    480
gcagctaacc ggcgggtgct gggcgacggt ggaggagtat cgtctcgctg ctgcccgagt    540
cagggctgag tcacccagct gatgtagaca gtggctgcct tccgaagagt gcgtgtttgc    600
atgtgtgtga ctctgcggct gctcaactcc caacaaacca gaggaccagc cacaaactta    660
accaacatcc ccaaacccga gttcacagat gtgggagagc tgtagaaccc tgagtgtcat    720
cgactgggcc ttcttatgat tgttgtttta agattagctg aagatctctg aaacgctgaa    780
ttttctgcac tgagcgtttt gacagaattc attgagagaa cagagaacat gacaagtact    840
tctagctcag cactgctcca actactgaag ctgattttca aggctactta aaaaaatctg    900
cagcgtacat taatggattt ctgttgtgtt taaattctcc acagattgta ttgtaaatat    960
tttatgaagt agagcatatg tatatattta tatatacgtg cacatacatt agtagcacta   1020
cctttggaag tctcagctct tgcttttcgg gactgaagcc agttttgcat gataaaagtg   1080
gccttgttac gggagataat tgtgttctgt tgggacttta gacaaaactc acctgcaaaa   1140
aactgacagg cattaactac tggaacttcc aaataatgtg tttgctgatc gttttactct   1200
```

```
tcgcataaat attttaggaa gtgtatgaga attttgcctt caggaacttt tctaacagcc   1260

aaagacagaa cttaacctct gcaagcaaga ttcgtggaag atagtctcca ctttttaatg   1320

cactaagcaa tcggttgcta ggagcccatc ctgggtcaga ggccgatccg cagaaccaga   1380

acgttttccc ctcctggact gttagtaact tagtctccct cctcccctaa ccacccccgc   1440

cccccccac cccccgcagt aataaaggcc cctgaacgtg tatgttggtc tcccgggagc   1500

tgcttgctga agatccgcgc ccctgtcgcc gtctggtagg agctgtttgc agggtcctaa   1560

ctcaatcggc ttgttgtgat gcgtatcccc gtagatgcca gcacgagccg ccgcttcacg   1620

ccgccttcca ccgcgctgag cccaggcaag atgagcgagg cgttgccgct gggcgccccg   1680

gacgccggcg ctgccctggc cggcaagctg aggagcggcg accgcagcat ggtggaggtg   1740

ctggccgacc acccgggcga gctggtgcgc accgacagcc ccaacttcct ctgctccgtg   1800

ctgcctacgc actggcgctg caacaagacc ctgcccatcg ctttcaaggt ggtggcccta   1860

ggggatgttc cagatggcac tctggtcact gtgatggctg gcaatgatga aaactactcg   1920

gctgagctga gaaatgctac cgcagccatg aagaaccagg ttgcaagatt taatgacctc   1980

aggtttgtcg gtcgaagtgg aagagggaaa agcttcactc tgaccatcac tgtcttcaca   2040

aacccaccgc aagtcgccac ctaccacaga gccatcaaaa tcacagtgga tgggccccga   2100

gaacctcgaa gacatcggca gaaactagat gatcagacca agcccgggag cttgtccttt   2160

tccgagcggc tcagtgaact ggagcagctg cggcgcacag ccatgagggt cagcccacac   2220

cacccagccc ccacgcccaa ccctcgtgcc tccctgaacc actccactgc ctttaaccct   2280

cagcctcaga gtcagatgca ggaggaagac acagcaccct ggagatgtta aggcagaagt   2340

cagttcttct gtccatccct ctccccagcc aggatagagc tatcttttcc atctcatcct   2400

cagaagagac tcagaagaaa gatgacagcc ctcagaatgc acgttatgag gaaggcagaa   2460

tgtgggtctg taattcctcc gtgtcccttc tccccctctg caaaccgtcg taacaataat   2520

agttcctaac acatgggaca attgtgagga ttaaatgagt tagcctgcag aaatcacttg   2580

atgcacagca catgggaagc attgtgtgta tttattaatc cttcacaaag tctttgagat   2640

atatttttat caaatattta gcatggatcc cggtacactt tcaatactta ataaatggtc   2700

aatgttattc tttttcacta tt                                              2722
```

<210> SEQ ID NO 69
<211> LENGTH: 2746
<212> TYPE: DNA
<213> ORGANISM: Homo sapiens

<400> SEQUENCE: 69

```
ggctccgact tggactccct gctccgctgc tgccgcttcg gccccgcacg cagccagccg     60

ccagccgccc gcccggccca gctcccgccg cggccccttg ccgcggtccc tctcctggtc    120

ccctcccggt tggtccgggg gtgcgcaggg ggcagggcgg gcgcccaggg gaagctcgag    180

ggacgcgcgc gcgaaggctc ctttgtggac ttcacggccg ccaacatctg ggcgcagcgc    240

gggccaccgc tggccgtctc gccgccgcgt cgccttgggg acccgagggg gctcagcccc    300

aaggacggag acttcgattc gggaccagcc ccccgggatg cggtagcggc cgctgtgcgg    360

aggccgcgaa gcagctgcag ccgccgccgc gcagatccac gctggctccg tgcgccatgg    420

tcacccacag caagtttccc gccgccggga tgagccgccc cctggacacc agcctgcgcc    480

tcaagacctt cagctccaag agcgagtacc agctggtggt gaacgcagtg cgcaagctgc    540

aggagagcgg cttctactgg agcgcagtga ccggcggcga ggcgaacctg ctgctcagtg    600
```

```
ccgagcccgc cggcaccttt ctgatccgcg acagctcgga ccagcgccac ttcttcacgc    660
tcagcgtcaa gacccagtct gggaccaaga acctgcgcat ccagtgtgag gggggcagct    720
tctctctgca gagcgatccc cggagcacgc agcccgtgcc ccgcttcgac tgcgtgctca    780
agctggtgca ccactacatg ccgccccctg gagccccctc cttcccctcg ccacctactg    840
aaccctcctc cgaggtgccc gagcagccgt ctgcccagcc actccctggg agtcccccca    900
gaagagccta ttacatctac tccgggggcg agaagatccc cctggtgttg agccggcccc    960
tctcctccaa cgtggccact cttcagcatc tctgtcggaa gaccgtcaac ggccacctgg   1020
actcctatga gaaagtcacc cagctgccgg ggcccattcg ggagttcctg gaccagtacg   1080
atgccccgct ttaaggggta aagggcgcaa agggcatggg tcgggagagg ggacgcaggc   1140
ccctctcctc cgtggcacat ggcacaagca caagaagcca accaggagag agtcctgtag   1200
ctctgggggg aaagagggcg gacaggcccc tccctctgcc ctctccctgc agaatgtggc   1260
aggcggacct ggaatgtgtt ggagggaagg gggagtacca cctgagtctc cagcttctcc   1320
ggaggagcca gctgtcctgg tgggacgata gcaaccacaa gtggattctc cttcaattcc   1380
tcagcttccc ctctgcctcc aaacagggga cacttcggga atgctgaact aatgagaact   1440
gccagggaat cttcaaactt tccaacggaa cttgtttgct ctttgatttg gtttaaacct   1500
gagctggttg tggagcctgg gaaaggtgga agagagagag gtcctgaggg ccccagggct   1560
gcgggctggc gaaggaaatg gtcacacccc ccgcccaccc caggcgagga tcctggtgac   1620
atgctcctct ccctggctcc ggggagaagg gcttggggtg acctgaaggg aaccatcctg   1680
gtaccccaca tcctctcctc cgggacagtc accgaaaaca caggttccaa agtctacctg   1740
gtgcctgaga gcccagggcc cttcctccgt tttaaggggg aagcaacatt tggaggggat   1800
ggatgggctg gtcagctggt ctccttttcc tactcatact ataccttcct gtacctgggt   1860
ggatggagcg ggaggatgga ggagacggga catctttcac ctcaggctcc tggtagagaa   1920
gacaggggat tctactctgt gcctcctgac tatgtctggc taagagattc gccttaaatg   1980
ctccctgtcc catggagagg gacccagcat aggaaagcca catactcagc ctggatgggt   2040
ggagaggctg agggactcac tggagggcac caagccagcc cacagccagg gaagtgggga   2100
ggggggcgg aaacccatgc ctcccagctg agcactggga atgtcagccc agtaagtatt   2160
ggccagtcag gcgcctcgtg gtcagagcag agccaccagg tcccactgcc ccgagccctg   2220
cacagccctc cctcctgcct gggtggggga ggctggaggt cattggagag gctggactgc   2280
tgccaccccg ggtgctcccg ctctgccata gcactgatca gtgacaattt acaggaatgt   2340
agcagcgatg gaattacctg gaacagtttt ttgtttttgt ttttgttttt gtttttgtgg   2400
ggggggcaa ctaaacaaac acaaagtatt ctgtgtcagg tattgggctg gacagggcag   2460
ttgtgtgttg gggtggtttt tttctctatt tttttgtttg tttcttgttt tttaataatg   2520
tttacaatct gcctcaatca ctctgtcttt tataaagatt ccacctccag tcctctctcc   2580
tccccctac tcaggccctt gaggctatta ggagatgctt gaagaactca acaaaatccc   2640
aatccaagtc aaactttgca catatttata tttatattca gaaaagaaac atttcagtaa   2700
tttataataa agagcactat tttttaatga aaaaaaaaaa aaaaaa                  2746
```

<210> SEQ ID NO 70
<211> LENGTH: 1709
<212> TYPE: DNA
<213> ORGANISM: Homo sapiens

<400> SEQUENCE: 70

```
agaacactgg cggccgatcc caacgaggct ccctggagcc cgacgcagag cagcgccctg     60
gccgggccaa gcaggagccg gcatcatgga ttccttcaaa gtagtgctgg aggggccagc    120
accttggggc ttccggctgc aagggggcaa ggacttcaat gtgcccctct ccatttcccg    180
gctcactcct gggggcaaag cggcgcaggc cggagtggcc gtgggtgact gggtgctgag    240
catcgatggc gagaatgcgg gtagcctcac acacatcgaa gctcagaaca agatccgggc    300
ctgcggggag cgcctcagcc tgggcctcag cagggcccag ccggttcaga gcaaaccgca    360
gaaggcctcc gcccccgccg cggaccctcc gcggtacacc tttgcaccca gcgtctccct    420
caacaagacg gcccggccct ttggggcgcc cccgcccgct gacagcgccc cgcagcagaa    480
tggacagccg ctccgaccgc tggtcccaga tgccagcaag cagcggctga tggagaacac    540
agaggactgg cggccgcggc cggggacagg ccagtcgcgt tccttccgca tccttgccca    600
cctcacaggc accgagttca tgcaagaccc ggatgaggag cacctgaaga aatcaagcca    660
ggtgcccagg acagaagccc cagccccagc ctcatctaca ccccaggagc cctggcctgg    720
ccctaccgcc cccagcccta ccagccgccc gccctgggct gtggaccctg cgtttgccga    780
gcgctatgcc ccggacaaaa cgagcacagt gctgacccgg cacagccagc cggccacgcc    840
cacgccgctg cagagccgca cctccattgt gcaggcagct gccggagggg tgccaggagg    900
gggcagcaac aacggcaaga ctcccgtgtg tcaccagtgc cacaaggtca tccggggccg    960
ctacctggtg gcgctgggcc acgcgtacca cccggaggag tttgtgtgta gccagtgtgg   1020
gaaggtcctg gaagagggtg gcttctttga ggagaagggc gccatcttct gcccaccatg   1080
ctatgacgtg cgctatgcac ccagctgtgc caagtgcaag aagaagatta caggcgagat   1140
catgcacgcc ctgaagatga cctggcacgt gcactgcttt acctgtgctg cctgcaagac   1200
gcccatccgg aacagggcct tctacatgga ggagggcgtg ccctattgcg agcgagacta   1260
tgagaagatg tttggcacga aatgccatgg ctgtgacttc aagatcgacg ctggggaccg   1320
cttcctggag gccctgggct tcagctggca tgacacctgc ttcgtctgtg cgatatgtca   1380
gatcaacctg gaaggaaaga ccttctactc caagaaggac aggcctctct gcaagagcca   1440
tgccttctct catgtgtgag cccttctgc ccacagctgc cgcggtggcc cctagcctga   1500
ggggcctgga gtcgtggccc tgcatttctg ggtagggctg gcaatggttg ccttaaccct   1560
ggctcctggc ccgagcctgg ggctccctgg gccctgcccc acccacctta tcctcccacc   1620
ccactccctc caccaccaca gcacaccggt gctggccaca ccagcccct ttcacctcca   1680
gtgccacaat aaacctgtac ccagctgtg                                      1709
```

<210> SEQ ID NO 71
<211> LENGTH: 1607
<212> TYPE: DNA
<213> ORGANISM: Homo sapiens

<400> SEQUENCE: 71

```
agaacactgg cggccgatcc caacgaggct ccctggagcc cgacgcagag cagcgccctg     60
gccgggccaa gcaggagccg gcatcatgga ttccttcaaa gtagtgctgg aggggccagc    120
accttggggc ttccggctgc aagggggcaa ggacttcaat gtgcccctct ccatttcccg    180
gctcactcct gggggcaaag cggcgcaggc cggagtggcc gtgggtgact gggtgctgag    240
catcgatggc gagaatgcgg gtagcctcac acacatcgaa gctcagaaca agatccgggc    300
ctgcggggag cgcctcagcc tgggcctcag cagggcccag ccggttcaga gcaaaccgca    360
```

```
gaaggtgcag accccctgaca aacagccgct ccgaccgctg gtcccagatg ccagcaagca    420

gcggctgatg gagaacacag aggactggcg gccgcggccg gggacaggcc agtcgcgttc    480

cttccgcatc cttgcccacc tcacaggcac cgagttcatg caagacccgg atgaggagca    540

cctgaagaaa tcaagccagg tgcccaggac agaagcccca gccccagcct catctacacc    600

ccaggagccc tggcctggcc ctaccgcccc cagccctacc agccgcccgc cctgggctgt    660

ggaccctgcg tttgccgagc gctatgcccc ggacaaaacg agcacagtgc tgacccggca    720

cagccagccg gccacgccca cgccgctgca gagccgcacc tccattgtgc aggcagctgc    780

cggaggggtg ccaggagggg gcagcaacaa cggcaagact cccgtgtgtc accagtgcca    840

caaggtcatc cggggccgct acctggtggc gctgggccac gcgtaccacc cggaggagtt    900

tgtgtgtagc cagtgtggga aggtcctgga agagggtggc ttctttgagg agaagggcgc    960

catcttctgc ccaccatgct atgacgtgcg ctatgcaccc agctgtgcca agtgcaagaa   1020

gaagattaca ggcgagatca tgcacgccct gaagatgacc tggcacgtgc actgctttac   1080

ctgtgctgcc tgcaagacgc ccatccggaa cagggccttc tacatggagg agggcgtgcc   1140

ctattgcgag cgagactatg agaagatgtt tggcacgaaa tgccatggct gtgacttcaa   1200

gatcgacgct ggggaccgct tcctggaggc cctgggcttc agctggcatg acacctgctt   1260

cgtctgtgcg atatgtcaga tcaacctgga aggaaagacc ttctactcca agaaggacag   1320

gcctctctgc aagagccatg ccttctctca tgtgtgagcc ccttctgccc acagctgccg   1380

cggtggcccc tagcctgagg ggcctggagt cgtggccctg catttctggg tagggctggc   1440

aatggttgcc ttaaccctgg ctcctggccc gagcctgggg ctccctgggc cctgccccac   1500

ccaccttatc ctcccacccc actccctcca ccaccacagc acaccggtgc tggccacacc   1560

agccccccttt cacctccagt gccacaataa acctgtaccc agctgtg                1607
```

<210> SEQ ID NO 72
<211> LENGTH: 1005
<212> TYPE: DNA
<213> ORGANISM: Homo sapiens

<400> SEQUENCE: 72

```
agaacactgg cggccgatcc caacgaggct ccctggagcc cgacgcagag cagcgccctg     60

gccgggccaa gcaggagccg gcatcatgga ttccttcaaa gtagtgctgg aggggccagc    120

accttggggc ttccggctgc aagggggcaa ggacttcaat gtgcccctct ccatttcccg    180

gctcactcct gggggcaaag cggcgcaggc cggagtggcc gtgggtgact gggtgctgag    240

catcgatggc gagaatgcgg gtagcctcac acacatcgaa gctcagaaca agatccgggc    300

ctgcggggag cgcctcagcc tgggcctcag cagggcccag ccggttcaga gcaaaccgca    360

gaaggcctcc gcccccgccg cggaccctcc gcggtacacc tttgcaccca gcgtctccct    420

caacaagacg gcccggccct ttggggcgcc cccgcccgct gacagcgccc cgcagcagaa    480

tggacagccg ctccgaccgc tggtcccaga tgccagcaag cagcggctga tggagaacac    540

agaggactgg cggccgcggc cggggacagg ccagtcgcgt tccttccgca tccttgccca    600

cctcacaggc accgagttca tgcaagaccc ggatgaggag cacctgaaga aatcaaggga    660

aaagtatgtc ctggagctgc agagcccacg ctacacccgc ctccgggact ggcaccacca    720

gcgctctgcc cacgtgctca acgtgcagtc gtagcccggc cctctccagc cggctgccct    780

ctctgcctcc ctctttctgt tcctcctgcc cagggcaccc ccttagtgcc tccagcttct    840
```

```
gcctacctca cccccccttt cgtgcccctg gcctgagcct cctgctggcc tggccctggc    900

cgcccacctg ggttcatctg acactgcctt ccctctttgc cctgtggtac tgctgtctgc    960

caggtctgtg ctgccttggg catggaataa acattctcag ccctg                   1005
```

<210> SEQ ID NO 73
<211> LENGTH: 5455
<212> TYPE: DNA
<213> ORGANISM: Homo sapiens

<400> SEQUENCE: 73

```
atttgggcgg agccctttct gagtcagtct gtcggccgac ttcctgcttg gggcctgggc     60

agccacactg cacgcaggct gggccgactg aggggctcag aggccaggct ctgaggccca    120

cgcagggcct agggtgggaa gatggcaggt gggggcggcg acctgagcac caggaggctg    180

aatgaatgta tttcaccagt agcaaatgag atgaaccatc ttcctgcaca cagccacgat    240

ttgcaaagga tgttcacgga agaccagggt gtagatgaca ggctgctcta tgacattgta    300

ttcaagcact tcaaaagaaa taaggtggag atttcaaatg caataaaaaa gacatttcca    360

ttcctcgagg gcctccgtga tcgtgatctc atcacaaata aaatgtttga agattctcaa    420

gattcttgta gaaacctggt ccctgtacag agagtggtgt acaatgttct tagtgaactg    480

gagaagacat ttaacctgcc agttctggaa gcactgttca gcgatgtcaa catgcaggaa    540

taccccgatt taattcacat ttataaaggc tttgaaaatg taatccatga caaattgcct    600

ctccaagaaa gtgaagaaga agagagggag gagaggtctg gcctccaact aagtcttgaa    660

caaggaactg gtgaaaactc ttttcgaagc ctgacttggc caccttcggg ttccccatct    720

catgctggta caaccccacc tgaaaatgga ctctcagagc acccctgtga aacagaacag    780

ataaatgcaa agagaaaaga tacaaccagt gacaaagatg attcgctagg aagccaacaa    840

acaaatgaac aatgtgctca aaaggctgag ccaacagagt cctgcgaaca aattgctgtc    900

caagtgaata atggggatgc tggaagggag atgccctgcc cgttgccctg tgatgaagaa    960

agcccagagg cagagctaca caaccatgga atccaaatta attcctgttc tgtgcgactg   1020

gtggatataa aaaaggaaaa gccattttct aattcaaaag ttgagtgcca agcccaagca   1080

agaactcatc ataaccaggc atctgacata atagtcatca gcagtgagga ctctgaagga   1140

tccactgacg ttgatgagcc cttagaagtc ttcatctcag caccgagaag tgagcctgtg   1200

atcaataatg acaacccttt agaatcaaat gatgaaaagg agggccaaga agccacttgc   1260

tcacgacccc agattgtacc agagcccatg gatttcagaa aattatctac attcagagaa   1320

agttttaaga aaagagtgat aggacaagac cacgactttt cagaatccag tgaggaggag   1380

gcgcccgcag aagcctcgag cggggcactg agaagcaagc atggtgagaa ggctcctatg   1440

acttctagaa gtacatctac ttggagaata cccagcagga agagacgttt cagcagtagt   1500

gacttttcag acctgagtaa tggagaagag cttcaggaaa cctgcagctc atccctaaga   1560

agagggtcag gatcacagcc acaagaacct gaaaataaga agtgctcctg tgtcatgtgt   1620

tttccaaaag gtgtgccaag aagccaagaa gcaaggactg aaagtagtca agcatctgac   1680

atgatggata ccatggatgt tgaaaacaat tctactttgg aaaaacacag tgggaaaaga   1740

agaaaaaaga gaaggcatag atctaaagta aatggtctcc aaagagggag aaagaaagac   1800

agacctagaa aacatttaac tctgaataac aaagtccaaa agaaaagatg gcaacaaaga   1860

ggaagaaaag ccaacactag acctttgaaa agaagaagaa aaagaggtcc aagaattccc   1920

aaagatgaaa atattaattt taaacaatct gaacttcctg tgacctgtgg tgaggtgaag   1980
```

```
ggcactctat ataaggagcg attcaaacaa ggaacctcaa agaagtgtat acagagtgag   2040
gataaaaagt ggttcactcc cagggaattt gaaattgaag gagaccgcgg agcatccaag   2100
aactggaagc taagtatacg ctgcggtgga tataccctga aagtcctgat ggagaacaaa   2160
tttctgccag aaccaccaag cacaagaaaa aagagaatac tggaatctca caacaatacc   2220
ttagttgacc cttgtccgga aaactcaaat atatgtgagg tgtgcaacaa atggggacgg   2280
ctgttctgct gcgacacttg tccaagatcc tttcatgagc actgccacat cccatccgtg   2340
gaagctaaca agaacccgtg gagttgcatc ttctgcagga taaagactat tcaggaaaga   2400
tgcccagaaa gccaatcagg tcatcaggaa tctgaagtcc tgatgaggca gatgctgcct   2460
gaggagcagt tgaaatgtga attcctcctc ttgaaggtct actgtgattc gaaaagctgc   2520
tttttcgcct cagaaccgta ttataacaga gaggggtctc agggcccaca gaagcccatg   2580
tggttaaaca aagtcaagac aagtttgaat gagcagatgt acacccgagt agaagggttt   2640
gtgcaggaca tgcgtctcat ctttcataac cacaaggaat tttacaggga agataaattc   2700
accagactgg gaattcaagt acaggacatc tttgagaaga atttcagaaa catttttgca   2760
attcaggaaa caagcaagaa cattataatg tttatttagc cattcttatc tcctcccttc   2820
agatcctctg gcagctagct acgcaatgtg cctgtggtcc cactaatctg tgactgctcc   2880
tgtggaaact ccacatcaca attctccaaa atttatcatt gccattttaa aaccgtcttt   2940
tcagctttca ataaaattca acaccccttc atgttaaaaa ttctcaataa gctaggtatt   3000
gaggaacata tcccaaaata ataagagcca tttatgacaa acccacagac aacattatat   3060
ggaatgcgca aaagaagcat tccccttgaa aacaagcaca agacaaggat tccctctctc   3120
accactccta ttcaacaaag tattggaagt cctggtcaga gcagtcagga agcagaaaaa   3180
aataaagggt atctaaatag gcaaagagga agtcaaacta tccctgtttg cacacaacat   3240
tgattctata tctagaaaac cccctagtct cagcccagaa gctccttctg ctgataaaca   3300
atttcagaga tgtttcagaa tacaaaatta gtatatgaaa attactagta ttcctataca   3360
ccagcaatag ccaagccaag agccaaatca ggaaggcaat ctcattcaca attgccacta   3420
aaagaataaa atacctagga atacagctaa tcagggaggt gagagagttc tacaatgaga   3480
attacgaaac actgctcaaa gagattggag atgacacaaa caaatggaaa aacatcccat   3540
gctcctgtgt agaaacagtc aatatcatta aaatgaccat actgcccaaa gcagtttaca   3600
ggttcaatgt tattcctatc aaaccaccaa tgacattctt cacagaacta gataaaacta   3660
ttttaaaatt catacagaac caaaaaagag cccaaatagc caaggcaatc ctaagcaaaa   3720
agaacaaagc tgaaggcatc acgttacccc acttcaaact atattacagg gcttcagtaa   3780
ccaaaacagc atggtactgg taccaaaaaa aaagccacat agaccaatgg aacagaacga   3840
agagcacaga ataagaccac actcctatga ccatctgatc gtcgataaaa acaagcaatg   3900
ggaaaaagac tccctatttt ataaatggtg ctgggataac tgggatagaa gattgaagct   3960
agacctcttc cttacaccat atacaaaaat caactcaaga tcaattaaag acttaatgta   4020
aaatcaaaaa ctatgaagac tctggaagac aacctaggca ataccatcct ggacatagga   4080
acaggcaaag atttcatgat aaagacaaaa gcaatagcaa caaaagcaaa atttgacaaa   4140
tgggatctaa ttaaacttaa gagattctgc acagcaaaag aaacaatcaa cagagtaaac   4200
agacaaccta caaaatggga gaaaatattt gcacactatg catctgacaa aggtctaata   4260
gccagcttct atagggaact taaacaaatt tacaagacaa aaagaaataa ccccattaaa   4320
```

```
aagtgggcaa aggacatgaa agacactttt ttttttaag atggagtttc actcttgttg   4380
cccaggccag agtgcaatgg cgtgatcttg gctcaccaca acctctgcct cccgggttca   4440
agcaattctc ctgcctcagc ctcccaggtg gctgggatta caggcatgca ccacctgact   4500
gattttgtat tttagtagag acggggtttc tccacattgg tcaggctggt cttgaactcc   4560
cgacctcagg tgatccaccc acctcggcct cccaaagtgc tgggattaca ggcatcagcc   4620
accatgcccg gatgaaaaga cactttccaa aagaagatac acatgcggcc aacaagcatg   4680
ttttaaaagc tcaatatcac tgatcgttag agacatgcaa attaaaacta caatgagaca   4740
ccatctcaca ccagtcaaaa tgcctctttc taaaaagtca aaaaataaca gctagtaagg   4800
ttgtggagaa aagggaacat ttatacacta ttgatgggag tgtaaattag ttcaaccact   4860
gtggaaagca gtgtggcaac tcctcatagt gctaaaagca gaactgccat tccacccagc   4920
aatcccatta ctgggtacat acccagagga atataaatca ttctaccata aagacacatg   4980
catgcaaatg tccactgcag cactattcac aatagcaaag atacagaatc aacctaagtg   5040
cccatcagta acagattgga taaagaaaat atggtacaca tacaccatgg aatagtatgc   5100
agccataaga aacaatgaga tcatgtctca ggaacatgga tagagctgga ggctattatc   5160
cttagcaaac taattcagga acagaaaacc aaataccaca ggttctcagt tgtgagtggg   5220
agctaaatga tgagaactca tgaacacaat gaagggaaca gacactaggg tctacttgag   5280
ggtggaggat gggaagaggg agaggagcag aaaaagtacc tattggtgat gaagtactct   5340
gtacaacaaa cccgtgacaa gagtttccct atataacaaa ccttcacata taccccctgaa   5400
cctaaaagtt tttttaattg taaataaatg gatcattaaa aaaaatttta ataat        5455
```

<210> SEQ ID NO 74
<211> LENGTH: 3688
<212> TYPE: DNA
<213> ORGANISM: Homo sapiens

<400> SEQUENCE: 74

```
atttgggcgg agccctttct gagtcagtct gtcggccgac ttcctgcttg ggcctgggc      60
agccacactg cacgcaggct gggccgactg aggggctcag aggccaggct ctgaggccca    120
cgcagggcct agggtgggaa gatggcaggt gggggcggcg acctgagcac caggaggctg    180
aatgaatgta tttcaccagt agcaaatgag atgaaccatc ttcctgcaca cagccacgat    240
ttgcaaagga tgttcacgga agaccagggt gtagatgaca ggctgctcta tgacattgta    300
ttcaagcact tcaaaagaaa taaggtggag atttcaaatg caataaaaaa gacatttcca    360
ttcctcgagg gcctccgtga tcgtgatctc atcacaaata aaatgtttga agattctcaa    420
gattcttgta gaaacctggt ccctgtacag agagtggtgt acaatgttct tagtgaactg    480
gagaagacat ttaacctgcc agttctggaa gcactgttca gcgatgtcaa catgcaggaa    540
taccccgatt taattcacat ttataaaggc tttgaaaatg taatccatga caaattgcct    600
ctccaagaaa gtgaagaaga agagagggag gagaggtctg gcctccaact aagtcttgaa    660
caaggaactg gtgaaaactc ttttcgaagc ctgacttggc caccttcggg ttccccatct    720
catgctggta caaccccacc tgaaaatgga ctctcagagc acccctgtga aacagaacag    780
ataaatgcaa agagaaaaga tacaaccagt gacaaagatg attcgctagg aagccaacaa    840
acaaatgaac aatgtgctca aaaggctgag ccaacagagt cctgcgaaca aattgctgtc    900
caagtgaata atggggatgc tggaagggag atgccctgcc cgttgccctg tgatgaagaa    960
agcccagagg cagagctaca caaccatgga atccaaatta attcctgttc tgtgcgactg   1020
```

```
gtggatataa aaaaggaaaa gccattttct aattcaaaag ttgagtgcca agcccaagca   1080
agaactcatc ataaccaggc atctgacata atagtcatca gcagtgagga ctctgaagga   1140
tccactgacg ttgatgagcc cttagaagtc ttcatctcag caccgagaag tgagcctgtg   1200
atcaataatg acaacccttt agaatcaaat gatgaaaagg agggccaaga agccacttgc   1260
tcacgacccc agattgtacc agagcccatg gatttcagaa aattatctac attcagagaa   1320
agttttaaga aaagagtgat aggacaagac cacgactttt cagaatccag tgaggaggag   1380
gcgcccgcag aagcctcgag cggggcactg agaagcaagc atggtgagaa ggctcctatg   1440
acttctagaa gtacatctac ttggagaata cccagcagga agagacgttt cagcagtagt   1500
gacttttcag acctgagtaa tggagaagag cttcaggaaa cctgcagctc atccctaaga   1560
agagggtcag gatcacagcc acaagaacct gaaaataaga agtgctcctg tgtcatgtgt   1620
tttccaaaag gtgtgccaag aagccaagaa gcaaggactg aaagtagtca agcatctgac   1680
atgatggata ccatggatgt tgaaaacaat tctactttgg aaaaacacag tgggaaaaga   1740
agaaaaaaga gaaggcatag atctaaagta aatggtctcc aaagagggag aaagaaagac   1800
agacctagaa aacatttaac tctgaataac aaagtccaaa agaaaagatg gcaacaaaga   1860
ggaagaaaag ccaacactag acctttgaaa agaagaagaa aaagaggtcc aagaattccc   1920
aaagatgaaa atattaattt taaacaatct gaacttcctg tgacctgtgg tgaggtgaag   1980
ggcactctat ataaggagcg attcaaacaa ggaacctcaa agaagtgtat acagagtgag   2040
gataaaaagt ggttcactcc cagggaattt gaaattgaag gagaccgcgg agcatccaag   2100
aactggaagc taagtatacg ctgcggtgga tataccctga aagtcctgat ggagaacaaa   2160
tttctgccag aaccaccaag cacaagaaaa aagagaatac tggaatctca caacaatacc   2220
ttagttgacc cttgtgagga gcataagaag aagaacccag atgcttcagt caagttctca   2280
gagtttttaa agaagtgctc agagacatgg aagaccattt ttgctaaaga gaaaggaaaa   2340
tttgaagata tggcaaaggc ggacaaggcc cattatgaaa gagaaatgaa aacctatatc   2400
cctcctaaag gggagaaaaa aaagaagttc aaggatccca atgcacccaa gaggcctcct   2460
ttggcctttt tcctgttctg ctctgagtat cgcccaaaaa tcaaaggaga acatcctggc   2520
ctgtccattg atgatgttgt gaagaaactg gcagggatgt ggaataacac cgctgcagct   2580
gacaagcagt tttatgaaaa gaaggctgca aagctgaagg aaaaatacaa aaaggatatt   2640
gctgcatatc gagctaaagg aaagcctaat tcagcaaaaa agagagttgt caaggctgaa   2700
aaaagcaaga aaaagaagga agaggaagaa gatgaagagg atgaacaaga ggaggaaaat   2760
gaagaagatg atgataaata agttgcttct agtgcagttt ttttcttgtc tataaagcat   2820
ttaagctgcc tgtacacaac tcactccttt taaagaaaaa aacttcaacg taagactgtg   2880
taagatttgt ttttaaaccg tacactgtgt ttttttgtat agttaaccac taccgaatgt   2940
gtcttcagat agccctgtcc tggtggtatt tagccactaa cctttgcctg gtacagtatg   3000
ggggttgtaa attggcatgg aaatttaaag caggttcttg ttagtgcaca gcacaaatta   3060
gttgtatatg aggatggtag ttttttcacc ttcagttgtc tctgatgtag cttatacaaa   3120
acatttgttg ttctgttaac tgaatgccac tctgtaattg caaaaaaaaa aaacagttgc   3180
agctgttttg ttgacattct gaatgcttct aagtaaatac aatttttaaa aaaccgtatg   3240
agggaactgt gtagacaagg taccaggtca gtcttcttcc atgtctatta gctccacaaa   3300
gccaatctca atccctcaaa acaatcttgt catacttgaa aatatgacac tctagtcaaa   3360
```

```
gccttggtaa aataatcagt gtttccaatc tgtcctgtta caaaagaaac agattattat   3420

tgaacttatg caaataacca ttgtcataag aatgtttatg aatagtttcc aaattatggc   3480

aaattcatgt agagagagaa aagtaactgt tttggttttg ctcacaaaag tctactttac   3540

ctaagggctg tcagatataa gtaacttaaa agaaagagaa gttttcttga cttttgaaaa   3600

caaaatatga aaagaatcgg caatgtttca aacaaaaagt cataaaagtc actttattcc   3660

tccatcaaaa aaaaaaaaaa aaaaaaaa                                      3688
```

```
<210> SEQ ID NO 75
<211> LENGTH: 2313
<212> TYPE: DNA
<213> ORGANISM: Homo sapiens

<400> SEQUENCE: 75

atttgggcgg agccctttct gagtcagtct gtcggccgac ttcctgcttg gggcctgggc     60

agccacactg cacgcaggct gggccgactg aggggctcag aggccaggct ctgaggccca    120

cgcagggcct agggtgggaa gatggcaggt gggggcggcg acctgagcac caggaggctg    180

aatgaatgta tttcaccagt agcaaatgag atgaaccatc ttcctgcaca cagccacgat    240

ttgcaaagga tgttcacgga agaccagggt gtagatgaca ggctgctcta tgacattgta    300

ttcaagcact tcaaaagaaa taaggtggag atttcaaatg caataaaaaa gacatttcca    360

ttcctcgagg gcctccgtga tcgtgatctc atcacaaata aaatgtttga agattctcaa    420

gattcttgta gaaacctggt ccctgtacag agagtggtgt acaatgttct tagtgaactg    480

gagaagacat ttaacctgcc agttctggaa gcactgttca gcgatgtcaa catgcaggaa    540

taccccgatt taattcacat ttataaaggc tttgaaaatg taatccatga caaattgcct    600

ctccaagaaa gtgaagaaga agagagggag gagaggtctg gcctccaact aagtcttgaa    660

caaggaactg gtgaaaactc ttttcgaagc ctgacttggc caccttcggg ttccccatct    720

catgctggta caaccccacc tgaaaatgga ctctcagagc acccctgtga aacagaacag    780

ataaatgcaa agagaaaaga tacaaccagt gacaaagatg attcgctagg aagccaacaa    840

acaaatgaac aatgtgctca aaaggctgag ccaacagagt cctgcgaaca aattgctgtc    900

caagtgaata atggggatgc tggaagggag atgccctgcc cgttgccctg tgatgaagaa    960

agcccagagg cagagctaca caaccatgga atccaaatta attcctgttc tgtgcgactg   1020

gtggatataa aaaaggaaaa gccattttct aattcaaaag ttgagtgcca agcccaagca   1080

agaactcatc ataaccaggc atctgacata atagtcatca gcagtgagga ctctgaagga   1140

tccactgacg ttgatgagcc cttagaagtc ttcatctcag caccgagaag tgagcctgtg   1200

atcaataatg acaacccttt agaatcaaat gatgaaaagg agggccaaga agccacttgc   1260

tcacgacccc agattgtacc agagcccatg gatttcagaa aattatctac attcagagaa   1320

agttttaaga aaagagtgat aggacaagac cacgactttt cagaatccag tgaggaggag   1380

gcgcccgcag aagcctcgag cggggcactg agaagcaagc atggtgagaa ggctcctatg   1440

acttctagaa gtacatctac ttggagaata cccagcagga agagacgttt cagcagtagt   1500

gacttttcag acctgagtaa tggagaagag cttcaggaaa cctgcagctc atccctaaga   1560

agagggtcag gatcacagcc acaagaacct gaaaataaga agtgctcctg tgtcatgtgt   1620

tttccaaaag gtgtgccaag aagccaagaa gcaaggactg aaagtagtca agcatctgac   1680

atgatggata ccatggatgt tgaaaacaat tctactttgg aaaaacacag tgggaaaaga   1740

agaaaaaaga gaaggcatag atctaaagta aatggtctcc aaagagggag aaagaaagac   1800
```

```
agacctagaa aacatttaac tctgaataac aaagtccaaa agaaaagatg gcaacaaaga   1860

ggaagaaaag ccaacactag acctttgaaa agaagaagaa aaagaggtcc aagaattccc   1920

aaagatgaaa atattaattt taaacaatct gaacttcctg tgacctgtgg tgaggtgaag   1980

ggcactctat ataaggagcg attcaaacaa ggaacctcaa agaagtgtat acagagtgag   2040

gataaaaagt ggttcactcc cagggaattt gaaattgaag gagaccgcgg agcatccaag   2100

aactggaagc taagtatacg ctgcggtgga tataccctga aagtcctgat ggagaacaaa   2160

tttctgccag aaccaccaag cacaagaaaa aaggtgatga tcaagtgatc ttctgccaat   2220

gtctcgtcta ttatgttgtt gattttctat ctctgtggac ttacagtctt taaattgacc   2280

catcatcata aaatttgatt ttataataaa aaa                                2313
```

```
<210> SEQ ID NO 76
<211> LENGTH: 2015
<212> TYPE: DNA
<213> ORGANISM: Homo sapiens

<400> SEQUENCE: 76

atttgggcgg agccctttct gagtcagtct gtcggccgac ttcctgcttg gggcctgggc     60

agccacactg cacgcaggct gggccgactg aggggctcag aggccaggct ctgaggccca    120

cgcagggcct agggtgggaa gatggcaggt gggggcggcg acctgagcac caggaggctg    180

aatgaatgta tttcaccagt agcaaatgag atgaaccatc ttcctgcaca cagccacgat    240

ttgcaaagga tgttcacgga agaccagggt gtagatgaca ggctgctcta tgacattgta    300

ttcaagcact tcaaaagaaa taaggtggag atttcaaatg caataaaaaa gacatttcca    360

ttcctcgagg gcctccgtga tcgtgatctc atcacaaata aaatgtttga agattctcaa    420

gattcttgta gaaacctggt ccctgtacag agagtggtgt acaatgttct tagtgaactg    480

gagaagacat ttaacctgcc agttctggaa gcactgttca gcgatgtcaa catgcaggaa    540

taccccgatt taattcacat ttataaaggc tttgaaaatg taatccatga caaattgcct    600

ctccaagaaa gtgaagaaga agagagggag gagaggtctg gcctccaact aagtcttgaa    660

caaggaactg gtgaaaactc ttttcgaagc ctgacttggc caccttcggg ttccccatct    720

catgctggta caaccccacc tgaaaatgga ctctcagagc acccctgtga aacagaacag    780

ataaatgcaa agagaaaaga tacaaccagt gacaaagatg attcgctagg aagccaacaa    840

acaaatgaac aatgtgctca aaaggctgag ccaacagagt cctgcgaaca aattgctgtc    900

caagtgaata atggggatgc tggaagggag atgccctgcc cgttgccctg tgatgaagaa    960

agcccagagg cagagctaca caaccatgga atccaaatta attcctgttc tgtgcgactg   1020

gtggatataa aaaaggaaaa gccattttct aattcaaaag ttgagtgcca agcccaagca   1080

agaactcatc ataaccaggc atctgacata atagtcatca gcagtgagga ctctgaagga   1140

tccactgacg ttgatgagcc cttagaagtc ttcatctcag caccgagaag tgagcctgtg   1200

atcaataatg acaacccttt agaatcaaat gatgaaaagg agggccaaga agccacttgc   1260

tcacgacccc agattgtacc agagcccatg gatttcagaa aattatctac attcagagaa   1320

agttttaaga aaagagtgat aggacaagac cacgactttt cagaatccag tgaggaggag   1380

gcgcccgcag aagcctcgag cggggcactg agaagcaagc atggtgagaa ggctcctatg   1440

acttctagaa gtacatctac ttggagaata cccagcagga agagacgttt cagcagtagt   1500

gacttttcag acctgagtaa tggagaagag cttcaggaaa cctgcagctc atccctaaga   1560
```

```
agagggtcag gtaaagaaga ttaggatgcc aagacttggc ctgcagaatg tcaggaatgt   1620

gaattaaaag ctgctgtttc cagacgcttt ttattctgag caccttcact accttgtatc   1680

cagttcatct gggaactcct ttttgcattt tagaaaatgg aaagaggcag gaaattatga   1740

taaactcatg tttaacagaa agagtttcac tgactaaatg tatgtaatta tattttgttg   1800

ttgtagaaga aataaatagc aaatttgtgg tattcttttt tttaaacctg ctctcattcc   1860

tattaacact aagatcttag atttttatag tgataaatgg gttgacatca ttgtcatttg   1920

taattgtaaa gcctcaaaag acaactgttc ctactatgta attatagaca gaaataaaaa   1980

cttcagatca aacactctca aacgttaaaa aaaaa                              2015
```

<210> SEQ ID NO 77
<211> LENGTH: 1931
<212> TYPE: DNA
<213> ORGANISM: Homo sapiens

<400> SEQUENCE: 77

```
atttgggcgg agccctttct gagtcagtct gtcggccgac ttcctgcttg gggcctgggc     60

agccacactg cacgcaggct gggccgactg aggggctcag aggccaggct ctgaggccca    120

cgcagggcct agggtgggaa gatggcaggt gggggcggcg acctgagcac caggatgttc    180

acggaagacc agggtgtaga tgacaggctg ctctatgaca ttgtattcaa gcacttcaaa    240

agaaataagg tggagatttc aaatgcaata aaaaagacat ttccattcct cgagggcctc    300

cgtgatcgtg atctcatcac aaataaaatg tttgaagatt ctcaagattc ttgtagaaac    360

ctggtccctg tacagagagt ggtgtacaat gttcttagtg aactggagaa gacatttaac    420

ctgccagttc tggaagcact gttcagcgat gtcaacatgc aggaataccc cgatttaatt    480

cacatttata aaggctttga aaatgtaatc catgacaaat tgcctctcca agaaagtgaa    540

gaagaagaga gggaggagag gtctggcctc caactaagtc ttgaacaagg aactggtgaa    600

aactcttttc gaagcctgac ttggccacct tcgggttccc catctcatgc tggtacaacc    660

ccacctgaaa atggactctc agagcacccc tgtgaaacag aacagataaa tgcaaagaga    720

aaagatacaa ccagtgacaa agatgattcg ctaggaagcc aacaaacaaa tgaacaatgt    780

gctcaaaagg ctgagccaac agagtcctgc gaacaaattg ctgtccaagt gaataatggg    840

gatgctggaa gggagatgcc ctgcccgttg ccctgtgatg aagaaagccc agaggcagag    900

ctacacaacc atggaatcca aattaattcc tgttctgtgc gactggtgga tataaaaaag    960

gaaaagccat tttctaattc aaaagttgag tgccaagccc aagcaagaac tcatcataac   1020

caggcatctg acataatagt catcagcagt gaggactctg aaggatccac tgacgttgat   1080

gagcccttag aagtcttcat ctcagcaccg agaagtgagc ctgtgatcaa taatgacaac   1140

cctttagaat caaatgatga aaaggagggc caagaagcca cttgctcacg accccagatt   1200

gtaccagagc ccatggattt cagaaaatta tctacattca gagaaagttt taagaaaaga   1260

gtgataggac aagaccacga cttttcagaa tccagtgagg aggaggcgcc cgcagaagcc   1320

tcgagcgggg cactgagaag caagcatgct cctatgactt ctagaagtac atctacttgg   1380

agaataccca gcaggaagag acgtttcagc agtagtgact tttcagacct gagtaatgga   1440

gaagagcttc aggaaacctg cagctcatcc ctaagaagag ggtcaggtaa agaagattag   1500

gatgccaaga cttggcctgc agaatgtcag gaatgtgaat taaaagctgc tgtttccaga   1560

cgctttttat tctgagcacc ttcactacct tgtatccagt tcatctggga actccttttt   1620

gcattttaga aaatggaaag aggcaggaaa ttatgataaa ctcatgttta acagaaagag   1680
```

```
tttcactgac taaatgtatg taattatatt ttgttgttgt agaagaaata aatagcaaat   1740

ttgtggtatt cttttttta aacctgctct cattcctatt aacactaaga tcttagattt   1800

ttatagtgat aaatgggttg acatcattgt catttgtaat tgtaaagcct caaaagacaa   1860

ctgttcctac tatgtaatta tagacagaaa taaaaacttc agatcaaaca ctctcaaacg   1920

ttaaaaaaaa a                                                         1931


<210> SEQ ID NO 78
<211> LENGTH: 2050
<212> TYPE: DNA
<213> ORGANISM: Homo sapiens

<400> SEQUENCE: 78

agacgctgtg gtctcacctg tcctggcaag gggcctctgc cggctgttcc catgactggc     60

tcagggtctg agttcttatt ccatcaacct tgatcaaaag aaggaaaggg aagaaaaagg    120

cccagggagg ctgaatgaat gtatttcacc agtagcaaat gagatgaacc atcttcctgc    180

acacagccac gatttgcaaa ggtttttgga gaggaataaa tttaatgaaa gatgtacatg    240

acttctaaaa actataagca gtgctgggta aaattaaaca catgatgttc acggaagacc    300

agggtgtaga tgacaggctg ctctatgaca ttgtattcaa gcacttcaaa agaaataagg    360

tggagatttc aaatgcaata aaaaagacat ttccattcct cgagggcctc cgtgatcgtg    420

atctcatcac aaataaaatg tttgaagatt ctcaagattc ttgtagaaac ctggtccctg    480

tacagagagt ggtgtacaat gttcttagtg aactggagaa gacatttaac ctgccagttc    540

tggaagcact gttcagcgat gtcaacatgc aggaataccc cgatttaatt cacatttata    600

aaggctttga aaatgtaatc catgacaaat tgcctctcca agaaagtgaa gaagaagaga    660

gggaggagag gtctggcctc caactaagtc ttgaacaagg aactggtgaa aactcttttc    720

gaagcctgac ttggccacct tcgggttccc catctcatgc tggtacaacc ccacctgaaa    780

atggactctc agagcacccc tgtgaaacag aacagataaa tgcaaagaga aaagatacaa    840

ccagtgacaa agatgattcg ctaggaagcc aacaaacaaa tgaacaatgt gctcaaaagg    900

ctgagccaac agagtcctgc gaacaaattg ctgtccaagt gaataatggg gatgctggaa    960

gggagatgcc ctgcccgttg ccctgtgatg aagaaagccc agaggcagag ctacacaacc   1020

atggaatcca aattaattcc tgttctgtgc gactggtgga tataaaaaag gaaaagccat   1080

tttctaattc aaaagttgag tgccaagccc aagcaagaac tcatcataac caggcatctg   1140

acataatagt catcagcagt gaggactctg aaggatccac tgacgttgat gagcccttag   1200

aagtcttcat ctcagcaccg agaagtgagc ctgtgatcaa taatgacaac cctttagaat   1260

caaatgatga aaaggagggc caagaagcca cttgctcacg accccagatt gtaccagagc   1320

ccatggattt cagaaaatta tctacattca gagaaagttt taagaaaaga gtgataggac   1380

aagaccacga cttttcagaa tccagtgagg aggaggcgcc cgcagaagcc tcgagcgggg   1440

cactgagaag caagcatggt gagaaggctc ctatgacttc tagaagtaca tctacttgga   1500

gaatacccag caggaagaga cgtttcagca gtagtgactt ttcagacctg agtaatggag   1560

aagagcttca ggaaacctgc agctcatccc taagaagagg gtcaggtaaa gaagattagg   1620

atgccaagac ttggcctgca gaatgtcagg aatgtgaatt aaaagctgct gtttccagac   1680

gctttttatt ctgagcacct tcactacctt gtatccagtt catctgggaa ctcctttttg   1740

cattttagaa aatggaaaga ggcaggaaat tatgataaac tcatgtttaa cagaaagagt   1800
```

```
ttcactgact aaatgtatgt aattatattt tgttgttgta gaagaaataa atagcaaatt   1860

tgtggtattc tttttttttaa acctgctctc attcctatta acactaagat cttagatttt   1920

tatagtgata aatgggttga catcattgtc atttgtaatt gtaaagcctc aaaagacaac   1980

tgttcctact atgtaattat agacagaaat aaaaacttca gatcaaacac tctcaaacgt   2040

taaaaaaaaa                                                         2050
```

<210> SEQ ID NO 79
<211> LENGTH: 3833
<212> TYPE: DNA
<213> ORGANISM: Homo sapiens

<400> SEQUENCE: 79

```
gcgggctgag cgcggatccg cggcgggcgc aggatacggg ccggggcgcg agccgagcgc     60

agtctgccgg gccgagcggg cggagcgagc cgagtggggc tgagcgcgcc ggcggcggcg    120

ggcggagcgg agcgcggcgc gccggggccg ccgccggggg gatgcggctg cctccccggg    180

ccggggtgta gagagggcgg gtccccggcc tcgggagcac ggcggtggag gggacatagg    240

aggcggccat ggcgaccccc ggcaacctag ggtcctctgt cctggcgagc aagaccaaga    300

ccaagaagaa gcacttcgta gcgcagaaag tgaagctgtt tcgggccagc gacccgctgc    360

tcagcgtcct catgtggggg gtaaaccact cgatcaatga actgagccat gttcaaatcc    420

ctgttatgtt gatgccagat gacttcaaag cctattcaaa aataaaggtg gacaatcacc    480

tttttaacaa agaaaacatg ccgagccatt tcaagtttaa ggaatactgc ccgatggtct    540

tccgtaacct gcgggagagg tttggaattg atgatcaaga tttccagaat tccctgacca    600

ggagcgcacc cctccccaac gactcccagg cccgcagtgg agctcgtttt cacacttcct    660

acgacaaaag atacatcatc aagactatta ccagtgaaga cgtggccgaa atgcacaaca    720

tcctgaagaa ataccaccag tacatagtgg aatgtcatgg gatcaccctt cttccccagt    780

tcttgggcat gtaccggctt aatgttgatg gagttgaaat atatgtgata gttacaagaa    840

atgtattcag ccaccgtttg tctgtgtata ggaaatacga cttaaagggc tctacagtgg    900

ctagagaagc tagtgacaaa gaaaaggcca aagaactgcc aactctgaaa gataatgatt    960

tcattaatga gggccaaaag atttatattg atgacaacaa caagaaggtc ttcctggaaa   1020

aactaaaaaa ggatgttgag tttctggccc agctgaagct catggactac agtctgctgg   1080

tgggaattca tgatgtggag agagccgaac aggaggaagt ggagtgtgag gagaacgatg   1140

gggaggagga gggcgagagc gatggcaccc acccggtggg aacccccccca gatagccccg   1200

ggaatacact gaacagctca ccacccctgg ctcccgggga gttcgatccg aacatcgacg   1260

tctatggaat taagtgccat gaaaactcgc ctaggaagga ggtgtacttc atggcaatta   1320

ttgacatcct tactcattat gatgcaaaaa agaaagctgc ccatgctgca aaaactgtta   1380

aacatggcgc tggcgcggag atctccaccg tgaacccaga acagtattca aagcgctttt   1440

tggactttat tggccacatc ttgacgtaac ctcctgcgca gcctcggaca gacatgaaca   1500

ttggatggac agaggtggct tcggtgtagg aaaaatgaaa accaaactca gtgaagtact   1560

catcttgcag gaagcaaacc tccttgttta catcttcagg ccaagatgac tgatttgggg   1620

gctactcgct ttacagctac ctgattttcc cagcatcgtt ctagctattt ctgactttgt   1680

gtatatgtgt gtgtgtgtgt gttggggggg ggtgagtgtg tgcgcgcgtg tgcattttaa   1740

aagtcataaa ttaattaaaa cagatccact tcggtcagta tgtgtcccaa caaagaccct   1800

ttgattccag ctatggccga atgaatgagt gagtgagtga gtgagtgaat gaacacacgt   1860
```

```
gtgggggagg ggagaaggaa gtgcatgatg tcaggcaccg tgttggcatc acacaacaaa   1920

ctgtggatca gttttttttt tttttttttt tttttggagt tgaaagatgt gagacagtat   1980

tcagaataat gaagataata atgatgatta ttataataat gatgatgatt ccaaggaaaa   2040

aacctacagc gaatgttcca tttctacccc gcacgcagac actctcccta acactgataa   2100

cctgagcccc cagcactgga cggaagaatg ctggcgtctc cgtgtgtact ggttcagggt   2160

tctggcccca gccttgtcag gaccccctgg tgtccagagc cccccacccct cccgcaacaa   2220

gcagctgatg ccccagtgat tctctataca tttttcacct cggccaatat gtccaggaaa   2280

actgcttact tctcttttct tgcctggagc cttcattgtt caccccttacg ttgcaatata   2340

ggaattaatg ctacaaaata aaagtaaagc ttacctgaaa agtgcatagt ttggggcaat   2400

ggtatctaca tctcccactg tgggaaaacc agcaaagcat caaaactctc aattctcctg   2460

ttaccaaatg cagatctgaa ttataagatg tttatgtttg accattgttt caacaatggg   2520

attttgttac gaattatccc tttaactgaa accctcagtt ttactgttta cattattagg   2580

aaaacaggga tatcttttga atctaaaaat ttgatgtaca gcatgtgatt tttgaagttt   2640

acatgtaaag tcacagtata ggtgaaataa cgtttgtcat attttgagac gtatcctgca   2700

gccatgtttt tacgtgagtg ttttagtcaa agtacatggt agacagtctt tcacaataaa   2760

aggaaaagga tttttttttc ctccaaatgt acatttatca acctaatgat tgattttttt   2820

aaaaagagat ttcgccccag tctggtttat gaaagttcat tgccctaaac tgtgctgatt   2880

gtttttaatc aagttataaa tttccaacct agatcatgta tctaccaact ctcctgcatt   2940

ttccaaaagg cattgagctt aaatattagt cttgcttaga gtaggttatc cacttacatg   3000

ctgcgctaaa gccatgcctt tgaaactcct tgtttaaaac atgatatgat ttttgtgggc   3060

agtttcagaa aagaaaacaa acaaacaaaa atcgaccctt taattattac ttgcaactca   3120

acagatctcc ctgccgtact gccttttcca ggaactttac ttcagggctg tccagattgc   3180

agctgtgccc cgtgtatgtg gatctagttc acagagtctt tggaagccag cagtcgtgcc   3240

ctccgtatac tgtccactca ttttatgtag atttggtatc ctcagcagcc agtgttaaca   3300

ccactgtcac gtagtgtaca gattcatctt ttatgtattt aaagtaatcc atactatgat   3360

ttggtttttc cctgcaccat taattctggc atcagatcag tttttgtgtt gtgaagttct   3420

actgtggttt gacccaagac cacaaccatg agaccctgaa gtaaagataa ggtacacata   3480

cattatttga gtaactgttt ccttgggggc caatctgtgt atgcttttag aagtttacag   3540

aatgctttta tttttgtcta taacaaacag tctgtcattt atttctgttg ataaaccatt   3600

tggacagagt gaggacgttt gccctgttat ctcctagtgc taacaataca ctccagtcat   3660

gagccgggct ttacaaataa agcacttttg atgactcaca agatgaatcc ttttttcctc   3720

tgtcccaatt gtgtgtctct gttccaaaca cattttaaat actcggtcct gacagtgtct   3780

ttagctaatc cttgaagaaa tgaaagtgga attgaatctt tttagtttct aga          3833
```

<210> SEQ ID NO 80
<211> LENGTH: 4912
<212> TYPE: DNA
<213> ORGANISM: Homo sapiens

<400> SEQUENCE: 80

```
attggggtct gctctaagct gcagcaagag aaactgtgtg tgaggggaag aggcctgttt     60

cgctgtcggg tctctagttc ttgcacgctc tttaagagtc tgcactggag gaactcctgc    120
```

```
cattaccagc tcccttcttg cagaagggag ggggaaacat acatttattc atgccagtct    180
gttgcatgca ggctttttgg cttcctacct tgcaacaaaa taattgcacc aactccttag    240
tgccgattcc gcccacagag agtcctggag ccacagtctt ttttgctttg cattgtagga    300
gagggactaa gtgctagaga ctatgtcgct ttcctgagct accgagagcg ctcgtgaact    360
ggaatcaact gcttcaggga aaaagaaaaa aaaaaaaaaa agacttgcct gggaggccgc    420
gagaaacttg cattggaagc ttcagcaacc agcattcgag aaactcctct ctactttagc    480
acggtctcca gactcagccg agagacagca aactgcagcg cggtgagaga gcgagagaga    540
gggagagaga gactctccag cctgggaact ataactcctc tgcgagaggc ggagaactcc    600
ttccccaaat cttttgggga cttttctctc tttacccacc tccgcccctg cgaggagttg    660
aggggccagt tcggccgccg cgcgcgtctt cccgttcggc gtgtgcttgg cccggggaac    720
cgggagggcc cggcgatcgc gcggcggccg ccgcgagggt gtgagcgcgc gtgggcgccc    780
gccgagccga ggccatggtg cagcaaacca acaatgccga gaacacggaa gcgctgctgg    840
ccggcgagag ctcggactcg ggcgccggcc tcgagctggg aatcgcctcc tcccccacgc    900
ccggctccac cgcctccacg ggcggcaagg ccgacgaccc gagctggtgc aagaccccga    960
gtgggcacat caagcgaccc atgaacgcct tcatggtgtg gtcgcagatc gagcggcgca   1020
agatcatgga gcagtcgccc gacatgcaca acgccgagat ctccaagcgg ctgggcaaac   1080
gctggaagct gctcaaagac agcgacaaga tccctttcat tcgagaggcg gagcggctgc   1140
gcctcaagca catggctgac taccccgact acaagtaccg gcccaggaag aaggtgaagt   1200
ccggcaacgc caactccagc tcctcggccg ccgcctcctc caagccgggg gagaagggag   1260
acaaggtcgg tggcagtggc gggggcggcc atgggggcgg cggcggcggc gggagcagca   1320
acgcgggggg aggaggcggc ggtgcgagtg gcggcggcgc caactccaaa ccggcgcaga   1380
aaaagagctg cggctccaaa gtggcgggcg gcgcgggcgg tggggttagc aaaccgcacg   1440
ccaagctcat cctggcaggc ggcggcggcg gcgggaaagc agcggctgcc gccgccgcct   1500
ccttcgccgc cgaacaggcg gggggccgcg ccctgctgcc cctgggcgcc gccgccgacc   1560
accactcgct gtacaaggcg cggactccca gcgcctcggc ctccgcctcc tcggcagcct   1620
cggcctccgc agcgctcgcg gccccgggca agcacctggc ggagaagaag gtgaagcgcg   1680
tctacctgtt cggcggcctg ggcacgtcgt cgtcgcccgt gggcggcgtg ggcgcgggag   1740
ccgaccccag cgaccccctg ggcctgtacg aggaggaggg cgcgggctgc tcgcccgacg   1800
cgcccagcct gagcggccgc agcagcgccg cctcgtcccc cgccgccggc cgctcgcccg   1860
ccgaccaccg cggctacgcc agcctgcgcg ccgcctcgcc cgccccgtcc agcgcgccct   1920
cgcacgcgtc ctcctcggcc tcgtcccact cctcctcttc ctcctcctcg ggctcctcgt   1980
cctccgacga cgagttcgaa gacgacctgc tcgacctgaa ccccagctca aactttgaga   2040
gcatgtccct gggcagcttc agttcgtcgt cggcgctcga ccgggacctg gattttaact   2100
tcgagcccgg ctccggctcg cacttcgagt tcccggacta ctgcacgccc gaggtgagcg   2160
agatgatctc gggagactgg ctcgagtcca gcatctccaa cctggttttc acctactgaa   2220
gggcgcgcag gcagggagaa gggccggggg gggtaggaga ggagaaaaaa aaagtgaaaa   2280
aaagaaacga aaaggacaga cgaagagttt aaagagaaaa gggaaaaaag aaagaaaaag   2340
taagcagggc tggcttcgcc cgcgttctcg tcgtcggatc aaggagcgcg gcggcgtttt   2400
ggacccgcgc tcccatcccc caccttcccg ggccggggac ccactctgcc cagccggagg   2460
gacgcggagg aggaagaggg tagacagggg cgacctgtga ttgttgttat tgatgttgtt   2520
```

```
gttgatggca aaaaaaaaaa agcgacttcg agtttgctcc cctttgcttg aagagacccc   2580
ctccccccttc caacgagctt ccggacttgt ctgcaccccc agcaagaagg cgagttagtt   2640
ttctagagac ttgaaggagt ctcccccttc ctgcatcacc accttggttt tgttttattt   2700
tgcttcttgg tcaagaaagg aggggagaac ccagcgcacc cctccccccc tttttttaaa   2760
cgcgtgatga agacagaagg ctccggggtg acgaatttgg ccgatggcag atgttttggg   2820
ggaacgccgg gactgagaga ctccacgcag gcgaattccc gtttggggct ttttttttcct   2880
ccctcttttc cccttgcccc ctctgcagcc ggaggaggag atgttgaggg gaggaggcca   2940
gccagtgtga ccggcgctag gaaatgaccc gagaaccccg ttggaagcgc agcagcggga   3000
gctaggggcg ggggcggagg aggacacgaa ctggaagggg gttcacggtc aaactgaaat   3060
ggatttgcac gttggggagc tggcggcggc ggctgctggg cctccgcctt cttttctacg   3120
tgaaatcagt gaggtgagac ttcccagacc ccggaggcgt ggaggagagg agactgtttg   3180
atgtggtaca ggggcagtca gtggagggcg agtggtttcg gaaaaaaaaa aagaaaaaaa   3240
gaaaaaaaaa gaaaaaaaaa agattttttt cttctcttaa tcggaatcgt gatggtgttg   3300
gattatttca atggtggggt taatatagca tgttatcctg tctatctttt aaagatttct   3360
gtataagact gttgagcagt ttttaaaata gtgtaggata atataaaaag cagatagatg   3420
gcgctatgtt tgattcctac aacgaaatta tcaccagctt tttttcattc ttaactcttt   3480
aaaggattca aacgcaactc aaatctgtgc tggactttaa aaaaacaatt caggaccaaa   3540
tttttctca gtgtgtgtgt ttattcctta taggtgtaaa tgagaagacg tgtttttttc   3600
cttcaccgat gctccatcct cgtatttctt tttccttgta aatgtaatca gatgccattt   3660
tatatgtgga cgtatttata ctggccaaac atattttttc ttttgtccct tttttttcttt   3720
cctttctttt tacttccttt atttctttat tccttccttt tcctttttttt cttttttttt   3780
tcttttttttt ttttttttttt tggtagttgt tgttacccac gccattttac gtctccttca   3840
ctgaagggct agagttttaa cttttaattt tttatattta aatgtagact tttgacactt   3900
ttaaaaaaca aaaaaagaca agagagatga aaacgtttga ttattttctc agtgtatttt   3960
tgtaaaaaat atataaaggg ggtgttaatc ggtgtaaatc gctgtttgga tttcctgatt   4020
ttataacagg gcggctggtt aatatctcac acagtttaaa aatcagccc ctaatttctc   4080
catgtttaca cttcaatctg caggcttctt aaagtgacag tatcccttaa cctgccacca   4140
gtgtccaccc tccggccccc gtcttgtaaa aaggggagga gaattagcca aacactgtaa   4200
gcttttaaga aaaacaaagt tttaaacgaa atactgctct gtccagaggc tttaaaactg   4260
gtgcaattac agcaaaaagg gattctgtag ctttaacttg taaaccacat ctttttttgca   4320
ctttttttat aagcaaaaac gtgccgttta aaccactgga tctatctaaa tgccgatttg   4380
agttcgcgac actatgtact gcgtttttca ttcttgtatt tgactattta atcctttcta   4440
cttgtcgcta aatataattg ttttagtctt atggcatgat gatagcatat gtgttcaggt   4500
ttatagctgt tgtgtttaaa aattgaaaaa agtggaaaac atctttgtac atttaagtct   4560
gtattataat aagcaaaaag attgtgtgta tgtatgttta atataacatg acaggcacta   4620
ggacgtctgc ctttttaagg cagttccgtt aagggttttt gtttttaaac tttttttttgc   4680
catccatcct gtgcaatatg ccgtgtagaa tatttgtctt aaaattcaag gccacaaaaa   4740
caatgtttgg gggaaaaaaa agaaaaaatc atgccagcta atcatgtcaa gttcactgcc   4800
tgtcagattg ttgatatata ccttctgtaa ataacttttt ttgagaagga aataaaatca   4860
```

```
gctggaactg aaccctaaaa aaaaaaaaaa aaaaaaaaaa aaaaaaaaaa aa          4912


<210> SEQ ID NO 81
<211> LENGTH: 2970
<212> TYPE: DNA
<213> ORGANISM: Homo sapiens

<400> SEQUENCE: 81

gttttaaacg cgcagccgag ggccgcgcgc aggagtaggg agggcctagg gcggcggagc     60

cgactcgtcg cggccgaggc gcgcgcggtc cgtgccggcg tcagtctggg attggccggc    120

ccgcgacttc ctccgccccc tgccaatcgc cggggacgac ttccgtgggt ttttccggct    180

cccccgcgtc gctaaggagc gacgggctgt cggccagacc ccgagttctc ggtgcgctca    240

gcggccgccg acgctaggag gccgcgctcc gcccccgcta ccatgaggcc ccggaaagcc    300

ttcctgctcc tgctgctctt ggggctggtg cagctgctgg ccgtggcggg tgccgagggc    360

ccggacgagg attcttctaa cagagaaaat gccattgagg atgaagagga ggaggaggag    420

gaagatgatg atgaggaaga agacgacttg gaagttaagg aagaaaatgg agtcttggtc    480

ctaaatgatg caaactttga taattttgtg gctgacaaag acacagtgct gctggagttt    540

tatgctccat ggtgtggaca ttgcaagcag tttgctccgg aatatgaaaa aattgccaac    600

atattaaagg ataaagatcc tcccattcct gttgccaaga tcgatgcaac ctcagcgtct    660

gtgctggcca gcaggtttga tgtgagtggc taccccacca tcaagatcct taagaagggg    720

caggctgtag actacgaggg ctccagaacc caggaagaaa ttgttgccaa ggtcagagaa    780

gtctcccagc ccgactggac gcctccacca gaagtcacgc ttgtgttgac caaagagaac    840

tttgatgaag ttgtgaatga tgcagatatc attctggtgg agttttatgc cccatggtgt    900

ggacactgca agaaacttgc cccgagtat gagaaggccg ccaaggagct cagcaagcgt     960

tctcctccaa ttcccctggc aaaggtcgac gccaccgcag aaacagacct ggccaagagg   1020

tttgatgtct ctggctatcc caccctgaaa attttccgca aaggaaggcc ttatgactac   1080

aacggcccac gagaaaaata tggaatcgtt gattacatga tcgagcagtc cgggcctccc   1140

tccaaggaga ttctgaccct gaagcaggtc caggagttcc tgaaggatgg agacgatgtc   1200

atcatcatcg gggtctttaa gggggagagt gacccagcct accagcaata ccaggatgcc   1260

gctaacaacc tgagagaaga ttacaaattt caccacactt tcagcacaga aatagcaaag   1320

ttcttgaaag tctcccaggg gcagttggtt gtaatgcagc ctgagaaatt ccagtccaag   1380

tatgagcccc ggagccacat gatggacgtc cagggctcca cccaggactc ggccatcaag   1440

gacttcgtgc tgaagtacgc cctgcccctg gttggccacc gcaaggtgtc aaacgatgct   1500

aagcgctaca ccaggcgccc cctggtggtc gtctactaca gtgtggactt cagctttgat   1560

tacagagctg caactcagtt ttggcggagc aaagtcctag aggtggccaa ggacttccct   1620

gagtacacct ttgccattgc ggacgaagag gactatgctg gggaggtgaa ggacctgggg   1680

ctcagcgaga gtggggagga tgtcaatgcc gccatcctgg acgagagtgg gaagaagttc   1740

gccatggagc cagaggagtt tgactctgac accctccgcg agtttgtcac tgctttcaaa   1800

aaaggaaaac tgaagccagt catcaaatcc cagccagtgc ccaagaacaa caagggaccc   1860

gtcaaggtcg tggtgggaaa gacctttgac tccattgtga tggaccccaa gaaggacgtc   1920

ctcatcgagt tctacgcgcc atggtgcggg cactgcaagc agctagagcc cgtgtacaac   1980

agcctggcca agaagtacaa gggccaaaag ggcctggtca tcgccaagat ggacgccact   2040

gccaacgacg tccccagcga ccgctataag gtggagggct tccccaccat ctacttcgcc   2100
```

```
cccagtgggg acaaaaagaa cccagttaaa tttgagggtg gagacagaga tctggagcat   2160

ttgagcaagt ttatagaaga acatgccaca aaactgagca ggaccaagga agagctttga   2220

aggcctgagg tctgcggaag gtgggaggag gcagacgccc tgcgtggccc atggtcgggg   2280

cgtccacgcc gaggccggca acaaacgaca gtatctcgga ttcctttttt ttttttttta   2340

atttttttata ctttggtgtt tcacttcatg ctctgaatac tgaataacca tgaatgactg   2400

aatagtttag tccagatttt tacagaggat acatctattt ttatcattat ttggggtttg   2460

aaaaattttt ttttacacct tctaatttct ttatttctca aagcagataa ttcttctgtg   2520

tgaaaatgtt ttcttttttt aatttaaggt ttaaaattcc ttttccaaat catgttgatt   2580

ttgctctttg ctttttcgtt gtctgagaaa ttgttggcgt agatttggct tctggtatgt   2640

gtttctgatt gcttcctgtt gagcacaaag tgagagctgc cactgagcag ccctgccagg   2700

ggtgctgttt caggctgggc atcgccaggc ggcctccctg caaaccaagg gctgggggca   2760

aaggggcatg atccagggtc ccccagggtg ggctcagctc cagggagagg ccacccacgt   2820

ggcagcccca cctcttgaga gcccccagtg ccggagcaga aaggaccctg gacccagagg   2880

cagatactgc ggggtggtag aaaaggtaga gtaggctgtg gcaatggaat aaaacacgat   2940

taaaaacgtt aaaaaaaaaa aaaaaaaaaa                                    2970
```

<210> SEQ ID NO 82
<211> LENGTH: 3791
<212> TYPE: DNA
<213> ORGANISM: Homo sapiens

<400> SEQUENCE: 82

```
aagaggggc ggggcggaag cggcggcggc gcgcgcaaag ctgcagcgtc tggaaaaaag     60

cgacttgtgg cggtcgagcg tggcgcaggc gaatcctcgg cactaagcaa atatggacct    120

cgcggcggca gcggagccgg gcgccggcag ccagcacctg gaggtccgcg acgaggtggc    180

cgagaagtgc cagaaactgt tcctggactt cttggaggag tttcagagca gcgatggaga    240

aattaaatac ttgcaattag cagaggaact gattcgtcct gagagaaaca cattggttgt    300

gagttttgtg gacctggaac aatttaacca gcaactttcc accaccattc aagaggagtt    360

ctatagagtt taccccttacc tgtgtcgggc cttgaaaaca ttcgtcaaag accgtaaaga    420

gatccctctt gccaaggatt tttatgttgc attccaagac ctgcctacca gacacaagat    480

tcgagagctc acctcatcca gaattggttt gctcactcgc atcagtgggc aggtggtgcg    540

gactcaccca gttcacccag agcttgtgag cggaactttt ctgtgcttgg actgtcagac    600

agtgatcagg gatgtagaac agcagttcaa atacacacag ccaaacatct gccgaaatcc    660

agtttgtgcc aacaggagga gattcttact ggatacaaat aaatcaagat ttgttgattt    720

tcaaaaggtt cgtattcaag agacccaagc tgagcttcct cgagggagta tcccccgcag    780

tttagaagta attttaaggg ctgaagctgt ggaatcagct caagctggtg acaagtgtga    840

ctttacaggg acactgattg ttgtgcctga cgtctccaag cttagcacac caggagcacg    900

tgcagaaact aattcccgtg tcagtggtgt tgatggatat gagacagaag gcattcgagg    960

actccgggcc cttggtgtta gggacctttc ttataggctg gtctttcttg cctgctgtgt   1020

tgcgccaacc aacccaaggt ttgggggggaa agagctcaga gatgaggaac agacagctga   1080

gagcattaag aaccaaatga ctgtgaaaga atgggagaaa gtgtttgaga tgagtcaaga   1140

taaaaatcta taccacaatc tttgtaccag cctgttccct actatacatg gcaatgatga   1200
```

```
agtaaaacgg ggtgtcctgc tgatgctctt tggtggcgtt ccaaagacaa caggagaagg   1260
gacctctctt cgaggggaca taaatgtttg cattgttggt gacccaagta cagctaagag   1320
ccaatttctc aagcacgtgg aggagttcag ccccagagct gtctacacca gtggtaaagc   1380
gtccagtgct gctggcttaa cagcagctgt tgtgagagat gaagaatctc atgagtttgt   1440
cattgaggct ggagctttga tgttggctga taatggtgtg tgttgtattg atgaatttga   1500
taagatggac gtgcgggatc aagttgctat tcatgaagct atggaacagc agaccatatc   1560
catcactaaa gcaggagtga aggctactct gaacgcccgg acgtccattt tggcagcagc   1620
aaacccaatc agtggacact atgacagatc aaaatcattg aaacagaata taaatttgtc   1680
agctcccatc atgtcccgat tcgatctctt ctttatcctt gtggatgaat gtaatgaggt   1740
tacagattat gccattgcca ggcgcatagt agatttgcat tcaagaattg aggaatcaat   1800
tgatcgtgtc tattccctcg atgatatcag aagatatctt ctctttgcaa gacagtttaa   1860
acccaagatt tccaaagagt cagaggactt cattgtggag caatataaac atctccgcca   1920
gagagatggt tctggagtga ccaagtcttc atggaggatt acagtgcgac agcttgagag   1980
catgattcgt ctctctgaag ctatggctcg gatgcactgc tgtgatgagg tccaacctaa   2040
acatgtgaag gaagctttcc ggttactgaa taaatcaatc atccgtgtgg aaacacctga   2100
tgtcaatcta gatcaagagg aagagatcca gatggaggta gatgagggtg ctggtggcat   2160
caatggtcat gctgacagcc ctgctcctgt gaacgggatc aatggctaca atgaagacat   2220
aaatcaagag tctgctccca aagcctcctt aaggctgggc ttctctgagt actgccgaat   2280
ctctaacctt attgtgcttc acctcagaaa ggtggaagaa gaagaggacg agtcagcatt   2340
aaagaggagc gagcttgtta actggtactt gaaggaaatc gaatcagaga tagactctga   2400
agaagaactt ataaataaaa aaagaatcat agagaaagtt attcatcgac tcacacacta   2460
tgatcatgtt ctaattgagc tcacccaggc tggattgaaa ggctccacag agggaagtga   2520
gagctatgaa gaagatccct acttggtagt taaccctaac tacttgctcg aagattgaga   2580
tagtgaaagt aactgaccag agctgaggaa ctgtggcaca gcacctcgtg gcctggagcc   2640
tggctggagc tctgctaggg acagaagtgt ttctggaagt gatgcttcca ggatttgttt   2700
tcagaaacaa gaattgagtt gatggtccta tgtgtcacat tcatcacagg tttcatacca   2760
acacaggctt cagcacttcc tttggtgtgt ttcctgtccc agtgaagttg gaaccaaata   2820
atgtgtagtc tctataacca atacctttgt tttcatgtgt aagaaaaggc ccattacttt   2880
taaggtatgt gctgtcctat tgagcaaata actttttttc aattgccagc tactgctttt   2940
attcatcaaa ataaaataac ttgttctgaa gttgtctatt ggatttcttt ctactgtacc   3000
ctgattatta cttccatcta cttctgaatg tgagactttc cctttttgct taacctggag   3060
tgaagaggta gaactgtggt attatggatg aggtttctat gagaaggagt cattagagaa   3120
ctcatatgaa agctagaggc cttagagatg actttccaag gttaattcca gttgtttttt   3180
ttttttttta agtttataaa agtttattat actttttttaa aattactctt tagtaattta   3240
ttttacttct gtgtcctaag ggtaatttct caggattgtt ttcaaattgc ttttttaggg   3300
gaaataggtc atttgctata ttacaagcaa tccccaaatt ttatggtctt ccaggaaaag   3360
ttattaccgt ttatgatact aacagttcct gagacttagc tatgatcagt atgttcatga   3420
ggtggagcag ttcctgtgtt gcagctttta acaacagatg gcattcatta aatcacaaag   3480
tatgttaaag gtcacaaaag caaaataact gtctgaggct aaggcccacg tgggacagtc   3540
taatacccat gagtactcaa cttgccttga tgtctgagct ttccagtgca atgtgaattt   3600
```

```
gagcagccag aaatctatta gtagaaagca agacagatta atataggtta aaacaatgat   3660

ttaaatatgt ttctcccaat aattatctct ttccctggaa tcaacttgta tgaaaccttg   3720

tcaaaatgta ctccacaagt atgtacaatt aagtatttta aaaataaatg gcaaacatta   3780

aaaacaaaaa a                                                        3791
```

<210> SEQ ID NO 83
<211> LENGTH: 3720
<212> TYPE: DNA
<213> ORGANISM: Homo sapiens

<400> SEQUENCE: 83

```
aggatacagc ggcttctgcg cgacttataa gagctccttg tgcggcgcca ttttaagcct     60

ctcggtctgt ggcagcagcg ttggcccggc cccgggagcg gagagcgagg ggaggcggag    120

acggaggaag gtctgaggag cagcttcagt ccccgccgag ccgccaccgc aggtcgagga    180

cggtcggact cccgcggcgg gaggagcctg ttcccctgag ggtatttgaa gtataccata    240

caactgtttt gaaaatccag cgtggacaat ggctactcaa gctgatttga tggagttgga    300

catggccatg gaaccagaca gaaaagcggc tgttagtcac tggcagcaac agtcttacct    360

ggactctgga atccattctg gtgccactac cacagctcct tctctgagtg gtaaaggcaa    420

tcctgaggaa gaggatgtgg atacctccca agtcctgtat gagtgggaac agggattttc    480

tcagtccttc actcaagaac aagtagctga tattgatgga cagtatgcaa tgactcgagc    540

tcagagggta cgagctgcta tgttccctga gacattagat gagggcatgc agatcccatc    600

tacacagttt gatgctgctc atcccactaa tgtccagcgt ttggctgaac catcacagat    660

gctgaaacat gcagttgtaa acttgattaa ctatcaagat gatgcagaac ttgccacacg    720

tgcaatccct gaactgacaa aactgctaaa tgacgaggac caggtggtgg ttaataaggc    780

tgcagttatg gtccatcagc tttctaaaaa ggaagcttcc agacacgcta tcatgcgttc    840

tcctcagatg gtgtctgcta ttgtacgtac catgcagaat acaaatgatg tagaaacagc    900

tcgttgtacc gctgggacct tgcataacct ttcccatcat cgtgagggct tactggccat    960

ctttaagtct ggaggcattc ctgccctggt gaaaatgctt ggttcaccag tggattctgt   1020

gttgttttat gccattacaa ctctccacaa cctttttatta catcaagaag gagctaaaat   1080

ggcagtgcgt ttagctggtg ggctgcagaa aatggttgcc ttgctcaaca aaacaaatgt   1140

taaattcttg gctattacga cagactgcct tcaaatttta gcttatggca accaagaaag   1200

caagctcatc atactggcta gtggtggacc ccaagcttta gtaaatataa tgaggaccta   1260

tacttacgaa aaactactgt ggaccacaag cagagtgctg aaggtgctat ctgtctgctc   1320

tagtaataag ccggctattg tagaagctgg tggaatgcaa gctttaggac ttcacctgac   1380

agatccaagt caacgtcttg ttcagaactg tctttggact ctcaggaatc tttcagatgc   1440

tgcaactaaa caggaaggga tggaaggtct ccttgggact cttgttcagc ttctgggttc   1500

agatgatata aatgtggtca cctgtgcagc tggaattctt tctaacctca cttgcaataa   1560

ttataagaac aagatgatgg tctgccaagt gggtggtata gaggctcttg tgcgtactgt   1620

ccttcgggct ggtgacaggg aagacatcac tgagcctgcc atctgtgctc ttcgtcatct   1680

gaccagccga caccaagaag cagagatggc ccagaatgca gttcgccttc actatggact   1740

accagttgtg gttaagctct tacacccacc atcccactgg cctctgataa aggctactgt   1800

tggattgatt cgaaatcttg ccctttgtcc cgcaaatcat gcacctttgc gtgagcaggg   1860
```

-continued

```
tgccattcca cgactagttc agttgcttgt tcgtgcacat caggataccc agcgccgtac   1920
gtccatgggt gggacacagc agcaatttgt ggaggggggtc cgcatggaag aaatagttga   1980
aggttgtacc ggagcccttc acatcctagc tcgggatgtt cacaaccgaa ttgttatcag   2040
aggactaaat accattccat tgtttgtgca gctgctttat tctcccattg aaaacatcca   2100
aagagtagct gcaggggtcc tctgtgaact tgctcaggac aaggaagctg cagaagctat   2160
tgaagctgag ggagccacag ctcctctgac agagttactt cactctagga atgaaggtgt   2220
ggcgacatat gcagctgctg ttttgttccg aatgtctgag gacaagccac aagattacaa   2280
gaaacggctt tcagttgagc tgaccagctc tctcttcaga acagagccaa tggcttggaa   2340
tgagactgct gatcttggac ttgatattgg tgcccaggga gaaccccttg gatatcgcca   2400
ggatgatcct agctatcgtt cttttcactc tggtggatat ggccaggatg ccttgggtat   2460
ggaccccatg atggaacatg agatgggtgg ccaccaccct ggtgctgact atccagttga   2520
tgggctgcca gatctggggc atgcccagga cctcatggat gggctgcctc caggtgacag   2580
caatcagctg gcctggtttg atactgacct gtaaatcatc ctttaggtaa gaagttttaa   2640
aaagccagtt tgggtaaaat acttttactc tgcctacaga acttcagaaa gacttggttg   2700
gtagggtggg agtggtttag gctatttgta aatctgccac aaaaacaggt atatactttg   2760
aaaggagatg tcttggaaca ttggaatgtt ctcagatttc tggttgttat gtgatcatgt   2820
gtggaagtta ttaactttaa tgtttttttgc cacagctttt gcaacttaat actcaaatga   2880
gtaacatttg ctgttttaaa cattaatagc agcctttctc tctttataca gctgtattgt   2940
ctgaacttgc attgtgattg gcctgtagag ttgctgagag ggctcgaggg gtgggctggt   3000
atctcagaaa gtgcctgaca cactaaccaa gctgagtttc ctatgggaac aattgaagta   3060
aactttttgt tctggtcctt tttggtcgag gagtaacaat acaaatggat tttgggagtg   3120
actcaagaag tgaagaatgc acaagaatgg atcacaagat ggaatttatc aaaccctagc   3180
cttgcttgtt aaattttttt ttttttttt ttaagaatat ctgtaatggt actgactttg   3240
cttgctttga agtagctctt ttttttttt ttttttttt tttgcagtaa ctgtttttta   3300
agtctctcgt agtgttaagt tatagtgaat actgctacag caatttctaa tttttaagaa   3360
ttgagtaatg gtgtagaaca ctaattcata atcactctaa ttaattgtaa tctgaataaa   3420
gtgtaacaat tgtgtagcct ttttgtataa aatagacaaa tagaaaatgg tccaattagt   3480
ttccttttta atatgcttaa aataagcagg tggatctatt tcatgttttt gatcaaaaac   3540
tatttgggat atgtatgggt agggtaaatc agtaagaggt gttatttgga accttgtttt   3600
ggacagttta ccagttgcct tttatcccaa agttgttgta acctgctgtg atacgatgct   3660
tcaagagaaa atgcggttat aaaaaatggt tcagaattaa acttttaatt cattcgattg   3720
```

<210> SEQ ID NO 84
<211> LENGTH: 434
<212> TYPE: DNA
<213> ORGANISM: Homo sapiens

<400> SEQUENCE: 84

```
acttccgctc gtccgcctaa taccgcgcct gcgcaccgcg tctcttcctt tctgggctcg     60
gacctaggtc gcggcgacat ggccaaacgt accaagaaag tcgggatcgt cggtaaatac    120
gggacccgct atggggcctc cctccggaaa atggtgaaga aaattgaaat cagccagcac    180
gccaagtaca cttgctcttt ctgtggcaaa accaagatga agagacgagc tgtggggatc    240
tggcactgtg gttcctgcat gaagacagtg gctggcggtg cctggacgta caataccact    300
```

```
tccgctgtca cggtaaagtc cgccatcaga agactgaagg agttgaaaga ccagtagacg    360

ctcctctact ctttgagaca tcactggcct ataataaatg ggttaattta tgtaacaaaa    420

aaaaaaaaaa aaaa                                                      434
```

<210> SEQ ID NO 85
<211> LENGTH: 1926
<212> TYPE: DNA
<213> ORGANISM: Homo sapiens

<400> SEQUENCE: 85

```
ggcgggggcc cggccgaggc aataagagcg gcggcggcgg cagcggcggc agcagctccc     60

gcagctcctg ctctggtccg cctcggcccg gcggcggcca tcagcccccct cggcctcggc   120

tcgaggggcg gggagctgcg cgcgccccctc ggtccgaccg acaccctccc cttcccgccc   180

gtccgcgcgc cccgcggccc gcggcccgca gtccgccccg cgcgctcctt gccgaggagc    240

cgagcccgcg cccggcccgc ccgcccggcg ctgccccggc cctcccggcc cgcgtgaggc    300

cgcccgcgcc cgccgccgcc gcagcccggc cgcgccccgc cgccgccgcc gccgccatgg    360

gctgcctcgg gaacagtaag accgaggacc agcgcaacga ggagaaggcg cagcgtgagg    420

ccaacaaaaa gatcgagaag cagctgcaga aggacaagca ggtctaccgg gccacgcacc    480

gcctgctgct gctgggtgct ggagaatctg gtaaaagcac cattgtgaag cagatgagga    540

tcctgcatgt taatgggttt aatggagagg gcggcgaaga ggacccgcag gctgcaagga    600

gcaacagcga tggtgagaag gcaaccaaag tgcaggacat caaaaacaac ctgaaagagg    660

cgattgaaac cattgtggcc gccatgagca acctggtgcc ccccgtggag ctggccaacc    720

ccgagaacca gttcagagtg gactacatcc tgagtgtgat gaacgtgcct gactttgact    780

tccctcccga attctatgag catgccaagg ctctgtggga ggatgaagga gtgcgtgcct    840

gctacgaacg ctccaacgag taccagctga ttgactgtgc ccagtacttc ctggacaaga    900

tcgacgtgat caagcaggct gactatgtgc cgagcgatca ggacctgctt cgctgccgtg    960

tcctgacttc tggaatcttt gagaccaagt tccaggtgga caaagtcaac ttccacatgt   1020

ttgacgtggg tggccagcgc gatgaacgcc gcaagtggat ccagtgcttc aacgatgtga   1080

ctgccatcat cttcgtggtg gccagcagca gctacaacat ggtcatccgg gaggacaacc   1140

agaccaaccg cctgcaggag gctctgaacc tcttcaagag catctggaac aacagatggc   1200

tgcgcaccat ctctgtgatc ctgttcctca acaagcaaga tctgctcgct gagaaagtcc   1260

ttgctgggaa atcgaagatt gaggactact ttccagaatt tgctcgctac actactcctg   1320

aggatgctac tcccgagccc ggagaggacc cacgcgtgac ccgggccaag tacttcattc   1380

gagatgagtt tctgaggatc agcactgcca gtggagatgg gcgtcactac tgctaccctc   1440

atttcacctg cgctgtggac actgagaaca tccgccgtgt gttcaacgac tgccgtgaca   1500

tcattcagcg catgcacctt cgtcagtacg agctgctcta agaagggaac ccccaaattt   1560

aattaaagcc ttaagcacaa ttaattaaaa gtgaaacgta attgtacaag cagttaatca   1620

cccaccatag ggcatgatta acaaagcaac ctttcccttc cccgagtga ttttgcgaaa    1680

ccccctttc ccttcagctt gcttagatgt tccaaattta gaaagcttaa ggcggcctac    1740

agaaaaagga aaaaaggcca caaaagttcc ctctcacttt cagtaaaaat aaataaaaca   1800

gcagcagcaa acaaataaaa tgaaataaaa gaaacaaatg aaataaatat tgtgttgtgc   1860

agcattaaaa aaaatcaaaa taaaaattaa atgtgagcaa agaatgaaaa aaaaaaaaaa   1920
```

aaaaaa 1926

<210> SEQ ID NO 86
<211> LENGTH: 3784
<212> TYPE: DNA
<213> ORGANISM: Homo sapiens

<400> SEQUENCE: 86
aggatagacc aaggaagagg ggctgggggg cagcctgggg gcatgaaaag tggccaggaa 60
ggagccaaga ctccaccagc aacaattgag ttgcttcagc ctcagtctag ggttccttcc 120
aggccttgaa ccccccaacc tcacaagggt tggaaagtga ggccggtgaa ctttccagct 180
ggtactttga ttttaaaata ataataataa ttttttcacc ctagttcggt tgggtgctcc 240
atcttacgga gccccaaact tattttgaga ggccgccacc gtgttatggg cgtgcgcaac 300
tgcctctacg gcaataatat gtcaggacaa cgcgatatcc cccctgaaat cggggaacag 360
cccgagcaac cacctttgga ggccccaggg gcagctgccc ccggtgctgg gcctagccca 420
gccgaagaga tggagaccga accgcctcac aacgagccca tccccgtcga gaatgatggc 480
gaggcctgtg gacccccaga ggtctccaga cccaactttc aggtcctcaa cccggcattc 540
agggaagctg gagcccatgg aagctacagc ccacctcctg aggaagcaat gcccttcgag 600
gctgaacagc ccagcttggg aggcttctgg cctacactgg agcagcctgg attccccagt 660
ggggtccatg caggccttga ggccttcggc ccagcactca tggagcccgg agccttcagt 720
ggtgccagac caggcctggg aggatacagc cctccaccag aagaagctat gccctttgag 780
tttgaccagc ctgcccagag aggctgcagt caacttctct tacaggtccc agaccttgct 840
ccaggaggcc caggtgctgc aggggtcccc ggagctcctc ccgaggagcc ccaagccctc 900
aggcctgcaa aggctggctc cagaggaggc tacagccctc cccctgagga gactatgcca 960
tttgagcttg atggagaagg atttggggac gacagcccac ccccggggct ttcccgagtt 1020
atcgcacaag tcgacggcag cagccagttc gcggcagtcg cggcctcgag tgcggtccgc 1080
ctcactcccg ccgcgaacgc gcctccccctc tgggtcccag gcgccatcgg cagcccatcc 1140
caagaggctg tcagacctcc ttctaacttc acgggcagca gcccctggat ggagatctcc 1200
ggacccccgt tcgagattgg cagcgccccc gctggggtcg acgacactcc cgtcaacatg 1260
gacagccccc caatcgcgct tgacggcccg cccatcaagg tctccggagc cccagataag 1320
agagagcgag cagagagacc cccagttgag gaggaagcag cagagatgga aggagccgct 1380
gatgccgcgg agggaggaaa agtaccctct ccggggtacg gatcccctgc cgccggggca 1440
gcctcagcgg ataccgctgc cagggcagcc cctgcagccc cagccgatcc tgactccggg 1500
gcaaccccag aagatcccga ctccgggaca gcaccagccg atcctgactc cggggcattc 1560
gcagccgatc ccgactccgg ggcagcccct gccgccccag ccgatcccga ctccggggcg 1620
gcccctgacg ccccagccga tcccgactcc ggggcggccc ctgacgcccc agccgatcca 1680
gatgccgggg cggcccctga ggctcccgcc gcccctgcgg ctgctgagac ccgggcagcc 1740
catgtcgccc cagctgcgcc agacgcaggg gctcccactg ccccagccgc ttctgccacc 1800
cgggcagccc aagtccgccg ggcggcctct gcagcccctg cctccggggc cagacgcaag 1860
atccatctca gacccccccag ccccgagatc caggctgccg atccgcctac tccgcggcct 1920
actcgcgcgt ctgcctggcg gggcaagtcc gagagcagcc gcggccgccg cgtgtactac 1980
gatgaagggg tggccagcag cgacgatgac tccagcggag acgagtccga cgatgggacc 2040
tccggatgcc tccgctggtt tcagcatcgg cgaaatcgcc gccgccgaaa gccccagcgc 2100

```
aacttactcc gcaactttct cgtgcaagcc ttcgggggct gcttcggtcg atctgagagt   2160

ccccagccca aagcctcgcg ctctctcaag gtcaagaagg taccccctggc ggagaagcgc   2220

agacagatgc gcaaagaagc cctggagaag cgggcccaga agcgcgcaga gaagaaacgc   2280

agtaagctca tcgacaaaca actccaggac gaaaagatgg gctacatgtg tacgcaccgc   2340

ctgctgcttc taggtgctgg agaatctggt aaaagcacca ttgtgaagca gatgaggatc   2400

ctgcatgtta atgggtttaa tggagagggc ggcgaagagg acccgcaggc tgcaaggagc   2460

aacagcgatg gtgagaaggc aaccaaagtg caggacatca aaaacaacct gaaagaggcg   2520

attgaaacca ttgtggccgc catgagcaac ctggtgcccc ccgtggagct ggccaacccc   2580

gagaaccagt tcagagtgga ctacatcctg agtgtgatga acgtgcctga ctttgacttc   2640

cctcccgaat tctatgagca tgccaaggct ctgtgggagg atgaaggagt gcgtgcctgc   2700

tacgaacgct ccaacgagta ccagctgatt gactgtgccc agtacttcct ggacaagatc   2760

gacgtgatca agcaggctga ctatgtgccg agcgatcagg acctgcttcg ctgccgtgtc   2820

ctgacttctg gaatctttga gaccaagttc caggtggaca aagtcaactt ccacatgttt   2880

gacgtgggtg gccagcgcga tgaacgccgc aagtggatcc agtgcttcaa cgatgtgact   2940

gccatcatct tcgtggtggc cagcagcagc tacaacatgg tcatccggga ggacaaccag   3000

accaaccgcc tgcaggaggc tctgaacctc ttcaagagca tctggaacaa cagatggctg   3060

cgcaccatct ctgtgatcct gttcctcaac aagcaagatc tgctcgctga gaaagtcctt   3120

gctgggaaat cgaagattga ggactacttt ccagaatttg ctcgctacac tactcctgag   3180

gatgctactc ccgagcccgg agaggaccca cgcgtgaccc gggccaagta cttcattcga   3240

gatgagtttc tgaggatcag cactgccagt ggagatgggc gtcactactg ctaccctcat   3300

ttcacctgcg ctgtggacac tgagaacatc cgccgtgtgt tcaacgactg ccgtgacatc   3360

attcagcgca tgcaccttcg tcagtacgag ctgctctaag aagggaaccc ccaaatttaa   3420

ttaaagcctt aagcacaatt aattaaaagt gaaacgtaat tgtacaagca gttaatcacc   3480

caccataggg catgattaac aaagcaacct ttcccttccc ccgagtgatt ttgcgaaacc   3540

ccctttttccc ttcagcttgc ttagatgttc caaatttaga aagcttaagg cggcctacag   3600

aaaaaggaaa aaaggccaca aaagttccct ctcactttca gtaaaaaataa ataaaacagc   3660

agcagcaaac aaataaaatg aaataaaaga aacaaatgaa ataaatattg tgttgtgcag   3720

cattaaaaaa aatcaaaata aaaattaaat gtgagcaaag aatgaaaaaa aaaaaaaaaa   3780

aaaa                                                               3784
```

<210> SEQ ID NO 87
<211> LENGTH: 1884
<212> TYPE: DNA
<213> ORGANISM: Homo sapiens

<400> SEQUENCE: 87

```
ggcgggggcc cggccgaggc aataagagcg gcggcggcgg cagcggcggc agcagctccc     60

gcagctcctg ctctggtccg cctcggcccg gcggcggcca tcagcccccct cggcctcggc    120

tcgaggggcg gggagctgcg cgcgcccctc ggtccgaccg acaccctccc cttcccgccc    180

gtccgcgcgc cccgcggccc gcggcccgca gtccgccccg cgcgctcctt gccgaggagc    240

cgagcccgcg cccggcccgc ccgcccggcg ctgccccggc cctcccggcc cgcgtgaggc    300

cgcccgcgcc cgccgccgcc gcagcccggc cgcgccccgc cgccgccgcc gccgccatgg    360
```

```
gctgcctcgg gaacagtaag accgaggacc agcgcaacga ggagaaggcg cagcgtgagg     420
ccaacaaaaa gatcgagaag cagctgcaga aggacaagca ggtctaccgg gccacgcacc     480
gcctgctgct gctgggtgct ggagaatctg gtaaaagcac cattgtgaag cagatgagga     540
tcctgcatgt taatgggttt aatggagaca gtgagaaggc aaccaaagtg caggacatca     600
aaaacaacct gaaagaggcg attgaaacca ttgtggccgc catgagcaac ctggtgcccc     660
ccgtggagct ggccaacccc gagaaccagt tcagagtgga ctacatcctg agtgtgatga     720
acgtgcctga ctttgacttc cctcccgaat tctatgagca tgccaaggct ctgtgggagg     780
atgaaggagt gcgtgcctgc tacgaacgct ccaacgagta ccagctgatt gactgtgccc     840
agtacttcct ggacaagatc gacgtgatca agcaggctga ctatgtgccg agcgatcagg     900
acctgcttcg ctgccgtgtc ctgacttctg gaatctttga gaccaagttc caggtggaca     960
aagtcaactt ccacatgttt gacgtgggtg gccagcgcga tgaacgccgc aagtggatcc    1020
agtgcttcaa cgatgtgact gccatcatct tcgtggtggc cagcagcagc tacaacatgg    1080
tcatccggga ggacaaccag accaaccgcc tgcaggaggc tctgaacctc ttcaagagca    1140
tctggaacaa cagatggctg cgcaccatct ctgtgatcct gttcctcaac aagcaagatc    1200
tgctcgctga gaaagtcctt gctgggaaat cgaagattga ggactacttt ccagaatttg    1260
ctcgctacac tactcctgag gatgctactc ccgagcccgg agaggaccca cgcgtgaccc    1320
gggccaagta cttcattcga gatgagtttc tgaggatcag cactgccagt ggagatgggc    1380
gtcactactg ctaccctcat ttcacctgcg ctgtggacac tgagaacatc cgccgtgtgt    1440
tcaacgactg ccgtgacatc attcagcgca tgcaccttcg tcagtacgag ctgctctaag    1500
aagggaaccc ccaaatttaa ttaaagcctt aagcacaatt aattaaaagt gaaacgtaat    1560
tgtacaagca gttaatcacc caccataggg catgattaac aaagcaacct ttcccttccc    1620
ccgagtgatt ttgcgaaacc ccccttttccc ttcagcttgc ttagatgttc caaatttaga    1680
aagcttaagg cggcctacag aaaaaggaaa aaaggccaca aaagttccct ctcactttca    1740
gtaaaaataa ataaaacagc agcagcaaac aaataaaatg aaataaaaga aacaaatgaa    1800
ataaatattg tgttgtgcag cattaaaaaa aatcaaaata aaaattaaat gtgagcaaag    1860
aatgaaaaaa aaaaaaaaaa aaaa                                           1884
```

<210> SEQ ID NO 88
<211> LENGTH: 2581
<212> TYPE: DNA
<213> ORGANISM: Homo sapiens

<400> SEQUENCE: 88

```
ctcgcctcag tctcctctgt cctctcccag gcaagaggac cggcggaggc acctctctcg      60
agtcttaggc tgcggaatct aagactcagc gagaggagcc cgggaggaga cagaactttc     120
ccctttttc ccatcccttc ttcttgctca gagaggcaag caaggcgcgg agctttagaa     180
agttcttaag tggtcaggaa ggtaggtgct tccctttttc tcctcacaag gaggtgaggc     240
tgggacctcc gggccagctt ctcacctcat agggtgtacc tttcccggct ccagcagcca     300
atgtgcttcg gagccactct ctgcagagcc agagggcagg ccggcttctc ggtgtgtgcc     360
taagaggatg gatcggaggt cccgggctca gcagtggcgc cgagctcgcc ataattacaa     420
cgacctgtgc ccgcccatag gccgccgggc agccaccgcg ctcctctggc tctcctgctc     480
catcgcgctc ctccgcgccc ttgccacctc caacgcccgt gcccagcagc gcgcggctgc     540
ccaacagcgc cggagcttcc ttaacgccca ccaccgctcc ggcgcccagg tattccctga     600
```

```
gtcccccgaa tcggaatctg accacgagca cgaggaggca gaccttgagc tgtccctccc    660

cgagtgccta gagtacgagg aagagttcga ctacgagacc gagagcgaga ccgagtccga    720

aatcgagtcc gagaccgact tcgagaccga gcctgagacc gcccccacca ctgagcccga    780

gaccgagcct gaagacgatc gcggcccggt ggtgcccaag cactccacct tcggccagtc    840

cctcacccag cgtctgcacg ctctcaagtt gcgaagcccc gacgcctccc caagtcgcgc    900

gccgcccagc actcaggagc cccagagccc cagggaaggg gaggagctca agcccgagga    960

caaagatcca agggaccccg aagagtcgaa ggagcccaag gaggagaagc agcggcgtcg   1020

ctgcaagcca aagaagccca cccgccgtga cgcgtccccg gagtcccctt ccaaaaaggg   1080

acccatcccc atccggcgtc actaatggag gacgccgtcc agattctcct tgttttcatg   1140

gattcaggtg ctggagaatc tggtaaaagc accattgtga agcagatgag gatcctgcat   1200

gttaatgggt ttaatggaga gggcggcgaa gaggacccgc aggctgcaag gagcaacagc   1260

gatggcagtg agaaggcaac caaagtgcag gacatcaaaa acaacctgaa agaggcgatt   1320

gaaaccattg tggccgccat gagcaacctg gtgccccccg tggagctggc caaccccgag   1380

aaccagttca gagtggacta catcctgagt gtgatgaacg tgcctgactt tgacttccct   1440

cccgaattct atgagcatgc caaggctctg tgggaggatg aaggagtgcg tgcctgctac   1500

gaacgctcca acgagtacca gctgattgac tgtgcccagt acttcctgga caagatcgac   1560

gtgatcaagc aggctgacta tgtgccgagc gatcaggacc tgcttcgctg ccgtgtcctg   1620

acttctggaa tctttgagac caagttccag gtggacaaag tcaacttcca catgtttgac   1680

gtgggtggcc agcgcgatga acgccgcaag tggatccagt gcttcaacga tgtgactgcc   1740

atcatcttcg tggtggccag cagcagctac aacatggtca tccgggagga caaccagacc   1800

aaccgcctgc aggaggctct gaacctcttc aagagcatct ggaacaacag atggctgcgc   1860

accatctctg tgatcctgtt cctcaacaag caagatctgc tcgctgagaa agtccttgct   1920

gggaaatcga agattgagga ctactttcca gaatttgctc gctacactac tcctgaggat   1980

gctactcccg agcccggaga ggacccacgc gtgacccggg ccaagtactt cattcgagat   2040

gagtttctga ggatcagcac tgccagtgga gatgggcgtc actactgcta ccctcatttc   2100

acctgcgctg tggacactga gaacatccgc cgtgtgttca acgactgccg tgacatcatt   2160

cagcgcatgc accttcgtca gtacgagctg ctctaagaag ggaacccccca aatttaatta   2220

aagccttaag cacaattaat taaaagtgaa acgtaattgt acaagcagtt aatcacccac   2280

catagggcat gattaacaaa gcaacctttc ccttcccccg agtgattttg cgaaacccccc   2340

ttttcccttc agcttgctta gatgttccaa atttagaaag cttaaggcgg cctacagaaa   2400

aaggaaaaaa ggccacaaaa gttccctctc actttcagta aaaataaata aaacagcagc   2460

agcaaacaaa taaaatgaaa taaaagaaac aaatgaaata aatattgtgt tgtgcagcat   2520

taaaaaaaat caaaataaaa attaaatgtg agcaaagaat gaaaaaaaaa aaaaaaaaaa   2580

a                                                                   2581
```

<210> SEQ ID NO 89
<211> LENGTH: 1929
<212> TYPE: DNA
<213> ORGANISM: Homo sapiens

<400> SEQUENCE: 89

```
ggcgggggcc cggccgaggc aataagagcg gcggcggcgg cagcggcggc agcagctccc     60
```

```
gcagctcctg ctctggtccg cctcggcccg gcggcggcca tcagccccct cggcctcggc    120
tcgaggggcg gggagctgcg cgcgcccctc ggtccgaccg acaccctccc cttcccgccc    180
gtccgcgcgc cccgcggccc gcggcccgca gtccgccccg cgcgctcctt gccgaggagc    240
cgagcccgcg cccggcccgc ccgcccggcg ctgccccggc cctcccggcc cgcgtgaggc    300
cgcccgcgcc cgccgccgcc gcagcccggc cgcgccccgc cgccgccgcc gccgccatgg    360
gctgcctcgg gaacagtaag accgaggacc agcgcaacga ggagaaggcg cagcgtgagg    420
ccaacaaaaa gatcgagaag cagctgcaga aggacaagca ggtctaccgg gccacgcacc    480
gcctgctgct gctgggtgct ggagaatctg gtaaaagcac cattgtgaag cagatgagga    540
tcctgcatgt taatgggttt aatggagagg gcggcgaaga ggacccgcag gctgcaagga    600
gcaacagcga tggcagtgag aaggcaacca aagtgcagga catcaaaaac aacctgaaag    660
aggcgattga aaccattgtg gccgccatga gcaacctggt gcccccgtg gagctggcca    720
accccgagaa ccagttcaga gtggactaca tcctgagtgt gatgaacgtg cctgactttg    780
acttccctcc cgaattctat gagcatgcca aggctctgtg ggaggatgaa ggagtgcgtg    840
cctgctacga acgctccaac gagtaccagc tgattgactg tgcccagtac ttcctggaca    900
agatcgacgt gatcaagcag gctgactatg tgccgagcga tcaggacctg cttcgctgcc    960
gtgtcctgac ttctggaatc tttgagacca agttccaggt ggacaaagtc aacttccaca   1020
tgtttgacgt gggtggccag cgcgatgaac gccgcaagtg gatccagtgc ttcaacgatg   1080
tgactgccat catcttcgtg gtggccagca gcagctacaa catggtcatc cgggaggaca   1140
accagaccaa ccgcctgcag gaggctctga acctcttcaa gagcatctgg aacaacagat   1200
ggctgcgcac catctctgtg atcctgttcc tcaacaagca agatctgctc gctgagaaag   1260
tccttgctgg gaaatcgaag attgaggact actttccaga atttgctcgc tacactactc   1320
ctgaggatgc tactcccgag cccggagagg acccacgcgt gacccgggcc aagtacttca   1380
ttcgagatga gtttctgagg atcagcactg ccagtggaga tgggcgtcac tactgctacc   1440
ctcatttcac ctgcgctgtg gacactgaga acatccgccg tgtgttcaac gactgccgtg   1500
acatcattca gcgcatgcac cttcgtcagt acgagctgct ctaagaaggg aacccccaaa   1560
tttaattaaa gccttaagca caattaatta aaagtgaaac gtaattgtac aagcagttaa   1620
tcacccacca tagggcatga ttaacaaagc aacctttccc ttcccccgag tgattttgcg   1680
aaacccccctt ttcccttcag cttgcttaga tgttccaaat ttagaaagct taaggcggcc   1740
tacagaaaaa ggaaaaaagg ccacaaaagt tccctctcac tttcagtaaa aataaataaa   1800
acagcagcag caaacaaata aaatgaaata aaagaaacaa atgaaataaa tattgtgttg   1860
tgcagcatta aaaaaaatca aaataaaaat taaatgtgag caaagaatga aaaaaaaaaa   1920
aaaaaaaaa                                                           1929
```

<210> SEQ ID NO 90
<211> LENGTH: 1881
<212> TYPE: DNA
<213> ORGANISM: Homo sapiens

<400> SEQUENCE: 90

```
ggcgggggcc cggccgaggc aataagagcg gcggcggcgg cagcggcggc agcagctccc     60
gcagctcctg ctctggtccg cctcggcccg gcggcggcca tcagccccct cggcctcggc    120
tcgaggggcg gggagctgcg cgcgcccctc ggtccgaccg acaccctccc cttcccgccc    180
gtccgcgcgc cccgcggccc gcggcccgca gtccgccccg cgcgctcctt gccgaggagc    240
```

```
cgagcccgcg cccggcccgc ccgcccggcg ctgccccggc cctcccggcc cgcgtgaggc    300

cgcccgcgcc cgccgccgcc gcagcccggc cgcgccccgc cgccgccgcc gccgccatgg    360

gctgcctcgg gaacagtaag accgaggacc agcgcaacga ggagaaggcg cagcgtgagg    420

ccaacaaaaa gatcgagaag cagctgcaga aggacaagca ggtctaccgg gccacgcacc    480

gcctgctgct gctgggtgct ggagaatctg gtaaaagcac cattgtgaag cagatgagga    540

tcctgcatgt taatgggttt aatggagatg agaaggcaac caaagtgcag gacatcaaaa    600

acaacctgaa agaggcgatt gaaaccattg tggccgccat gagcaacctg gtgccccccg    660

tggagctggc caaccccgag aaccagttca gagtggacta catcctgagt gtgatgaacg    720

tgcctgactt tgacttccct cccgaattct atgagcatgc caaggctctg tgggaggatg    780

aaggagtgcg tgcctgctac gaacgctcca acgagtacca gctgattgac tgtgcccagt    840

acttcctgga caagatcgac gtgatcaagc aggctgacta tgtgccgagc gatcaggacc    900

tgcttcgctg ccgtgtcctg acttctggaa tctttgagac caagttccag gtggacaaag    960

tcaacttcca catgtttgac gtgggtggcc agcgcgatga acgccgcaag tggatccagt   1020

gcttcaacga tgtgactgcc atcatcttcg tggtggccag cagcagctac aacatggtca   1080

tccgggagga caaccagacc aaccgcctgc aggaggctct gaacctcttc aagagcatct   1140

ggaacaacag atggctgcgc accatctctg tgatcctgtt cctcaacaag caagatctgc   1200

tcgctgagaa agtccttgct gggaaatcga agattgagga ctactttcca gaatttgctc   1260

gctacactac tcctgaggat gctactcccg agcccggaga ggacccacgc gtgacccggg   1320

ccaagtactt cattcgagat gagtttctga ggatcagcac tgccagtgga gatgggcgtc   1380

actactgcta ccctcatttc acctgcgctg tggacactga gaacatccgc cgtgtgttca   1440

acgactgccg tgacatcatt cagcgcatgc accttcgtca gtacgagctg ctctaagaag   1500

ggaaccccca aatttaatta aagccttaag cacaattaat taaaagtgaa acgtaattgt   1560

acaagcagtt aatcacccac catagggcat gattaacaaa gcaacctttc ccttcccccg   1620

agtgattttg cgaaaccccc ttttcccttc agcttgctta gatgttccaa atttagaaag   1680

cttaaggcgg cctacagaaa aaggaaaaaa ggccacaaaa gttccctctc actttcagta   1740

aaaataaata aaacagcagc agcaaacaaa taaaatgaaa taaaagaaac aaatgaaata   1800

aatattgtgt tgtgcagcat taaaaaaaat caaaataaaa attaaatgtg agcaaagaat   1860

gaaaaaaaaa aaaaaaaaaa a                                             1881
```

<210> SEQ ID NO 91
<211> LENGTH: 1638
<212> TYPE: DNA
<213> ORGANISM: Homo sapiens

<400> SEQUENCE: 91

```
aggctggggc gtcatcgggg ccggttagaa gctctgctcc ccggcgggga cactcagtcg     60

cgtcggcacc gcggagcggg ctgcgtcagg tggctggccg gcgcggcgct cccctgctct    120

ctggctccgg gctgcggcgc ggcggctgga gcgagcccct gtcccggcgc ggggcggcgg    180

cgggcggccg gcaggcgctg ccttgcgtgt gagtgcacct cactcacatg tgctggagaa    240

tctggtaaaa gcaccattgt gaagcagatg aggatcctgc atgttaatgg gtttaatgga    300

gagggcggcg aagaggaccc gcaggctgca aggagcaaca gcgatggtga gaaggcaacc    360

aaagtgcagg acatcaaaaa caacctgaaa gaggcgattg aaaccattgt ggccgccatg    420
```

```
agcaacctgg tgccccccgt ggagctggcc aaccccgaga accagttcag agtggactac    480
atcctgagtg tgatgaacgt gcctgacttt gacttccctc ccgaattcta tgagcatgcc    540
aaggctctgt gggaggatga aggagtgcgt gcctgctacg aacgctccaa cgagtaccag    600
ctgattgact gtgcccagta cttcctggac aagatcgacg tgatcaagca ggctgactat    660
gtgccgagcg atcaggacct gcttcgctgc cgtgtcctga cttctggaat ctttgagacc    720
aagttccagg tggacaaagt caacttccac atgtttgacg tgggtggcca gcgcgatgaa    780
cgccgcaagt ggatccagtg cttcaacgat gtgactgcca tcatcttcgt ggtggccagc    840
agcagctaca acatggtcat ccgggaggac aaccagacca accgcctgca ggaggctctg    900
aacctcttca agagcatctg gaacaacaga tggctgcgca ccatctctgt gatcctgttc    960
ctcaacaagc aagatctgct cgctgagaaa gtccttgctg ggaaatcgaa gattgaggac   1020
tactttccag aatttgctcg ctacactact cctgaggatg ctactcccga gcccggagag   1080
gacccacgcg tgacccgggc caagtacttc attcgagatg agtttctgag gatcagcact   1140
gccagtggag atgggcgtca ctactgctac cctcatttca cctgcgctgt ggacactgag   1200
aacatccgcc gtgtgttcaa cgactgccgt gacatcattc agcgcatgca ccttcgtcag   1260
tacgagctgc tctaagaagg gaacccccaa atttaattaa agccttaagc acaattaatt   1320
aaaagtgaaa cgtaattgta caagcagtta atcacccacc atagggcatg attaacaaag   1380
caacctttcc cttcccccga gtgattttgc gaaacccct tttcccttca gcttgcttag   1440
atgttccaaa tttagaaagc ttaaggcggc ctacagaaaa aggaaaaaag gccacaaaag   1500
ttccctctca ctttcagtaa aaataaataa aacagcagca gcaaacaaat aaaatgaaat   1560
aaaagaaaca aatgaaataa atattgtgtt gtgcagcatt aaaaaaaatc aaaataaaaa   1620
ttaaatgtga gcaaagaa                                                 1638
```

<210> SEQ ID NO 92
<211> LENGTH: 2217
<212> TYPE: DNA
<213> ORGANISM: Homo sapiens

<400> SEQUENCE: 92

```
ccccgccgcc gccgcccttc gcgccctggg ccatctccct cccacctccc tccgcggagc     60
agccagacag cgagggcccc ggccgggggc aggggggacg ccccgtccgg ggcacccccc    120
cggctctgag ccgcccgcgg ggccggcctc ggcccggagc ggaggaagga gtcgccgagg    180
agcagcctga ggccccagag tctgagacga gccgccgccg cccccgccac tgcggggagg    240
agggggagga ggagcgggag gagggacgag ctggtcggga gaagaggaaa aaaacttttg    300
agacttttcc gttgccgctg ggagccggag gcgcggggac ctcttggcgc gacgctgccc    360
cgcgaggagg caggacttgg ggaccccaga ccgcctccct ttgccgccgg ggacgcttgc    420
tccctccctg ccccctacac ggcgtccctc aggcgccccc attccggacc agccctcggg    480
agtcgccgac ccggcctccc gcaaagactt ttccccagac ctcgggcgca ccccctgcac    540
gccgccttca tccccggcct gtctcctgag cccccgcgca tcctagaccc tttctcctcc    600
aggagacgga tctctctccg acctgccaca gatcccctat tcaagaccac ccaccttctg    660
gtaccagatc gcgcccatct aggttatttc cgtgggatac tgagacaccc ccggtccaag    720
cctcccctcc accactgcgc ccttctccct gaggacctca gctttccctc gaggccctcc    780
tacctttgc cgggagaccc ccagcccctg caggggcggg gcctccccac cacaccagcc     840
ctgttcgcgc tctcggcagt gccgggggc gccgcctccc ccatgccgcc ctccgggctg     900
```

```
cggctgctgc cgctgctgct accgctgctg tggctactgg tgctgacgcc tggccggccg    960
gccgcgggac tatccacctg caagactatc gacatggagc tggtgaagcg gaagcgcatc   1020
gaggccatcc gcggccagat cctgtccaag ctgcggctcg ccagcccccc gagccagggg   1080
gaggtgccgc ccggcccgct gcccgaggcc gtgctcgccc tgtacaacag cacccgcgac   1140
cgggtggccg gggagagtgc agaaccggag cccgagcctg aggccgacta ctacgccaag   1200
gaggtcaccc gcgtgctaat ggtggaaacc cacaacgaaa tctatgacaa gttcaagcag   1260
agtacacaca gcatatatat gttcttcaac acatcagagc tccgagaagc ggtacctgaa   1320
cccgtgttgc tctcccgggc agagctgcgt ctgctgaggc tcaagttaaa agtggagcag   1380
cacgtggagc tgtaccagaa atacagcaac aattcctggc gatacctcag caaccggctg   1440
ctggcaccca gcgactcgcc agagtggtta tcttttgatg tcaccggagt tgtgcggcag   1500
tggttgagcc gtggagggga aattgagggc tttcgcctta gcgcccactg ctcctgtgac   1560
agcagggata acacactgca agtggacatc aacgggttca ctaccggccg ccgaggtgac   1620
ctggccacca ttcatggcat gaaccggcct ttcctgcttc tcatggccac cccgctggag   1680
agggcccagc atctgcaaag ctcccggcac cgccgagccc tggacaccaa ctattgcttc   1740
agctccacgg agaagaactg ctgcgtgcgg cagctgtaca ttgacttccg caaggacctc   1800
ggctggaagt ggatccacga gcccaagggc taccatgcca acttctgcct cgggccctgc   1860
ccctacattt ggagcctgga cacgcagtac agcaaggtcc tggccctgta caaccagcat   1920
aacccgggcg cctcggcggc gccgtgctgc gtgccgcagg cgctggagcc gctgcccatc   1980
gtgtactacg tgggccgcaa gcccaaggtg gagcagctgt ccaacatgat cgtgcgctcc   2040
tgcaagtgca gctgaggtcc cgccccgccc cgccccgccc cggcaggccc ggccccaccc   2100
cgccccgccc ccgctgcctt gcccatgggg gctgtattta aggacacccg tgccccaagc   2160
ccacctgggg ccccattaaa gatggagaga ggactgcgga aaaaaaaaaa aaaaaaa      2217
```

<210> SEQ ID NO 93
<211> LENGTH: 2276
<212> TYPE: DNA
<213> ORGANISM: Homo sapiens

<400> SEQUENCE: 93

```
gaacgtggta taaaaggggc gggaggccag gctcgtgccg ttttgcagac gccaccgccg     60
aggaaaaccg tgtactatta gccatggtca accccaccgt gttcttcgac attgccgtcg    120
acggcgagcc cttgggccgc gtctcctttg agctgtttgc agacaaggtc ccaaagacag    180
cagaaaattt tcgtgctctg agcactggag agaaaggatt tggttataag ggttcctgct    240
ttcacagaat tattccaggg tttatgtgtc agggtggtga cttcacacgc cataatggca    300
ctggtggcaa gtccatctat ggggagaaat ttgaagatga gaacttcatc ctaaagcata    360
cgggtcctgg catcttgtcc atggcaaatg ctggacccaa cacaaatggt tcccagtttt    420
tcatctgcac tgccaagact gagtggttgg atggcaagca tgtggtgttt ggcaaagtga    480
aagaaggcat gaatattgtg gaggccatgg agcgctttgg gtccaggaat ggcaagacca    540
gcaagaagat caccattgct gactgtggac aactcgaata agtttgactt gtgttttatc    600
ttaaccacca gatcattcct tctgtagctc aggagagcac ccctccaccc catttgctcg    660
cagtatccta gaatctttgt gctctcgctg cagttccctt tgggttccat gttttccttg    720
ttccctccca tgcctagctg gattgcagag ttaagtttat gattatgaaa taaaaactaa    780
```

```
ataacaattg tcctcgtttg agttaagagt gttgatgtag gctttatttt aagcagtaat    840
gggttacttc tgaaacatca cttgtttgct taattctaca cagtacttag attttttttta    900
ctttccagtc ccaggaagtg tcaatgtttg ttgagtggaa tattgaaaat gtaggcagca    960
actgggcatg gtggctcact gtctgtaatg tattacctga ggcagaagac cacctgaggg   1020
taggagtcaa gatcagcctg ggcaacatag tgagacgctg tctctacaaa aaataattag   1080
cctggcctgg tggtgcatgc ctagtcctag ctgatctgga ggctgacgtg ggaggattgc   1140
ttgagcctag agtgagctat tatcatgcca ctgtacagcc tgggtgttca cagatcttgt   1200
gtctcaaagg taggcagagg caggaaaagc aaggagccag aattaagagg ttgggtcagt   1260
ctgcagtgag ttcatgcatt tagaggtgtt cttcaagatg actaatgtca aaaattgaga   1320
catctgttgc ggtttttttt tttttttttt cccctggaat gcagtggcgt gatctcagct   1380
cactgcagcc tccgcctcct gggttcaagt gattctagtg cctcagcctc ctgagtagct   1440
gggataatgg gcgtgtgcca ccatgcccag ctaatttttg tatttttagt atagatgggg   1500
tttcatcatt ttgaccaggc tggtctcaaa ctcttgacct cagctgatgc gcctgccttg   1560
gcctcccaaa ctgctgagat tacagatgtg agccaccgca ccctacctca ttttctgtaa   1620
caaagctaag cttgaacact gttgatgttc ttgagggaag catattgggc tttaggctgt   1680
aggtcaagtt tatacatctt aattatggtg gaattcctat gtagagtcta aaaagccagg   1740
tacttggtgc tacagtcagt ctccctgcag agggttaagg cgcagactac ctgcagtgag   1800
gaggtactgc ttgtagcata tagagcctct ccctagcttt ggttatggag gctttgaggt   1860
tttgcaaacc tgaccaattt aagccataag atctggtcaa agggataccc ttcccactaa   1920
ggacttggtt tctcaggaaa ttatatgtac agtgcttgct ggcagttaga tgtcaggaca   1980
atctaagctg agaaaacccc ttctctgccc accttaacag acctctaggg ttcttaaccc   2040
agcaatcaag tttgcctatc ctagaggtgg cggatttgat catttggtgt gttgggcaat   2100
ttttgtttta ctgtctggtt ccttctgcgt gaattaccac caccaccact tgtgcatctc   2160
agtcttgtgt gttgtctggt tacgtattcc ctgggtgata ccattcaatg tcttaatgta   2220
cttgtggctc agacctgagt gcaaggtgga aataaacatc aaacatcttt tcatta       2276
```

<210> SEQ ID NO 94
<211> LENGTH: 5572
<212> TYPE: DNA
<213> ORGANISM: Homo sapiens

<400> SEQUENCE: 94

```
cctcccctcg cccggcgcgg tcccgtccgc ctctcgctcg cctcccgcct cccctcggtc     60
ttccgaggcg cccgggctcc cggcgcggcg gcggaggggg cgggcaggcc ggcgggcggt    120
gatgtggcgg gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cacctcccgc tcctggagcg gggggggagaa gcggcggcgg    540
cggcggccgc ggcggctgca gctccaggga gggggtctga gtcgcctgtc accatttcca    600
gggctgggaa cgccggagag ttggtctctc cccttctact gcctccaaca cggcggcggc    660
```

```
ggcggcggca catccaggga cccgggccgg ttttaaacct cccgtccgcc gccgccgcac    720
cccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
aagcggcggc agagcgaggg gcatcagcta ccgccaagtc cagagccatt tccatcctgc    960
agaagaagcc ccgccaccag cagcttctgc catctctctc ctcctttttc ttcagccaca   1020
ggctcccaga catgacagcc atcatcaaag agatcgttag cagaaacaaa aggagatatc   1080
aagaggatgg attcgactta gacttgacct atatttatcc aaacattatt gctatgggat   1140
ttcctgcaga aagacttgaa ggcgtataca ggaacaatat tgatgatgta gtaaggtttt   1200
tggattcaaa gcataaaaac cattacaaga tatacaatct ttgtgctgaa agacattatg   1260
acaccgccaa atttaattgc agagttgcac aatatccttt tgaagaccat aacccaccac   1320
agctagaact tatcaaaccc ttttgtgaag atcttgacca atggctaagt gaagatgaca   1380
atcatgttgc agcaattcac tgtaaagctg gaaagggacg aactggtgta atgatatgtg   1440
catatttatt acatcggggc aaatttttaa aggcacaaga ggccctagat ttctatgggg   1500
aagtaaggac cagagacaaa aagggagtaa ctattcccag tcagaggcgc tatgtgtatt   1560
attatagcta cctgttaaag aatcatctgg attatagacc agtggcactg ttgtttcaca   1620
agatgatgtt tgaaactatt ccaatgttca gtggcggaac ttgcaatcct cagtttgtgg   1680
tctgccagct aaaggtgaag atatattcct ccaattcagg acccacacga cgggaagaca   1740
agttcatgta ctttgagttc cctcagccgt tacctgtgtg tggtgatatc aaagtagagt   1800
tcttccacaa acagaacaag atgctaaaaa aggacaaaat gtttcacttt tgggtaaata   1860
cattcttcat accaggacca gaggaaacct cagaaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt ttttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
```

```
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
accctttgga ccttacacat tctattacaa tgaattttgc agttttgcac atttttttaaa  3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
aaaaaagaca tttgattttt cagtagaaat tgtcctacat gtgctttatt gatttgctat   3660
tgaaagaata gggttttttt tttttttttt tttttttttt ttaaatgtgc agtgttgaat   3720
catttcttca tagtgctccc ccgagttggg actagggctt caatttcact tcttaaaaaa   3780
aatcatcata tatttgatat gcccagactg catacgattt taagcggagt acaactacta   3840
ttgtaaagct aatgtgaaga tattattaaa aaggtttttt tttccagaaa tttggtgtct   3900
tcaaattata ccttcacctt gacatttgaa tatccagcca ttttgtttct taatggtata   3960
aaattccatt ttcaataact tattggtgct gaaattgttc actagctgtg gtctgaccta   4020
gttaatttac aaatacagat tgaataggac ctactagagc agcatttata gagtttgatg   4080
gcaaatagat taggcagaac ttcatctaaa atattcttag taaataatgt tgacacgttt   4140
tccatacctt gtcagtttca ttcaacaatt tttaaatttt taacaaagct cttaggattt   4200
acacatttat atttaaacat tgatatatag agtattgatt gattgctcat aagttaaatt   4260
ggtaaagtta gagacaacta ttctaacacc tcaccattga aatttatatg ccaccttgtc   4320
tttcataaaa gctgaaaatt gttacctaaa atgaaaatca acttcatgtt ttgaagatag   4380
ttataaatat tgttctttgt tacaatttcg ggcaccgcat attaaaacgt aactttattg   4440
ttccaatatg taacatggag ggccaggtca taaataatga cattataatg ggcttttgca   4500
ctgttattat ttttcctttg gaatgtgaag gtctgaatga gggttttgat tttgaatgtt   4560
tcaatgtttt tgagaagcct tgcttacatt ttatggtgta gtcattggaa atggaaaaat   4620
ggcattatat atattatata tataaatata tattatacat actctcctta ctttatttca   4680
gttaccatcc ccatagaatt tgacaagaat tgctatgact gaaaggtttt cgagtcctaa   4740
ttaaaacttt atttatggca gtattcataa ttagcctgaa atgcattctg taggtaatct   4800
ctgagtttct ggaatatttt cttagacttt ttggatgtgc agcagcttac atgtctgaag   4860
ttacttgaag gcatcacttt taagaaagct tacagttggg ccctgtacca tcccaagtcc   4920
tttgtagctc ctcttgaaca tgtttgccat acttttaaaa gggtagttga ataaatagca   4980
tcaccattct ttgctgtggc acaggttata aacttaagtg gagtttaccg gcagcatcaa   5040
atgtttcagc tttaaaaaat aaaagtaggg tacaagttta atgtttagtt ctagaaattt   5100
tgtgcaatat gttcataacg atggctgtgg ttgccacaaa gtgcctcgtt tacctttaaa   5160
tactgttaat gtgtcatgca tgcagatgga aggggtggaa ctgtgcacta aagtgggggc   5220
tttaactgta gtatttggca gagttgcctt ctacctgcca gttcaaaagt tcaacctgtt   5280
ttcatataga atatatatac taaaaaattt cagtctgtta aacagcctta ctctgattca   5340
gcctcttcag atactcttgt gctgtgcagc agtggctctg tgtgtaaatg ctatgcactg   5400
```

aggatacaca aaaataccaa tatgatgtgt acaggataat gcctcatccc aatcagatgt 5460
ccatttgtta ttgtgtttgt taacaaccct ttatctctta gtgttataaa ctccacttaa 5520
aactgattaa agtctcattc ttgtcaaaaa aaaaaaaaaa aaaaaaaaaa aa 5572

<210> SEQ ID NO 95
<211> LENGTH: 2080
<212> TYPE: DNA
<213> ORGANISM: Homo sapiens

<400> SEQUENCE: 95
ggagggcagt ctccgagttt cggaggggct tggagtgagt ggacgcactc gggaattgta 60
ggaggacgag gctcagctct tgccaggcca aattgagaca tgtctgacac aagcgagagt 120
ggtgcaggtc taactcgctt ccaggctgaa gcttcagaaa aggacagtag ctcgatgatg 180
cagactctgt tgacagtgac ccagaatgtg gaggtcccag agacaccgaa ggcctcaaag 240
gcactggagg tctcagagga tgtgaaggtc tcaaaagcct ctggggtctc aaaggccaca 300
gaggtctcaa agaccccaga ggctcgggag gcacctgcca cccaggcctc atctactact 360
cagctgactg atacccaggt tctggcagct gaaaacaaga gtctagcagc tgacaccaag 420
aaacagaatg ctgacccgca ggctgtgaca atgcctgcca ctgagaccaa aaaggtcagc 480
catgtggctg atacaaaggt caatacaaag gctcaggaga ctgaggctgc accctctcag 540
gccccagcag atgaacctga gcctgagagt gcagctgccc agtctcagga gaatcaggat 600
actcggccca aggtcaaagc caagaaagcc cgaaaggtga agcatctgga tggggaagag 660
gatggcagca gtgatcagag tcaggcttct ggaaccacag gtggccgaag ggtctcaaag 720
gccctaatgg cctcaatggc ccgcagggct tcaaggggtc ccatagcctt ttgggcccgc 780
agggcatcaa ggactcggtt ggctgcttgg gcccggagag ccttgctctc cctgagatca 840
cctaaagccc gtaggggcaa ggctcgccgt agagctgcca agctccagtc atcccaagag 900
cctgaagcac caccacctcg ggatgtggcc cttttgcaag ggagggcaaa tgatttggtg 960
aagtaccttt tggctaaaga ccagacgaag attcccatca agcgctcgga catgctgaag 1020
gacatcatca aagaatacac tgatgtgtac cccgaaatca ttgaacgagc aggctattcc 1080
ttggagaagg tatttgggat tcaattgaag gaaattgata agaatgacca cttgtacatt 1140
cttctcagca ccttagagcc cactgatgca ggcatactgg gaacgactaa ggactcaccc 1200
aagctgggtc tgctcatggt gcttcttagc atcatcttca tgaatggaaa tcggtccagt 1260
gaggctgtca tctgggaggt gctgcgcaag ttggggctgc gccctgggat acatcattca 1320
ctctttgggg acgtgaagaa gctcatcact gatgagtttg tgaagcagaa gtacctggac 1380
tatgccagag tccccaatag caatccccct gaatatgagt tcttctgggg cctgcgctct 1440
tactatgaga ccagcaagat gaaagtcctc aagtttgcct gcaaggtaca aaagaaggat 1500
cccaaggaat gggcagctca gtaccgagag gcgatggaag cggatttgaa ggctgcagct 1560
gaggctgcag ctgaagccaa ggctagggcc gagattagag ctcgaatggg cattgggctc 1620
ggctcggaga atgctgccgg gccctgcaac tgggacgaag ctgatatcgg accctgggcc 1680
aaagcccgga tccaggcggg agcagaagct aaagccaaag cccaagagag tggcagtgcc 1740
agcactggtg ccagtaccag taccaataac agtgccagtg ccagtgccag caccagtggt 1800
ggcttcagtg ctggtgccag cctgaccgcc actctcacat ttgggctctt cgctggcctt 1860
ggtggagctg gtgccagcac cagtggcagc tctggtgcct gtggtttctc ctacaagtga 1920

```
gattttagat attgttaatc ctgccagtct ttctcttcaa gccagggtgc atcctcagaa   1980

acctactcaa cacagcactc taggcagcca ctatcaatca attgaagttg acactctgca   2040

ttaaatctat ttgccatttc aaaaaaaaaa aaaaaaaaaa                         2080


<210> SEQ ID NO 96
<211> LENGTH: 2092
<212> TYPE: DNA
<213> ORGANISM: Homo sapiens

<400> SEQUENCE: 96

ggaggctgag acttcgagag ggacttagag aaggcagacg catcccgaac tcgctggagg     60

acaaggctca gctcttgcca ggccaaattg agacatgtct gacacaagcg agagtggtgc    120

aggtctaact cgcttccagg ctgaagcttc agaaaaggac agtagctcga tgatgcagac    180

tctgttgaca gtgacccaga atgtggaggt cccagagaca ccgaaggcct caaaggcact    240

ggaggtctca gaggatgtga aggtctcaaa agcctctggg gtctcaaagg ccacagaggt    300

ctcaaagacc ccagaggctc gggaggcacc tgccacccag gcctcatcta ctactcagct    360

gactgatacc caggttctgg cagctgaaaa caagagtcta gcagctgaca ccaagaaaca    420

gaatgctgac ccgcaggctg tgacaatgcc tgccactgag accaaaaagg tcagccatgt    480

ggctgataca aaggtcaata caaaggctca ggagactgag gctgcaccct ctcaggcccc    540

agcagatgaa cctgagcctg agagtgcagc tgcccagtct caggagaatc aggatactcg    600

gcccaaggtc aaagccaaga aagcccgaaa ggtgaagcat ctggatgggg aagaggatgg    660

cagcagtgat cagagtcagg cttctggaac cacaggtggc cgaagggtct caaaggccct    720

aatggcctca atggcccgca gggcttcaag gggtcccata gccttttggg cccgcagggc    780

atcaaggact cggttggctg cttgggcccg gagagccttg ctctccctga gatcacctaa    840

agcccgtagg ggcaaggctc gccgtagagc tgccaagctc cagtcatccc aagagcctga    900

agcaccacca cctcgggatg tggccctttt gcaagggagg gcaaatgatt tggtgaagta    960

ccttttggct aaagaccaga cgaagattcc catcaagcgc tcggacatgc tgaaggacat   1020

catcaaagaa tacactgatg tgtaccccga aatcattgaa cgagcaggct attccttgga   1080

gaaggtattt gggattcaat tgaaggaaat tgataagaat gaccacttgt acattcttct   1140

cagcacctta gagcccactg atgcaggcat actgggaacg actaaggact cacccaagct   1200

gggtctgctc atggtgcttc ttagcatcat cttcatgaat ggaaatcggt ccagtgaggc   1260

tgtcatctgg gaggtgctgc gcaagttggg gctgcgccct gggatacatc attcactctt   1320

tggggacgtg aagaagctca tcactgatga gtttgtgaag cagaagtacc tggactatgc   1380

cagagtcccc aatagcaatc cccctgaata tgagttcttc tggggcctgc gctcttacta   1440

tgagaccagc aagatgaaag tcctcaagtt tgcctgcaag gtacaaaaga aggatcccaa   1500

ggaatgggca gctcagtacc gagaggcgat ggaagcggat ttgaaggctg cagctgaggc   1560

tgcagctgaa gccaaggcta gggccgagat tagagctcga atgggcattg ggctcggctc   1620

ggagaatgct gccgggccct gcaactggga cgaagctgat atcggaccct gggccaaagc   1680

ccggatccag gcgggagcag aagctaaagc caaagcccaa gagagtggca gtgccagcac   1740

tggtgccagt accagtacca ataacagtgc cagtgccagt gccagcacca gtggtggctt   1800

cagtgctggt gccagcctga ccgccactct cacatttggg ctcttcgctg gccttggtgg   1860

agctggtgcc agcaccagtg gcagctctgg tgcctgtggt ttctcctaca agtgagattt   1920

tagatattgt taatcctgcc agtctttctc ttcaagccag ggtgcatcct cagaaaccta   1980
```

```
ctcaacacag cactctaggc agccactatc aatcaattga agttgacact ctgcattaaa   2040

tctatttgcc atttcaaaaa aaaaaaaaaa aaaaaaaaaa aaaaaaaaaa aa           2092


<210> SEQ ID NO 97
<211> LENGTH: 2174
<212> TYPE: DNA
<213> ORGANISM: Homo sapiens

<400> SEQUENCE: 97

gggaaaaggg gcggggtcct cagagctgcc gcgctggcac atcttcctgg agaaggggag     60

ggtgcggctg cagagaattg agacttagaa gctttgaatt cctgtatctg agaacggagt    120

cgttgggggt ggtggagggg gttggaattg gggacctacg gaaggctcag ctcttgccag    180

gccaaattga gacatgtctg acacaagcga gagtggtgca ggtctaactc gcttccaggc    240

tgaagcttca gaaaaggaca gtagctcgat gatgcagact ctgttgacag tgacccagaa    300

tgtggaggtc ccagagacac cgaaggcctc aaaggcactg gaggtctcag aggatgtgaa    360

ggtctcaaaa gcctctgggg tctcaaaggc cacagaggtc tcaaagaccc cagaggctcg    420

ggaggcacct gccacccagg cctcatctac tactcagctg actgataccc aggttctggc    480

agctgaaaac aagagtctag cagctgacac caagaaacag aatgctgacc cgcaggctgt    540

gacaatgcct gccactgaga ccaaaaaggt cagccatgtg gctgatacaa aggtcaatac    600

aaaggctcag gagactgagg ctgcaccctc tcaggcccca gcagatgaac ctgagcctga    660

gagtgcagct gcccagtctc aggagaatca ggatactcgg cccaaggtca aagccaagaa    720

agcccgaaag gtgaagcatc tggatgggga agaggatggc agcagtgatc agagtcaggc    780

ttctggaacc acaggtggcc gaagggtctc aaaggcccta atggcctcaa tggcccgcag    840

ggcttcaagg ggtcccatag ccttttgggc ccgcagggca tcaaggactc ggttggctgc    900

ttgggcccgg agagccttgc tctccctgag atcacctaaa gcccgtaggg gcaaggctcg    960

ccgtagagct gccaagctcc agtcatccca agagcctgaa gcaccaccac ctcgggatgt   1020

ggcccttttg caagggaggg caaatgattt ggtgaagtac cttttggcta aagaccagac   1080

gaagattccc atcaagcgct cggacatgct gaaggacatc atcaaagaat acactgatgt   1140

gtaccccgaa atcattgaac gagcaggcta ttccttggag aaggtatttg ggattcaatt   1200

gaaggaaatt gataagaatg accacttgta cattcttctc agcaccttag agcccactga   1260

tgcaggcata ctgggaacga ctaaggactc acccaagctg ggtctgctca tggtgcttct   1320

tagcatcatc ttcatgaatg gaaatcggtc cagtgaggct gtcatctggg aggtgctgcg   1380

caagttgggg ctgcgccctg ggatacatca ttcactcttt ggggacgtga agaagctcat   1440

cactgatgag tttgtgaagc agaagtacct ggactatgcc agagtcccca atagcaatcc   1500

ccctgaatat gagttcttct ggggcctgcg ctcttactat gagaccagca agatgaaagt   1560

cctcaagttt gcctgcaagg tacaaaagaa ggatcccaag gaatgggcag ctcagtaccg   1620

agaggcgatg gaagcggatt tgaaggctgc agctgaggct gcagctgaag ccaaggctag   1680

ggccgagatt agagctcgaa tgggcattgg gctcggctcg gagaatgctg ccgggccctg   1740

caactgggac gaagctgata tcggaccctg ggccaaagcc cggatccagg cgggagcaga   1800

agctaaagcc aaagcccaag agagtggcag tgccagcact ggtgccagta ccagtaccaa   1860

taacagtgcc agtgccagtg ccagcaccag tggtggcttc agtgctggtg ccagcctgac   1920

cgccactctc acatttgggc tcttcgctgg ccttggtgga gctggtgcca gcaccagtgg   1980
```

```
cagctctggt gcctgtggtt tctcctacaa gtgagatttt agatattgtt aatcctgcca   2040
gtctttctct tcaagccagg gtgcatcctc agaaacctac tcaacacagc actctaggca   2100
gccactatca atcaattgaa gttgacactc tgcattaaat ctatttgcca tttcaaaaaa   2160
aaaaaaaaaa aaaa                                                      2174
```

<210> SEQ ID NO 98
<211> LENGTH: 2162
<212> TYPE: DNA
<213> ORGANISM: Homo sapiens

<400> SEQUENCE: 98

```
cgagttccgg cgaggcttca gggtacagct cccccgcagc cagaagccgg gcctgcagcg     60
cctcagcacc gctccgggac accccacccg cttcccaggc gtgacctgtc aacagcaact    120
tcgcggtgtg gtgaactctc tgaggaaaaa ccattttgat tattactctc agacgtgcgt    180
ggcaacaagt gactgagacc tagaaatcca agcgttggag gtcctgaggc cagcctaagt    240
cgcttcaaaa tggaacgaag gcgtttgtgg ggttccattc agagccgata catcagcatg    300
agtgtgtgga caagcccacg gagacttgtg gagctggcag ggcagagcct gctgaaggat    360
gaggccctgg ccattgccgc cctggagttg ctgcccaggg agctcttccc gccactcttc    420
atggcagcct ttgacgggag acacagccag accctgaagg caatggtgca ggcctggccc    480
ttcacctgcc tccctctggg agtgctgatg aagggacaac atcttcacct ggagaccttc    540
aaagctgtgc ttgatggact tgatgtgctc cttgcccagg aggttcgccc caggaggtgg    600
aaacttcaag tgctggattt acggaagaac tctcatcagg acttctggac tgtatggtct    660
ggaaacaggg ccagtctgta ctcatttcca gagccagaag cagctcagcc catgacaaag    720
aagcgaaaag tagatggttt gagcacagag gcagagcagc ccttcattcc agtagaggtg    780
ctcgtagacc tgttcctcaa ggaaggtgcc tgtgatgaat tgttctccta cctcattgag    840
aaagtgaagc gaaagaaaaa tgtactacgc ctgtgctgta agaagctgaa gatttttgca    900
atgcccatgc aggatatcaa gatgatcctg aaaatggtgc agctggactc tattgaagat    960
ttggaagtga cttgtacctg gaagctaccc accttggcga aattttctcc ttacctgggc   1020
cagatgatta atctgcgtag actcctcctc tcccacatcc atgcatcttc ctacatttcc   1080
ccggagaagg aagagcagta tatcgcccag ttcacctctc agttcctcag tctgcagtgc   1140
ctgcaggctc tctatgtgga ctctttattt ttccttagag gccgcctgga tcagttgctc   1200
aggcacgtga tgaacccctt ggaaaccctc tcaataacta actgccggct ttcggaaggg   1260
gatgtgatgc atctgtccca gagtcccagc gtcagtcagc taagtgtcct gagtctaagt   1320
ggggtcatgc tgaccgatgt aagtcccgag cccctccaag ctctgctgga gagagcctct   1380
gccaccctcc aggacctggt ctttgatgag tgtgggatca cggatgatca gctccttgcc   1440
ctcctgcctt ccctgagcca ctgctcccag cttacaacct taagcttcta cgggaattcc   1500
atctccatat ctgccttgca gagtctcctg cagcacctca tcgggctgag caatctgacc   1560
cacgtgctgt atcctgtccc cctggagagt tatgaggaca tccatggtac cctccacctg   1620
gagaggcttg cctatctgca tgccaggctc agggagttgc tgtgtgagtt ggggcggccc   1680
agcatggtct ggcttagtgc caacccctgt cctcactgtg gggacagaac cttctatgac   1740
ccggagccca tcctgtgccc ctgtttcatg cctaactagc tgggtgcaca tatcaaatgc   1800
ttcattctgc atacttggac actaaagcca ggatgtgcat gcatcttgaa gcaacaaagc   1860
agccacagtt tcagacaaat gttcagtgtg agtgaggaaa acatgttcag tgaggaaaaa   1920
```

```
acattcagac aaatgttcag tgaggaaaaa aaggggaagt tggggatagg cagatgttga   1980
cttgaggagt taatgtgatc tttggggaga tacatcttat agagttagaa atagaatctg   2040
aatttctaaa gggagattct ggcttgggaa gtacatgtag gagttaatcc ctgtgtagac   2100
tgttgtaaag aaactgttga aaataaagag aagcaatgtg aagcaaaaaa aaaaaaaaaa   2160
aa                                                                  2162
```

<210> SEQ ID NO 99
<211> LENGTH: 2776
<212> TYPE: DNA
<213> ORGANISM: Homo sapiens

<400> SEQUENCE: 99

```
cgagttccgg cgaggcttca gggtacagct cccccgcagc cagaagccgg gcctgcagcg     60
cctcagcacc gctccgggac accccacccg cttcccaggc gtgacctgtc aacagcaact    120
tcgcggtgtg gtgaactctc tgaggaaaaa cgtaagttcg agccctgatt cctccgcttc    180
cccgcagggt gaccttgggc ttgtgccccc ggcaccaccc ctgtcccggg tccctgtttt    240
ctctctggaa atgggttgaa gaccaaagaa aataatgtgc gccacttggg tcaccccggg    300
ccgcctgccc cggaaaattg gccccagttg aggagttgtg gctgtaagga tgccttgaac    360
cgaggcggcg gtgctcgtgg ttggagctct ccagggtggg tgcgcatttg taatgcggtg    420
gatgctctgg gactcggccc ctctgaaggt gctgggggtt ggggacggcc caggcagtgg    480
cgtaggcgtc ctaggaaggc gggagcagag gcagaaatgt cgctgcaaga ccgtagtcag    540
ggtccttgac cacaggggtc acttgtgacc aaccacatgg tctgttgttc ctcctgcccc    600
ctggttcagc ccaggaaaca ctggtgctca ggtttggagc cagagatttg cactgaaagg    660
gcgggattga gtcgccagtt gtcagtttcc tcagcagtat ttgcggaggt tttcacagga    720
ggccgttgct tcgtaaatat tatacatgta ttcttctttt tggagcattt tgattattac    780
tctcagacgt gcgtggcaac aagtgactga gacctagaaa tccaagcgtt ggaggtcctg    840
aggccagcct aagtcgcttc aaaatggaac gaaggcgttt gtggggttcc attcagagcc    900
gatacatcag catgagtgtg tggacaagcc cacggagact tgtggagctg gcagggcaga    960
gcctgctgaa ggatgaggcc ctggccattg ccgccctgga gttgctgccc agggagctct   1020
tcccgccact cttcatggca gcctttgacg ggagacacag ccagaccctg aaggcaatgg   1080
tgcaggcctg gcccttcacc tgcctccctc tgggagtgct gatgaaggga caacatcttc   1140
acctggagac cttcaaagct gtgcttgatg gacttgatgt gctccttgcc caggaggttc   1200
gccccaggag gtggaaactt caagtgctgg atttacggaa gaactctcat caggacttct   1260
ggactgtatg gtctggaaac agggccagtc tgtactcatt tccagagcca gaagcagctc   1320
agcccatgac aaagaagcga aaagtagatg gtttgagcac agaggcagag cagcccttca   1380
ttccagtaga ggtgctcgta gacctgttcc tcaaggaagg tgcctgtgat gaattgttct   1440
cctacctcat tgagaaagtg aagcgaaaga aaaatgtact acgcctgtgc tgtaagaagc   1500
tgaagatttt tgcaatgccc atgcaggata tcaagatgat cctgaaaatg gtgcagctgg   1560
actctattga agatttggaa gtgacttgta cctggaagct acccaccttg gcgaaatttt   1620
ctccttacct gggccagatg attaatctgc gtagactcct cctctcccac atccatgcat   1680
cttcctacat ttccccggag aaggaagagc agtatatcgc ccagttcacc tctcagttcc   1740
tcagtctgca gtgcctgcag gctctctatg tggactcttt atttttcctt agaggccgcc   1800
```

```
tggatcagtt gctcaggcac gtgatgaacc ccttggaaac cctctcaata actaactgcc   1860
ggctttcgga aggggatgtg atgcatctgt cccagagtcc cagcgtcagt cagctaagtg   1920
tcctgagtct aagtggggtc atgctgaccg atgtaagtcc cgagcccctc caagctctgc   1980
tggagagagc ctctgccacc ctccaggacc tggtctttga tgagtgtggg atcacggatg   2040
atcagctcct tgccctcctg ccttccctga gccactgctc ccagcttaca accttaagct   2100
tctacgggaa ttccatctcc atatctgcct tgcagagtct cctgcagcac ctcatcgggc   2160
tgagcaatct gacccacgtg ctgtatcctg tcccctgga gagttatgag gacatccatg    2220
gtaccctcca cctggagagg cttgcctatc tgcatgccag gctcagggag ttgctgtgtg   2280
agttggggcg gcccagcatg gtctggctta gtgccaaccc ctgtcctcac tgtggggaca   2340
gaaccttcta tgacccggag cccatcctgt gcccctgttt catgcctaac tagctgggtg   2400
cacatatcaa atgcttcatt ctgcatactt ggacactaaa gccaggatgt gcatgcatct   2460
tgaagcaaca aagcagccac agtttcagac aaatgttcag tgtgagtgag gaaaacatgt   2520
tcagtgagga aaaaacattc agacaaatgt tcagtgagga aaaaaagggg aagttgggga   2580
taggcagatg ttgacttgag gagttaatgt gatctttggg gagatacatc ttatagagtt   2640
agaaatagaa tctgaatttc taaagggaga ttctggcttg ggaagtacat gtaggagtta   2700
atccctgtgt agactgttgt aaagaaactg ttgaaaataa agagaagcaa tgtgaagcaa   2760
aaaaaaaaaa aaaaaa                                                   2776

<210> SEQ ID NO 100
<211> LENGTH: 2141
<212> TYPE: DNA
<213> ORGANISM: Homo sapiens

<400> SEQUENCE: 100

cgagttccgg cgaggcttca gggtacagct cccccgcagc cagaagccgg gcctgcagcg     60
cctcagcacc gctccgggac accccacccg cttcccaggc gtgacctgtc aacagcaact    120
tcgcggtgtg gtgaactctc tgaggaaaaa cacgtgcgtg gcaacaagtg actgagacct    180
agaaatccaa gcgttggagg tcctgaggcc agcctaagtc gcttcaaaat ggaacgaagg    240
cgtttgtggg gttccattca gagccgatac atcagcatga gtgtgtggac aagcccacgg    300
agacttgtgg agctggcagg gcagagcctg ctgaaggatg aggccctggc cattgccgcc    360
ctggagttgc tgcccaggga gctcttcccg ccactcttca tggcagcctt tgacgggaga    420
cacagccaga ccctgaaggc aatggtgcag gcctggccct tcacctgcct ccctctggga    480
gtgctgatga agggacaaca tcttcacctg gagaccttca aagctgtgct tgatggactt    540
gatgtgctcc ttgcccagga ggttcgcccc aggaggtgga aacttcaagt gctggattta    600
cggaagaact ctcatcagga cttctggact gtatggtctg gaaacagggc cagtctgtac    660
tcatttccag agccagaagc agctcagccc atgacaaaga agcgaaaagt agatggtttg    720
agcacagagg cagagcagcc cttcattcca gtagaggtgc tcgtagacct gttcctcaag    780
gaaggtgcct gtgatgaatt gttctcctac ctcattgaga aagtgaagcg aaagaaaaat    840
gtactacgcc tgtgctgtaa gaagctgaag atttttgcaa tgcccatgca ggatatcaag    900
atgatcctga aaatggtgca gctggactct attgaagatt tggaagtgac ttgtacctgg    960
aagctaccca ccttggcgaa attttctcct tacctgggcc agatgattaa tctgcgtaga   1020
ctcctcctct cccacatcca tgcatcttcc tacatttccc cggagaagga agagcagtat   1080
atcgcccagt tcacctctca gttcctcagt ctgcagtgcc tgcaggctct ctatgtggac   1140
```

```
tctttatttt tccttagagg ccgcctggat cagttgctca ggcacgtgat gaaccccttg   1200
gaaaccctct caataactaa ctgccggctt tcggaagggg atgtgatgca tctgtcccag   1260
agtcccagcg tcagtcagct aagtgtcctg agtctaagtg gggtcatgct gaccgatgta   1320
agtcccgagc ccctccaagc tctgctggag agagcctctg ccaccctcca ggacctggtc   1380
tttgatgagt gtgggatcac ggatgatcag ctccttgccc tcctgccttc cctgagccac   1440
tgctcccagc ttacaacctt aagcttctac gggaattcca tctccatatc tgccttgcag   1500
agtctcctgc agcacctcat cggggctgagc aatctgaccc acgtgctgta tcctgtcccc   1560
ctggagagtt atgaggacat ccatggtacc ctccacctgg agaggcttgc ctatctgcat   1620
gccaggctca gggagttgct gtgtgagttg ggcggcccca gcatggtctg gcttagtgcc   1680
aacccctgtc ctcactgtgg ggacagaacc ttctatgacc cggagcccat cctgtgcccc   1740
tgtttcatgc ctaactagct gggtgcacat atcaaatgct tcattctgca tacttggaca   1800
ctaaagccag gatgtgcatg catcttgaag caacaaagca gccacagttt cagacaaatg   1860
ttcagtgtga gtgaggaaaa catgttcagt gaggaaaaaa cattcagaca aatgttcagt   1920
gaggaaaaaa aggggaagtt ggggataggc agatgttgac ttgaggagtt aatgtgatct   1980
ttggggagat acatcttata gagttagaaa tagaatctga atttctaaag ggagattctg   2040
gcttgggaag tacatgtagg agttaatccc tgtgtagact gttgtaaaga aactgttgaa   2100
aataaagaga agcaatgtga agcaaaaaaa aaaaaaaaaa a                       2141
```

<210> SEQ ID NO 101
<211> LENGTH: 2220
<212> TYPE: DNA
<213> ORGANISM: Homo sapiens

<400> SEQUENCE: 101

```
aatgtaggga aagcagggcg gagtcctctg caggctcggg ggagggggagg ggcgtgaatg     60
cgtggatttc tgtggagagt ggaaacacgg ggagtcgagg ggagcatgcg cgggcctcag    120
aaagttctgg gaaaccgact cctgggagca gggaggaacg cgcgctccag agacaacttc    180
gcggtgtggt gaactctctg aggaaaaacc attttgatta ttactctcag acgtgcgtgg    240
caacaagtga ctgagaccta gaaatccaag cgttggaggt cctgaggcca gcctaagtcg    300
cttcaaaatg gaacgaaggc gtttgtgggg ttccattcag agccgataca tcagcatgag    360
tgtgtggaca agcccacgga gacttgtgga gctggcaggg cagagcctgc tgaaggatga    420
ggccctggcc attgccgccc tggagttgct gcccagggag ctcttcccgc cactcttcat    480
ggcagccttt gacgggagac acagccagac cctgaaggca atggtgcagg cctggccctt    540
cacctgcctc cctctgggag tgctgatgaa gggacaacat cttcacctgg agaccttcaa    600
agctgtgctt gatggacttg atgtgctcct tgcccaggag gttcgcccca ggaggtggaa    660
acttcaagtg ctggatttac ggaagaactc tcatcaggac ttctggactg tatggtctgg    720
aaacagggcc agtctgtact catttccaga gccagaagca gctcagccca tgacaaagaa    780
gcgaaaagta gatggtttga gcacagaggc agagcagccc ttcattccag tagaggtgct    840
cgtagacctg ttcctcaagg aaggtgcctg tgatgaattg ttctcctacc tcattgagaa    900
agtgaagcga aagaaaaatg tactacgcct gtgctgtaag aagctgaaga tttttgcaat    960
gcccatgcag gatatcaaga tgatcctgaa aatggtgcag ctggactcta ttgaagattt   1020
ggaagtgact tgtacctgga agctacccac cttggcgaaa ttttctcctt acctgggcca   1080
```

```
gatgattaat ctgcgtagac tcctcctctc ccacatccat gcatcttcct acatttcccc   1140

ggagaaggaa gagcagtata tcgcccagtt cacctctcag ttcctcagtc tgcagtgcct   1200

gcaggctctc tatgtggact ctttattttt ccttagaggc cgcctggatc agttgctcag   1260

gcacgtgatg aacccettgg aaaccctctc aataactaac tgccggcttt cggaagggga   1320

tgtgatgcat ctgtcccaga gtcccagcgt cagtcagcta agtgtcctga gtctaagtgg   1380

ggtcatgctg accgatgtaa gtcccgagcc cctccaagct ctgctggaga gagcctctgc   1440

caccctccag gacctggtct ttgatgagtg tgggatcacg gatgatcagc tccttgccct   1500

cctgccttcc ctgagccact gctcccagct tacaacctta agcttctacg ggaattccat   1560

ctccatatct gccttgcaga gtctcctgca gcacctcatc gggctgagca atctgaccca   1620

cgtgctgtat cctgtccccc tggagagtta tgaggacatc catggtaccc tccacctgga   1680

gaggcttgcc tatctgcatg ccaggctcag ggagttgctg tgtgagttgg ggcggcccag   1740

catggtctgg cttagtgcca acccctgtcc tcactgtggg gacagaacct tctatgaccc   1800

ggagcccatc ctgtgcccct gtttcatgcc taactagctg ggtgcacata tcaaatgctt   1860

cattctgcat acttggacac taaagccagg atgtgcatgc atcttgaagc aacaaagcag   1920

ccacagtttc agacaaatgt tcagtgtgag tgaggaaaac atgttcagtg aggaaaaaac   1980

attcagacaa atgttcagtg aggaaaaaaa ggggaagttg gggataggca gatgttgact   2040

tgaggagtta atgtgatctt tggggagata catcttatag agttagaaat agaatctgaa   2100

tttctaaagg gagattctgg cttgggaagt acatgtagga gttaatccct gtgtagactg   2160

ttgtaaagaa actgttgaaa ataaagagaa gcaatgtgaa gcaaaaaaaa aaaaaaaaaa   2220
```

<210> SEQ ID NO 102
<211> LENGTH: 2197
<212> TYPE: DNA
<213> ORGANISM: Homo sapiens

<400> SEQUENCE: 102

```
aatgtaggga aagcagggcg gagtcctctg caggctcggg ggaggggagg ggcgtgaatg     60

cgtggatttc tgtggagagt ggaaacacgg ggagtcgagg ggagcatgcg cgggcctcag    120

aaagttctgg gaaaccgact cctgggagca gggaggaacg cgcgctccag agacaacttc    180

gcggtgtggt gaactctctg aggaaaaaca cgtgcgtggc aacaagtgac tgagacctag    240

aaatccaagc gttggaggtc ctgaggccag cctaagtcgc ttcaaaatgg aacgaaggcg    300

tttgtggggt tccattcaga gccgatacat cagcatgagt gtgtggacaa gcccacggag    360

acttgtggag ctggcagggc agagcctgct gaaggatgag gccctggcca ttgccgccct    420

ggagttgctg cccagggagc tcttcccgcc actcttcatg gcagcctttg acgggagaca    480

cagccagacc ctgaaggcaa tggtgcaggc ctggcccttc acctgcctcc ctctgggagt    540

gctgatgaag ggacaacatc ttcacctgga gaccttcaaa gctgtgcttg atggacttga    600

tgtgctcctt gcccaggagg ttcgccccag gaggtggaaa cttcaagtgc tggatttacg    660

gaagaactct catcaggact tctggactgt atggtctgga aacagggcca gtctgtactc    720

atttccagag ccagaagcag ctcagcccat gacaaagaag cgaaaagtag atggtttgag    780

cacagaggca gagcagccct tcattccagt agaggtgctc gtagacctgt tcctcaagga    840

aggtgcctgt gatgaattgt tctcctacct cattgagaaa gtgaagcgaa agaaaaatgt    900

actacgcctg tgctgtaaga agctgaagat ttttgcaatg cccatgcagg atatcaagat    960

gatcctgaaa atggtgcagc tggactctat tgaagatttg gaagtgactt gtacctggaa   1020
```

```
gctacccacc ttggcgaaat tttctcctta cctgggccag atgattaatc tgcgtagact   1080

cctcctctcc cacatccatg catcttccta catttccccg gagaaggaag agcagtatat   1140

cgcccagttc acctctcagt tcctcagtct gcagtgcctg caggctctct atgtggactc   1200

tttatttttc cttagaggcc gcctggatca gttgctcagg cacgtgatga acccettgga   1260

aaccctctca ataactaact gccggctttc ggaaggggat gtgatgcatc tgtcccagag   1320

tcccagcgtc agtcagctaa gtgtcctgag tctaagtggg gtcatgctga ccgatgtaag   1380

tcccgagccc ctccaagctc tgctggagag agcctctgcc accctccagg acctggtctt   1440

tgatgagtgt gggatcacgg atgatcagct ccttgccctc ctgccttccc tgagccactg   1500

ctcccagctt acaaccttaa gcttctacgg gaattccatc tccatatctg ccttgcagag   1560

tctcctgcag cacctcatcg ggctgagcaa tctgacccac gtgctgtatc ctgtccccct   1620

ggagagttat gaggacatcc atggtaccct ccacctggag aggcttgcct atctgcatgc   1680

caggctcagg gagttgctgt gtgagttggg gcggcccagc atggtctggc ttagtgccaa   1740

cccctgtcct cactgtgggg acagaacctt ctatgacccg gagcccatcc tgtgcccctg   1800

tttcatgcct aactagctgg gtgcacatat caaatgcttc attctgcata cttggacact   1860

aaagccagga tgtgcatgca tcttgaagca acaaagcagc cacagtttca gacaaatgtt   1920

cagtgtgagt gaggaaaaca tgttcagtga ggaaaaaaca ttcagacaaa tgttcagtga   1980

ggaaaaaaag ggaagttgg ggataggcag atgttgactt gaggagttaa tgtgatcttt   2040

ggggagatac atcttataga gttagaaata gaatctgaat ttctaaaggg agattctggc   2100

ttgggaagta catgtaggag ttaatccctg tgtagactgt tgtaaagaaa ctgttgaaaa   2160

taaagagaag caatgtgaag caaaaaaaaa aaaaaaa                            2197
```

<210> SEQ ID NO 103
<211> LENGTH: 4309
<212> TYPE: DNA
<213> ORGANISM: Homo sapiens

<400> SEQUENCE: 103

```
actcggcgcg cttctctccc agtgcgcagt ggcctggtgg gtcagccggc ggcggctgga     60

gcgcggggcc ggccctgcgc acgaatgaat gggcgcccgg gggacgcgcg cgctcggggc    120

tgaagggcat taggaccgtg aggatcgctc cgcgatcctg tctctcccta tcaccccccc    180

gcccccccac ctctctcctt tttctgctct gcaggactga gcagctaggc gcgagcgaaa    240

acaaacagct ggggctgcga gcgcccccgc cccggccccg agagcacgcc ggcccagtcc    300

cccacctggg gcgcccgtct gcccaccatg aggaagatcc gcgccaatgc catcgccatc    360

ctgaccgtag cctggatcct gggcactttc tactacttat ggcaggacaa ccgagcccac    420

gcagcatcct ccggcggccg gggcgcgcag agggcaggca ggaggtcgga gcagctccgc    480

gaggaccgca ccatcccgct cattgtgaca ggaactccct cgaaaggctt tgatgagaag    540

gcctacctgt cggccaagca gctgaaggct ggagaggacc cctacagaca gcacgccttc    600

aaccagctgg agagtgacaa gctgagccca gaccggccca tccgggacac ccgccattac    660

agctgcccat ctgtgtccta ctcctcggac ctgccagcca ccagcgtcat catcaccttc    720

cacaatgagg cccgttccac cctgctgcgc acagtgaaga gtgtcctgaa ccgaactcct    780

gccaacttga tccaggagat cattttagtg gatgacttca gctcagatcc ggaagactgt    840

ctactcctga ccaggatccc caaggtcaag tgcctgcgca atgatcggcg ggaagggctg    900
```

```
atccggtccc gagtgcgtgg ggcggacgtg gctgcagcta ccgttctcac ctttctggat    960
agccactgcg aagtgaacac cgagtggctg ccgcccatgc tgcagcgggt gaaggaggac   1020
cacacccgcg tggtgagtcc catcattgat gtcatcagtc tggataattt tgcctacctt   1080
gcagcatctg ctgaccttcg tggagggttc gactggagcc tgcatttcaa gtgggagcag   1140
atccctcttg agcagaagat gacccggaca gaccccacca ggcccataag gacgcctgtc   1200
atagctggag gaatcttcgt gatcgacaag tcctggttta accacttggg aaagtatgat   1260
gcccagatgg acatctgggg gggagagaat tttgagctct ccttcagggt gtggatgtgt   1320
ggtggcagtc tggagatcgt cccctgcagc cgggtgggcc atgtcttcag gaaacggcac   1380
ccctacaact tccctgaggg taatgccctc acctacatca ggaatactaa gcgcactgca   1440
gaagtgtgga tggatgaata caagcaatac tactatgagg cccggccctc ggccatcggg   1500
aaggccttcg gcagtgtggc tacgcggata gagcagagga agaagatgaa ctgcaagtcc   1560
ttccgctggt acctggagaa cgtctaccca gagctcacgg tccccgtgaa ggaagcactc   1620
cccggcatca ttaagcaggg ggtgaactgc ttagaatctc agggccagaa cacagctggt   1680
gacttcctgc ttggaatggg gatctgcaga gggtctgcca agaacccgca gcccgcccag   1740
gcatggctgt tcagtgacca cctcatccag cagcagggga agtgcctggc tgccacctcc   1800
accttaatgt cctcccctgg atccccagtc atactgcaga tgtgcaaccc tagagaaggc   1860
aagcagaaat ggaggagaaa aggatctttc atccagcatt cagtcagtgg cctctgcctg   1920
gagacaaagc ctgcccagct ggtgaccagc aagtgtcagg ctgacgccca ggcccagcag   1980
tggcagctgt tgccacacac atgacggtag ccctggggcc tcctgtacct tttgcatgag   2040
acttcgggac cggaaggggg ttagggtggg ggagtgcaaa gtgggctgtt cccatctcct   2100
cacatttctg ccaggaccat cagcaaatac ccaccatgac acacgttctc caaagcttgt   2160
tctaggaggg cgcaggcggg cacgccccga tgccctcagt gctgtcctgg ccttgccccg   2220
ggagaggaga tggtcagggt gctggactgt tgctgggtag agactgagta ggtgcccctg   2280
gccctttgtc ctctcccttg gcgcttcttg ggctgggac aatagtgtgt ggtctctccc   2340
ttgttgcccg gagaaagcaa ggacagaagc ccacacaggg gtcttttggg tcatgaggcc   2400
cagctgtgca ggcaggcagg gccaggggaa attgggcagc atggatggag aggctgaagg   2460
ctgggaagag ggaaggggag aggggcagcc tgcaggggta gctgaagaac aggaaggagg   2520
tgagaagccc ggtgacctgt cagagatgcc aagcccaggg tggcactggg ttgggtgggg   2580
acggatggtg tcttggcagc aaaggatggg taatttgcaa atgaacatgg atagaagagc   2640
agcaaagcac caaaagaaca aggtctctta cccaggacac agtcccttcc acactttacc   2700
agccccaggg tctgagcccg acgctgcctc ttccggtcct gtgcctgtgg gtgcccacat   2760
tcttagcaag aggctgcaga gggatcttta ggggaagatt cgggcgtagt ttattaaaca   2820
gactccactt ctatttggcc atgtgtcagg ctgagacctc tctctcgggc attaatgaac   2880
agctagtgcc ctgtccctgc cgccaggacc cactgaaagg acgggtagcc acacacatcc   2940
ctgagtagtc ccagcctcat ttgtcatttt tgactcctgc tttctcaaag gtttttgcct   3000
ctgtcaatac agcatcatgg gtggttggaa agaagggaac ttcccttctg gaccaagaac   3060
agcccctaag tcattagggt tcaacctcac ccttattccc ctccccgcta caggagcccc   3120
taagtcatta gggctcaacc tcacccttat tcccctccct actacaggag ggattttctt   3180
gaagggtcag ctattgcact gtgctgggag gctggctgtg gctcctgttt gtgaagagaa   3240
ctcccagttc cttttcacag ccgctgagaa cacatccaca catctacccc acggccttgt   3300
```

```
cttggaactg ctcctgctat ccccacaccc tgcttcctca ccccactggc tcttgggcaa   3360
atgactgttg gtaccaggac cctgggggtc tcccctacaa agcagaccag cctggggcag   3420
atatacctac cacaggagcc ccctgtcttt cataggccaa ggatccacat acccatagag   3480
ttcatggatt ctagagggtc taggaatctc ttgaaattgt ccctaaaata ctgcatgtgt   3540
gtgcatacat gcattttcct ggggaaaaag tccatggctt ctaaaagagg tccctgatcc   3600
ccaaagggcc tgaacctctg ctctggattg aagccactgt ctgcccaagc tgccaccccc   3660
taatcttcct ccctggcgtg ctcaaactgc catcgcctgc tccctccaca cggcccttgg   3720
ggtcagcagc caagtgtctg tggtccgcag cacctgctct ggagggctct ccagcagttt   3780
cgcctcctga ctctcaccag cgtcctctcg gcagcactcc cgtgcccaag tgcacccctc   3840
tggacttgcc agcgcaggcc ccttcgctcc cagggccatg ctttgcctgt cctctgtcgt   3900
gatgtttctt ccgcagccag gtgcagcctc agatcccctg ttcatctggg aagcctcctg   3960
ccacagctta ggacagaact gggcccaggg caaaggcctc tccccagagg atggactaga   4020
aggcctgggc cacactcggg catggacctt tggggctggg gagccggggc tgcgcctgtt   4080
gaatgtaaga ggactgctga ccagagggcc ttcaagaggg tctctctgtc ctttgctgtg   4140
gtcagatcag gctctgcact tatcagccgg tcctttgtgg caacgcagcc ctgttctgtt   4200
tttgcttttc ctcttcttga ccaaagcatg tgccactagc tgtccttgag gacctcgtct   4260
ttatgaaaca cacacctgga ataaaaccac ttcttacatg tccacatgc              4309
```

<210> SEQ ID NO 104
<211> LENGTH: 3148
<212> TYPE: DNA
<213> ORGANISM: Homo sapiens

<400> SEQUENCE: 104

```
actcggcgcg cttctctccc agtgcgcagt ggcctggtgg gtcagccggc ggcggctgga     60
gcgcggggcc ggccctgcgc acgaatgaat gggcgcccgg gggacgcgcg cgctcggggc    120
tgaagggcat taggaccgtg aggatcgctc cgcgatcctg tctctcccta tcaccccccc    180
gcccccccac ctctctcctt tttctgctct gcaggactga gcagctaggc gcgagcgaaa    240
acaaacagct ggggctgcga gcgcccccgc cccggccccg agagcacgcc ggcccagtcc    300
cccacctggg gcgcccgtct gcccaccatg aggaagatcc gcgccaatgc catcgccatc    360
ctgaccgtag cctggatcct gggcactttc tactacttat ggcaggacaa ccgagcccac    420
gcagcatcct ccggcggccg gggcgcgcag agggcaggca ggaggtcgga gcagctccgc    480
gaggaccgca ccatcccgct cattgtgaca ggaactccct cgaaaggctt tgatgagaag    540
gcctacctgt cggccaagca gctgaaggct ggagaggacc cctacagaca gcacgccttc    600
aaccagctgg agagtgacaa gctgagccca gaccggccca tccgggacac ccgccattac    660
agctgcccat ctgtgtccta ctcctcggac ctgccagcca ccagcgtcat catcaccttc    720
cacaatgagg cccgttccac cctgctgcgc acagtgaaga gtgtcctgaa ccgaactcct    780
gccaacttga tccaggagat cattttagtg gatgacttca gctcagatcc ggaagactgt    840
ctactcctga ccaggatccc caaggtcaag tgcctgcgca atgatcggcg ggaagggctg    900
atccggtccc gagtgcgtgg ggcggacgtg gctgcagcta ccgttctcac ctttctggat    960
agccactgcg aagtgaacac cgagtggctg ccgcccatgc tgcagcgggt gaaggaggac   1020
cacacccgcg tggtgagtcc catcattgat gtcatcagtc tggataattt tgcctacctt   1080
```

gcagcatctg ctgaccttcg tggagggttc gactggagcc tgcatttcaa gtgggagcag 1140
atccctcttg agcagaagat gacccggaca gaccccacca ggcccataag gacgcctgtc 1200
atagctggag gaatcttcgt gatcgacaag tcctggttta accacttggg aaagtatgat 1260
gcccagatgg acatctgggg gggagagaat tttgagctct ccttcagggt gtggatgtgt 1320
ggtggcagtc tggagatcgt cccctgcagc cgggtgggcc atgtcttcag gaaacggcac 1380
ccctacaact tccctgaggg taatgccctc acctacatca ggaatactaa gcgcactgca 1440
gaagtgtgga tggatgaata caagcaatac tactatgagg cccggccctc ggccatcggg 1500
aaggccttcg gcagtgtggc tacgcggata gagcagagga agaagatgaa ctgcaagtcc 1560
ttccgctggt acctggagaa cgtctaccca gagctcacgg tccccgtgaa ggaagcactc 1620
cccggcatca ttaagcaggg ggtgaactgc ttagaatctc agggccagaa cacagctggt 1680
gacttcctgc ttggaatggg gatctgcaga gggtctgcca agaacccgca gcccgcccag 1740
gcatggctgt tcagtgacca cctcatccag cagcagggga agtgcctggc tgccacctcc 1800
accttaatgt cctcccctgg atccccagtc atactgcaga tgtgcaaccc tagagaaggc 1860
aagcagaaat ggaggagaaa aggatctttc atccagcatt cagtcagtgg cctctgcctg 1920
gagacaaagc ctgcccagct ggtgaccagc aagtgtcagg ctgacgccca ggcccagcag 1980
tggcagctgt tgccacacac atgacggagg gattttcttg aagggtcagc tattgcactg 2040
tgctgggagg ctggctgtgg ctcctgtttg tgaagagaac tcccagttcc ttttcacagc 2100
cgctgagaac acatccacac atctacccca cggccttgtc ttggaactgc tcctgctatc 2160
cccacaccct gcttcctcac cccactggct cttgggcaaa tgactgttgg taccaggacc 2220
ctgggggtct cccctacaaa gcagaccagc ctggggcaga tatacctacc acaggagccc 2280
cctgtctttc ataggccaag gatccacata cccatagagt tcatggattc tagagggtct 2340
aggaatctct tgaaattgtc cctaaaatac tgcatgtgtg tgcatacatg cattttcctg 2400
gggaaaaagt ccatggcttc taaaagaggt ccctgatccc caaagggcct gaacctctgc 2460
tctggattga agccactgtc tgcccaagct gccaccccct aatcttcctc cctggcgtgc 2520
tcaaactgcc atcgcctgct ccctccacac ggcccttggg gtcagcagcc aagtgtctgt 2580
ggtccgcagc acctgctctg gagggctctc cagcagtttc gcctcctgac tctcaccagc 2640
gtcctctcgg cagcactccc gtgcccaagt gcacccctct ggacttgcca gcgcaggccc 2700
cttcgctccc agggccatgc tttgcctgtc ctctgtcgtg atgtttcttc cgcagccagg 2760
tgcagcctca gatcccctgt tcatctggga agcctcctgc cacagcttag gacagaactg 2820
ggcccagggc aaaggcctct ccccagagga tggactagaa ggcctgggcc acactcgggc 2880
atggaccttt ggggctgggg agccggggct gcgcctgttg aatgtaagag gactgctgac 2940
cagagggcct tcaagagggt ctctctgtcc tttgctgtgg tcagatcagg ctctgcactt 3000
atcagccggt cctttgtggc aacgcagccc tgttctgttt ttgcttttcc tcttcttgac 3060
caaagcatgt gccactagct gtccttgagg acctcgtctt tatgaaacac acacctggaa 3120
taaaaccact tcttacatgt ccacatgc 3148

<210> SEQ ID NO 105
<211> LENGTH: 1979
<212> TYPE: DNA
<213> ORGANISM: Homo sapiens

<400> SEQUENCE: 105
aacggcctga cgtcggcgga gggaagcagg cgcaggctcc gtgaggaggc aaggtaagac 60

```
gccgagggag gactgaggcg ggcctcaccc cagacagagg gcccccaata atccagcgct    120
gcctctgctg ccgggcctgg accaccctgc aggggaagac ttctcaggct cagtcgccac    180
cacctcaccc cgccaccccc cgccgcttta accgcaggga actctggcat ctcagggagt    240
tgatgacctt gttttcagaa ggtgactcag gtcaacacag gggcccccat ctggtcgaca    300
gatgcagtgg ttctaggatc tgccaagcat ccaggtggag agcctgaggt tctgaggggg    360
acaggctgac aagtaggacc cgaggcactg gaggagcatt gaaggagaag atctgcctgt    420
gggtcttcat tgcccagctc ctgcccgcac tcctgcctgc tgccctgacc agagtcatca    480
tgcctcttga gcagaggagt cagcactgca agcctgaaga aggccttgag gcccgaggag    540
aggccctggg cctggtgggt gcgcaggctc ctgctactga ggagcagcag accgcttctt    600
cctcttctac tctagtggaa gttaccctgg gggaggtgcc tgctgccgac tcaccgagtc    660
ctccccacag tcctcaggga gcctccagct tctcgactac catcaactac actctttgga    720
gacaatccga tgagggctcc agcaaccaag aagaggaggg gccaagaatg tttcccgacc    780
tggagtccga gttccaagca gcaatcagta ggaagatggt tgagttggtt cattttctgc    840
tcctcaagta tcgagccagg gagccggtca caaaggcaga aatgctggag agtgtcctca    900
gaaattgcca ggacttcttt cccgtgatct tcagcaaagc ctccgagtac ttgcagctgg    960
tctttggcat cgaggtggtg gaagtggtcc ccatcagcca cttgtacatc cttgtcacct   1020
gcctgggcct ctcctacgat ggcctgctgg gcgacaatca ggtcatgccc aagacaggcc   1080
tcctgataat cgtcctggcc ataatcgcaa tagagggcga ctgtgcccct gaggagaaaa   1140
tctgggagga gctgagtatg ttggaggtgt ttgaggggag ggaggacagt gtcttcgcac   1200
atcccaggaa gctgctcatg caagatctgg tgcaggaaaa ctacctggag taccggcagg   1260
tgcccggcag tgatcctgca tgctacgagt tcctgtgggg tccaagggcc ctcattgaaa   1320
ccagctatgt gaaagtcctg caccatacac taaagatcgg tggagaacct cacatttcct   1380
acccacccct gcatgaacgg gctttgagag agggagaaga gtgagtctca gcacatgttg   1440
cagccagggc cagtgggagg gggtctgggc cagtgcacct tccagggccc catccattag   1500
cttccactgc ctcgtgtgat atgaggccca ttcctgcctc tttgaagaga gcagtcagca   1560
ttcttagcag tgagtttctg ttctgttgga tgactttgag atttatcttt gtttcctgtt   1620
ggaattgttc aaatgttcct tttaacaaat ggttggatga acttcagcat ccaagtttat   1680
gaatgacagt agtcacacat agtgctgttt atatagttta ggggtaagag tcctgttttt   1740
tattcagatt gggaaatcca ttccattttg tgagttgtca cataataaca gcagtggaat   1800
atgtatttgc ctatattgtg aacgaattag cagtaaaata catgatacaa ggaactcaaa   1860
agatagttaa ttcttgcctt atacctcagt ctattatgta aaattaaaaa tatgtgtatg   1920
tttttgcttc tttgagaatg caaaagaaat taaatctgaa taaataattc ttcctgttc    1979
```

```
<210> SEQ ID NO 106
<211> LENGTH: 1965
<212> TYPE: DNA
<213> ORGANISM: Homo sapiens

<400> SEQUENCE: 106

aacggcctga cgtcggcgga gggaagcagg cgcaggctcc gtgaggaggc aagggaactc     60
tggcgtaaga gctttgtgtg accagggcag ggctggttag aagtgctcag ggcccagact    120
cagccaggaa tcaagaatcc gggctttgcc cctgcaatca acccacggaa gctccgggaa    180
```

```
tggcggccaa gcacgcggat cctgacgttc acatatctca gggagttgat gaccttgttt    240

tcagaaggtg actcaggtca acacaggggc ccccatctgg tcgacagatg cagtggttct    300

aggatctgcc aagcatccag gtggagagcc tgaggttctg agggggacag gctgacaagt    360

aggacccgag gcactggagg agcattgaag gagaagatct gcctgtgggt cttcattgcc    420

cagctcctgc ccgcactcct gcctgctgcc ctgaccagag tcatcatgcc tcttgagcag    480

aggagtcagc actgcaagcc tgaagaaggc cttgaggccc gaggagaggc cctgggcctg    540

gtgggtgcgc aggctcctgc tactgaggag cagcagaccg cttcttcctc ttctactcta    600

gtggaagtta ccctgggga ggtgcctgct gccgactcac cgagtcctcc ccacagtcct    660

cagggagcct ccagcttctc gactaccatc aactacactc tttggagaca atccgatgag    720

ggctccagca accaagaaga ggaggggcca agaatgtttc ccgacctgga gtccgagttc    780

caagcagcaa tcagtaggaa gatggttgag ttggttcatt ttctgctcct caagtatcga    840

gccagggagc cggtcacaaa ggcagaaatg ctggagagtg tcctcagaaa ttgccaggac    900

ttctttcccg tgatcttcag caaagcctcc gagtacttgc agctggtctt tggcatcgag    960

gtggtggaag tggtccccat cagccacttg tacatccttg tcacctgcct gggcctctcc   1020

tacgatggcc tgctgggcga caatcaggtc atgcccaaga caggcctcct gataatcgtc   1080

ctggccataa tcgcaataga gggcgactgt gcccctgagg agaaaatctg ggaggagctg   1140

agtatgttgg aggtgtttga ggggagggag gacagtgtct tcgcacatcc caggaagctg   1200

ctcatgcaag atctggtgca ggaaaactac ctggagtacc ggcaggtgcc cggcagtgat   1260

cctgcatgct acgagttcct gtggggtcca agggccctca ttgaaaccag ctatgtgaaa   1320

gtcctgcacc atacactaaa gatcggtgga gaacctcaca tttcctaccc acccctgcat   1380

gaacgggctt tgagagaggg agaagagtga gtctcagcac atgttgcagc cagggccagt   1440

gggagggggt ctgggccagt gcaccttcca gggccccatc cattagcttc cactgcctcg   1500

tgtgatatga ggcccattcc tgcctctttg aagagagcag tcagcattct tagcagtgag   1560

tttctgttct gttggatgac tttgagattt atctttgttt cctgttggaa ttgttcaaat   1620

gttcctttta acaaatggtt ggatgaactt cagcatccaa gtttatgaat gacagtagtc   1680

acacatagtg ctgtttatat agtttagggg taagagtcct gtttttttatt cagattggga   1740

aatccattcc attttgtgag ttgtcacata ataacagcag tggaatatgt atttgcctat   1800

attgtgaacg aattagcagt aaaatacatg atacaaggaa ctcaaaagat agttaattct   1860

tgccttatac ctcagtctat tatgtaaaat taaaaatatg tgtatgtttt tgcttctttg   1920

agaatgcaaa agaaattaaa tctgaataaa taattcttcc tgttc                   1965
```

<210> SEQ ID NO 107
<211> LENGTH: 1981
<212> TYPE: DNA
<213> ORGANISM: Homo sapiens

<400> SEQUENCE: 107

```
aacggcctga cgtcggcgga gggaagcagg cgcaggctcc gtgaggaggc aagaatccgg     60

gctttgcccc tgcaatcaac ccacggaagc tccgggaatg gcggccaagc acgcggatcc    120

tgacgttcac atatctcagg gagttgatga ccttgttttc agaaggtgac tcaggtcaac    180

acaggggccc ccatctggtc gacagatgca gtggttctag gatctgccaa gcatccaggt    240

ggagagcctg aggaatcagg agctccagga accaggcagt gaggccttgg tctgagtcag    300

tgtcctcagg tcacagagca gaggggacgc agacagtgcc aacactgaag gttctgaggg    360
```

```
ggacaggctg acaagtagga cccgaggcac tggaggagca ttgaaggaga agatctgcct    420
gtgggtcttc attgcccagc tcctgcccgc actcctgcct gctgccctga ccagagtcat    480
catgcctctt gagcagagga gtcagcactg caagcctgaa gaaggccttg aggcccgagg    540
agaggccctg ggcctggtgg gtgcgcaggc tcctgctact gaggagcagc agaccgcttc    600
ttcctcttct actctagtgg aagttaccct gggggaggtg cctgctgccg actcaccgag    660
tcctccccac agtcctcagg gagcctccag cttctcgact accatcaact acactctttg    720
gagacaatcc gatgagggct ccagcaacca agaagaggag ggggccaagaa tgtttcccga    780
cctggagtcc gagttccaag cagcaatcag taggaagatg gttgagttgg ttcattttct    840
gctcctcaag tatcgagcca gggagccggt cacaaaggca gaaatgctgg agagtgtcct    900
cagaaattgc caggacttct ttcccgtgat cttcagcaaa gcctccgagt acttgcagct    960
ggtctttggc atcgaggtgg tggaagtggt ccccatcagc cacttgtaca tccttgtcac   1020
ctgcctgggc ctctcctacg atggcctgct gggcgacaat caggtcatgc ccaagacagg   1080
cctcctgata atcgtcctgg ccataatcgc aatagagggc gactgtgccc ctgaggagaa   1140
aatctgggag gagctgagta tgttggaggt gtttgagggg agggaggaca gtgtcttcgc   1200
acatcccagg aagctgctca tgcaagatct ggtgcaggaa aactacctgg agtaccggca   1260
ggtgcccggc agtgatcctg catgctacga gttcctgtgg ggtccaaggg ccctcattga   1320
aaccagctat gtgaaagtcc tgcaccatac actaaagatc ggtggagaac ctcacatttc   1380
ctacccaccc ctgcatgaac gggctttgag agagggagaa gagtgagtct cagcacatgt   1440
tgcagccagg gccagtggga gggggtctgg gccagtgcac cttccagggc cccatccatt   1500
agcttccact gcctcgtgtg atatgaggcc cattcctgcc tctttgaaga gagcagtcag   1560
cattcttagc agtgagtttc tgttctgttg gatgactttg agatttatct ttgtttcctg   1620
ttggaattgt tcaaatgttc cttttaacaa atggttggat gaacttcagc atccaagttt   1680
atgaatgaca gtagtcacac atagtgctgt ttatatagtt taggggtaag agtcctgttt   1740
tttattcaga ttgggaaatc cattccattt tgtgagttgt cacataataa cagcagtgga   1800
atatgtattt gcctatattg tgaacgaatt agcagtaaaa tacatgatac aaggaactca   1860
aaagatagtt aattcttgcc ttatacctca gtctattatg taaaattaaa aatatgtgta   1920
tgtttttgct tctttgagaa tgcaaaagaa attaaatctg aataaataat tcttcctgtt   1980
c                                                                   1981
```

<210> SEQ ID NO 108
<211> LENGTH: 1390
<212> TYPE: DNA
<213> ORGANISM: Homo sapiens

<400> SEQUENCE: 108

```
gggagagaga tcttcctctc tcttcgggcg tgttaagaca gcggggttgg cctgtacttc     60
ctctggccct ggctgaagag ggctagtgaa accgttaaac ccctaggcga tcatggcctt    120
gagacctgag gaccccagta gcgggttccg gcatagcaac gtggtggcct tcatcaacga    180
gaaaatggcc aggcacacga aaggccccga gttctatctt gagaatatat ccttatcctg    240
ggagaaggtg gaagacaagc tgagggccat actggaggac agcgaggtgc ccagtgaggt    300
caaagaggcc tgcacctggg gcagcctggc cttgggagtg cgctttgccc acaggcaggc    360
acagctacaa aggcacaggg tgcggtggct gcacggcttc gccaaactgc acaaatcagc    420
```

```
cgcacaggcc ttggcatcag acctgaagaa gctcagggag cagcaggaga cggaacgcaa    480
ggaggcggcc tcccggctaa gaatggccca gaccagcctc gtggaggtgc agaaagagag    540
agacaaggag ctggtgtctc cccatgagtg ggagcagggg gcagggtggc caggcctggc    600
cactgccgga ggggtttgca cagaaggagc agctgaggag gaagaagagg cggcggtggc    660
tgctgctggt gctgctggag gaaaaggagc agaagaagag cagagggatg tggaggttgt    720
ggctgcccct gtggaggcca tggctccccc tgtggaggct ggggctgccc ccatggagac    780
ccagttcccc cacgtggagg ccagggctgc ctccatggag accacagaga agctggagag    840
aatcctcctg cagctccttg gagatgctga tcaggaaaag tacacctatt gggggcagaa    900
ggagggagat ctccggtcgg tcgaaacagc cacatcttat ttctctggaa ccacgaaccc    960
ctggtccaga gcctcatcag aacctcttcc tgtccagctc cctgcctcat actcatactc   1020
atactcaagc ccttttttcct ccttctcaga catacccact atatcccctc cacaagcaac  1080
agtcacagca ccagttccgc ctcagctgcc ttccgactgg gaggcctttg atactagcct   1140
gtggtctgat ggggggcccc acagaataga ccatcaggag cacccaagag acaggagata   1200
ctccgaacct catcagcaaa gacctccagt atatcgcagg ccaggggact gggactgccc   1260
ttggtgtaac gctgtgaatt tttcacggag ggatacttgc ttcgactgtg ggaagggaat   1320
ctggctgcaa aaacctcatt gagtgcagaa atgcaaaata gaaccgaagc atgtataaaa   1380
aaaaaaaaaa                                                          1390
```

<210> SEQ ID NO 109
<211> LENGTH: 10197
<212> TYPE: DNA
<213> ORGANISM: Homo sapiens

<400> SEQUENCE: 109

```
ctgcggggcg ctgttgctgt ggctgagatt tggccgccgc ctccccccacc cggcctgcgc    60
cctccctctc cctcggcgcc cgcccgcccg ctcgcggccc gcgctcgctc ctctccctcg    120
cagccggcag ggcccccgac ccccgtccgg gccctcgccg gcccggccgc ccgtgcccgg    180
ggctgttttc gcgagcaggt gaaaatggct gagaacttgc tggacggacc gcccaacccc    240
aaaagagcca aactcagctc gcccggtttc tcggcgaatg acagcacaga ttttggatca    300
ttgtttgact tggaaaatga tcttcctgat gagctgatac ccaatggagg agaattaggc    360
cttttaaaca gtgggaacct tgttccagat gctgcttcca aacataaaca actgtcggag    420
cttctacgag gaggcagcgg ctctagtatc aacccaggaa taggaaatgt gagcgccagc    480
agccccgtgc agcagggcct gggtggccag gctcaagggc agccgaacag tgctaacatg    540
gccagcctca gtgccatggg caagagccct ctgagccagg gagattcttc agcccccagc    600
ctgcctaaac aggcagccag cacctctggg cccacccccg ctgcctccca agcactgaat    660
ccgcaagcac aaaagcaagt ggggctggcg actagcagcc ctgccacgtc acagactgga    720
cctggtatct gcatgaatgc taactttaac cagacccacc caggcctcct caatagtaac    780
tctggccata gcttaattaa tcaggcttca caagggcagg cgcaagtcat gaatggatct    840
cttggggctg ctggcagagg aaggggagct ggaatgccgt accctactcc agccatgcag    900
ggcgcctcga gcagcgtgct ggctgagacc ctaacgcagg tttccccgca aatgactggt    960
cacgcgggac tgaacaccgc acaggcagga ggcatggcca agatgggaat aactgggaac   1020
acaagtccat ttggacagcc ctttagtcaa gctggagggc agccaatggg agccactgga   1080
gtgaaccccc agttagccag caaacagagc atggtcaaca gtttgcccac cttccctaca   1140
```

```
gatatcaaga atacttcagt caccaacgtg ccaaatatgt ctcagatgca aacatcagtg   1200
ggaattgtac ccacacaagc aattgcaaca ggccccactg cagatcctga aaaacgcaaa   1260
ctgatacagc agcagctggt tctactgctt catgctcata agtgtcagag acgagagcaa   1320
gcaaacggag aggttcgggc ctgctcgctc ccgcattgtc gaaccatgaa aaacgttttg   1380
aatcacatga cgcattgtca ggctgggaaa gcctgccaag ttgcccattg tgcatcttca   1440
cgacaaatca tctctcattg gaagaactgc acacgacatg actgtcctgt ttgcctccct   1500
ttgaaaaatg ccagtgacaa gcgaaaccaa caaaccatcc tggggtctcc agctagtgga   1560
attcaaaaca caattggttc tgttggcaca gggcaacaga atgccacttc tttaagtaac   1620
ccaaatccca tagaccccag ctccatgcag cgagcctatg ctgctctcgg actcccctac   1680
atgaaccagc cccagacgca gctgcagcct caggttcctg gccagcaacc agcacagcct   1740
caaacccacc agcagatgag gactctcaac cccctgggaa ataatccaat gaacattcca   1800
gcaggaggaa taacaacaga tcagcagccc ccaaacttga tttcagaatc agctcttccg   1860
acttccctgg gggccacaaa cccactgatg aacgatggct ccaactctgg taacattgga   1920
accctcagca ctataccaac agcagctcct ccttctagca ccggtgtaag gaaaggctgg   1980
cacgaacatg tcactcagga cctgcggagc catctagtgc ataaactcgt ccaagccatc   2040
ttcccaacac ctgatcccgc agctctaaag gatcgccgca tggaaaacct ggtagcctat   2100
gctaagaaag tggaaggga catgtacgag tctgccaaca gcagggatga atattatcac   2160
ttattagcag agaaaatcta caagatacaa aaagaactag aagaaaaacg gaggtcgcgt   2220
ttacataaac aaggcatctt ggggaaccag ccagccttac cagccccggg ggctcagccc   2280
cctgtgattc cacaggcaca acctgtgaga cctccaaatg gacccctgtc cctgccagtg   2340
aatcgcatgc aagtttctca agggatgaat tcatttaacc ccatgtcctt ggggaacgtc   2400
cagttgccac aagcacccat gggacctcgt gcagcctccc caatgaacca ctctgtccag   2460
atgaacagca tgggctcagt gccagggatg gccatttctc cttcccgaat gcctcagcct   2520
ccgaacatga tgggtgcaca caccaacaac atgatggccc aggcgcccgc tcagagccag   2580
tttctgccac agaaccagtt cccgtcatcc agcggggcga tgagtgtggg catggggcag   2640
ccgccagccc aaacaggcgt gtcacaggga caggtgcctg gtgctgctct tcctaaccct   2700
ctcaacatgc tggggcctca ggccagccag ctaccttgcc ctccagtgac acagtcacca   2760
ctgcacccaa caccgcctcc tgcttccacg gctgctggca tgccatctct ccagcacacg   2820
acaccacctg ggatgactcc tccccagcca gcagctccca ctcagccatc aactcctgtg   2880
tcgtcttccg ggcagactcc caccccgact cctggctcag tgcccagtgc tacccaaacc   2940
cagagcaccc ctacagtcca ggcagcagcc caggcccagg tgaccccgca gcctcaaacc   3000
ccagttcagc cccgtctgt ggctacccct cagtcatcgc agcaacagcc gacgcctgtg   3060
cacgcccagc ctcctggcac accgctttcc caggcagcag ccagcattga taacagagtc   3120
cctacccct cctcggtggc cagcgcagaa accaattccc agcagccagg acctgacgta   3180
cctgtgctgg aaatgaagac ggagacccaa gcagaggaca ctgagcccga tcctggtgaa   3240
tccaaagggg agcccaggtc tgagatgatg gaggaggatt tgcaaggagc ttcccaagtt   3300
aaagaagaaa cagacatagc agagcagaaa tcagaaccaa tggaagtgga tgaaaagaaa   3360
cctgaagtga aagtagaagt taaagaggaa gaagagagta gcagtaacgg cacagcctct   3420
cagtcaacat ctccttcgca gccgcgcaaa aaaatcttta aaccagagga gttacgccag   3480
```

-continued

```
gccctcatgc caaccctaga agcactgtat cgacaggacc cagagtcatt acctttccgg   3540
cagcctgtag atccccagct cctcggaatt ccagactatt ttgacatcgt aaagaatccc   3600
atggacctct ccaccatcaa gcggaagctg gacacagggc aataccaaga gccctggcag   3660
tacgtggacg acgtctggct catgttcaac aatgcctggc tctataatcg caagacatcc   3720
cgagtctata agttttgcag taagcttgca gaggtctttg agcaggaaat tgaccctgtc   3780
atgcagtccc ttggatattg ctgtggacgc aagtatgagt tttccccaca gactttgtgc   3840
tgctatggga agcagctgtg taccattcct cgcgatgctg cctactacag ctatcagaat   3900
aggtatcatt tctgtgagaa gtgtttcaca gagatccagg gcgagaatgt gaccctgggt   3960
gacgaccctt cacagcccca gacgacaatt tcaaaggatc agtttgaaaa gaagaaaaat   4020
gataccttag accccgaacc tttcgttgat tgcaaggagt gtggccggaa gatgcatcag   4080
atttgcgttc tgcactatga catcatttgg ccttcaggtt ttgtgtgcga caactgcttg   4140
aagaaaactg gcagacctcg aaaagaaaac aaattcagtg ctaagaggct gcagaccaca   4200
agactgggaa accacttgga agaccgagtg aacaaatttt tgcggcgcca gaatcaccct   4260
gaagccgggg aggtttttgt ccgagtggtg gccagctcag acaagacggt ggaggtcaag   4320
cccgggatga agtcacggtt tgtggattct ggggaaatgt ctgaatcttt cccatatcga   4380
accaaagctc tgtttgcttt tgaggaaatt gacggcgtgg atgtctgctt ttttggaatg   4440
cacgtccaag aatacggctc tgattgcccc cctccaaaca cgaggcgtgt gtacatttct   4500
tatctggata gtattcattt cttccggcca cgttgcctcc gcacagccgt ttaccatgag   4560
atccttattg gatatttaga gtatgtgaag aaattagggt atgtgacagg gcacatctgg   4620
gcctgtcctc caagtgaagg agatgattac atcttccatt gccacccacc tgatcaaaaa   4680
atacccaagc caaaacgact gcaggagtgg tacaaaaaga tgctggacaa ggcgtttgca   4740
gagcggatca tccatgacta caaggatatt ttcaaacaag caactgaaga caggctcacc   4800
agtgccaagg aactgcccta ttttgaaggt gatttctggc ccaatgtgtt agaagagagc   4860
attaaggaac tagaacaaga agaagaggag aggaaaaagg aagagagcac tgcagccagt   4920
gaaaccactg agggcagtca gggcgacagc aagaatgcca agaagaagaa caacaagaaa   4980
accaacaaga acaaaagcag catcagccgc gccaacaaga agaagcccag catgcccaac   5040
gtgtccaatg acctgtccca gaagctgtat gccaccatgg agaagcacaa ggaggtcttc   5100
ttcgtgatcc acctgcacgc tgggcctgtc atcaacaccc tgccccccat cgtcgacccc   5160
gacccccctgc tcagctgtga cctcatggat gggcgcgacg ccttcctcac cctcgccaga   5220
gacaagcact gggagttctc ctccttgcgc cgctccaagt ggtccacgct ctgcatgctg   5280
gtggagctgc acacccaggg ccaggaccgc tttgtctaca cctgcaacga gtgcaagcac   5340
cacgtggaga cgcgctggca ctgcactgtg tgcgaggact acgacctctg catcaactgc   5400
tataacacga agagccatgc ccataagatg gtgaagtggg ggctgggcct ggatgacgag   5460
ggcagcagcc agggcgagcc acagtcaaag agcccccagg agtcacgccg gctgagcatc   5520
cagcgctgca tccagtcgct ggtgcacgcg tgccagtgcc gcaacgccaa ctgctcgctg   5580
ccatcctgcc agaagatgaa gcgggtggtg cagcacacca agggctgcaa acgcaagacc   5640
aacgggggct gcccggtgtg caagcagctc atcgccctct gctgctacca cgccaagcac   5700
tgccaagaaa acaaatgccc cgtgcccttc tgcctcaaca tcaaacacaa gctccgccag   5760
cagcagatcc agcaccgcct gcagcaggcc cagctcatgc gccggcggat ggccaccatg   5820
aacacccgca acgtgcctca gcagagtctg ccttctccta cctcagcacc gcccgggacc   5880
```

```
cccacacagc agcccagcac accccagacg ccgcagcccc ctgcccagcc ccaaccctca   5940

cccgtgagca tgtcaccagc tggcttcccc agcgtggccc ggactcagcc ccccaccacg   6000

gtgtccacag ggaagcctac cagccaggtg ccggcccccc cacccccggc ccagcccccct   6060

cctgcagcgg tggaagcggc tcggcagatc gagcgtgagg cccagcagca gcagcacctg   6120

taccgggtga acatcaacaa cagcatgccc ccaggacgca cgggcatggg gaccccgggg   6180

agccagatgg cccccgtgag cctgaatgtg ccccgaccca accaggtgag cgggcccgtc   6240

atgcccagca tgcctcccgg gcagtggcag caggcgcccc ttccccagca gcagcccatg   6300

ccaggcttgc ccaggcctgt gatatccatg caggcccagg cggccgtggc tgggccccgg   6360

atgcccagcg tgcagccacc caggagcatc tcacccagcg ctctgcaaga cctgctgcgg   6420

accctgaagt cgcccagctc ccctcagcag caacagcagg tgctgaacat tctcaaatca   6480

aacccgcagc taatggcagc tttcatcaaa cagcgcacag ccaagtacgt ggccaatcag   6540

cccggcatgc agccccagcc tggcctccag tcccagcccg gcatgcaacc ccagcctggc   6600

atgcaccagc agcccagcct gcagaacctg aatgccatgc aggctggcgt gccgcggccc   6660

ggtgtgcctc cacagcagca ggcgatggga ggcctgaacc cccagggcca ggccttgaac   6720

atcatgaacc caggacacaa ccccaacatg gcgagtatga atccacagta ccgagaaatg   6780

ttacggaggc agctgctgca gcagcagcag caacagcagc agcaacaaca gcagcaacag   6840

cagcagcagc aagggagtgc cggcatggct gggggcatgg cggggcacgg ccagttccag   6900

cagcctcaag gacccggagg ctacccaccg gccatgcagc agcagcagcg catgcagcag   6960

catctccccc tccagggcag ctccatgggc cagatggcgg ctcagatggg acagcttggc   7020

cagatggggc agccggggct gggggcagac agcaccccca acatccagca agccctgcag   7080

cagcggattc tgcagcaaca gcagatgaag cagcagattg ggtccccagg ccagccgaac   7140

cccatgagcc cccagcaaca catgctctca ggacagccac aggcctcgca tctccctggc   7200

cagcagatcg ccacgtccct tagtaaccag gtgcggtctc cagcccctgt ccagtctcca   7260

cggccccagt cccagcctcc acattccagc ccgtcaccac ggatacagcc ccagccttcg   7320

ccacaccacg tctcacccca gactggttcc ccccaccccg gactcgcagt caccatggcc   7380

agctccatag atcagggaca cttggggaac cccgaacaga gtgcaatgct cccccagctg   7440

aacaccccca gcaggagtgc gctgtccagc gaactgtccc tggtcgggga caccacgggg   7500

gacacgctag agaagtttgt ggagggcttg tagcattgtg agagcatcac cttttccctt   7560

tcatgttctt ggaccttttg tactgaaaat ccaggcatct aggttctttt tattcctaga   7620

tggaactgcg acttccgagc catggaaggg tggattgatg tttaaagaaa caatacaaag   7680

aatatatttt tttgttaaaa accagttgat ttaaatatct ggtctctctc tttggttttt   7740

ttttggcggg ggggtggggg gggttctttt ttttccgttt tgtttttgtt tggggggagg   7800

ggggttttgt ttggattctt tttgtcgtca ttgctggtga ctcatgcctt tttttaacgg   7860

gaaaaacaag ttcattatat tcatattttt tatttgtatt ttcaagactt taaacattta   7920

tgtttaaaag taagaagaaa aataatattc agaactgatt cctgaaataa tgcaagctta   7980

taatgtatcc cgataacttt gtgatgtttc gggaagattt ttttctatag tgaactctgt   8040

gggcgtctcc cagtattacc ctggatgata ggaattgact ccggcgtgca cacacgtaca   8100

cacccacaca catctatcta tacataatgg ctgaagccaa acttgtcttg cagatgtaga   8160

aattgttgct ttgtttctct gataaaactg gttttagaca aaaaataggg atgatcactc   8220
```

```
ttagaccatg ctaatgttac tagagaagaa gccttctttt ctttcttcta tgtgaaactt   8280

gaaatgagga aaagcaattc tagtgtaaat catgcaagcg ctctaattcc tataaatacg   8340

aaactcgaga agattcaatc actgtataga atggtaaaat accaactcat ttcttatatc   8400

atattgttaa ataaactgtg tgcaacagac aaaaagggtg gtccttcttg aattcatgta   8460

catggtatta acacttagtg ttcggggttt tttgttatga aaatgctgtt ttcaacattg   8520

tatttggact atgcatgtgt tttttcccca ttgtatataa agtaccgctt aaaattgata   8580

taaattactg aggtttttaa catgtattct gttctttaag atccctgtaa gaatgtttaa   8640

ggtttttatt tatttatata tatttttga gtctgttctt tgtaagacat ggttctggtt    8700

gttcgctcat agcggagagg ctggggctgc ggttgtggtt gtggcggcgt gggtggtggc   8760

tgggaactgt ggcccaggct tagcggccgc ccggaggctt ttcttcccgg agactgaggt   8820

gggcgactga ggtgggcggc tcagcgttgg ccccacacat tcgaggctca caggtgattg   8880

tcgctcacac agttagggtc gtcagttggt ctgaaactgc atttggccca ctcctccatc   8940

ctccctgtcc gtcgtagctg ccacccccag aggcggcgct tcttcccgtg ttcaggcggc   9000

tccccccccc cgtacacgac tcccagaatc tgaggcagag agtgctccag gctcgcgagg   9060

tgctttctga cttcccccca aatcctgccg ctgccgcgca gcatgtcccg tgtggcgttt   9120

gaggaaatgc tgagggacag acaccttgga gcaccagctc cggtccctgt tacagtgaga   9180

aaggtccccc acttcggggg atacttgcac ttagccacat ggtcctgcct cccttggagt   9240

ccagttccag gctcccttac tgagtgggtg agacaagttc acaaaaaccg taaaactgag   9300

aggaggacca tgggcagggg agctgaagtt catcccctaa gtctaccacc cccagcaccc   9360

agagaaccca ctttatccct agtcccccaa caaaggctgg tctaggtggg ggtgatggta   9420

attttagaaa tcacgcccca aatagcttcc gtttgggccc ttacattcac agataggttt   9480

taaatagctg aatacttggt ttgggaatct gaattcgagg aacctttcta agaagttgga   9540

aaggtccgat ctagttttag cacagagctt tgaaccttga gttataaaat gcagaataat   9600

tcaagtaaaa ataagaccac catctggcac ccctgaccag cccccattca ccccatccca   9660

ggaggggaag cacaggccgg gcctccggtg gagattgctg ccactgctcg gcctgctggg   9720

ttcttaacct ccagtgtcct cttcatcttt tccacccgta gggaaacctt gagccatgtg   9780

ttcaaacaag aagtggggct agagcccgag agcagcagct ctaagcccac actcagaaag   9840

tggcgccctc ctggttgtgc agccttttaa tgtgggcagt ggaggggcct ctgtttcagg   9900

ttatcctgga attcaaaacg ttatgtacca acctcatcct ctttggagtc tgcatcctgt   9960

gcaaccgtct tgggcaatcc agatgtcgaa ggatgtgacc gagagcatgg tctgtggatg  10020

ctaaccctaa gtttgtcgta aggaaatttc tgtaagaaac ctggaaagcc ccaacgctgt  10080

gtctcatgct gtatacttaa gaggagaaga aaaagtccta tatttgtgat caaaaagagg  10140

aaacttgaaa tgtgatggtg tttataataa aagatggtaa aactacttgg attcaaa     10197
```

<210> SEQ ID NO 110
<211> LENGTH: 10083
<212> TYPE: DNA
<213> ORGANISM: Homo sapiens

<400> SEQUENCE: 110

```
ctgcggggcg ctgttgctgt ggctgagatt tggccgccgc ctcccccacc cggcctgcgc     60

cctccctctc cctcggcgcc cgcccgcccg ctcgcggccc gcgctcgctc ctctccctcg    120

cagccggcag ggcccccgac ccccgtccgg gccctcgccg gcccggccgc ccgtgcccgg    180
```

```
ggctgttttc gcgagcaggt gaaaatggct gagaacttgc tggacggacc gcccaacccc    240
aaaagagcca aactcagctc gcccggtttc tcggcgaatg acagcacaga ttttggatca    300
ttgtttgact tggaaaatga tcttcctgat gagctgatac ccaatggagg agaattaggc    360
cttttaaaca gtgggaacct tgttccagat gctgcttcca aacataaaca actgtcggag    420
cttctacgag gaggcagcgg ctctagtatc aacccaggaa taggaaatgt gagcgccagc    480
agccccgtgc agcagggcct gggtggccag gctcaagggc agccgaacag tgctaacatg    540
gccagcctca gtgccatggg caagagccct ctgagccagg gagattcttc agcccccagc    600
ctgcctaaac aggcagccag cacctctggg cccacccccg ctgcctccca agcactgaat    660
ccgcaagcac aaaagcaagt ggggctggcg actagcagcc ctgccacgtc acagactgga    720
cctggtatct gcatgaatgc taactttaac cagacccacc caggcctcct caatagtaac    780
tctggccata gcttaattaa tcaggcttca caagggcagg cgcaagtcat gaatggatct    840
cttggggctg ctggcagagg aaggggagct ggaatgccgt accctactcc agccatgcag    900
ggcgcctcga gcagcgtgct ggctgagacc ctaacgcagg tttccccgca aatgactggt    960
cacgcgggac tgaacaccgc acaggcagga ggcatggcca agatgggaat aactgggaac   1020
acaagtccat ttggacagcc ctttagtcaa gctggagggc agccaatggg agccactgga   1080
gtgaaccccc agttagccag caaacagagc atggtcaaca gtttgcccac cttccctaca   1140
gatatcaaga atacttcagt caccaacgtg ccaaatatgt ctcagatgca aacatcagtg   1200
ggaattgtac ccacacaagc aattgcaaca ggccccactg cagatcctga aaaacgcaaa   1260
ctgatacagc agcagctggt tctactgctt catgctcata agtgtcagag acgagagcaa   1320
gcaaacggag aggttcgggc ctgctcgctc ccgcattgtc gaaccatgaa aaacgttttg   1380
aatcacatga cgcattgtca ggctgggaaa gcctgccaag ccatcctggg gtctccagct   1440
agtggaattc aaaacacaat tggttctgtt ggcacagggc aacagaatgc cacttcttta   1500
agtaacccaa atcccataga ccccagctcc atgcagcgag cctatgctgc tctcggactc   1560
ccctacatga accagcccca gacgcagctg cagcctcagg ttcctggcca gcaaccagca   1620
cagcctcaaa cccaccagca gatgaggact ctcaaccccc tgggaaataa tccaatgaac   1680
attccagcag gaggaataac aacagatcag cagcccccaa acttgatttc agaatcagct   1740
cttccgactt ccctgggggc cacaaaccca ctgatgaacg atggctccaa ctctggtaac   1800
attggaaccc tcagcactat accaacagca gctcctcctt ctagcaccgg tgtaaggaaa   1860
ggctggcacg aacatgtcac tcaggacctg cggagccatc tagtgcataa actcgtccaa   1920
gccatcttcc caacacctga tcccgcagct ctaaaggatc gccgcatgga aaacctggta   1980
gcctatgcta agaaagtgga aggggacatg tacgagtctg ccaacagcag ggatgaatat   2040
tatcacttat tagcagagaa aatctacaag atacaaaaag aactagaaga aaaacggagg   2100
tcgcgtttac ataaacaagg catcttgggg aaccagccag ccttaccagc cccgggggct   2160
cagccccctg tgattccaca ggcacaacct gtgagacctc caaatggacc cctgtccctg   2220
ccagtgaatc gcatgcaagt ttctcaaggg atgaattcat ttaaccccat gtccttgggg   2280
aacgtccagt tgccacaagc acccatggga cctcgtgcag cctccccaat gaaccactct   2340
gtccagatga acagcatggg ctcagtgcca gggatggcca tttctccttc ccgaatgcct   2400
cagcctccga acatgatggg tgcacacacc aacaacatga tggcccaggc gcccgctcag   2460
agccagtttc tgccacagaa ccagttcccg tcatccagcg gggcgatgag tgtgggcatg   2520
```

```
gggcagccgc cagcccaaac aggcgtgtca cagggacagg tgcctggtgc tgctcttcct   2580
aaccctctca acatgctggg gcctcaggcc agccagctac cttgccctcc agtgacacag   2640
tcaccactgc acccaacacc gcctcctgct tccacggctg ctggcatgcc atctctccag   2700
cacacgacac cacctgggat gactcctccc cagccagcag ctcccactca gccatcaact   2760
cctgtgtcgt cttccgggca gactcccacc ccgactcctg gctcagtgcc cagtgctacc   2820
caaacccaga gcacccctac agtccaggca gcagcccagg cccaggtgac cccgcagcct   2880
caaaccccag ttcagccccc gtctgtggct acccctcagt catcgcagca acagccgacg   2940
cctgtgcacg cccagcctcc tggcacaccg ctttcccagg cagcagccag cattgataac   3000
agagtcccta ccccctcctc ggtggccagc gcagaaacca attcccagca gccaggacct   3060
gacgtacctg tgctggaaat gaagacggag acccaagcag aggacactga gcccgatcct   3120
ggtgaatcca aaggggagcc caggtctgag atgatggagg aggatttgca aggagcttcc   3180
caagttaaag aagaaacaga catagcagag cagaaatcag aaccaatgga agtggatgaa   3240
aagaaacctg aagtgaaagt agaagttaaa gaggaagaag agagtagcag taacggcaca   3300
gcctctcagt caacatctcc ttcgcagccg cgcaaaaaaa tctttaaacc agaggagtta   3360
cgccaggccc tcatgccaac cctagaagca ctgtatcgac aggacccaga gtcattacct   3420
ttccggcagc ctgtagatcc ccagctcctc ggaattccag actattttga catcgtaaag   3480
aatcccatgg acctctccac catcaagcgg aagctggaca cagggcaata ccaagagccc   3540
tggcagtacg tggacgacgt ctggctcatg ttcaacaatg cctggctcta taatcgcaag   3600
acatcccgag tctataagtt ttgcagtaag cttgcagagg tctttgagca ggaaattgac   3660
cctgtcatgc agtcccttgg atattgctgt ggacgcaagt atgagttttc cccacagact   3720
ttgtgctgct atgggaagca gctgtgtacc attcctcgcg atgctgccta ctacagctat   3780
cagaataggt atcatttctg tgagaagtgt ttcacagaga tccagggcga gaatgtgacc   3840
ctgggtgacg acccttcaca gccccagacg acaatttcaa aggatcagtt tgaaaagaag   3900
aaaaatgata ccttagaccc cgaacctttc gttgattgca aggagtgtgg ccggaagatg   3960
catcagattt gcgttctgca ctatgacatc atttggcctt caggttttgt gtgcgacaac   4020
tgcttgaaga aaactggcag acctcgaaaa gaaaacaaat tcagtgctaa gaggctgcag   4080
accacaagac tgggaaacca cttggaagac cgagtgaaca aatttttgcg gcgccagaat   4140
caccctgaag ccggggaggt tttgtccgga gtggtggcca gctcagacaa gacggtggag   4200
gtcaagcccg ggatgaagtc acggtttgtg gattctgggg aaatgtctga atctttccca   4260
tatcgaacca aagctctgtt tgcttttgag gaaattgacg gcgtggatgt ctgctttttt   4320
ggaatgcacg tccaagaata cggctctgat tgcccccctc caaacacgag gcgtgtgtac   4380
atttcttatc tggatagtat tcatttcttc cggccacgtt gcctccgcac agccgtttac   4440
catgagatcc ttattggata tttagagtat gtgaagaaat tagggtatgt gacagggcac   4500
atctgggcct gtcctccaag tgaaggagat gattacatct tccattgcca cccacctgat   4560
caaaaaatac ccaagccaaa acgactgcag gagtggtaca aaaagatgct ggacaaggcg   4620
tttgcagagc ggatcatcca tgactacaag gatattttca aacaagcaac tgaagacagg   4680
ctcaccagtg ccaaggaact gccctatttt gaaggtgatt tctggcccaa tgtgttagaa   4740
gagagcatta aggaactaga acaagaagaa gaggagagga aaaaggaaga gagcactgca   4800
gccagtgaaa ccactgaggg cagtcagggc gacagcaaga atgccaagaa gaagaacaac   4860
aagaaaacca acaagaacaa aagcagcatc agccgcgcca acaagaagaa gcccagcatg   4920
```

```
cccaacgtgt ccaatgacct gtcccagaag ctgtatgcca ccatggagaa gcacaaggag   4980

gtcttcttcg tgatccacct gcacgctggg cctgtcatca acaccctgcc ccccatcgtc   5040

gaccccgacc ccctgctcag ctgtgacctc atggatgggc gcgacgcctt cctcaccctc   5100

gccagagaca agcactggga gttctcctcc ttgcgccgct ccaagtggtc cacgctctgc   5160

atgctggtgg agctgcacac ccagggccag gaccgctttg tctacacctg caacgagtgc   5220

aagcaccacg tggagacgcg ctggcactgc actgtgtgcg aggactacga cctctgcatc   5280

aactgctata acacgaagag ccatgcccat aagatggtga agtgggggct gggcctggat   5340

gacgagggca gcagccaggg cgagccacag tcaaagagcc cccaggagtc acgccggctg   5400

agcatccagc gctgcatcca gtcgctggtg cacgcgtgcc agtgccgcaa cgccaactgc   5460

tcgctgccat cctgccagaa gatgaagcgg gtggtgcagc acaccaaggg ctgcaaacgc   5520

aagaccaacg gggggctgccc ggtgtgcaag cagctcatcg ccctctgctg ctaccacgcc   5580

aagcactgcc aagaaaacaa atgccccgtg cccttctgcc tcaacatcaa acacaagctc   5640

cgccagcagc agatccagca ccgcctgcag caggcccagc tcatgcgccg gcggatggcc   5700

accatgaaca cccgcaacgt gcctcagcag agtctgcctt ctcctacctc agcaccgccc   5760

gggaccccca cacagcagcc cagcacaccc cagacgccgc agccccctgc ccagccccaa   5820

ccctcacccg tgagcatgtc accagctggc ttccccagcg tggcccggac tcagcccccc   5880

accacggtgt ccacagggaa gcctaccagc caggtgccgg cccccccacc cccggcccag   5940

ccccctcctg cagcggtgga agcggctcgg cagatcgagc gtgaggccca gcagcagcag   6000

cacctgtacc gggtgaacat caacaacagc atgcccccag gacgcacggg catggggacc   6060

ccggggagcc agatggcccc cgtgagcctg aatgtgcccc gacccaacca ggtgagcggg   6120

cccgtcatgc ccagcatgcc tcccgggcag tggcagcagg cgccccttcc ccagcagcag   6180

cccatgccag gcttgcccag gcctgtgata tccatgcagg cccaggcggc cgtggctggg   6240

ccccggatgc ccagcgtgca gccacccagg agcatctcac ccagcgctct gcaagacctg   6300

ctgcggaccc tgaagtcgcc cagctcccct cagcagcaac agcaggtgct gaacattctc   6360

aaatcaaacc cgcagctaat ggcagctttc atcaaacagc gcacagccaa gtacgtggcc   6420

aatcagcccg gcatgcagcc ccagcctggc ctccagtccc agcccggcat gcaaccccag   6480

cctggcatgc accagcagcc cagcctgcag aacctgaatg ccatgcaggc tggcgtgccg   6540

cggcccggtg tgcctccaca gcagcaggcg atgggaggcc tgaaccccca gggccaggcc   6600

ttgaacatca tgaacccagg acacaacccc aacatggcga gtatgaatcc acagtaccga   6660

gaaatgttac ggaggcagct gctgcagcag cagcagcaac agcagcagca acaacagcag   6720

caacagcagc agcagcaagg gagtgccggc atggctgggg gcatggcggg gcacggccag   6780

ttccagcagc ctcaaggacc cggaggctac ccaccggcca tgcagcagca gcagcgcatg   6840

cagcagcatc tcccctcca gggcagctcc atgggccaga tggcggctca gatgggacag   6900

cttggccaga tggggcagcc ggggctgggg gcagacagca cccccaacat ccagcaagcc   6960

ctgcagcagc ggattctgca gcaacagcag atgaagcagc agattgggtc cccaggccag   7020

ccgaacccca tgagccccca gcaacacatg ctctcaggac agccacaggc ctcgcatctc   7080

cctggccagc agatcgccac gtcccttagt aaccaggtgc ggtctccagc ccctgtccag   7140

tctccacggc cccagtccca gcctccacat tccagcccgt caccacggat acagccccag   7200

ccttcgccac accacgtctc accccagact ggttcccccc accccggact cgcagtcacc   7260
```

```
atggccagct ccatagatca gggacacttg gggaaccccg aacagagtgc aatgctcccc   7320
cagctgaaca cccccagcag gagtgcgctg tccagcgaac tgtccctggt cggggacacc   7380
acgggggaca cgctagagaa gtttgtggag ggcttgtagc attgtgagag catcaccttt   7440
tccctttcat gttcttggac cttttgtact gaaaatccag gcatctaggt tctttttatt   7500
cctagatgga actgcgactt ccgagccatg gaagggtgga ttgatgttta aagaaacaat   7560
acaaagaata tatttttttg ttaaaaacca gttgatttaa atatctggtc tctctctttg   7620
gttttttttt ggcggggggg tggggggggt tctttttttt ccgttttgtt tttgtttggg   7680
gggagggggg ttttgtttgg attctttttg tcgtcattgc tggtgactca tgcctttttt   7740
taacgggaaa aacaagttca ttatattcat atttttttatt tgtattttca agactttaaa   7800
catttatgtt taaaagtaag aagaaaaata atattcagaa ctgattcctg aaataatgca   7860
agcttataat gtatcccgat aactttgtga tgtttcggga agattttttt ctatagtgaa   7920
ctctgtgggc gtctcccagt attaccctgg atgataggaa ttgactccgg cgtgcacaca   7980
cgtacacacc cacacacatc tatctataca taatggctga agccaaactt gtcttgcaga   8040
tgtagaaatt gttgctttgt ttctctgata aaactggttt tagacaaaaa atagggatga   8100
tcactcttag accatgctaa tgttactaga gaagaagcct tcttttcttt cttctatgtg   8160
aaacttgaaa tgaggaaaag caattctagt gtaaatcatg caagcgctct aattcctata   8220
aatacgaaac tcgagaagat tcaatcactg tatagaatgg taaaatacca actcatttct   8280
tatatcatat tgttaaataa actgtgtgca acagacaaaa agggtggtcc ttcttgaatt   8340
catgtacatg gtattaacac ttagtgttcg gggtttttttg ttatgaaaat gctgttttca   8400
acattgtatt tggactatgc atgtgttttt tccccattgt atataaagta ccgcttaaaa   8460
ttgatataaa ttactgaggt ttttaacatg tattctgttc tttaagatcc ctgtaagaat   8520
gtttaaggtt tttatttatt tatatatatt ttttgagtct gttctttgta agacatggtt   8580
ctggttgttc gctcatagcg gagaggctgg ggctgcggtt gtggttgtgg cggcgtgggt   8640
ggtggctggg aactgtggcc caggcttagc ggccgcccgg aggcttttct tcccggagac   8700
tgaggtgggc gactgaggtg ggcggctcag cgttggcccc acacattcga ggctcacagg   8760
tgattgtcgc tcacacagtt agggtcgtca gttggtctga aactgcattt ggcccactcc   8820
tccatcctcc ctgtccgtcg tagctgccac ccccagaggc ggcgcttctt cccgtgttca   8880
ggcggctccc cccccccgta cacgactccc agaatctgag gcagagagtg ctccaggctc   8940
gcgaggtgct ttctgacttc cccccaaatc ctgccgctgc cgcgcagcat gtcccgtgtg   9000
gcgtttgagg aaatgctgag ggacagacac cttggagcac cagctccggt ccctgttaca   9060
gtgagaaagg tcccccactt cggggggatac ttgcacttag ccacatggtc ctgcctccct   9120
tggagtccag ttccaggctc ccttactgag tgggtgagac aagttcacaa aaaccgtaaa   9180
actgagagga ggaccatggg caggggagct gaagttcatc ccctaagtct accaccccca   9240
gcacccagag aacccacttt atccctagtc ccccaacaaa ggctggtcta ggtgggggtg   9300
atggtaattt tagaaatcac gccccaaata gcttccgttt gggcccttac attcacagat   9360
aggttttaaa tagctgaata cttggtttgg gaatctgaat tcgaggaacc tttctaagaa   9420
gttggaaagg tccgatctag ttttagcaca gagctttgaa ccttgagtta taaaatgcag   9480
aataattcaa gtaaaaataa gaccaccatc tggcacccct gaccagcccc cattcacccc   9540
atcccaggag gggaagcaca ggccgggcct ccggtggaga ttgctgccac tgctcggcct   9600
gctgggttct taacctccag tgtcctcttc atcttttcca cccgtaggga aaccttgagc   9660
```

```
catgtgttca aacaagaagt ggggctagag cccgagagca gcagctctaa gcccacactc   9720

agaaagtggc gccctcctgg ttgtgcagcc ttttaatgtg ggcagtggag gggcctctgt   9780

ttcaggttat cctggaattc aaaacgttat gtaccaacct catcctcttt ggagtctgca   9840

tcctgtgcaa ccgtcttggg caatccagat gtcgaaggat gtgaccgaga gcatggtctg   9900

tggatgctaa ccctaagttt gtcgtaagga aatttctgta agaaacctgg aaagccccaa   9960

cgctgtgtct catgctgtat acttaagagg agaagaaaaa gtcctatatt tgtgatcaaa  10020

aagaggaaac ttgaaatgtg atggtgttta taataaaaga tggtaaaact acttggattc  10080

aaa                                                                10083
```

<210> SEQ ID NO 111
<211> LENGTH: 1194
<212> TYPE: DNA
<213> ORGANISM: Homo sapiens

<400> SEQUENCE: 111

```
ataaatgggg aggggagagc ccactgggta gaaggaacag ggagcggcca ggatgctgaa     60

tctgctgctg ctggcgctgc ccgtcctggc gagccgcgcc tacgcggccc ctgccccagg    120

ccaggccctg cagcgagtgg gcatcgtcgg gggtcaggag gcccccagga gcaagtggcc    180

ctggcaggtg agcctgagag tccacggccc atactggatg cacttctgcg gggctccct    240

catccacccc cagtgggtgc tgaccgcagc gcactgcgtg ggaccggacg tcaaggatct    300

ggccgccctc agggtgcaac tgcgggagca gcacctctac taccaggacc agctgctgcc    360

ggtcagcagg atcatcgtgc acccacagtt ctacaccgcc cagatcggag cggacatcgc    420

cctgctggag ctggaggagc cggtgaacgt ctccagccac gtccacacgg tcaccctgcc    480

ccctgcctca gagaccttcc ccccggggat gccgtgctgg gtcactggct ggggcgatgt    540

ggacaatgat gagcgcctcc caccgccatt tcctctgaag caggtgaagg tccccataat    600

ggaaaaccac atttgtgacg caaaatacca ccttggcgcc tacacgggag acgacgtccg    660

catcgtccgt gacgacatgc tgtgtgccgg gaacacccgg agggactcat gccagggcga    720

ctccggaggg cccctggtgt gcaaggtgaa tggcacctgg ctgcaggcgg gcgtggtcag    780

ctggggcgag ggctgtgccc agcccaaccg gcctggcatc tacacccgtg tcacctacta    840

cttggactgg atccaccact atgtccccaa aaagccgtga gtcaggcctg ggttggccac    900

ctgggtcact ggaggaccaa cccctgctgt ccaaaacacc actgcttcct acccaggtgg    960

cgactgcccc ccacaccttc cctgccccgt cctgagtgcc ccttcctgtc ctaagccccc   1020

tgctctcttc tgagcccctt cccctgtcct gaggaccctt ccctatcctg agccccttc   1080

cctgtcctaa gcctgacgcc tgcaccgggc cctccagccc tcccctgccc agatagctgg   1140

tggtgggcgc taatcctcct gagtgctgga cctcattaaa gtgcatggaa atca         1194
```

<210> SEQ ID NO 112
<211> LENGTH: 2325
<212> TYPE: DNA
<213> ORGANISM: Homo sapiens

<400> SEQUENCE: 112

```
gcgggaagca ggggcggggc ctctggtggc ggtcgggaac tcggtgggag gcggcaacat     60

tgtttcaagt tggccaaatt gacaagagcg agaggtatac tgcgttccat cccgacccgg    120

ggccacggta ctgggccctg tttcccccctc ctcggccccc gagagccagg gtccgccttc    180
```

```
tgcagggttc ccaggccccc gctccagggc cgggctgacc cgactcgctg gcgcttcatg    240
gagaacttcc aaaaggtgga aaagatcgga gagggcacgt acggagttgt gtacaaagcc    300
agaaacaagt tgacgggaga ggtggtggcg cttaagaaaa tccgcctgga cactgagact    360
gagggtgtgc ccagtactgc catccgagag atctctctgc ttaaggagct taaccatcct    420
aatattgtca agctgctgga tgtcattcac acagaaaata aactctacct ggtttttgaa    480
tttctgcacc aagatctcaa gaaattcatg gatgcctctg ctctcactgg cattcctctt    540
cccctcatca agagctatct gttccagctg ctccagggcc tagctttctg ccattctcat    600
cgggtcctcc accgagacct taaacctcag aatctgctta ttaacacaga gggggccatc    660
aagctagcag actttggact agccagagct tttggagtcc ctgttcgtac ttacacccat    720
gaggtggtga ccctgtggta ccgagctcct gaaatcctcc tgggctgcaa atattattcc    780
acagctgtgg acatctggag cctgggctgc atctttgctg agatggtgac tcgccgggcc    840
ctattccctg gagattctga gattgaccag ctcttccgga tctttcggac tctggggacc    900
ccagatgagg tggtgtggcc aggagttact tctatgcctg attacaagcc aagtttcccc    960
aagtgggccc ggcaagattt tagtaaagtt gtacctcccc tggatgaaga tggacggagc   1020
ttgttatcgc aaatgctgca ctacgaccct aacaagcgga tttcggccaa ggcagccctg   1080
gctcaccctt tcttccagga tgtgaccaag ccagtacccc atcttcgact ctgatagcct   1140
tcttgaagcc cccagcccta atctcaccct ctcctccagt gtgggcttga ccaggcttgg   1200
ccttgggcta tttggactca ggtgggccct ctgaacttgc cttaaacact caccttctag   1260
tcttggccag ccaactctgg gaatacaggg gtgaaagggg ggaaccagtg aaaatgaaag   1320
gaagtttcag tattagatgc acttaagtta gcctccacca ccctttcccc cttctcttag   1380
ttattgctga agagggttgg tataaaaata attttaaaaa agccttccta cacgttagat   1440
ttgccgtacc aatctctgaa tgccccataa ttattatttc cagtgtttgg gatgaccagg   1500
atcccaagcc tcctgctgcc acaatgttta taaaggccaa atgatagcgg gggctaagtt   1560
ggtgcttttg agaaccaagt aaaacaaaac cactgggagg agtctatttt aaagaattcg   1620
gttgaaaaaa tagatccaat cagtttatac cctagttagt gttttgcctc acctaatagg   1680
ctgggagact gaagactcag cccgggtggg gctgcagaaa aatgattggc cccagtcccc   1740
ttgtttgtcc cttctacagg catgaggaat ctgggaggcc ctgagacagg gattgtgctt   1800
cattccaatc tattgcttca ccatggcctt atgaggcagg tgagagatgt ttgaattttt   1860
ctcttccttt tagtattctt agttgttcag ttgccaagga tccctgatcc catttttcctc   1920
tgacgtccac ctcctacccc ataggagtta gaagttaggg tttaggcatc attttgagaa   1980
tgctgacact tttcagggc tgtgattgag tgagggcatg ggtaaaaata tttctttaaa   2040
agaaggatga acaattatat ttatatttca ggttatatcc aatagtagag ttggcttttt   2100
ttttttttt ttggtcatag tgggtggatt tgttgccatg tgcaccttgg ggttttgtaa   2160
tgacagtgct aaaaaaaaaa agcatttttt ttttatgatt tgtctctgtc acccttgtcc   2220
ttgagtgctc ttgctattaa cgttatttgt aatttagttt gtagctcatt aaaaaaatgt   2280
gcctagtttt ataaaaaaaa aaaaaaaaaa caaaaaaaaa aaaaa                   2325
```

<210> SEQ ID NO 113
<211> LENGTH: 2223
<212> TYPE: DNA
<213> ORGANISM: Homo sapiens

<400> SEQUENCE: 113

```
gcgggaagca ggggcggggc ctctggtggc ggtcgggaac tcggtgggag gcggcaacat     60
tgtttcaagt tggccaaatt gacaagagcg agaggtatac tgcgttccat cccgacccgg    120
ggccacggta ctgggccctg tttccccctc ctcggccccc gagagccagg gtccgccttc    180
tgcagggttc ccaggccccc gctccagggc cgggctgacc cgactcgctg gcgcttcatg    240
gagaacttcc aaaaggtgga aaagatcgga gagggcacgt acggagttgt gtacaaagcc    300
agaaacaagt tgacgggaga ggtggtggcg cttaagaaaa tccgcctgga cactgagact    360
gagggtgtgc ccagtactgc catccgagag atctctctgc ttaaggagct taaccatcct    420
aatattgtca agctgctgga tgtcattcac acagaaaata aactctacct ggtttttgaa    480
tttctgcacc aagatctcaa gaaattcatg gatgcctctg ctctcactgg cattcctctt    540
cccctcatca agagctatct gttccagctg ctccagggcc tagctttctg ccattctcat    600
cgggtcctcc accgagacct taaacctcag aatctgctta ttaacacaga gggggccatc    660
aagctagcag actttggact agccagagct tttggagtcc ctgttcgtac ttacacccat    720
gaggtgactc gccgggccct attccctgga gattctgaga ttgaccagct cttccggatc    780
tttcggactc tggggacccc agatgaggtg gtgtggccag gagttacttc tatgcctgat    840
tacaagccaa gtttccccaa gtgggcccgg caagatttta gtaaagttgt acctcccctg    900
gatgaagatg gacggagctt gttatcgcaa atgctgcact acgaccctaa caagcggatt    960
tcggccaagg cagccctggc tcaccctttc ttccaggatg tgaccaagcc agtaccccat   1020
cttcgactct gatagccttc ttgaagcccc cagccctaat ctcaccctct cctccagtgt   1080
gggcttgacc aggcttggcc ttgggctatt tggactcagg tgggccctct gaacttgcct   1140
taaacactca ccttctagtc ttggccagcc aactctggga atacaggggt gaaagggggg   1200
aaccagtgaa aatgaaagga agtttcagta ttagatgcac ttaagttagc ctccaccacc   1260
ctttcccccct tctcttagtt attgctgaag agggttggta taaaaataat tttaaaaaag   1320
ccttcctaca cgttagattt gccgtaccaa tctctgaatg ccccataatt attatttcca   1380
gtgtttggga tgaccaggat cccaagcctc ctgctgccac aatgtttata aaggccaaat   1440
gatagcgggg gctaagttgg tgcttttgag aaccaagtaa aacaaaacca ctgggaggag   1500
tctattttaa agaattcggt tgaaaaaata gatccaatca gtttataccc tagttagtgt   1560
tttgcctcac ctaataggct gggagactga agactcagcc cgggtggggc tgcagaaaaa   1620
tgattggccc cagtcccctt gtttgtccct tctacaggca tgaggaatct gggaggccct   1680
gagacaggga ttgtgcttca ttccaatcta ttgcttcacc atggccttat gaggcaggtg   1740
agagatgttt gaatttttct cttcctttta gtattcttag ttgttcagtt gccaaggatc   1800
cctgatccca ttttcctctg acgtccacct cctaccccat aggagttaga agttagggtt   1860
taggcatcat tttgagaatg ctgacacttt ttcagggctg tgattgagtg agggcatggg   1920
taaaaatatt tctttaaaag aaggatgaac aattatattt atatttcagg ttatatccaa   1980
tagtagagtt ggcttttttt ttttttttt ggtcatagtg ggtggatttg ttgccatgtg   2040
caccttgggg ttttgtaatg acagtgctaa aaaaaaaaag catttttttt ttatgatttg   2100
tctctgtcac ccttgtcctt gagtgctctt gctattaacg ttatttgtaa tttagtttgt   2160
agctcattaa aaaaatgtgc ctagttttat aaaaaaaaaa aaaaaaaaca aaaaaaaaaa   2220
aaa                                                                 2223
```

<210> SEQ ID NO 114

<211> LENGTH: 4576
<212> TYPE: DNA
<213> ORGANISM: Homo sapiens

<400> SEQUENCE: 114

```
tggcagccag tgtcggggtg gcggctggga atgggggccg ctccggactt ccgctgccaa     60
ctacaagggg gcgggtccga ggggggttag ccgaagttgt aggcggggcg cgaggttcta    120
gtacccgagc tcatactagg gacgggaagt cgcgaccaga gccattggag ggcgcgggga    180
ctgcaaccct aatcagagcc caaatggcgc agtgggaaat gctgcagaat cttgacagcc    240
cctttcagga tcagctgcac cagctttact cgcacagcct cctgcctgtg gacattcgac    300
agtacttggc tgtctggatt gaagaccaga actggcagga agctgcactt gggagtgatg    360
attccaaggc taccatgcta ttcttccact tcttggatca gctgaactat gagtgtggcc    420
gttgcagcca ggacccagag tccttgttgc tgcagcacaa tttgcggaaa ttctgccggg    480
acattcagcc cttttcccag gatcctaccc agttggctga gatgatcttt aacctccttc    540
tggaagaaaa aagaattttg atccaggctc agagggccca attggaacaa ggagagccag    600
ttctcgaaac acctgtggag agccagcaac atgagattga atcccggatc ctggatttaa    660
gggctatgat ggagaagctg gtaaaatcca tcagccaact gaaagaccag caggatgtct    720
tctgcttccg atataagatc caggccaaag ggaagacacc ctctctggac ccccatcaga    780
ccaaagagca gaagattctg caggaaactc tcaatgaact ggacaaaagg agaaaggagg    840
tgctggatgc ctccaaagca ctgctaggcc gattaactac cctaatcgag ctactgctgc    900
caaagttgga ggagtggaag gcccagcagc aaaaagcctg catcagagct cccattgacc    960
acgggttgga acagctggag acatggttca cagctggagc aaagctgttg tttcacctga   1020
ggcagctgct gaaggagctg aagggactga gttgcctggt tagctatcag gatgaccctc   1080
tgaccaaagg ggtggaccta cgcaacgccc aggtcacaga gttgctacag cgtctgctcc   1140
acagagcctt tgtggtagaa acccagccct gcatgcccca aactccccat cgacccctca   1200
tcctcaagac tggcagcaag ttcaccgtcc gaacaaggct gctggtgaga ctccaggaag   1260
gcaatgagtc actgactgtg gaagtctcca ttgacaggaa tcctcctcaa ttacaaggct   1320
tccggaagtt caacattctg acttcaaacc agaaaacttt gacccccgag aaggggcaga   1380
gtcagggttt gatttgggac tttggttacc tgactctggt ggagcaacgt tcaggtggtt   1440
caggaaaggg cagcaataag gggccactag gtgtgacaga ggaactgcac atcatcagct   1500
tcacggtcaa atatacctac cagggtctga agcaggagct gaaaacggac accctccctg   1560
tggtgattat ttccaacatg aaccagctct caattgcctg ggcttcagtt ctctggttca   1620
atttgctcag cccaaacctt cagaaccagc agttcttctc caaccccccc aaggccccct   1680
ggagcttgct gggccctgct ctcagttggc agttctcctc ctatgttggc cgaggcctca   1740
actcagacca gctgagcatg ctgagaaaca agctgttcgg gcagaactgt aggactgagg   1800
atccattatt gtcctgggct gacttcacta agcgagagag ccctcctggc aagttaccat   1860
tctggacatg gctggacaaa attctggagt tggtacatga ccacctgaag gatctctgga   1920
atgatggacg catcatgggc tttgtgagtc ggagccagga gcgccggctg ctgaagaaga   1980
ccatgtctgg cacctttcta ctgcgcttca gtgaatcgtc agaagggggc attacctgct   2040
cctgggtgga gcaccaggat gatgacaagg tgctcatcta ctctgtgcaa ccgtacacga   2100
aggaggtgct gcagtcactc ccgctgactg aaatcatccg ccattaccag ttgctcactg   2160
aggagaatat acctgaaaac ccactgcgct tcctctatcc ccgaatcccc cgggatgaag   2220
```

```
cttttgggtg ctactaccag gagaaagtta atctccagga acggaggaaa tacctgaaac   2280
acaggctcat tgtggtctct aatagacagg tggatgaact gcaacaaccg ctggagctta   2340
agccagagcc agagctggag tcattagagc tggaactagg gctggtgcca gagccagagc   2400
tcagcctgga cttagagcca ctgctgaagg cagggctgga tctggggcca gagctagagt   2460
ctgtgctgga gtccactctg gagcctgtga tagagcccac actatgcatg gtatcacaaa   2520
cagtgccaga gccagaccaa ggacctgtat cacagccagt gccagagcca gatttgccct   2580
gtgatctgag acatttgaac actgagccaa tggaaatctt cagaaactgt gtaaagattg   2640
aagaaatcat gccgaatggt gacccactgt tggctggcca gaacaccgtg gatgaggttt   2700
acgtctcccg ccccagccac ttctacactg atggaccctt gatgccttct gacttctagg   2760
aaccacattt cctctgttct tttcatatct cttgcccttc ctactcctca tagcatgata   2820
ttgttctcca aggatgggaa tcaggcatgt gtcccttcca agctgtgtta actgttcaaa   2880
ctcaggcctg tgtgactcca ttggggtgag aggtgaaagc ataacatggg tacagagggg   2940
acaacaatga atcagaacag atgctgagcc ataggtctaa ataggatcct ggaggctgcc   3000
tgctgtgctg ggaggtatag gggtcctggg ggcaggccag ggcagttgac aggtacttgg   3060
agggctcagg gcagtggctt ctttccagta tggaaggatt tcaacatttt aatagttggt   3120
taggctaaac tggtgcatac tggcattggc ccttggtggg gagcacagac acaggatagg   3180
actccatttc tttcttccat tccttcatgt ctaggataac ttgctttctt ctttccttta   3240
ctcctggctc aagccctgaa tttcttcttt tcctgcaggg gttgagagct ttctgcctta   3300
gcctaccatg tgaaactcta ccctgaagaa agggatggat aggaagtaga cctctttttc   3360
ttaccagtct cctcccctac tctgccccta agctggctgt acctgttcct cccccataaa   3420
atgatcctgc caatctaatg tgagtgtgaa gctttgcaca ctagtttatg ctacctagtc   3480
tccactttct caatgcttag gagacagatc actcctggag gctggggatg gtaggattgc   3540
tggggatttt ttttttttta aacagggtct cactctgttg cccaggctag agtgcaatgg   3600
tgcaatcaca gctcactgca gcctcaacct cctgggttca agcaatcctc ctacctcagc   3660
ctcctgggta gctagcacca tggcatgcgc caccatgccc tatttttttt ttttaaagac   3720
agggtcttgc tatattgccc aggctggtct tgaactgggc tcaagtgatc ctcacgcctt   3780
ggcctcccaa agtgctggga ttataggcat gagccactgt gcttggccag gatttttttt   3840
tttttttttt tgagatggag tttctctctt gttgtccagg ctggagtgca atggtgtgat   3900
ctcggctcac tgcaacctcc gccttccggg ttcaagtgac tctcctgcct cagcctcccc   3960
agtagctggg attacagatc tgcaccacca tgcccagcta attttgtatt tttagtagag   4020
acggggtttc tccatgttgg tcaggctggt ctcgaactcc tgacctcaag tgatctgtcc   4080
acctcggcct cccagagtgc tgggattaca ggcgtgagcc actgttccca gcaggaattt   4140
ctttttttata gtattggata aagtttggtg tttttacaga ggagaagcaa tgggtcttag   4200
ctctttctct attatgttat catcctccct tttttgtaca atatgttgtt tacctgaaag   4260
gaaggtttct attcgttggt tgtggacctg gacaaagtcc aagtctgtgg aacttaaaac   4320
cttgaaggtc tgtcatagga ctctggacaa tctcacacct tagctattcc cagggaaccc   4380
cagggggcaa ctgacattgc tccaagatgt tctcctgatg tagcttgaga tataaaggaa   4440
aggccctgca caggtggctg tttcttgtct gttatgtcag aggaacagtc ctgttcagaa   4500
aggggctctt ctgagcagaa atggctaata aactttgtgc tgatctggaa aaaaaaaaaa   4560
```

aaaaaaaaaa aaaaaa 4576

<210> SEQ ID NO 115
<211> LENGTH: 4564
<212> TYPE: DNA
<213> ORGANISM: Homo sapiens

<400> SEQUENCE: 115
tggcagccag tgtcggggtg gcggctggga atgggggccg ctccggactt ccgctgccaa 60
ctacaagggg gcgggtccga ggggggttag ccgaagttgt aggcggggcg cgaggttcta 120
gtacccgagc tcatactagg gacgggaagt cgcgaccaga gccattggag ggcgcgggga 180
ctgcaaccct aatcagagcc caaatggcgc agtgggaaat gctgcagaat cttgacagcc 240
cctttcagga tcagctgcac cagctttact cgcacagcct cctgcctgtg gacattcgac 300
agtacttggc tgtctggatt gaagaccaga actggcagga agctgcactt gggagtgatg 360
attccaaggc taccatgcta ttcttccact tcttggatca gctgaactat gagtgtggcc 420
gttgcagcca ggacccagag tccttgttgc tgcagcacaa tttgcggaaa ttctgccggg 480
acattcagga tcctacccag ttggctgaga tgatctttaa cctccttctg gaagaaaaaa 540
gaattttgat ccaggctcag agggcccaat tggaacaagg agagccagtt ctcgaaacac 600
ctgtggagag ccagcaacat gagattgaat cccggatcct ggatttaagg gctatgatgg 660
agaagctggt aaaatccatc agccaactga aagaccagca ggatgtcttc tgcttccgat 720
ataagatcca ggccaaaggg aagacaccct ctctggaccc ccatcagacc aaagagcaga 780
agattctgca ggaaactctc aatgaactgg acaaaaggag aaaggaggtg ctggatgcct 840
ccaaagcact gctaggccga ttaactaccc taatcgagct actgctgcca aagttggagg 900
agtggaaggc ccagcagcaa aaagcctgca tcagagctcc cattgaccac gggttggaac 960
agctggagac atggttcaca gctggagcaa agctgttgtt tcacctgagg cagctgctga 1020
aggagctgaa gggactgagt tgcctggtta gctatcagga tgaccctctg accaaagggg 1080
tggacctacg caacgcccag gtcacagagt tgctacagcg tctgctccac agagcctttg 1140
tggtagaaac ccagccctgc atgccccaaa ctccccatcg acccctcatc ctcaagactg 1200
gcagcaagtt caccgtccga acaaggctgc tggtgagact ccaggaaggc aatgagtcac 1260
tgactgtgga agtctccatt gacaggaatc ctcctcaatt acaaggcttc cggaagttca 1320
acattctgac ttcaaaccag aaaactttga cccccgagaa ggggcagagt cagggtttga 1380
tttgggactt tggttacctg actctggtgg agcaacgttc aggtggttca ggaaagggca 1440
gcaataaggg gccactaggt gtgacagagg aactgcacat catcagcttc acggtcaaat 1500
atacctacca gggtctgaag caggagctga aaacggacac cctccctgtg gtgattattt 1560
ccaacatgaa ccagctctca attgcctggg cttcagttct ctggttcaat ttgctcagcc 1620
caaaccttca gaaccagcag ttcttctcca acccccccaa ggcccccctgg agcttgctgg 1680
gccctgctct cagttggcag ttctcctcct atgttggccg aggcctcaac tcagaccagc 1740
tgagcatgct gagaaacaag ctgttcgggc agaactgtag gactgaggat ccattattgt 1800
cctgggctga cttcactaag cgagagagcc ctcctggcaa gttaccattc tggacatggc 1860
tggacaaaat tctggagttg gtacatgacc acctgaagga tctctggaat gatggacgca 1920
tcatgggctt tgtgagtcgg agccaggagc gccggctgct gaagaagacc atgtctggca 1980
cctttctact gcgcttcagt gaatcgtcag aagggggcat tacctgctcc tgggtggagc 2040
accaggatga tgacaaggtg ctcatctact ctgtgcaacc gtacacgaag gaggtgctgc 2100

```
agtcactccc gctgactgaa atcatccgcc attaccagtt gctcactgag gagaatatac   2160
ctgaaaaccc actgcgcttc ctctatcccc gaatccccg ggatgaagct tttgggtgct    2220
actaccagga gaaagttaat ctccaggaac ggaggaaata cctgaaacac aggctcattg   2280
tggtctctaa tagacaggtg gatgaactgc aacaaccgct ggagcttaag ccagagccag   2340
agctggagtc attagagctg gaactagggc tggtgccaga gccagagctc agcctggact   2400
tagagccact gctgaaggca gggctggatc tggggccaga gctagagtct gtgctggagt   2460
ccactctgga gcctgtgata gagcccacac tatgcatggt atcacaaaca gtgccagagc   2520
cagaccaagg acctgtatca cagccagtgc cagagccaga tttgccctgt gatctgagac   2580
atttgaacac tgagccaatg gaaatcttca gaaactgtgt aaagattgaa gaaatcatgc   2640
cgaatggtga cccactgttg gctggccaga acaccgtgga tgaggtttac gtctcccgcc   2700
ccagccactt ctacactgat ggacccttga tgccttctga cttctaggaa ccacatttcc   2760
tctgttcttt tcatatctct tgcccttcct actcctcata gcatgatatt gttctccaag   2820
gatgggaatc aggcatgtgt cccttccaag ctgtgttaac tgttcaaact caggcctgtg   2880
tgactccatt ggggtgagag gtgaaagcat aacatgggta cagaggggac aacaatgaat   2940
cagaacagat gctgagccat aggtctaaat aggatcctgg aggctgcctg ctgtgctggg   3000
aggtataggg gtcctggggg caggccaggg cagttgacag gtacttggag ggctcagggc   3060
agtggcttct ttccagtatg gaaggatttc aacattttaa tagttggtta ggctaaactg   3120
gtgcatactg gcattggccc ttggtgggga gcacagacac aggataggac tccatttctt   3180
tcttccattc cttcatgtct aggataactt gctttcttct ttcctttact cctggctcaa   3240
gccctgaatt tcttcttttc ctgcaggggt tgagagcttt ctgccttagc ctaccatgtg   3300
aaactctacc ctgaagaaag ggatggatag gaagtagacc tctttttctt accagtctcc   3360
tcccctactc tgcccctaag ctggctgtac ctgttcctcc cccataaaat gatcctgcca   3420
atctaatgtg agtgtgaagc tttgcacact agtttatgct acctagtctc cactttctca   3480
atgcttagga gacagatcac tcctggaggc tggggatggt aggattgctg ggatttttt    3540
ttttttaaa cagggtctca ctctgttgcc caggctagag tgcaatggtg caatcacagc    3600
tcactgcagc ctcaacctcc tgggttcaag caatcctcct acctcagcct cctgggtagc   3660
tagcaccatg gcatgcgcca ccatgcccta ttttttttt ttaaagacag ggtcttgcta    3720
tattgcccag gctggtcttg aactgggctc aagtgatcct cacgccttgg cctcccaaag   3780
tgctgggatt ataggcatga gccactgtgc ttggccagga ttttttttt ttttttttg     3840
agatggagtt tctctcttgt tgtccaggct ggagtgcaat ggtgtgatct cggctcactg   3900
caacctccgc cttccgggtt caagtgactc tcctgcctca gcctccccag tagctgggat   3960
tacagatctg caccaccatg cccagctaat tttgtatttt tagtagagac ggggtttctc   4020
catgttggtc aggctggtct cgaactcctg acctcaagtg atctgtccac ctcggcctcc   4080
cagagtgctg ggattacagg cgtgagccac tgttcccagc aggaatttct tttttatagt   4140
attggataaa gtttggtgtt tttacagagg agaagcaatg ggtcttagct ctttctctat   4200
tatgttatca tcctcccttt tttgtacaat atgttgttta cctgaaagga aggtttctat   4260
tcgttggttg tggacctgga caaagtccaa gtctgtggaa cttaaaacct tgaaggtctg   4320
tcataggact ctggacaatc tcacacctta gctattccca gggaacccca gggggcaact   4380
gacattgctc caagatgttc tcctgatgta gcttgagata taaaggaaag gccctgcaca   4440
```

```
ggtggctgtt tcttgtctgt tatgtcagag gaacagtcct gttcagaaag gggctcttct   4500

gagcagaaat ggctaataaa ctttgtgctg atctggaaaa aaaaaaaaaa aaaaaaaaaa   4560

aaaa                                                                 4564
```

<210> SEQ ID NO 116
<211> LENGTH: 2923
<212> TYPE: DNA
<213> ORGANISM: Homo sapiens

<400> SEQUENCE: 116

```
cctctcgagg cggggcgggg cctccgcgtt cgctacaaaa gccgcgcggc ggctgcgacc     60

gggacggccc gttttccgcc agctcgccgc tcgctatggc gtcgctcacc gtgaaggcct    120

accttctggg caaggaggac gcggcgcgcg agattcgccg cttcagcttc tgctgcagcc    180

ccgagcctga ggcggaagcc gaggctgcgg cgggtccggg accctgcgag cggctgctga    240

gccgggtggc cgccctgttc cccgcgctgc ggcctggcgg cttccaggcg cactaccgcg    300

atgaggacgg ggacttggtt gccttttcca gtgacgagga attgacaatg gccatgtcct    360

acgtgaagga tgacatcttc cgaatctaca ttaaagagaa aaaagagtgc cggcgggacc    420

accgcccacc gtgtgctcag gaggcgcccc gcaacatggt gcaccccaat gtgatctgcg    480

atggctgcaa tgggcctgtg gtaggaaccc gctacaagtg cagcgtctgc ccagactacg    540

acttgtgtag cgtctgcgag ggaaagggct tgcaccgggg gcacaccaag ctcgcattcc    600

ccagcccctt cgggcacctg tctgagggct tctcgcacag ccgctggctc cggaaggtga    660

aacacggaca cttcgggtgg ccaggatggg aaatgggtcc accaggaaac tggagcccac    720

gtcctcctcg tgcaggggag gcccgccctg gccccacggc agaatcagct tctggtccat    780

cggaggatcc gagtgtgaat ttcctgaaga acgttgggga gagtgtggca gctgccctta    840

gccctctggg cattgaagtt gatatcgatg tggagcacgg agggaaaaga agccgcctga    900

cccccgtctc tccagagagt tccagcacag aggagaagag cagctcacag ccaagcagct    960

gctgctctga ccccagcaag ccgggtggga atgttgaggg cgccacgcag tctctggcgg   1020

agcagatgag gaagatcgcc ttggagtccg aggggcgccc tgaggaacag atggagtcgg   1080

ataactgttc aggaggagat gatgactgga cccatctgtc ttcaaaagaa gtggacccgt   1140

ctacaggtga actccagtcc ctacagatgc cagaatccga agggccaagc tctctggacc   1200

cctcccagga gggacccaca gggctgaagg aagctgcctt gtacccacat ctcccgccag   1260

aggctgaccc gcggctgatt gagtccctct cccagatgct gtccatgggc ttctctgatg   1320

aaggcggctg gctcaccagg ctcctgcaga ccaagaacta tgacatcgga gcggctctgg   1380

acaccatcca gtattcaaag catcccccgc cgttgtgacc acttttgccc acctcttctg   1440

cgtgcccctc ttctgtctca tagttgtgtt aagcttgcgt agaattgcag gtctctgtac   1500

gggccagttt ctctgccttc ttccaggatc aggggttagg gtgcaagaag ccatttaggg   1560

cagcaaaaca agtgacatga agggagggtc cctgtgtgtg tgtgtgctga tgtttcctgg   1620

gtgccctggc tccttgcagc agggctgggc ctgcgagacc caaggctcac tgcagcgcgc   1680

tcctgacccc tccctgcagg ggctacgtta gcagcccagc acatagcttg cctaatggct   1740

ttcactttct cttttgtttt aaatgactca taggtccctg acatttagtt gattattttc   1800

tgctacagac ctggtacact ctgattttag ataaagtaag cctaggtgtt gtcagcaggc   1860

aggctgggga ggccagtgtt gtgggcttcc tgctgggact gagaaggctc acgaagggca   1920

tccgcaatgt tggtttcact gagagctgcc tcctggtctc ttcaccactg tagttctctc   1980
```

```
atttccaaac catcagctgc ttttaaaata agatctcttt gtagccatcc tgttaaattt   2040

gtaaacaatc taattaaatg gcatcagcac tttaaccaat gacgtttgca tagagagaaa   2100

tgattgacag taagtttatt gttaatggtt cttacagagt atctttaaaa gtgccttagg   2160

ggaaccctgt ccctcctaac aagtgtatct cgattaataa cctgccagtc ccagatcaca   2220

catcatcatc gaagtcttcc ccagttataa agaggtcaca tagtcgtgtg ggtcgaggat   2280

tctgtgcctc caggaccagg ggcccaccct ctgcccaggg agtccttgcg tcccatgagg   2340

tcttcccgca aggcctctca gacccagatg tgacggggtg tgtggcccga ggaagctgga   2400

cagcggcagt gggcctgctg aggccttctc ttgaggcctg tgctctgggg gtcccttgct   2460

tagcctgtgc tggaccagct ggcctggggt ccctctgaag agaccttggc tgctcactgt   2520

ccacatgtga actttttcta ggtggcagga caaattgcgc ccatttagag gatgtggctg   2580

taacctgctg gatgggactc catagctcct tcccaggacc cctcagctcc ccggcactgc   2640

agtctgcaga gttctcctgg aggcaggggc tgctgccttg tttcaccttc catgtcaggc   2700

cagcctgtcc ctgaaagaga agatggccat gccctccatg tgtaagaaca atgccagggc   2760

ccaggaggac cgcctgccct gcctgggcct tggctgggcc tctggttctg acactttctg   2820

ctggaagctg tcaggctggg acaggctttg attttgaggg ttagcaagac aaagcaaata   2880

aatgccttcc acctcaccgc aaaaaaaaaa aaaaaaaaaa aaa                     2923
```

<210> SEQ ID NO 117
<211> LENGTH: 2931
<212> TYPE: DNA
<213> ORGANISM: Homo sapiens

<400> SEQUENCE: 117

```
gcgtcggctt ccggccgcct tccgcggcca ccgccgggcc cgctcccgcc gccgacgccc     60

aggtgcgcca ggtgcgggcc gggcgggggt cgcgctcacc tttctggccg ctgagtgccg    120

cgtaccagga cagcgagagg aaggcgcaca ggcagaagag cagcagcgtc aggaaggtgc    180

cattgcggag cctcatctcc tcggtgtctg cgagattaat ctctcatggc cgctgcacaa    240

gaacctggct tttagctgaa ctaaggagaa agtcctacaa cagtttggcg tgcaacatgg    300

ggcttgagaa aggatgagga cggggacttg gttgcctttt ccagtgacga ggaattgaca    360

atggccatgt cctacgtgaa ggatgacatc ttccgaatct acattaaaga gaaaaaagag    420

tgccggcggg accaccgccc accgtgtgct caggaggcgc cccgcaacat ggtgcacccc    480

aatgtgatct gcgatggctg caatgggcct gtggtaggaa cccgctacaa gtgcagcgtc    540

tgcccagact acgacttgtg tagcgtctgc gagggaaagg gcttgcaccg ggggcacacc    600

aagctcgcat tccccagccc cttcgggcac ctgtctgagg gcttctcgca cagccgctgg    660

ctccggaagg tgaaacacgg acacttcggg tggccaggat gggaaatggg tccaccagga    720

aactggagcc cacgtcctcc tcgtgcaggg gaggcccgcc ctggccccac ggcagaatca    780

gcttctggtc catcggagga tccgagtgtg aatttcctga agaacgttgg ggagagtgtg    840

gcagctgccc ttagccctct gggcattgaa gttgatatcg atgtggagca cggagggaaa    900

agaagccgcc tgaccccccgt ctctccagag agttccagca cagaggagaa gagcagctca    960

cagccaagca gctgctgctc tgaccccagc aagccgggtg ggaatgttga gggcgccacg   1020

cagtctctgg cggagcagat gaggaagatc gccttggagt ccgaggggcg ccctgaggaa   1080

cagatggagt cggataactg ttcaggagga gatgatgact ggacccatct gtcttcaaaa   1140
```

```
gaagtggacc cgtctacagg tgaactccag tccctacaga tgccagaatc cgaagggcca   1200
agctctctgg acccctccca ggagggaccc acagggctga aggaagctgc cttgtaccca   1260
catctcccgc cagaggctga cccgcggctg attgagtccc tctcccagat gctgtccatg   1320
ggcttctctg atgaaggcgg ctggctcacc aggctcctgc agaccaagaa ctatgacatc   1380
ggagcggctc tggacaccat ccagtattca aagcatcccc cgccgttgtg accacttttg   1440
cccacctctt ctgcgtgccc ctcttctgtc tcatagttgt gttaagcttg cgtagaattg   1500
caggtctctg tacgggccag tttctctgcc ttcttccagg atcaggggtt agggtgcaag   1560
aagccattta gggcagcaaa acaagtgaca tgaagggagg gtccctgtgt gtgtgtgtgc   1620
tgatgtttcc tgggtgccct ggctccttgc agcagggctg ggcctgcgag acccaaggct   1680
cactgcagcg cgctcctgac ccctccctgc aggggctacg ttagcagccc agcacatagc   1740
ttgcctaatg gctttcactt tctcttttgt tttaaatgac tcataggtcc ctgacattta   1800
gttgattatt ttctgctaca gacctggtac actctgattt tagataaagt aagcctaggt   1860
gttgtcagca ggcaggctgg ggaggccagt gttgtgggct tcctgctggg actgagaagg   1920
ctcacgaagg gcatccgcaa tgttggtttc actgagagct gcctcctggt ctcttcacca   1980
ctgtagttct ctcatttcca aaccatcagc tgcttttaaa ataagatctc tttgtagcca   2040
tcctgttaaa tttgtaaaca atctaattaa atggcatcag cactttaacc aatgacgttt   2100
gcatagagag aaatgattga cagtaagttt attgttaatg gttcttacag agtatcttta   2160
aaagtgcctt aggggaaccc tgtccctcct aacaagtgta tctcgattaa taacctgcca   2220
gtcccagatc acacatcatc atcgaagtct tccccagtta taaagaggtc acatagtcgt   2280
gtgggtcgag gattctgtgc ctccaggacc aggggcccac cctctgccca gggagtcctt   2340
gcgtcccatg aggtcttccc gcaaggcctc tcagacccag atgtgacggg gtgtgtggcc   2400
cgaggaagct ggacagcggc agtgggcctg ctgaggcctt ctcttgaggc ctgtgctctg   2460
ggggtccctt gcttagcctg tgctggacca gctggcctgg ggtccctctg aagagacctt   2520
ggctgctcac tgtccacatg tgaacttttt ctaggtggca ggacaaattg cgcccattta   2580
gaggatgtgg ctgtaacctg ctggatggga ctccatagct ccttcccagg accccctcagc   2640
tccccggcac tgcagtctgc agagttctcc tggaggcagg ggctgctgcc ttgtttcacc   2700
ttccatgtca ggccagcctg tccctgaaag agaagatggc catgccctcc atgtgtaaga   2760
acaatgccag ggcccaggag gaccgcctgc cctgcctggg ccttggctgg gcctctggtt   2820
ctgacacttt ctgctggaag ctgtcaggct gggacaggct ttgattttga gggttagcaa   2880
gacaaagcaa ataaatgcct tccacctcac cgcaaaaaaa aaaaaaaaaa a            2931
```

<210> SEQ ID NO 118
<211> LENGTH: 2848
<212> TYPE: DNA
<213> ORGANISM: Homo sapiens

<400> SEQUENCE: 118

```
ggatttaaag gggccgcagc accgccgtcg ccggcgccgc gagggggtgg ggtgggggcc     60
ggcggccggg atcccgatcg gctcccgcag ccccgcgtgg gctcgtgcga gtcggcctca    120
gtgtctgcga gattaatctc tcatggccgc tgcacaagaa cctggctttt agctgaacta    180
aggagaaagt cctacaacag tttggcgtgc aacatggggc ttgagaaagg atgaggacgg    240
ggacttggtt gccttttcca gtgacgagga attgacaatg gccatgtcct acgtgaagga    300
tgacatcttc cgaatctaca ttaaagagaa aaaagagtgc cggcgggacc accgcccacc    360
```

```
gtgtgctcag gaggcgcccc gcaacatggt gcaccccaat gtgatctgcg atggctgcaa    420
tgggcctgtg gtaggaaccc gctacaagtg cagcgtctgc ccagactacg acttgtgtag    480
cgtctgcgag ggaaagggct tgcaccgggg gcacaccaag ctcgcattcc ccagcccctt    540
cgggcacctg tctgagggct tctcgcacag ccgctggctc cggaaggtga aacacggaca    600
cttcgggtgg ccaggatggg aaatgggtcc accaggaaac tggagcccac gtcctcctcg    660
tgcaggggag gcccgccctg gccccacggc agaatcagct tctggtccat cggaggatcc    720
gagtgtgaat ttcctgaaga acgttgggga gagtgtggca gctgccctta gccctctggg    780
cattgaagtt gatatcgatg tggagcacgg agggaaaaga agccgcctga cccccgtctc    840
tccagagagt tccagcacag aggagaagag cagctcacag ccaagcagct gctgctctga    900
ccccagcaag ccgggtggga atgttgaggg cgccacgcag tctctggcgg agcagatgag    960
gaagatcgcc ttggagtccg aggggcgccc tgaggaacag atggagtcgg ataactgttc   1020
aggaggagat gatgactgga cccatctgtc ttcaaaagaa gtggacccgt ctacaggtga   1080
actccagtcc ctacagatgc cagaatccga agggccaagc tctctggacc cctcccagga   1140
gggacccaca gggctgaagg aagctgcctt gtacccacat ctcccgccag aggctgaccc   1200
gcggctgatt gagtccctct cccagatgct gtccatgggc ttctctgatg aaggcggctg   1260
gctcaccagg ctcctgcaga ccaagaacta tgacatcgga gcggctctgg acaccatcca   1320
gtattcaaag catcccccgc cgttgtgacc acttttgccc acctcttctg cgtgcccctc   1380
ttctgtctca tagttgtgtt aagcttgcgt agaattgcag gtctctgtac gggccagttt   1440
ctctgccttc ttccaggatc aggggttagg gtgcaagaag ccatttaggg cagcaaaaca   1500
agtgacatga agggagggtc cctgtgtgtg tgtgtgctga tgtttcctgg gtgccctggc   1560
tccttgcagc agggctgggc ctgcgagacc caaggctcac tgcagcgcgc tcctgacccc   1620
tccctgcagg ggctacgtta gcagcccagc acatagcttg cctaatggct ttcactttct   1680
cttttgtttt aaatgactca taggtccctg acatttagtt gattattttc tgctacagac   1740
ctggtacact ctgattttag ataaagtaag cctaggtgtt gtcagcaggc aggctgggga   1800
ggccagtgtt gtgggcttcc tgctgggact gagaaggctc acgaagggca tccgcaatgt   1860
tggtttcact gagagctgcc tcctggtctc ttcaccactg tagttctctc atttccaaac   1920
catcagctgc ttttaaaata agatctcttt gtagccatcc tgttaaattt gtaaacaatc   1980
taattaaatg gcatcagcac tttaaccaat gacgtttgca tagagagaaa tgattgacag   2040
taagtttatt gttaatggtt cttacagagt atctttaaaa gtgccttagg ggaaccctgt   2100
ccctcctaac aagtgtatct cgattaataa cctgccagtc ccagatcaca catcatcatc   2160
gaagtcttcc ccagttataa agaggtcaca tagtcgtgtg ggtcgaggat tctgtgcctc   2220
caggaccagg ggcccaccct ctgcccaggg agtccttgcg tcccatgagg tcttcccgca   2280
aggcctctca gacccagatg tgacggggtg tgtggcccga ggaagctgga cagcggcagt   2340
gggcctgctg aggccttctc ttgaggcctg tgctctgggg gtcccttgct tagcctgtgc   2400
tggaccagct ggcctggggt ccctctgaag agaccttggc tgctcactgt ccacatgtga   2460
actttttcta ggtggcagga caaattgcgc ccatttagag gatgtggctg taacctgctg   2520
gatgggactc catagctcct tcccaggacc cctcagctcc ccggcactgc agtctgcaga   2580
gttctcctgg aggcaggggc tgctgccttg tttcaccttc catgtcaggc cagcctgtcc   2640
ctgaaagaga agatggccat gccctccatg tgtaagaaca atgccagggc ccaggaggac   2700
```

cgcctgccct gcctgggcct tggctgggcc tctggttctg acactttctg ctggaagctg 2760
tcaggctggg acaggctttg attttgaggg ttagcaagac aaagcaaata aatgccttcc 2820
acctcaccgc aaaaaaaaaa aaaaaaaa 2848

<210> SEQ ID NO 119
<211> LENGTH: 987
<212> TYPE: DNA
<213> ORGANISM: Homo sapiens

<400> SEQUENCE: 119
aatataagtg gaggcgtcgc gctggcgggc attcctgaag ctgacagcat tcgggccgag 60
atgtctcgct ccgtggcctt agctgtgctc gcgctactct ctctttctgg cctggaggct 120
atccagcgta ctccaaagat tcaggtttac tcacgtcatc cagcagagaa tggaaagtca 180
aatttcctga attgctatgt gtctgggttt catccatccg acattgaagt tgacttactg 240
aagaatggag agagaattga aaaagtggag cattcagact tgtctttcag caaggactgg 300
tctttctatc tcttgtacta cactgaattc acccccactg aaaaagatga gtatgcctgc 360
cgtgtgaacc atgtgacttt gtcacagccc aagatagtta agtgggatcg agacatgtaa 420
gcagcatcat ggaggtttga agatgccgca tttggattgg atgaattcca aattctgctt 480
gcttgctttt taatattgat atgcttatac acttacactt tatgcacaaa atgtagggtt 540
ataataatgt taacatggac atgatcttct ttataattct actttgagtg ctgtctccat 600
gtttgatgta tctgagcagg ttgctccaca ggtagctcta ggagggctgg caacttagag 660
gtggggagca gagaattctc ttatccaaca tcaacatctt ggtcagattt gaactcttca 720
atctcttgca ctcaaagctt gttaagatag ttaagcgtgc ataagttaac ttccaattta 780
catactctgc ttagaatttg gggaaaatt tagaaatata attgacagga ttattggaaa 840
tttgttataa tgaatgaaac attttgtcat ataagattca tatttacttc ttatacattt 900
gataaagtaa ggcatggttg tggttaatct ggtttatttt tgttccacaa gttaaataaa 960
tcataaaact tgatgtgtta tctctta 987

<210> SEQ ID NO 120
<211> LENGTH: 1782
<212> TYPE: DNA
<213> ORGANISM: Homo sapiens

<400> SEQUENCE: 120
ggagagatga tgtttaggtc cgggactgtc agtcagtgcg cggccaggta cgggccgacg 60
ggcccgcggg gccggcgccg ccatggcggc cgtgtttgat ttggatttgg agacggagga 120
aggcagcgag ggcgagggcg agccagagct cagccccgcg gacgcatgtc cccttgccga 180
gttgagggca gctggcctag agcctgtggg acactatgaa gaggtggagc tgactgagac 240
cagcgtgaac gttggcccag agcgcatcgg gccccactgc tttgagctgc tgcgtgtgct 300
gggcaagggg ggctatggca aggtgttcca ggtgcgaaag gtgcaaggca ccaacttggg 360
caaaatatat gccatgaaag tcctaaggaa ggccaaaatt gtgcgcaatg ccaaggacac 420
agcacacaca cgggctgagc ggaacattct agagtcagtg aagcacccct ttattgtgga 480
actggcctat gccttccaga ctggtggcaa actctacctc atccttgagt gcctcagtgg 540
tggcgagctc ttcacgcatc tggagcgaga gggcatcttc ctggaagata cggcctgctt 600
ctacctggct gagatcacgc tggccctggg ccatctccac tcccagggca tcatctaccg 660
ggacctcaag cccgagaaca tcatgctcag cagccagggc cacatcaaac tgaccgactt 720

```
tggactctgc aaggagtcta tccatgaggg cgccgtcact cacaccttct gcggcaccat    780
tgagtacatg gcccctgaga ttctggtgcg cagtggccac aaccgggctg tggactggtg    840
gagcctgggg gccctgatgt acgacatgct cactggatcg ccgcccttca ccgcagagaa    900
ccggaagaaa accatggata agatcatcag ggcaagctg gcactgcccc cctacctcac     960
cccagatgcc cgggaccttg tcaaaaagtt tctgaaacgg aatcccagcc agcggattgg   1020
gggtggccca ggggatgctg ctgatgtgca gagacatccc tttttccggc acatgaattg   1080
ggacgacctt ctggcctggc gtgtggaccc ccctttcagg ccctgtctgc agtcagagga   1140
ggacgtgagc cagtttgata cccgcttcac acggcagacg ccggtggaca gtcctgatga   1200
cacagccctc agcgagagtg ccaaccaggc cttcctgggc ttcacatacg tggcgccgtc   1260
tgtcctggac agcatcaagg agggcttctc cttccagccc aagctgcgct cacccaggcg   1320
cctcaacagt agcccccggg cccccgtcag ccccctcaag ttctcccctt ttgaggggtt   1380
tcggcccagc cccagcctgc cggagcccac ggagctacct ctacctccac tcctgccacc   1440
gccgccgccc tcgaccaccg cccctctccc catccgtccc ccctcaggga ccaagaagtc   1500
caagaggggc cgtgggcgtc cagggcgcta ggaagccggg tgggggtgag ggtagccctt   1560
gagccctgtc cctgcggctg tgagagcagc aggaccctgg gccagttcca gagacctggg   1620
ggtgtgtctg gggtggggt gtgagtgcgt atgaaagtgt gtgtctgctg ggcagctgt    1680
gcccctgaat catgggcacg gagggccgcc cgccacgccc cgcgctcaac tgctcccgtg   1740
gaagattaaa gggctgaatc atggtgctga aaaaaaaaaa aa                      1782
```

<210> SEQ ID NO 121
<211> LENGTH: 2405
<212> TYPE: DNA
<213> ORGANISM: Homo sapiens

<400> SEQUENCE: 121

```
tccggcgtgg tgcgcaggcg cggtatcccc cctcccccgc cagctcgacc ccggtgtggt     60
gcgcaggcgc agtctgcgca gggactggcg ggactgcgcg gcggcaacag cagacatgtc    120
gggggtccgg ggcctgtcgc ggctgctgag cgctcggcgc ctggcgctgg ccaaggcgtg    180
gccaacagtg ttgcaaacag gaacccgagg ttttcacttc actgttgatg ggaacaagag    240
ggcatctgct aaagtttcag attccatttc tgctcagtat ccagtagtgg atcatgaatt    300
tgatgcagtg gtggtaggcg ctggaggggc aggcttgcga gctgcatttg gcctttctga    360
ggcagggttt aatacagcat gtgttaccaa gctgtttcct accaggtcac acactgttgc    420
agcacaggga ggaatcaatg ctgctctggg gaacatggag gaggacaact ggaggtggca    480
tttctacgac accgtgaagg gctccgactg gctgggggac caggatgcca tccactacat    540
gacggagcag gcccccgccg ccgtggtcga gctagaaaat tatggcatgc cgtttagcag    600
aactgaagat gggaagattt atcagcgtgc atttggtgga cagagcctca agtttggaaa    660
gggcgggcag gcccatcggt gctgctgtgt ggctgatcgg actggccact cgctattgca    720
caccttatat ggaaggtctc tgcgatatga taccagctat tttgtggagt attttgcctt    780
ggatctcctg atggagaatg gggagtgccg tggtgtcatc gcactgtgca tagaggacgg    840
gtccatccat cgcataagag caaagaacac tgttgttgcc acaggaggct acgggcgcac    900
ctacttcagc tgcacgtctg cccacaccag cactggcgac ggcacggcca tgatcaccag    960
ggcaggcctt ccttgccagg acctagagtt tgttcagttc caccctacag gcatatatgg   1020
```

```
tgctggttgt ctcattacgg aaggatgtcg tggagaggga ggcattctca ttaacagtca   1080

aggcgaaagg tttatggagc gatacgcccc tgtcgcgaag gacctggcgt ctagagatgt   1140

ggtgtctcgg tccatgactc tggagatccg agaaggaaga ggctgtggcc ctgagaaaga   1200

tcacgtctac ctgcagctgc accacctacc tccagagcag ctggccacgc gcctgcctgg   1260

catttcagag acagccatga tcttcgctgg cgtggacgtc acgaaggagc cgatccctgt   1320

cctccccacc gtgcattata acatgggcgg cattcccacc aactacaagg ggcaggtcct   1380

gaggcacgtg aatggccagg atcagattgt gcccggcctg tacgcctgtg gggaggccgc   1440

ctgtgcctcg gtacatggtg ccaaccgcct cggggcaaac tcgctcttgg acctggttgt   1500

ctttggtcgg gcatgtgccc tgagcatcga agagtcatgc aggcctggag ataaagtccc   1560

tccaattaaa ccaaacgctg ggaagaatc tgtcatgaat cttgacaaat tgagatttgc    1620

tgatggaagc ataagaacat cggaactgcg actcagcatg cagaagtcaa tgcaaaatca   1680

tgctgccgtg ttccgtgtgg gaagcgtgtt gcaagaaggt tgtgggaaaa tcagcaagct   1740

ctatggagac ctaaagcacc tgaagacgtt cgaccgggga atggtctgga acacggacct   1800

ggtggagacc ctggagctgc agaacctgat gctgtgtgcg ctgcagacca tctacggagc   1860

agaggcacgg aaggagtcac ggggcgcgca tgccagggaa gactacaagg tgcggattga   1920

tgagtacgat tactccaagc ccatccaggg gcaacagaag aagccctttg aggagcactg   1980

gaggaagcac accctgtcct atgtggacgt tggcactggg aaggtcactc tggaatatag   2040

acccgtgatc gacaaaactt tgaacgaggc tgactgtgcc accgtcccgc cagccattcg   2100

ctcctactga tgagacaaga tgtggtgatg acagaatcag cttttgtaat tatgtataat   2160

agctcatgca tgtgtccatg tcataactgt cttcatacgc ttctgcactc tggggaagaa   2220

ggagtacatt gaagggagat tggcacctag tggctgggag cttgccagga acccagtggc   2280

cagggagcgt ggcacttacc tttgtccctt gcttcattct tgtgagatga taaaactggg   2340

cacagctctt aaataaaata taaatgaaca aactttcttt tatttccaaa aaaaaaaaaa   2400

aaaaa                                                               2405
```

```
<210> SEQ ID NO 122
<211> LENGTH: 2148
<212> TYPE: DNA
<213> ORGANISM: Arabidopsis thaliana

<400> SEQUENCE: 122

agatcccaac ggattcaaac agcaaatttg tgctttgctc ttctctctta ttataatatc     60

ctctcaaaaa ccctctccta tatcctccta aagccccccct tccttgtttc tctaccgcaa  120

caaagaaaaa acaaaagttt gagaaaaatg gtgtgttcgt tgtgtaacca atgattgggt    180

tttagcttac tacttcgaga gattataaga aagaaagagt gaagatacat tatagaaaga    240

agagaagcag aaaccaaaaa aagaaaccat gaagtctttt tgtgataatg atgataataa    300

tcatagcaac acgactaatt tgttagggtt ctcattgtct tcaaatatga tgaaaatggg    360

aggtagagga ggtagagaag ctatttactc atcttcaact tcttcagctg caacttcttc    420

ttcttctgtt ccacctcaac ttgttgttgg tgacaacact agcaactttg gtgtttgcta    480

tggatctaac ccaaatggag gaatctattc tcacatgtct gtgatgccac tcagatctga    540

tggttctctt tgcttaatgg aagctctcaa cagatcttct cactcgaatc accatcaaga    600

ttcatctcca aaggtggagg atttctttgg gacccatcac aacaacacaa gtcacaaaga    660

agccatggat cttagcttag atagtttatt ctacaacacc actcatgagc ccaacacgac    720
```

```
tacaaacttt caagagttct ttagcttccc tcaaaccaga aaccatgagg aagaaactag    780

aaattacggg aatgacccta gtttgacaca tggagggtct tttaatgtag gggtatatgg    840

ggaatttcaa cagtcactga gcttatccat gagccctggg tcacaatcta gctgcatcac    900

tggctctcac caccaccaac aaaaccaaaa ccaaaaccac caaagccaaa accaccagca    960

gatctctgaa gctcttgtgg agacaagcgt tgggtttgag acgacgacaa tggcggctgc   1020

gaagaagaag aggggacaag aggatgttgt agttgttggt cagaaacaga ttgttcatag   1080

aaaatctatc gatacttttg gacaacgaac ttctcaatac cgaggcgtta caagacatag   1140

atggactggt agatatgaag ctcatctatg ggacaatagt ttcaagaagg aaggtcacag   1200

tagaaaagga agacaagttt atctgggagg ttatgatatg gaggagaaag ctgctcgagc   1260

atatgatctt gctgcactca agtactgggg tccctctact cacaccaatt tctctgcgga   1320

gaattatcag aaagagattg aagacatgaa gaacatgact agacaagaat atgttgcaca   1380

tttgagaagg aagagcagtg gtttctctag ggtgcttcc atctatagag gagtcacaag    1440

acatcaccag catggaaggt ggcaagcacg gattggtaga gtcgctggaa acaaagatct   1500

ctaccttgga acttttggaa cccaagaaga agctgcagaa gcttacgatg tagcagcaat   1560

taagttccgt ggcacaaatg ctgtgactaa ctttgatatc acgaggtacg atgttgatcg   1620

tatcatgtct agtaacacac tcttgtctgg agagttagcg cgaaggaaca acaacagcat   1680

tgtcgtcagg aatactgaag accaaaccgc tctaaatgct gttgtggaag gtggttccaa   1740

caaagaagtc agtactcccg agagactctt gagttttccg gcgattttcg cgttgcctca   1800

agttaatcaa aagatgttcg gatcaaatat gggcggaaat atgagtcctt ggacatcaaa   1860

ccctaatgct gagcttaaga ccgtcgctct tactttgcct cagatgccgg ttttcgctgc   1920

ttgggctgat tcttgatcaa cttcaatgac taactctggt ttcttggtt tagttgctaa    1980

gtgttttggt ttatctccgg ttttatccgg tttgaactac aattcggttt agtttcgtcg   2040

gtataaatag tatttgctta ggagcggtat atgtttcttt tgagtagtat tcatgtgaaa   2100

cagaatgaat ctctctataa catattattt taatgaatct cctttgct                2148
```

```
<210> SEQ ID NO 123
<211> LENGTH: 50
<212> TYPE: DNA
<213> ORGANISM: Artificial
<220> FEATURE:
<223> OTHER INFORMATION: Oligonucleotide probe

<400> SEQUENCE: 123

gaagaagccc tttgaggagc actggaggaa gcacaccctg tcctatgtgg                50


<210> SEQ ID NO 124
<211> LENGTH: 50
<212> TYPE: DNA
<213> ORGANISM: Artificial
<220> FEATURE:
<223> OTHER INFORMATION: Oligonucleotide probe

<400> SEQUENCE: 124

gcttcacata cgtggcgccg tctgtcctgg acagcatcaa ggagggcttc                50


<210> SEQ ID NO 125
<211> LENGTH: 50
<212> TYPE: DNA
<213> ORGANISM: Homo sapiens
```

<400> SEQUENCE: 125
gtcttggaac ctgagcccag gctggacctg gcaaaggcgc tcagtggtag 50

<210> SEQ ID NO 126
<211> LENGTH: 50
<212> TYPE: DNA
<213> ORGANISM: Homo sapiens

<400> SEQUENCE: 126
cgatgcgctt gagacactcg ctcagcttct tggtggacgc atcctgaggc 50

<210> SEQ ID NO 127
<211> LENGTH: 50
<212> TYPE: DNA
<213> ORGANISM: Homo sapiens

<400> SEQUENCE: 127
ctcaggctct ccacctggat gcttggcaga tcctagaacc actgcatctg 50

<210> SEQ ID NO 128
<211> LENGTH: 50
<212> TYPE: DNA
<213> ORGANISM: Homo sapiens

<400> SEQUENCE: 128
cgccacagct gccacgtgct ccttcaggca gctggcgatg cggttctgca 50

<210> SEQ ID NO 129
<211> LENGTH: 50
<212> TYPE: DNA
<213> ORGANISM: Homo sapiens

<400> SEQUENCE: 129
cacatcaaac ctgctggcca gcacagacgc tgaggttgca tcgatcttgg 50

<210> SEQ ID NO 130
<211> LENGTH: 50
<212> TYPE: DNA
<213> ORGANISM: Homo sapiens

<400> SEQUENCE: 130
gtctggctgt gtctcccgtc aaaggctgcc atgaagagtg gcgggaagag 50

<210> SEQ ID NO 131
<211> LENGTH: 50
<212> TYPE: DNA
<213> ORGANISM: Homo sapiens

<400> SEQUENCE: 131
gcagagtcac acacatgcaa acacgcactc ttcggaaggc agccactgtc 50

<210> SEQ ID NO 132
<211> LENGTH: 50
<212> TYPE: DNA
<213> ORGANISM: Homo sapiens

<400> SEQUENCE: 132
gtcttctcta ccaggagcct gaggtgaaag atgtcccgtc tcctccatcc 50

<210> SEQ ID NO 133
<211> LENGTH: 50
<212> TYPE: DNA
<213> ORGANISM: Homo sapiens

<400> SEQUENCE: 133
atttcaaaca tgcaacaacg ccactggtaa taaagctttg gaatgggtgc 50

<210> SEQ ID NO 134
<211> LENGTH: 50
<212> TYPE: DNA
<213> ORGANISM: Homo sapiens

<400> SEQUENCE: 134
cttcgatgtg tgtgaggcta cccgcattct cgccatcgat gctcagcacc 50

<210> SEQ ID NO 135
<211> LENGTH: 50
<212> TYPE: DNA
<213> ORGANISM: Homo sapiens

<400> SEQUENCE: 135
gcacaggctc acagaagccg agatccacat caccgcctgg catgcaaagg 50

<210> SEQ ID NO 136
<211> LENGTH: 50
<212> TYPE: DNA
<213> ORGANISM: Homo sapiens

<400> SEQUENCE: 136
ggccatttct gtgtgtaagc atttctctca tttcctcatg gtcacatgga 50

<210> SEQ ID NO 137
<211> LENGTH: 50
<212> TYPE: DNA
<213> ORGANISM: Homo sapiens

<400> SEQUENCE: 137
caaagaagtt gatgaaccgg tcctttacag atgaaaggac tttggctccc 50

<210> SEQ ID NO 138
<211> LENGTH: 50
<212> TYPE: DNA
<213> ORGANISM: Homo sapiens

<400> SEQUENCE: 138
ggactactgg gaatgctctc ggtaagattt ggtatcacac cagagggcac 50

<210> SEQ ID NO 139
<211> LENGTH: 50
<212> TYPE: DNA
<213> ORGANISM: Homo sapiens

<400> SEQUENCE: 139
agtgggaagg ctctgtgtag atcggaataa gggcttggcc actccaggag 50

<210> SEQ ID NO 140
<211> LENGTH: 50
<212> TYPE: DNA
<213> ORGANISM: Homo sapiens

<400> SEQUENCE: 140
gaggttgcag tgagccaaga tcgcgccagc ctggcgacag agtgagactc 50

<210> SEQ ID NO 141
<211> LENGTH: 50
<212> TYPE: DNA

<213> ORGANISM: Homo sapiens

<400> SEQUENCE: 141
tccatcatct ctcccttcaa tttgtcttcg atgacatcaa caagagcaag 50

<210> SEQ ID NO 142
<211> LENGTH: 50
<212> TYPE: DNA
<213> ORGANISM: Homo sapiens

<400> SEQUENCE: 142
gacaggctgg ctgtatatta aggttggttg cgtcattaca ggaacacttc 50

<210> SEQ ID NO 143
<211> LENGTH: 50
<212> TYPE: DNA
<213> ORGANISM: Homo sapiens

<400> SEQUENCE: 143
gaagttcgct gtgaggaagc caactctgaa gaaactgagc agtggttaga 50

<210> SEQ ID NO 144
<211> LENGTH: 50
<212> TYPE: DNA
<213> ORGANISM: Homo sapiens

<400> SEQUENCE: 144
gtttctccaa ctgcttgtgt tctgccggag tcataaagcc tgcttgcacc 50

<210> SEQ ID NO 145
<211> LENGTH: 22
<212> TYPE: DNA
<213> ORGANISM: Artificial sequence
<220> FEATURE:
<223> OTHER INFORMATION: nuclease protection probe

<400> SEQUENCE: 145
caaacaccat tgtcacactc ca 22

<210> SEQ ID NO 146
<211> LENGTH: 24
<212> TYPE: DNA
<213> ORGANISM: Artificial sequence
<220> FEATURE:
<223> OTHER INFORMATION: nuclease protection probe

<400> SEQUENCE: 146
actgctggtc ttcagtcagg gcca 24

<210> SEQ ID NO 147
<211> LENGTH: 23
<212> TYPE: DNA
<213> ORGANISM: Artificial sequence
<220> FEATURE:
<223> OTHER INFORMATION: nuclease protection probe

<400> SEQUENCE: 147
cagctgcttt tgggattccg ttg 23

<210> SEQ ID NO 148
<211> LENGTH: 23
<212> TYPE: DNA
<213> ORGANISM: Artificial sequence
<220> FEATURE:
<223> OTHER INFORMATION: nuclease protection probe

<400> SEQUENCE: 148
tcagttttgc atggatttgc aca 23

<210> SEQ ID NO 149
<211> LENGTH: 22
<212> TYPE: DNA
<213> ORGANISM: Artificial sequence
<220> FEATURE:
<223> OTHER INFORMATION: nuclease protection probe

<400> SEQUENCE: 149
acatcgttac cagacagtgt ta 22

<210> SEQ ID NO 150
<211> LENGTH: 23
<212> TYPE: DNA
<213> ORGANISM: Artificial sequence
<220> FEATURE:
<223> OTHER INFORMATION: nuclease protection probe

<400> SEQUENCE: 150
tccatcatta cccggcagta tta 23

<210> SEQ ID NO 151
<211> LENGTH: 22
<212> TYPE: DNA
<213> ORGANISM: Artificial sequence
<220> FEATURE:
<223> OTHER INFORMATION: nuclease protection probe

<400> SEQUENCE: 151
ctagtggtcc taaacatttc ac 22

<210> SEQ ID NO 152
<211> LENGTH: 22
<212> TYPE: DNA
<213> ORGANISM: Artificial sequence
<220> FEATURE:
<223> OTHER INFORMATION: nuclease protection probe

<400> SEQUENCE: 152
cagactccgg tggaatgaag ga 22

<210> SEQ ID NO 153
<211> LENGTH: 22
<212> TYPE: DNA
<213> ORGANISM: Artificial sequence
<220> FEATURE:
<223> OTHER INFORMATION: nuclease protection probe

<400> SEQUENCE: 153
tcaacatcag tctgataagc ta 22

<210> SEQ ID NO 154
<211> LENGTH: 21
<212> TYPE: DNA
<213> ORGANISM: Artificial sequence
<220> FEATURE:
<223> OTHER INFORMATION: nuclease protection probe

<400> SEQUENCE: 154
ggtaatccct ggcaatgtga t 21

<210> SEQ ID NO 155

<211> LENGTH: 22
<212> TYPE: DNA
<213> ORGANISM: Artificial sequence
<220> FEATURE:
<223> OTHER INFORMATION: nuclease protection probe

<400> SEQUENCE: 155
taaccgattt caaatggtgc ta 22

<210> SEQ ID NO 156
<211> LENGTH: 23
<212> TYPE: DNA
<213> ORGANISM: Artificial sequence
<220> FEATURE:
<223> OTHER INFORMATION: nuclease protection probe

<400> SEQUENCE: 156
acgggtgcga tttctgtgtg aga 23

<210> SEQ ID NO 157
<211> LENGTH: 22
<212> TYPE: DNA
<213> ORGANISM: Artificial sequence
<220> FEATURE:
<223> OTHER INFORMATION: nuclease protection probe

<400> SEQUENCE: 157
tcacgcgagc cgaacgaaca aa 22

<210> SEQ ID NO 158
<211> LENGTH: 20
<212> TYPE: DNA
<213> ORGANISM: Artificial sequence
<220> FEATURE:
<223> OTHER INFORMATION: nuclease protection probe

<400> SEQUENCE: 158
aggggcctca gcctcctggt 20

<210> SEQ ID NO 159
<211> LENGTH: 22
<212> TYPE: DNA
<213> ORGANISM: Artificial sequence
<220> FEATURE:
<223> OTHER INFORMATION: nuclease protection probe

<400> SEQUENCE: 159
cacatctcac tgtagcctca aa 22

<210> SEQ ID NO 160
<211> LENGTH: 21
<212> TYPE: DNA
<213> ORGANISM: Artificial sequence
<220> FEATURE:
<223> OTHER INFORMATION: nuclease protection probe

<400> SEQUENCE: 160
agtagtgctt tctactttat g 21

<210> SEQ ID NO 161
<211> LENGTH: 24
<212> TYPE: DNA
<213> ORGANISM: Artificial sequence
<220> FEATURE:
<223> OTHER INFORMATION: nuclease protection probe

<400> SEQUENCE: 161

```
actgcaggct ccagcttcca ggct                                              24


<210> SEQ ID NO 162
<211> LENGTH: 22
<212> TYPE: DNA
<213> ORGANISM: Artificial sequence
<220> FEATURE:
<223> OTHER INFORMATION: nuclease protection probe

<400> SEQUENCE: 162

aactatacaa cctactacct ca                                                22


<210> SEQ ID NO 163
<211> LENGTH: 22
<212> TYPE: DNA
<213> ORGANISM: Artificial sequence
<220> FEATURE:
<223> OTHER INFORMATION: nuclease protection probe

<400> SEQUENCE: 163

ctaccatagg gtaaaaccac tg                                                22


<210> SEQ ID NO 164
<211> LENGTH: 22
<212> TYPE: DNA
<213> ORGANISM: Artificial sequence
<220> FEATURE:
<223> OTHER INFORMATION: nuclease protection probe

<400> SEQUENCE: 164

agtgaattct accagtgcca ta                                                22
```

MOLECULAR MALIGNANCY IN MELANOCYTIC LESIONS

CROSS-REFERENCE TO RELATED APPLICATION

This is the U.S. National Stage of International Application No. PCT/US2013/047354, filed Jun. 24, 2013, which was published in English under PCT Article 21(2), which in turn claims priority to U.S. Provisional Application No. 61/663,428 filed Jun. 22, 2012, herein incorporated by reference in its entirety.

FIELD

This disclosure concerns biomarkers for characterizing melanocytic lesions as benign or malignant. In particular, this disclosure concerns the identification of biomarkers (including mRNA and/or miRNA) that are significantly differentially expressed in nevi and primary melanoma samples, clinically predictive algorithms based on the expression of such biomarkers, and methods of and compositions for their use.

PARTIES TO JOINT RESEARCH AGREEMENT

HTG Molecular Diagnostics and the John Wayne Cancer Institute are parties to a joint research agreement governing inventions disclosed herein.

BACKGROUND

Skin cancer is the most common of all cancers in the United States. Melanoma, a cancer originating in melanocytes, accounts for a relatively small percentage of skin cancers. However, melanoma causes the most skin cancer deaths making it one of the most dangerous types of skin cancer. In 2012, melanoma will account for more than 75,000 skin cancer cases.

Melanocytes also are found in organs other than skin, including the eye (e.g., in or on the uvea, ciliary body, conjunctiva, eyelid, iris, or orbit), the inner ear, meninges, bones, and heart. Ocular melanoma is the most common type of eye tumor in adults and the second most common type of primary malignant melanoma in the body. Ocular melanoma has an incidence of about five cases per one-million people in the United States.

To diagnose melanoma, suspect tissue is biopsied and examined under a microscope by a pathologist, preferably (but often not) one who is specially trained to identify melanoma in tissue biopsies. If the pathologist reports finding a melanoma, a number of factors (including the depth of the tumor in millimeters, the presence or absence of ulceration, the mitotic rate, and/or whether the tumor has spread) are used in determining a person's prognosis and course of treatment(s). When the tumor has not spread, a wider local excision is often performed to ensure that the entire lesion was removed along with a clear margin of normal tissue around the melanoma. If more extreme treatments are indicated, the patient also may receive lymphadenectomy, immunotherapy, chemotherapy, or radiation therapy.

Melanoma is almost always curable when it is found in its very early stages. Unfortunately, misdiagnoses of this disease are common (Piepkorn et al., *J. Am. Acad. Dermatol.,* 30:707, 1994; Farmer et al., *Hum. Pathol.,* 27:528, 1996; Corona et al., *J. Clin. Oncol.* 14:1218, 1996; Barnhill et al., *Hum. Pathol.,* 30:513, 1990; Brochez et al., *J. Pathol.* 196:459, 2002). Diagnostic errors have a number of root causes (e.g., see Ruiter et al., *Sem. Cutaneous Med. Surg.,* 22:33, 2003), including difficulties in differentiating between benign melanocytic nevi and early melanoma and between atypical and dysplastic nevi.

Mistakes in melanoma diagnosis have a significant adverse impact on the patients, their families, and society in general. Patients mistakenly diagnosed with a melanoma may undergo inappropriate and potentially dangerous therapy(ies), may live a life in constant fear of relapse, and may not be able to obtain life or health insurance. On the other hand, patients mistakenly diagnosed with a nevus instead of a melanoma are deprived of appropriate therapy for their malignancy, and may have their lives prematurely cut short. Finally, the societal toll of this problem is demonstrated by the fact that misdiagnosis of melanoma is the second only to misdiagnosis of breast cancer as the most common reason for cancer-based medical malpractice claims in the United States (McDonald et al., *Internet J. Fam. Practice,* 7(2), 2009; Troxel, *Am. J. Surg. Pathol.,* 27:1278, 200).

Given the limitations of histopathology alone, it is of critical importance in medical science to have additional tools for the proper diagnosis of melanoma. In particular, tools are needed to determine which biopsies (e.g., dysplastic or indeterminate nevi) may, in fact, be misdiagnosed melanoma, and/or which biopsies (e.g., nevi) may demonstrate molecular characteristics of melanoma or progression to melanoma.

SUMMARY

Disclosed are methods for characterizing a melanocyte-containing sample, for example determining whether a sample is a benign nevi or a malignant melanoma. In some examples, these methods include characterizing a melanocyte-containing sample by determining an expression level (such as a nucleic acid or protein level) for (i) at least two of the biomarkers selected from MAGEA2, PRAME, PDIA4, NR4A1, PDLIM7, B4GALT1, SAT1, RUNX1, SOCS3 and those in Table 13 and (ii) at least one normalization biomarker(s), in the melanocyte-containing sample obtained from a subject (such as a nevi sample), thereby generating raw expression values for each of the at least two biomarkers and the at least one normalization biomarker(s). The raw expression values for each of the at least two biomarkers are normalized to the raw expression values for the at least one normalization biomarker(s) to generate normalized expression values for each of the at least two biomarkers. The normalized expression values are used in a regression or machine learning algorithm to generate an output value. The resulting output value is compared to a cut-off value, which can be derived from normalized expression values for the at least two biomarkers in a plurality of melanocyte-containing samples known in advance to be benign or malignant. The melanocyte-containing sample obtained from the subject is then characterized, for example as benign if the output value is on the same side of the cut-off value as the plurality of known benign samples or as malignant if the output value is on the same side of the cut-off value as the plurality of known malignant samples.

Also provided are methods for determining malignancy in a melanocyte-containing sample. Such a method can include determining an expression level (such as a nucleic acid expression level) for at least two biomarkers selected from: B4GALT1, BAX, MAGEA2, NR4A1, PDIA4, PRAME, RUNX1, SOCS3, SAT1, PDLIM7, BIRC5, MET, MAGEC2, POLR2J3, ZFYVE16, and BEST1 in a melanocyte-containing sample obtained from a subject. The method can also include calculating an output from an algorithm that uses the expression levels of the at least two biomarkers as an input and determining from the algorithm output that the sample is or is not malignant by comparing the output to a reference standard from known malignant melanocyte-containing samples. The method can further include normalizing the expression levels of the at least two selected biomarkers to the expression level of at least one normalization biomarker, such as at least one of those in Table 3.

Also disclosed are arrays and kits for diagnosing a biological sample (such as a melanocyte-containing sample) as a benign nevi or a primary melanoma. For example, an array can include at least three addressable locations, each location having immobilized capture probes with the same specificity, and each location having capture probes with a specificity that is different from the capture probes at each other location, wherein the capture probes at two of the at least three locations are capable of directly or indirectly specifically hybridizing a biomarker that includes two or more of MAGEA2, PRAME, PDIA4, NR4A1, PDLIM7, B4GALT1, SAT1, RUNX1, SOCS3 and those in Table 13, and the capture probes at one of the at least three locations is capable of directly or indirectly specifically hybridizing to a normalization biomarker listed in Table 3, and wherein the specificity of each capture probe is identifiable by the addressable location the array. Kits are provided that include one or more arrays provided herein, as well as one or more of: a container containing lysis buffer; a container containing a nuclease specific for single-stranded nucleic acids; a container containing a plurality of nucleic acid programming linkers; a container containing a plurality of NPPs; a container containing a plurality of the bifunctional detection linker; a container containing a detection probe that specifically binds the bifunctional detection linkers; and a container containing a detection reagent.

The foregoing and other features of this disclosure will become more apparent from the following detailed description of a several embodiments which proceeds with reference to the accompanying figures.

BRIEF DESCRIPTION OF THE DRAWINGS

FIGS. 2A and 2B show box plots (top), mean plots (middle) and SAS diffograms (bottom) for the representative normalization genes indicated above the respective graphs (i.e., MFI2, RAP2B, BMP1 and NCOR2). Collectively, these results show that there were no statistically significant differences between nevi and primary melanoma samples for each normalizer gene, and that each such gene produced consistent results with low standard deviations.

FIG. 3 shows SAS output demonstrating the statistical significance of the representative B4GALT1 and NR4A1 (4-normalizer) model. Collectively, the output demonstrate that the model converged on a solution and, thus, that the results of the model were reliable. The model fit and test of global null hypotheses show that the overall model was statistically significant or that the probability that the observed results were far less likely than could be attributed to chance alone, Wald Chi-Square=15.856, 2df, p=0.0004. The Hosmer and Lemeshow test tests the null hypothesis that there is no lack of fit to the model; or the model accurately reproduces the data. No significance was found using the Hosmer and Lemeshow test further supporting the value of the model. It is noted that a significant Hosmer and Lemeshow p-value (e.g., less than 0.05) would suggest that there was some lack of fit to the model or that the proposed model, in some capacity, failed to fit the experimental data adequately.

FIG. 6 shows a continuation of the FIG. 5 classification table. These continued results show that lowering the cut-off threshold resulted in higher sensitivity with a minor tradeoff in specificity while still maintaining very high overall classification accuracy.

FIG. 7 shows that the representative B4GALT1 and NR4A1 (4-normalizer) model was highly significant even under multiple different estimation routines. One common assumption in regression-based models is equal variances. Unequal variances, especially when sample sizes are unequal, can cause standard estimation practices to give incorrect results. Although the Brown-Forsythe test for equality of variances showed no significant difference between the population variances (not shown), an Empirical Covariance "Sandwich" Estimator test, which is used when there may be unequal variances or some other violation of common assumption, was run. The Sandwich Estimator test (left box) confirmed that the original results obtained under the standard Fisher Scoring method were not due to violation of model assumptions. Similarly, the Firth bias reduction penalized likelihood model (right box) provided additional confirmation that the results were not sensitive to estimation procedure.

FIG. 8 shows that the B4GALT1 and NR4A1 (2-normalizer) model fit, as indicated by the Wald Chi-Square, was also highly significant. The ROC curve demonstrates that this model also had very high sensitivity and specificity. The very small change in the area under the curves (i.e., $\Delta$=0.0125) for the B4GALT1 and NR4A1 (2-normalizer) and B4GALT1 and NR4A1 (4-normalizer) models shows that the two models are very similar with respect to their abilities to correctly differentiate between nevi and primary melanoma samples.

SEQUENCES

Figure 1:
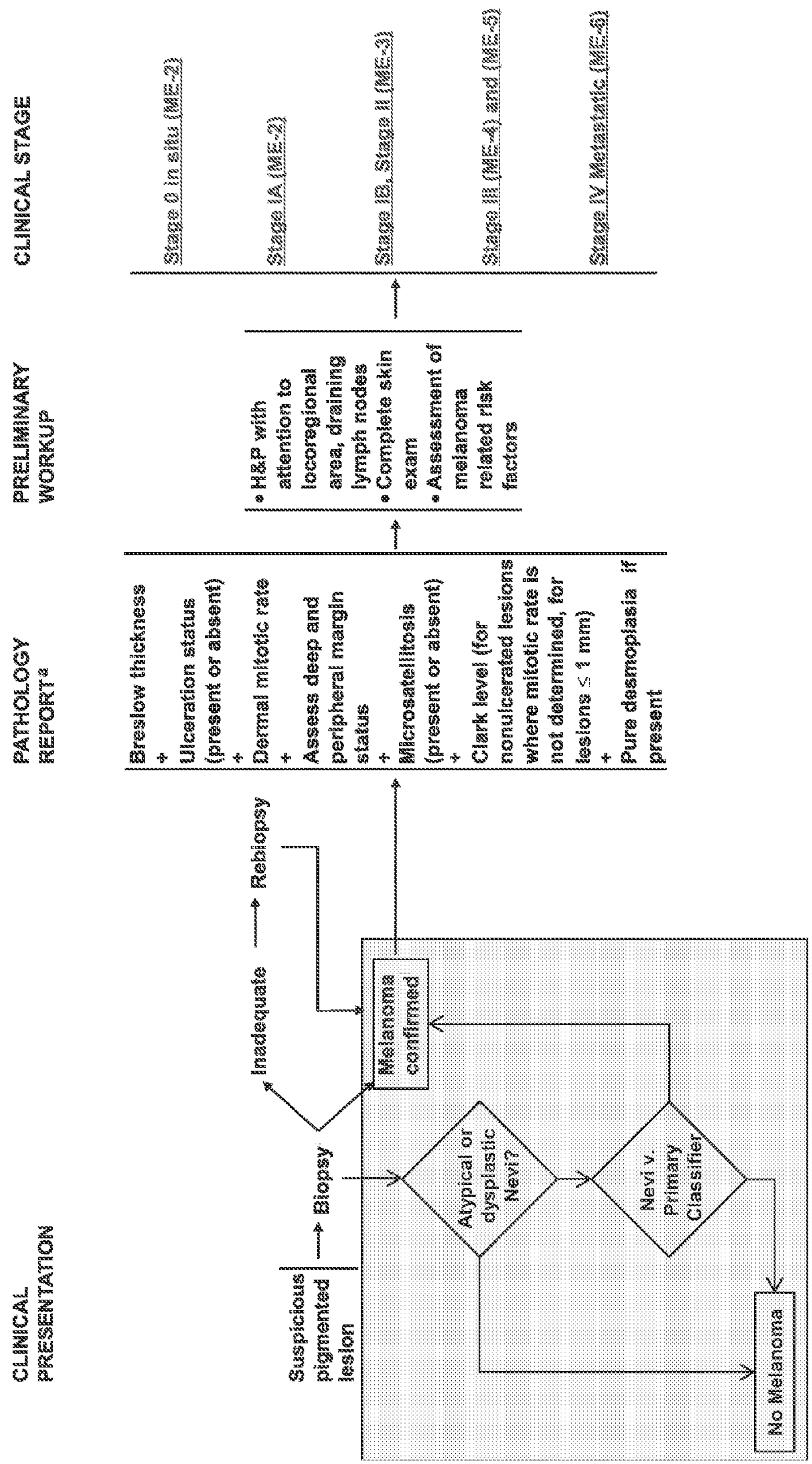
FIG. 1 is a flow diagram showing how embodiments of a diagnostic test disclosed herein (as indicated by the flowchart elements (in gray shaded) emanating from the arrow downward from the "Biopsy" point) fit into current Nation Comprehensive Cancer Network (NCCN) clinical recommendations for melanoma diagnosis.

The nucleic acid sequences listed herein are shown using standard letter abbreviations for nucleotide bases, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named "Sequence.txt" (~371 kb), which was created on Jun. 24, 2013, which is incorporated by reference herein.

In the provided sequences:

SEQ ID NOs. 1-36, 123, and 124 are representative nuclease protection probe (NPP) sequences.

SEQ ID NOs. 47-119 are GenBank mRNA RefSeqs for the genes disclosed as differentially expressed in nevi and primary melanoma.

SEQ ID NOs. 37-46, 120, and 121 are GenBank mRNA RefSeqs for disclosed normalizers.

SEQ ID NO. 122 is the GenBank mRNA RefSeq for a disclosed negative control plant gene (ANT).

SEQ ID NOs. 125-144 are representative NPP sequences for disclosed mRNA targets.

SEQ ID NOs. 145-164 are representative NPP sequences for disclosed miRNA targets.

DETAILED DESCRIPTION

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual, 3d ed.*, Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, Antibodies: A Laboratory Manual, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

All Genbank Numbers referenced herein are incorporated by reference, for the sequence available on Jun. 22, 2012.

To facilitate review of the various embodiments of this disclosure, the following explanations of specific terms are provided:

Antibody: A polypeptide ligand comprising at least a light chain or heavy chain immunoglobulin variable region which specifically recognizes and binds an epitope of an antigen or a fragment thereof, for example an epitope a biomarker shown in Table 3, 4, 11, or 13. The term antibody includes intact immunoglobulins and the variants and portions of them well known in the art, such as Fab' fragments, $F(ab)'_2$ fragments, single chain Fv proteins ("scFv"), and disulfide stabilized Fv proteins ("dsFv"). The term also includes genetically engineered forms such as chimeric antibodies, heteroconjugate antibodies (such as, bispecific antibodies). The term antibody includes both polyclonal and monoclonal antibodies. The preparation of polyclonal and monoclonal antibodies, molecularly engineered antibodies and antibody fragments is well known to those of ordinary skill in the art (see, e.g., Green et al., "Production of Polyclonal Antisera," in: *Immunochemical Protocols* pages 1-5, Manson, ed., Humana Press 1992; and Harlow et al., in: *Antibodies: a Laboratory Manual*, page 726, Cold Spring Harbor Pub., 1988).

Binding or stable binding (of an oligonucleotide): An oligonucleotide binds or stably binds to a target nucleic acid (such as a biomarker shown in Table 3, 4, 11, or 13) if a sufficient amount of the oligonucleotide forms base pairs or is hybridized to its target nucleic acid, for example the binding of an oligonucleotide, such as an probe or primer to the nucleic acid sequence of a gene shown in Table 3, 4, 11, or 13. Binding between a target and an oligonucleotide can be detected by any procedure known to one skilled in the art, including both functional (for example reduction in expression and/or activity) and physical binding assays.

Contacting: Placement in direct physical association including in solid and/or liquid form, for example contacting a sample (e.g., a sample suspended in buffer) with a nucleic acid probe, such as a probe specific for one of the biomarkers shown in Table 3, 4, 11, or 13. Contacting can occur in vitro, for example in a diagnostic assay, or, in other examples, ex situ.

Conditions sufficient to detect: Any environment that permits the desired activity, for example, that permits an antibody to bind an antigen (such as a biomarker shown in Table 3, 4, 11 or 13), and the interaction to be detected. In other examples, it is the detection of a nucleic acid, such as a biomarker shown in Table 3, 4, 11 or 13, for example by detecting hybridization of the biomarker to a nucleic acid probe.

Degenerate variant: A polynucleotide encoding a protein of interest (such as a biomarker shown in Table 3, 4, or 11) that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Detect: To determine if an agent (such as a signal or particular nucleic acid, nucleic acid probe, or protein, for example one of those in Table 3, 4, 11 or 13) is present or absent. In some examples, this can further include quantification, for example the quantification of the amount of the gene or protein, or a fraction of a sample, such as a particular cell or cells within a tissue.

Diagnostic: Identifying the presence or nature of a pathologic condition, such as, but not limited to cancer, such as melanoma. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides information (e.g., a positive indication) that aids in diagnosis.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to an mRNA, a DNA, or dsDNA encoded by one of the genes in Table 3, 4, 11, or 13.

"Specifically hybridizable" and "specifically complementary" are terms that indicate a sufficient degree of complementarity such that stable and specific binding occurs between the oligonucleotide (or it's analog) and the DNA or RNA target. The oligonucleotide or oligonucleotide analog need not be 100% complementary to its target sequence to be specifically hybridizable. An oligonucleotide or analog is specifically hybridizable when there is a sufficient degree of complementarity between the oligonucleotide or analog to the target DNA or RNA molecule (for example a DNA or RNA in Table 3, 4, 11, or 13) to avoid non-specific binding of the oligonucleotide or analog to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Hybridization of an oligonucleotide sequence can be modified by incorporating un-natural bases into the sequence, such as incorporating locked nucleic acids or peptide nucleic acids.

Isolated: An "isolated" biological component (such as a nucleic acid molecule, protein or organelle) has been substantially separated or purified away from other biological components in the cell of the organism in which the component naturally occurs, e.g., other chromosomal and extra-chromosomal DNA and RNA, proteins and/organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids, such as probes and primers, for example probes and primer for the detection and/or amplification of nucleic acids shown in Table 3, 4, 11, or 13.

Label: A detectable compound or composition, which can be conjugated directly or indirectly to another molecule, such as an antibody (for example an antibody that specifically binds a biomarker (e.g., protein) shown in Table 3, 4, 11, or 13) or a nucleic acid probe (for example a nucleic acid probe that specifically binds or indirectly binds to a nucleic acid in Table 3, 4, 11, or 13) or a protein, to facilitate detection of that molecule. Specific, non-limiting examples of labels, and methods of labeling nucleic acids and proteins are described throughout this disclosure.

Melanoma: A malignant tumor of melanocytes. Melanocytes are cells that produce the dark pigment, melanin, which is responsible for the color of skin. They predominantly occur in skin, but are also found in other parts of the body, including the bowel and the eye. Thus primary melanomas can occur in areas of the body other than the skin (e.g., uveal melanoma). A primary melanoma is neoplasia at the site of origin; even if the primary tumor has metastasized the original site remains primary and the distant site is the metastasis.

Nevus (plural nevi): A sharply circumscribed pigmented spot on the skin, or other part of the body, such as the bowel or eye. Nevi may be commonly referred to as birthmarks or moles. Nevi comprise melanocytes, which contribute to the nevi's pigmented appearance. Typically, nevi are considered benign. However, a dysplastic nevus (also sometimes referred to as an atypical mole) is a type of nevus with abnormal features. A dysplastic nevus may be bigger than and its color, surface, and border may be different from a non-dysplastic nevus. On the skin surface, a dysplastic nevus can appear as having a mixture of several colors (e.g., from pink to dark brown), a smooth or slightly scaly or pebbly surface, and irregular edges that may fade into the surrounding skin. Dysplastic nevi are more likely than "ordinary" nevi to develop into melanoma, and about half of melanomas arise from dysplastic nevi. However, most dysplastic nevi never become malignant; thus, it is important to be able to determine which nevi (whether dysplastic or non-dysplastic) may, in fact, mistakenly be or be biologically transforming (e.g., at the molecular level) to primary melanoma.

Nuclease: An enzyme that cleaves a phosphodiester bond. An endonuclease is an enzyme that cleaves an internal phosphodiester bond in a nucleotide chain (in contrast to exonucleases, which cleave a phosphodiester bond at the end of a nucleotide chain). Some nucleases have both endonuclease and exonuclease activities. Illustrative nucleases are described throughout this disclosure.

Primer: A short nucleic acid molecule, such as a DNA oligonucleotide, for example sequences of at least 15 nucleotides, which can be annealed to a complementary target nucleic acid molecule (such as one of the biomarkers in Table 3, 4, 11, or 13) by nucleic acid hybridization to form a hybrid between the primer and the target nucleic acid strand, for example under very high stringency hybridization conditions.

A primer can be extended along the target nucleic acid molecule by a polymerase enzyme. Therefore, primers can be used to amplify a target nucleic acid molecule (such as a portion of a nucleic acid molecule shown in Table 3, 4, 11, or 13), wherein the sequence of the primer is specific for the target nucleic acid molecule, for example so that the primer will hybridize to the target nucleic acid molecule under very high stringency hybridization conditions.

The specificity of a primer typically increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides of the target sequence.

In particular examples, a primer is at least 10 nucleotides in length, such as at least 15 contiguous nucleotides complementary to a target nucleic acid molecule. Particular lengths of primers that can be used to practice the methods of the present disclosure (for example, to amplify a region of a nucleic acid molecule shown in Table 3, 4, 11, or 13) include primers having at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, or more contiguous nucleotides complementary to the target nucleic acid molecule to be amplified, such as a primer of 10-60 nucleotides, 10-50 nucleotides, or 10-30 nucleotides.

Primer pairs can be used for amplification of a nucleic acid sequence, for example, by PCR, real-time PCR, or other nucleic-acid amplification methods known in the art and as described elsewhere in this disclosure. An "upstream" or "forward" primer is a primer 5' to a reference point on a nucleic acid sequence. A "downstream" or "reverse" primer is a primer 3' to a reference point on a nucleic acid sequence.

Probe: A probe comprises an isolated nucleic acid capable of hybridizing to a target nucleic acid (such as a nucleic acid sequence of a biomarker shown in Table 3, 4, 11, or 13), and a detectable label or reporter molecule can be attached to a nucleic acid molecule. For example, a label can be attached at the 5'- or 3'-end of the probe, or anywhere in between. In specific examples, the label is attached to the base at the 5'-end of the probe, the base at its 3'-end, the phosphate group at its 5'-end or a modified base, such as a T internal to the probe. Exemplary labels, methods for labeling and guidance in the choice of labels appropriate for various purposes are discussed elsewhere in this disclosure.

Probes are generally at least 15 nucleotides in length, such as at least 10, at least 15, at least 16, at least 17, at least 18, at least 19, least 20, at least 21, at least 22, at least 23, at least 24, at least 25, at least 30, at least 35, at least 40, at least 45, at least 50, at least 55, at least 60, at least 70, at least 80, at least 90, at least 100, at least 120, at least 140, at least 160, at least 180, at least 200, at least 250, at least 300, at least 350, at least 400, at least 450, at least 500, or more contiguous nucleotides complementary to the target nucleic acid molecule (such as those in Table 3, 4, 11, or 13), such as 20-500 nucleotides, 100-250 nucleotides, 20-50 nucleotides, or 20-30 nucleotides.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art; for example, Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet.

Homologs and variants of the sequences for those molecules shown in Table 4, 11, or 13 are encompassed by this disclosure typically characterized by possession of at least about 75%, for example at least about 80%, at least 85%, at least 90%, at least 91%, at least 92%, at least 93%, at least 94%, at least 95%, at least 96%, at least 97%, at least 98% or at least 99% sequence identity counted over the full length alignment with the amino acid or nucleic acid sequence of interest, and can retain the activity of the native protein or nucleic acid. One of skill in the art will appreciate that these sequence identity ranges are provided for guidance only; it is entirely possible that strongly significant homologs could be obtained that fall outside of the ranges provided.

One functional indication that two nucleic acid molecules are closely related is that the two molecules hybridize to each other under stringent conditions.

Methods and Compositions for Characterizing Melanocyte-Containing Samples

For most cancers, including melanoma, early detection has the greatest impact on survival and can contribute to better cure rates. In some cases, it is difficult to distinguish between a benign and malignant lesion based solely on classical methods (e.g., histopathology). Thus, methods that permit benign nevi to be distinguished from melanomas (e.g., primary melanomas) are needed. Evolving testing methods can help identify malignancies on the molecular level, e.g., before such malignancies can reliably be recognized at the microscopic or organismal level. Molecular testing involves identifying cancer phenotypes to clinically relevant gene expression patterns, as described herein for distinguishing a benign nevus from a malignant melanoma (e.g., primary melanoma). Such distinctions can avoid unnecessary therapies for those having only a benign nevus, and help to ensure those who have primary melanoma receive appropriate therapies after the initial biopsy.

Preparing to Collect Gene Expression Data

Gene expression is the process by which information encoded in the genome (gene) is transformed (e.g., via transcription and translation processes) into corresponding gene products (e.g., RNA (such as, mRNA and miRNA) and protein), which function interrelatedly to give rise to a set of characteristics (aka, phenotype). For purposes of this disclosure, gene expression may be measured by any technique known now or in the future. Commonly, gene expression is measured by detecting the products of the genes (e.g., mRNA, miRNA, and/or protein) expressed in samples collected from subjects of interest.

Subjects and Samples

Appropriate samples for use in the methods disclosed herein include any conventional biological sample containing melanocytes for which information about gene expression (e.g., mRNA, miRNA or protein expression; such as those in Table(s) 3, 4, 11, and/or 13) is desired.

Samples include those obtained from a subject, such as clinical samples obtained from a subject (including samples from a healthy or apparently healthy human subject or a human patient affected by a condition or disease to be diagnosed or investigated, such as melanoma). A subject is a living multicellular vertebrate organism, a category that includes, for example, mammals. A "mammal" includes both human and non-human mammals, such as dogs, mice or other veterinary subjects. In one example, the sample is from a subject who has no history of prior melanoma, or is from a subject who has previously had or been diagnosed with melanoma. In some examples, a subject is a patient, such as a patient presenting for skin cancer (e.g., melanoma) screening, or diagnosed with melanoma or at risk (or higher risk) for developing melanoma; for example, as described below. In some examples, the sample is from a subject who has no history of prior melanoma or from a subject who previously was diagnosed with melanoma.

The highest rates of melanoma in humans are reported in Australia (followed by New Zealand, Norway, Sweden, Switzerland, Denmark, United States, Austria, Iceland, Netherlands). Risk factors for a human subject developing melanoma include (a) family or personal history of melanoma; (b) multiple nevi (e.g., greater than 50 or 100 nevi), (c) multiple dysplastic nevi (e.g., at least three), (d) high exposure to sunlight (e.g., before age 10), (e) pale Caucasian skin, (f) red or blond hair, (g) history of at least one blistering sunburn, (h) higher socioeconomic class, (i) history of sunbed use (especially before age 30), (j) occupation as an airline crew member, and (k) pesticide exposure (MacKie et al., *Annals of Oncology,* 20(Supp. 6), vi1-7, 2009).

In some examples, a prior-used method was unable to reliably determine if the melanocyte-containing sample was malignant or benign. Thus, the disclosed methods can include using and/or determining that the sample to be analyzed cannot reliably be diagnosed as malignant or benign by another method; for example, by histopathology. Such an optional step can occur before determining levels of gene expression levels in the sample (e.g., gene expression of at least two different biomarkers in Table(s) 4, 11 and/or 13 (such as, gene combinations in Tables 6, 8 or 14), and/or at least one normalization biomarker(s)).

Exemplary samples include, without limitation, cells, cell lysates, cytocentrifuge preparations, cytology smears, tissue biopsies (e.g., skin biopsies, such as those that include a nevus or an ocular tissue biopsy), fine-needle aspirates, and/or tissue sections (e.g., cryostat tissue sections and/or paraffin-embedded tissue sections. Tissue is a plurality of functionally related cells. In particular examples, a tissue can be in suspension or intact. In one example the melanocyte-containing sample (such as, a tissue sample) includes a nevus, dysplastic nevus, atypical nevus, or suspected melanoma. In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). Thus, in some examples, the melanocyte-containing sample to be analyzed is fixed. Other method embodiments include fixing the sample (e.g., skin biopsy) in a fixative (e.g., formalin), embedding the sample (e.g., with paraffin), cutting or sectioning the sample, or combinations thereof.

Standard techniques for acquisition of samples useful in the present disclosure are available (see e.g., Schluger et al., *J. Exp. Med.* 176:1327-33 (1992); Bigby et al., *Am. Rev. Respir. Dis.* 133:515-18 (1986); Kovacs et al., *NEJM* 318: 589-93 (1988); and Ognibene et al., *Am. Rev. Respir. Dis.* 129:929-32 (1984)). In some examples, a sample is a skin sample or ocular tissue obtained by excisional biopsy, incisional biopsy, punch biopsy, saucerization biopsy or fine-needle aspiration biopsy. An excisional biopsy excises, or cuts away, the entire growth with a margin of normal surrounding skin or ocular tissue. Generally, an additional wide local excision of normal surrounding skin will be required if the biopsy is positive. The width of the margin will depend on the thickness of the cancer. An incisional biopsy, or core biopsy, removes only a sample of the growth. A punch biopsy removes a small, cylindrical shaped sample of skin or ocular tissue. It can include the epidermis, dermis, and parts of the underlying tissue. A saucerization biopsy removes the entire lesion by cutting under the lesion in a "scoop like" manner, and provides the practitioner with a complete specimen to better analyze the tumor architecture. A fine-needle aspiration biopsy is done with a very thin needle and syringe. It removes a very small sample of tissue. This type of biopsy can be done on a suspicious mole or skin or eye growth. In addition, it can be done on other deeper tissue, such as nearby lymph nodes or an internal organ, to see if melanoma has spread. It will appreciated that any method of obtaining tissue from a subject can be utilized, and that the selection of the method used will depend upon various factors such as the type of tissue, age of the subject, or procedures available to the practitioner.

In some embodiments, a sample containing melanocytes is a cell and/or tissue lysate. Cell lysate contains many of the proteins and nucleic acids contained in a cell, and include for example, the biomarkers shown in Table 3, 4, 11, or 13. Methods for obtaining a cell lysate are well known in the art and can be found for example in Ausubel et al. (In Current Protocols in Molecular Biology, John Wiley & Sons, New York, 1998). In some examples, cells in the sample are lysed or permeabilized in an aqueous solution (for example using a lysis buffer). The aqueous solution or lysis buffer may include detergent (such as sodium dodecyl sulfate) and one or more chaotropic agents (such as formamide, guanidinium HCl, guanidinium isothiocyanate, or urea). The solution may also contain a buffer (for example SSC). In some examples, the lysis buffer includes about 8% to 60% formamide (v/v) about 0.01% to 0.5% SDS, and about 0.5-6× SSC (for example, about 3×SSC). The buffer may optionally include tRNA at about 0.001 to about 2.0 mg/ml or a ribonuclease. The lysis buffer may also include a pH indicator, such as Phenol Red. Cells are incubated in the aqueous solution for a sufficient period of time (such as about 1 minute to about 60 minutes, for example about 5 minutes to about 20 minutes, or about 10 minutes) and at a sufficient temperature (such as about 22° C. to about 115° C., for example, about 37° C. to about 105° C., or about 90° C. to about 100° C.) to lyse or permeabilize the cell. In some examples, lysis is performed at about 95° C., for example if the nucleic acid to be detected is RNA. In other examples, lysis is performed at about 105° C., for example if the nucleic acid to be detected is DNA. In some examples, lysis conditions can be such that genomic DNA is not accessible to the probes whereas RNA (for example, mRNA) is, or such that the RNA is destroyed and only the DNA is accessible for probe hybridization. In some examples, the crude cell lysate is used directly without further purification.

Reference Standards

A reference standard also may be referred to as a "control." A control can be a known value or range of values indicative of basal levels or amounts of expression (such as expression of a biomarker shown in Table 4, 11, or 13) present in a tissue or a cell or populations thereof (such as a normal non-cancerous skin tissue or cell). A control can also be a cellular or tissue control.

Control samples include any suitable sample (e.g., cell, tissue or organ control sample) against which to compare expression of a melanoma biomarker shown in Table 4, 11 or 13, such as the normalization markers shown in Table 3. In some embodiments, the control sample is non-tumor tissue, such as a plurality of non-tumor tissue samples. In one example, non-tumor tissue is tissue known to be benign, such as benign nevus. In some examples, non-tumor tissue includes a skin sample that appears normal, that is it has the absence of nevi, benign lesion, or melanoma. In some examples, the non-tumor tissue is obtained from the same subject, such as non-tumor tissue that is adjacent or even distant from a malignant melanoma. In other examples, the non-tumor tissue is obtained from a healthy control subject or several healthy control subjects. For example, non-tumor tissue can be obtained from a plurality of healthy control subjects (e.g., those not having any cancers, including melanoma, such as samples containing benign nevi from a plurality of such subjects).

In some embodiments, the control sample is known tumor tissue, such as a plurality of known melanoma samples, such as a training set of melanoma (e.g., primary melanoma) samples. Other embodiments involve controls of tissue known to be benign nevi, such as a training set of nevi samples. Training sets of samples (e.g., nevi and melanoma) are useful, in some embodiments, to develop or "train" algorithms (e.g., machine learning algorithms) that distinguish between such sample types.

A difference between a test sample and a control can be an increase or conversely a decrease, for example a decrease or increase in the expression of a biomarker shown in Table 4, 11 or 13. The difference can be a qualitative difference or a quantitative difference, for example a statistically significant difference. In some examples, a difference is an increase or decrease in amount, relative to a control, of at least about 1%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In some embodiments, the control is a reference value or ranges of values, such as expected expression levels for the biomarkers shown in Table 4, 11, or 13 for a sample(s) known to be primary melanoma(s), or benign nevus(nevi). In other embodiments, a reference value obtained from control samples may be a population central tendency ("CT") (such as a mean (e.g., arithmetic or geometric mean), median, mode or average), or reference range of values such as plus and/or minus 0.5, 1.0, 1.5 or 2.0 standard deviation(s) around a population CT. For example, one or more reference values can be derived from the average expression values obtained from a group of healthy control subjects (e.g., from a plurality of known benign nevi) or from a group of cancer patients with melanoma (e.g., from a plurality of known malignant nevi).

Sample Analytical Options

In particular examples, the sample to be analyzed, such as a melanocyte-containing sample (e.g., skin biopsy) is or has been fixed. Fixation techniques may vary from site-to-site, country-to-country, investigator-to-investigator, etc. (Dissecting the Molecular Anatomy of Tissue, ed. by Emmert-Buck, Gillespie and Chuaqui, New York: Springer-Verlag, 244 pages (2010)) and may affect the integrity of and/or accessibility to the gene product(s) to be detected. Thus, in some disclosed methods involving fixed sample (e.g., methods embodiments with steps for isolating the gene expression product(s), such as PCR or nucleic acid sequencing), RNA recovery (e.g., using reversible cross linking agents, ethanol-based fixatives and/or RNA extraction or purification (in whole or in part)) may be advantageous. Notably, in other representative methods (e.g., involving qNPA) RNA recovery is optional or RNA recovery expressly is not needed. Similarly, tissue conditioning can be used to recover protein gene products from fixed tissue in some method embodiments and, thereby, aid in the detection of such protein products.

The percentage of tumor or suspected tumor (e.g., melanoma) in biological samples may vary; thus, in some disclosed embodiments, at least 5%, at least 10%, at least 25%, at least 50%, at least 75%, at least 80% or at least 90% of the sample area (or sample volume) or total cells in the sample are tumor or suspected tumor (e.g., melanoma). In other examples, samples may be enriched for tumor (or suspected tumor) cells, e.g., by macrodissecting areas or cells from a sample that are or appear to be abnormal (e.g., dysplastic). Optionally, a pathologist or other appropriately trained professional may review the sample (e.g., H&E-stained tissue section) to determine if sufficient abnormality (e.g., suspected tumor) is present in the sample for testing and/or mark the area to be macrodissected. In specific examples, macrodissection of sample to be tested avoids as much as possible necrotic and/or hemorrhagic areas. Samples useful in some disclosed methods will have less than 25%, 15%, 10%, 5%, 2%, or 1% necrosis by sample volume or area or total cells.

Sample load influences the amount and/or concentration of gene product (e.g., one or more of the biomarkers in Table 3, 4, 11, or 13) available for detection. In particular embodiments, at least 1 ng, 10 ng, 100 ng, 1 ug, 10 ug, 100 ug, 500 ug, 1 mg total RNA (e.g., mRNA or miRNA), at least 1 ng, 10 ng, 100 ng, 1 ug, 10 ug, 100 ug, 500 ug, 1 mg total DNA, or at least 0.01 ng, 0.1 ng, 1 ng, 10 ng, 100 ng, 1 ug, 10 ug, 100 ug, 500 ug, or 1 mg total protein is isolated from and/or present in a sample (such as a sample lysate). Some embodiments use tissue samples (e.g., FFPE sectioned skin biopsies) that are at least 3, 5, 8, or 10 μm (e.g., about 3 to about 10 μm) thick and/or at least 0.15, 0.2, 0.5, 1, 1.5, 2, 5 or 10 $cm^2$ in area. The concentration of sample suspended in buffer in some method embodiments is at least 0.006 $cm^2$/ul (e.g., 0.15 $cm^2$ FFPE tissue per 25 uL of buffer (e.g., lysis buffer)).

Genes and Gene Sets

Among the innovations disclosed herein are genes (also referred to as biomarkers) and sets of genes, the expression of which (e.g., as measured by mRNA, miRNA or protein expression) is useful in disclosed methods, arrays and kits for distinguishing between benign (e.g., nevi) and malignant (e.g., primary melanoma) melanocyte-containing samples. Also disclosed are genes and gene sets useful as normalizers (e.g., sample-to-sample controls) for nevus and melanoma (e.g., primary melanoma) samples.

In some examples, changes in expression (such as upregulation or downregulation) of at least two different biomarkers from any or all of Table(s) 4, 11 and/or 13 (including, without limitation, genes combinations in Tables 6, 8 or 14), for example normalized to at least one normalization marker (such as one or more of those in Table 3), can be used as specific markers of nevus or melanoma or as markers of the transition between a benign nevus and a primary melanoma. Such markers are useful for a variety of methods and compositions as describe in more detail in this disclosure and, for example, include methods for diagnosing a subject, such as a human subject, as having a benign nevus or as having melanoma, by measuring or detecting expression levels of two or more different biomarkers from any or all of Table(s) 4, 11 and/or 13 (including, e.g., genes combinations in Tables 6, 8 or 14). In one example, the human subject is at risk for developing melanoma.

This disclosure has identified significantly differentially expressed (SDE) genes in melanocyte-containing samples (populations) of interest (e.g., nevi vs. melanoma samples), and exemplary combinations of the identified SDE genes were analyzed to identify combinations of those SDE genes having predictive value to permit characterization of a melanocyte-containing sample as a benign nevus or primary melanoma (see, e.g., Example 2, 3 and 4). Although particular combinations of identified SDE genes are described herein, one ordinarily skilled in the art will appreciate that this disclosure now enables the identification of other combinations of the SDE genes shown in Table(s) 4, 11 and/or 13 that will robustly characterize a sample as a nevus or melanoma. For example, any non-repeating combination of biomarkers in any or all of Table(s) 4, 11 and/or 13 in which all predictor Xn variables (expression value for the selected biomarker) have a variance inflation factor (VIF) less than 10 are expected to have a useful predictive value for differentiating between samples from benign nevi versus those from primary melanoma and, accordingly, are contemplated by this disclosure. Additionally, nevi-melanoma classifiers of any combination of genes in Table(s) 4, 11 and/or 13 may be tested for acceptable classification performance (e.g., misclassification of fewer than 1%, 2%, 3%, 4%, 5%, 6%, 7%, 8% or 10% of samples, or classification accuracy of greater than or equal to 75%, 80%, 85%, 90%, 92%, 93%, 94%, 95%, 96%, 97%, 98% or 99%) using any of the methods disclosed herein (e.g., AUC) or commonly known in the art.

Particular method embodiments described throughout this disclosure include determining in a sample (e.g., a skin sample) obtained from a subject, an expression level (such as a nucleic acid or protein level) of at least two different (i.e., no repeated) biomarkers selected from any one or more (a)-(r) below and, in some cases, at least one normalization biomarker (such as listed in Table 3). Similarly, particular compositions embodiments described throughout this disclosure may include specific binding agents (e.g., probes, primers, aptamers, antibodies, etc.) that can be used to specifically measure an expression level (such as a nucleic acid or protein level) of at least two different (i.e., no repeated) biomarkers selected from any one or more (a)-(r) below and, in some cases, at least one normalization biomarker (such as listed in Table 3). In some examples, as applicable, an expression level (such as a nucleic acid or protein level) for at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, or all of the biomarkers listed in any one of (a)-(r) (such as 2 to 20, 2 to 10, 4 to 10, 4 to 15, or 2 to 5 of the biomarkers listed) is determined in the sample or can be specifically detected using a disclosed composition (e.g., array or kit). In other examples, an expression level (such as a nucleic acid or protein level) for at least two different (i.e., no repeated) biomarkers selected from any one or more (a)-(r) below are at least 50%, at least 75%, at least 80%, at least 90%, at least 95%, or at least 98% of the plurality of genes listed in the particular group (e.g., Table(s) 4, 11 and/or 13) from which the biomarkers are selected.

(a) Genes described in Table 4 (i.e., NR4A1, B4GALT1, SAT1, TP53, TADA3, BRAF, TFRC, RUNX1, SOCS3, PDLIM7, SP100, PIP4K2A, SOX4, PDIA4, MCM6, CTNNB1, RPL37A, GNAS, TGFB1, PPIA, PTEN, MAGED2, 1PRAME, GALNTL1, MAGEA2, TEX13A, CREBBP, TPSAB1, CDK2, STAT2, SQSTM1, and B2M); and/or (b) Genes described in Table 11 (i.e., B4GALT1, BAX, MAGEA2, NR4A1, PDIA4, PRAME, RUNX1, SOCS3, SAT1, PDLIM7, BIRC5, HIF1A, MET, MAGEC2, ERCC1, POLR2J3, LDHA, PICALM, ZFYVE16, and BEST1), and/or (c) Genes described in Table 13 (i.e., genes expressing the products hsa.miR.122, hsa.miR.1291, hsa.miR.191, hsa.miR.19b, hsa.miR.200a, hsa.miR.200c, hsa.miR.203, hsa.miR.205, hsa.miR.21, hsa.miR.23b, hsa.miR.29c, hsa.miR.342.3p, hsa.miR.375, hsa.miR.665, hsa.miR.1304, hsa.miR.142.5p, hsa.miR.1254, hsa.let.7a, hsa.miR.140.5p, and hsa.miR.183); and/or (d) NR4A1, B4GALT1, SOX4, SQSTM1, B2M, TFRC, TP53, GALNTL1, CREBBP, SOCS3 and CTNNB1; and/or (e) NR4A1, B4GALT1, SOX4, SQSTM1, B2M, TFRC, TP53, CREBBP, SOCS3, RPL37A, SAT1, BRAF, and TPSAB1; and/or (f) NR4A1, B4GALT1, SOX4, SQSTM1, B2M, TFRC, TP53, CREBBP, and SOCS3; and/or (g) NR4A1, B4GALT1, SOX4, SQSTM1, B2M, TFRC, TP53, SOCS3, and BRAF; and/or (h) NR4A1, B4GALT1, SOX4, SQSTM1, B2M, TFRC, TP53, CREBBP, SOCS3, and BFAF; and/or (i) MAGEA2, PRAME, PDIA4, NR4A1, PDLIM7, B4GALT1, SAT1, RUNX1, and SOCS3; and/or
(j) Any gene set described in Table 6; and/or
(k) Any gene set described in Table 8; and/or
(l) Any gene set described in Table 14; and/or
(m) Any of the specific combinations paired in square brackets ([ . . . ]) below:
[NR4A1,B4GALT1], [NR4A1,SOX4], [NR4A1, SQSTM1], [NR4A1,B2M], [NR4A1,TFRC], [NR4A1, TP53], [NR4A1,CREBBP], [NR4A1,SOCS3], [NR4A1,BRAF], [B4GALT1,SOX4], [B4GALT1, SQSTM1], [B4GALT1,B2M], [B4GALT1,TFRC], [B4GALT1,TP53], [B4GALT1,CREBBP], [B4GALT1,SOC53], [B4GALT1,BRAF], [SOX4, SQSTM1], [SOX4,B2M], [SOX4,TFRC], [SOX4, TP53], [SOX4,CREBBP], [SOX4,SOCS3], [SOX4, BRAF], [SQSTM1,B2M], [SQSTM1,TFRC], [SQSTM1,TP53], [SQSTM1,CREBBP], [SQSTM1, SOC53], [SQSTM1,BRAF], [B2M,TFRC], [B2M, TP53], [B2M,CREBBP], [B2M,SOCS3], [B2M, BRAF], [TFRC,TP53], [TFRC,CREBBP], [TFRC, SOCS3], [TFRC,BRAF], [TP53,CREBBP], [TP53, SOCS3], [TP53,BRAF], [CREBBP,SOCS3], [CREBBP,BRAF], and [SOCS3,BRAF]; and/or
(n) Combinations of three (or four) described by any of the pairs in (m) in combination with one (or two) other non-repetitive genes from the list of NR4A1, B4GALT1, SOX4, SQSTM1, B2M, TFRC, TP53, CREBBP, SOCS3, and BRAF; and/or
(o) Any of the specific combinations paired in square brackets ([ . . . ]) below:
[MAGEA2,PRAME], [MAGEA2,PDIA4], [MAGEA2, NR4A1], [MAGEA2,PDLIM7], [MAGEA2, B4GALT1], [MAGEA2,SAT1], [MAGEA2,RUNX1], [MAGEA2,SOCS3], [PRAME,PDIA4], [PRAME, NR4A1], [PRAME,PDLIM7], [PRAME,B4GALT1], [PRAME,SAT1], [PRAME,RUNX1], [PRAME, SOCS3], [PDIA4,NR4A1], [PDIA4,PDLIM7], [PDIA4,B4GALT1], [PDIA4,SAT1], [PDIA4, RUNX1], [PDIA4,SOCS3], [NR4A1,PDLIM7], [NR4A1,B4GALT1], [NR4A1,SAT1], [NR4A1, RUNX1], [NR4A1,SOCS3], [PDLIM7,B4GALT1], [PDLIM7,SAT1], [PDLIM7,RUNX1], [PDLIM7, SOCS3], [B4GALT1,SAT1], [B4GALT1,RUNX1], [B4GALT1,SOCS3], [SAT1,RUNX1], [SAT1, SOCS3], or [RUNX1,SOCS3]; and/or
(p) Combinations of three (or four) described by any of the pairs in (o) in combination with one (or two) other non-repetitive gene(s) from the list of MAGEA2, PRAME, PDIA4, NR4A1, PDLIM7, B4GALT1, SAT1, RUNX1, and SOCS3; and/or
(q) Any of the specific combinations paired in square brackets ([ . . . ]) below ("hsa" has been removed in each case but is intended as part of the identifier):
[miR.122, miR.1291], [miR.122, miR.191], [miR.122, miR.19b], [miR.122, miR.200a], [miR.122, miR.200c], [miR.122, miR.203], [miR.122, miR.205], [miR.122, miR.21], [miR.122, miR.23b], [miR.122, miR.29c], [miR.122, miR.342.3p], [miR.122, miR.375], [miR.122, miR.665], [miR.122, miR.1304], [miR.122, miR.142.5p], [miR.122, miR.1254], [miR.122, let.7a], [miR.122, miR.140.5p], [miR.122, miR.183], [miR.1291, miR.191], [miR.1291, miR.19b], [miR.1291, miR.200a], [miR.1291, miR.200c], [miR.1291, miR.203], [miR.1291, miR.205], [miR.1291, miR.21], [miR.1291, miR.23b], [miR.1291, miR.29c], [miR.1291, miR.342.3p], [miR.1291, miR.375], [miR.1291, miR.665], [miR.1291, miR.1304], [miR.1291, miR.142.5p], [miR.1291, miR.1254], [miR.1291, let.7a], [miR.1291, miR.140.5p], [miR.1291, miR.183], [miR.191, miR.19b], [miR.191, miR.200a], [miR.191, miR.200c], [miR.191, miR.203], [miR.191, miR.205], [miR.191, miR.21], [miR.191, miR.23b], [miR.191, miR.29c], [miR.191, miR.342.3p], [miR.191, miR.375], [miR.191, miR.665], [miR.191, miR.1304], [miR.191, miR.142.5p], [miR.191, miR.1254], [miR.191, let.7a], [miR.191, miR.140.5p], [miR.191, miR.183], [miR.19b, miR.200a], [miR.19b, miR.200c], [miR.19b, miR.203], [miR.19b, miR.205], [miR.19b, miR.21], [miR.19b, miR.23b], [miR.19b, miR.29c], [miR.19b, miR.342.3p], [miR.19b, miR.375], [miR.19b, miR.665], [miR.19b, miR.1304], [miR.19b, miR.142.5p], [miR.19b, miR.1254], [miR.19b, let.7a], [miR.19b, miR.140.5p], [miR.19b, miR.183], [miR.200a, miR.200c], [miR.200a, miR.203], [miR.200a, miR.205], [miR.200a, miR.21], [miR.200a, miR.23b], [miR.200a, miR.29c], [miR.200a, miR.342.3p], [miR.200a, miR.375], [miR.200a, miR.665], [miR.200a, miR.1304], [miR.200a, miR.142.5p], [miR.200a, miR.1254], [miR.200a, let.7a], [miR.200a, miR.140.5p], [miR.200a, miR.183], [miR.200c, miR.203], [miR.200c, miR.205], [miR.200c, miR.21], [miR.200c, miR.23b], [miR.200c, miR.29c], [miR.200c, miR.342.3p], [miR.200c, miR.375], [miR.200c, miR.665], [miR.200c, miR.1304], [miR.200c, miR.142.5p], [miR.200c, miR.1254], [miR.200c, let.7a], [miR.200c, miR.140.5p], [miR.200c, miR.183], [miR.203, miR.205], [miR.203, miR.21], [miR.203, miR.23b], [miR.203, miR.29c], [miR.203, miR.342.3p], [miR.203, miR.375], [miR.203, miR.665], [miR.203, miR.1304], [miR.203, miR.142.5p], [miR.203, miR.1254], [miR.203, let.7a], [miR.203, miR.140.5p], [miR.203, miR.183], [miR.205, miR.21], [miR.205, miR.23b], [miR.205, miR.29c], [miR.205, miR.342.3p], [miR.205, miR.375], [miR.205, miR.665], [miR.205, miR.1304], [miR.205, miR.142.5p], [miR.205, miR.1254], [miR.205, let.7a], [miR.205, miR.140.5p], [miR.205, miR.183], [miR.21, miR.23b], [miR.21, miR.29c], [miR.21, miR.342.3p], [miR.21, miR.375], [miR.21, miR.665], [miR.21, miR.1304], [miR.21, miR.142.5p], [miR.21, miR.1254], [miR.21, let.7a], [miR.21, miR.140.5p], [miR.21, miR.183], [miR.23b, miR.29c], [miR.23b, miR.342.3p], [miR.23b, miR.375], [miR.23b, miR.665], [miR.23b, miR.1304], [miR.23b, miR.142.5p], [miR.23b, miR.1254], [miR.23b, let.7a], [miR.23b, miR.140.5p], [miR.23b, miR.183], [miR.29c, miR.342.3p], [miR.29c, miR.375], [miR.29c, miR.665], [miR.29c, miR.1304], [miR.29c, miR.142.5p], [miR.29c, miR.1254], [miR.29c, let.7a], [miR.29c, miR.140.5p], [miR.29c, miR.183], [miR.342.3p, miR.375], [miR.342.3p, miR.665], [miR.342.3p, miR.1304], [miR.342.3p, miR.142.5p], [miR.342.3p, miR.1254], [miR.342.3p, let.7a], [miR.342.3p, miR.140.5p], [miR.342.3p, miR.183], [miR.375, miR.665], [miR.375, miR.1304], [miR.375, miR.142.5p], [miR.375, miR.1254], [miR.375, let.7a], [miR.375, miR.140.5p], [miR.375, miR.183], [miR.665, miR.1304], [miR.665, miR.142.5p], [miR.665, miR.1254], [miR.665, let.7a], [miR.665, miR.140.5p], [miR.665, miR.183], [miR.1304, miR.142.5p], [miR.1304, miR.1254], [miR.1304, let.7a], [miR.1304, miR.140.5p], [miR.1304, miR.183], [miR.142.5p, miR.1254], [miR.142.5p, let.7a], [miR.142.5p, miR.140.5p], [miR.142.5p, miR.183], [miR.1254, let.7a], [miR.1254, miR.140.5p], [miR.1254, miR.183], [let.7a, miR.140.5p], [let.7a, miR.183], or [miR.140.5p, miR.183]; and/or (r) Combinations of three (or four) described by any of the pairs in (q) in combination with one (or two) other non-repetitive miRNA(s) from the list of hsa.miR.122, hsa.miR.1291, hsa.miR.191, hsa.miR.19b, hsa.miR.200a, hsa.miR.200c, hsa.miR.203, hsa.miR.205, hsa.miR.21, hsa.miR.23b, hsa.miR.29c, hsa.miR.342.3p, hsa.miR.375, hsa.miR.665, hsa.miR.1304, hsa.miR.142.5p, hsa.miR.1254, hsa.let.7a, hsa.miR.140.5p, or hsa.miR.183.

Particular method embodiments include normalizing expression of the disease-specific biomarker(s) (e.g., see (a)-(r) above) to at least one normalization biomarker. As discussed in further detail elsewhere in this disclosure, normalization is a step included in some method embodiments that is useful to control for certain types of confounding variability in gene expression values. Adjusting the values of all disease-specific variables to the expression of specified normalization biomarkers (e.g., by division or subtraction) is one, non-limiting way to normalize such disease-specific variables. As a general rule, a specified normalization biomarker has no statistically significant difference in expression between the sample types of interest (such as between nevi and primary melanoma sample types). Exemplary normalization biomarkers for nevi and melanoma samples are listed in Table 3. Some disclosed methods contemplate normalizing disease-specific biomarker (see, e.g., Table(s) 4, 11, and/or 13) expression to an expression level for at least 2, at least 3, at least 4, at least 5, at least 6, at least 7, at least 8, or all of the normalization biomarker(s) listed in Table 3, or as selected from the group consisting of (i) MFI2, RAP2B, BMP1, NCOR2, RPS6KB2 and SDHA (ii) BMP-1, MFI2, NCOR2, and RAP2b; or (iii) RPS6KB2 and SDHA. While illustrative normalization biomarkers are specified here, other methods of normalization useful in the disclosed methods are discussed below.

Detecting Gene Expression

Disclosed methods further involve detecting the expression of the genes discovered herein (see Table(s) 4, 11 and/or 13) that distinguish benign (e.g., nevi) from malignant (e.g., primary melanoma) melanocyte-containing samples, or are suitable for normalizating expression levels in such sample types (see Table 3). A variety of techniques are (or may become) available for measuring gene expression in a sample of interest. However, the disclosure is not limited to particular methods of obtaining, measuring, or detecting gene expression. Many such techniques involve detecting the products of the genes (e.g., nucleic acids (such as mRNA or miRNA) and/or protein) expressed in such samples. It may also be (or become) possible to directly detect the activity of a gene or of chromosomal DNA (e.g., transcription rate) independent of measuring its resultant gene products and such techniques also are useful in methods disclosed herein.

Gene expression levels can be determined in the disclosed methods using a solution-based (i.e., ex situ) assay, such as PCR or a nuclease protection assay or nucleic acid sequencing. In other examples, expression levels are determined or detected using an in situ assay, for example using immunohistochemistry or in situ hybridization.

Detecting Nucleic-Acid Gene Products

Nucleic-acid gene products are, as the name suggests, products of gene expression that are nucleic acids. Exemplary nucleic acids whose expression can be detected include DNA or RNA, such as cDNA, protein-coding RNA (e.g., mRNA) or non-coding RNA (e.g., miRNA or lncRNA). In a particular examples, the method includes detecting mRNA expression, miRNA expression, or both. Base pairing between complementary strands of RNA or DNA (i.e., nucleic acid hybridization) forms all or part of the basis for a large representative class of techniques for detecting nucleic-acid gene products. Other representative detection techniques involve nucleic acid sequencing, which may or may not involve hybridization steps and/or bioinformatics steps (e.g., to associate nucleic acid sequence information to its corresponding gene). These and other methods of detecting nucleic acids are known in the art and, while representative techniques are described herein, this disclosure is not intended to be limited to particular methods of nucleic acid detection.

In some embodiments of the disclosed methods, determining the level of gene expression in a melanocyte-containing sample includes detecting two or more nucleic acids shown in Table(s) 4, 11, and/or 13 (and in some examples also one or more nucleic acids shown in Table 3), for example by determining the relative or actual amounts of such nucleic acids in the sample. Exemplary nucleic acids include DNA or RNA, such as cDNA, miRNA, or mRNA.

The level of expression of nucleic acid molecules can be detected or measured using, for instance, in vitro nucleic acid amplification and/or nucleic acid hybridization. The results of such detection methods can be quantified, for instance by determining the amount of hybridization or the amount of amplification. Thus, in some examples, determining the expression level of a biomarker (such as those in Table(s) 3, 4, 11, and/or 13, individually or in any combination, including the combinations in Tables 6, 8 or 14) in the methods provided herein can include contacting the sample with a plurality of nucleic acid probes (such as a nuclease protection probe, NPP) or paired amplification primers, wherein each probe or paired primers is/are specific and complementary to one of the least two, non-repeated biomarkers in Table(s) 4, 11, and/or 13, under conditions that permit the plurality of nucleic acid probes or paired primers to hybridize to its/their complementary at least two biomarkers in Table(s) 4, 11, and/or 13. In one example, the method can also include after contacting the sample with the plurality of nucleic acid probes (such as NPPs), contacting the sample with a nuclease that digests single-stranded nucleic acid molecules.

Optional Nucleic Acid Isolation

In some examples, nucleic acids are isolated or extracted from the melanocyte-containing sample prior to contacting such nucleic acids in the sample with a complementary nucleic acid probe or primer and/or otherwise detecting such nucleic acids in the sample. Nucleic acids (such as RNA (e.g., mRNA or miRNA) or DNA) can be isolated from the sample according to any of a number of methods. Representative methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993). Representative methods for RNA (e.g., mRNA or miRNA) extraction similarly are well known in the art and are disclosed in standard textbooks of molecular biology, including Ausubel et al., *Current Protocols of Molecular Biology*, John Wiley and Sons (1997).

Specific methods can include isolating total nucleic acid from a sample using, for example, an acid guanidinium-phenol-chloroform extraction method and/or isolating polyA+mRNA by oligo dT column chromatography or by (dT)n magnetic beads (see, for example, Sambrook et al, *Molecular Cloning: A Laboratory Manual* (2nd ed.), Vols. 1-3, Cold Spring Harbor Laboratory, (1989), or *Current Protocols in Molecular Biology*, F. Ausubel et al., ed. Greene Publishing and Wiley-Interscience, N.Y. (1987)). In other examples, nucleic acid isolation can be performed using purification kit, buffer set and protease from commercial manufacturers, such as QIAGEN® (Valencia, Calif.), according to the manufacturer's instructions. For example, total RNA from cells (such as those obtained from a subject) can be isolated using QIAGEN® RNeasy mini-columns. Other commercially available nucleic acid isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation. Methods for RNA extraction from paraffin embedded tissues are disclosed, for example, in Rupp and Locker, *Biotechniques* 6:56-60 (1988), and De Andres et al., *Biotechniques* 18:42-44 (1995).

After isolation or extraction of nucleic acids (e.g., RNA (such as mRNA or miRNA) or DNA) from a sample, any of a number of optional other steps may be performed to prepare such nucleic acids for detection, including measuring the concentration of the isolated nucleic acid, repair (or recovery) of degraded or damaged RNA, RNA reverse transcription, and/or amplification of RNA or DNA.

In other examples, a sample (e.g., FFPE melanocyte-containing tissue sample) is suspended in a buffer (e.g., lysis buffer) and nucleic acids (such as RNA or DNA) present in the suspended sample are not isolated or extracted (e.g., purified in whole or in part) from such suspended sample and are contacted in such suspension with one or more complementary nucleic acid probe(s) (e.g., nuclease protection probes); thereby, eliminating a need for isolation or extraction of nucleic acids (e.g., RNA) from the sample. This embodiment is particularly advantageous where the nucleic acids (such as RNA or DNA) present in the suspended sample are crosslinked or fixed to cellular structures and are not readily isolatable or extractable. Relatively short (e.g., less than 100 base pairs, such as 75-25 base pairs or 50-25 base pairs) probes for which no extension of such probe is required for detection are useful in some non-extraction method embodiments. An ordinarily skilled artisan will appreciate that methods requiring probe extension (e.g., PCR or primer extension) are not reliable where the nucleic acid template (e.g., RNA) for such extension is degraded or otherwise inaccessible. Specific methods (e.g., qNPA) for detecting nucleic acids (e.g., RNA) in a sample without prior extraction of such nucleic acids are described in detail elsewhere herein.

Nucleic Acid Hybridization

In some examples, determining the expression level of a disclosed biomarker (such as those in Table(s) 4, 11, and/or 13) or normalization biomarker (e.g., Table 3) in the methods provided herein can include contacting the sample with a plurality of nucleic acid probes (such as a nuclease protection probe, NPP, or adjoining ligatable probes) or paired amplification primers, wherein each probe (or set of ligatable probes) or paired primers in the plurality is/are specific and complementary to one of at least two biomarkers in Table(s) 4, 11, and/or 13 or a or normalization biomarker in Table 3, under conditions that permit the plurality of nucleic acid probes or paired primers to hybridize to its/their complementary biomarker in Table(s) 4, 11, and/or 13. In one example, the method can also include after contacting the sample with the plurality of nucleic acid probes (such as NPPs), contacting the sample with a nuclease that digests single-stranded nucleic acid molecules. In other examples, each of the at least two biomarkers in Table(s) 4, 11, and/or 13, or a or normalization biomarker in Table 3, is contacted with a "probe set" that consists of multiple (e.g., 2, 3, 4, 5, or 6) probes specific for each such biomarker, which design can be useful, for example, to increase the signal obtained from such gene product or to detect multiple variants of the same gene product.

In some examples, variable (e.g., Table(s) 4, 11, and/or 13) or normalization (e.g., Table 3) nucleic acids are detected by nucleic acid hybridization. Nucleic acid hybridization involves providing a denatured probe and target nucleic acid (e.g., those in Table(s) 4, 11, and/or 13) under conditions where the probe and its complementary target can form stable hybrid duplexes through complementary base pairing. In some examples, the nucleic acids that do not form hybrid duplexes are then removed (e.g., washed away, digested by nuclease or physically removed) leaving the hybridized nucleic acids to be detected, typically through detection of an (directly or indirectly) attached detectable label. In specific examples, nucleic acids that do not form hybrid duplexes, such as any excess probe that does not hybridize to its respective target, and the regions of the target sequence that are not complementary to the probes, can be digested away by addition of nuclease, leaving just the hybrid duplexes of target sequence of complementary probe.

It is generally recognized that nucleic acids are denatured by increasing the temperature and/or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions can be designed to provide different degrees of stringency. The strength of hybridization can be increased without lowering the stringency of hybridization, and thus the specificity of hybridization can be maintained in a high stringency buffer, by including unnatural bases in the probes, such as by including locked nucleic acids or peptide nucleic acids.

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridization complexes (e.g., as captured on an array surface) may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

Changes in expression of a nucleic acid and/or the presence of nucleic acid detected by these methods for instance can include increases or decreases in the level (amount) or functional activity of such nucleic acids, their expression or translation into protein, or in their localization or stability. An increase or a decrease, for example relative to a normalization biomarker (see, e.g., Table 3), can be, for example, at least a 1-fold, at least a 2-fold, or at least a 5-fold, such as about a 1-fold, 2-fold, 3-fold, 4-fold, 5-fold, change (increase or decrease) in the expression of and/or the presence of a particular nucleic acid, such as a nucleic acid corresponding to the biomarker shown in any of Table(s) 4, 11, and/or 13. In multiplexed method embodiments, the relative expression of non-normalizer genes (e.g., variable genes; for example, Table(s) 4, 11, and/or 13) also can be compared; particularly, when each such gene has been similarly normalized (e.g., to the expression of one or more co-detected normalizer genes; for example see Table 3). Hence, the normalized expression of one variable gene may be at least at least a 1-fold, at least a 2-fold, or at least a 5-fold, such as about a 1-fold, 1.5-fold, 2-fold, 3-fold, 4-fold, 5-fold higher or lower than the normalized expression of another variable gene.

Gene expression is measured using a multiplexed methodology and/or high throughput methodology in some embodiments. In multiplexed methods, a plurality of measurements (e.g., gene expression measurements) is made in a single sample. Various technologies have evolved that permit the monitoring of large numbers of genes in a single sample (e.g., traditional microarrays, multiplexed PCR, serial analysis of gene expression (SAGE; e.g., U.S. Pat. No. 5,866,330), multiplex ligation-dependent probe amplification (MLPA), high-throughput sequencing, labeled bead-based technology (e.g., U.S. Pat. Nos. 5,736,330 and 6,449,562), digital molecular barcoding technology (e.g, U.S. Pat. No. 7,473,767). In high-throughput methods, gene expression in multiple samples is measured contemporaneously. High-throughput methods can also be multiplexed (i.e., contemporaneously detecting multiple genes in each of multiple samples).

In some embodiments, expression levels of one or more biomarkers (such as two or more of those in Table(s) 4, 11, and/or 13 (e.g., any genes combination in Tables 6, 8 or 14) and/or at least one in Table 3) are determined contemporaneously in a single melanocyte-containing sample or in a plurality of melanocyte-containing samples (such as samples from different subjects). In one example, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or, as applicable, at least 20, at least 21, at least 22, at least 23, at least 24, at least 25, at least 26, at least 27, at least 28, at least 29, at least 30, at least 31, or all of the biomarkers listed in Table(s) 4, 11, and/or 13 (such as 2, 3, 4, 5, 6, 7, 8, 9, 10, 11, 12, 13, 14, 15, 16, 17, 18, 19, 20, or, as applicable, 21, 22, 23, 24, 25, 26, 27, 28, 29, 30, 31, or all of the biomarkers in Table(s) 4, 11, and/or 13), or, e.g., any of the gene combinations in Table 6, 8 or 14, can be detected contemporaneously in the same sample or in a plurality of samples, and in some examples, at least 2, at least 3, at least 4, at least 5, or all 6 of the normalization biomarkers listed in Table 3 (or other normalization biomarker(s) identified with the methods provided herein) are detected contemporaneously, for example contemporaneously with the at least two biomarkers in Table(s) 4, 11, and/or 13. The plurality of samples can be from multiple different subjects and/or be multiple samples from the same subject, such as at least 2 different samples (e.g., from at least 2 different subjects and/or from different areas of the same subject's tumor or body). In some examples, at least at least 2, at least 5, at least 10, at least 20, at least 50, at least 100, at least 500, at least 1000, at least 2000, at least 5000, or even at least 10,000 melanocyte-containing samples are analyzed contemporaneously (such as 10 to 100, 10 to 1000, 100 to 1000, 100 to 5000, or 1000 to 10,000 melanocyte-containing samples are analyzed contemporaneously).

This disclosure also includes methods utilizing integrated systems for high-throughput screening. The systems typically include a robotic armature that transfers fluid from a source to a destination, a controller that controls the robotic armature, a detector, a data storage unit that records detection, and an assay component such as a microtiter plate, for example including one or more programming linkers or one that includes one or more oligonucleotides that can directly hybridize to a target (such as two or more of the biomarkers in Table(s) 4, 11, and/or 13, and one or more of the normalization markers in Table 3).

Arrays are one useful (non-limiting) set of tools for multiplex detection of gene expression. An array is a systematic arrangement of elements (e.g., analyte capture reagents (such as, target-specific oligonucleotide probes, aptamers, or antibodies)) where a set of values (e.g., gene expression values) can be associated with an identification key. The arrayed elements may be systematically identified on a single surface (e.g., by spatial mapping or by differential tagging), using separately identifiable surfaces (e.g., flow channels or beads), or by a combination thereof.

Other examples of methods and assay systems that can be used to detect the disclosed biomarkers are high throughput assay techniques disclosed in International Patent Publication Nos. WO 2003/002750 and WO 2008/121927, WO 1999/032663, WO 2000/079008, WO/2000/037684, and WO 2000/037683 and U.S. Pat. Nos. 6,232,066, 6,458,533, 6,238,869, and 7,659,063, which are incorporated by reference herein in so far as they describe high throughput assay techniques.

In some array embodiments, nucleic acid probes (such as oligonucleotides), which are designed to capture (directly or indirectly) one or more products of the genes shown in Table(s) 3, 4, 11, and/or 13), are plated, or arrayed, on a microchip substrate. For example, the array can include oligonucleotides complementary to at least two of the genes shown in Table(s) 3, 4, 11, and/or 13 (such as at least 3, at least 5, at least 10, at least 20, or all of such genes, or any of the genes combinations in Tables 6, 8 or 14 or as otherwise disclosed herein) and, optionally, at least one of the genes shown in Table 3. In other examples, the array can include oligonucleotides complementary to a portion of a nuclease protection probe that is complementary to a product of at least two of the genes shown in Table(s) 3, 4, 11, and/or 13 (such as at least 3, at least 5, at least 10, at least 20, or all of such genes, or any of the genes combinations in Tables 6, 8 or 14 or as otherwise disclosed herein) and, optionally, at least one of the genes shown in Table 3.

The arrayed sequences are then hybridized with isolated nucleic acids (such as cDNA, miRNA or mRNA) from the test sample (e.g., melanocyte-containing sample obtained from a subject, whose characterization as benign nevus or malignant melanoma (e.g., primary melanoma) is desired). In one example, the isolated nucleic acids from the test sample are labeled, such that their hybridization with the specific complementary oligonucleotide on the array can be determined. Alternatively, the test sample nucleic acids are not labeled, and hybridization between the oligonucleotides on the array and the target nucleic acid is detected using a sandwich assay, for example using additional oligonucleotides complementary to the target that are labeled.

In one embodiment, the hybridized nucleic acids are detected by detecting one or more labels attached to the sample nucleic acids or attached to a nucleic acid probe that hybridizes directly or indirectly to the target nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification using a labeled nucleotide (such as fluorescein-labeled UTP and/or CTP) incorporates a label into the transcribed nucleic acids.

Detectable labels suitable for use in embodiments throughout this disclosure include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), chemiluminescent markers, radiolabels (for example, $^{3}H$, $^{125}I$, $^{35}S$, $^{14}C$, or $^{32}P$), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149; and U.S. Pat. No. 4,366,241. In some embodiments, labels are attached by spacer arms of various lengths to reduce potential steric hindrance.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology, Vol.* 24: *Hybridization With Nucleic Acid Probes*, P. Tijssen, ed. Elsevier, N.Y., 1993).

In situ hybridization (ISH), such as chromogenic in situ hybridization (CISH) or silver in situ hybridization (SISH), is an exemplary method for detecting and comparing expression of genes of interest (such as those in Table(s) 3, 4, 11, and/or 13). ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of the biomarkers in Table(s) 4, 11, and/or 13. Sample cells or tissues may be treated to increase their permeability to allow a probe, such as a probe specific for one or more of the biomarkers in Table(s) 4, 11, and/or 13, to enter the cells. The probe is added to the treated cells, allowed to hybridize at pertinent temperature, and excess probe is washed away. A complementary probe is labeled with a detectable label, such as a radioactive, fluorescent or antigenic tag, so that the probe's location and quantity in the tissue can be determined, for example using autoradiography, fluorescence microscopy or immunoassay.

In situ PCR is the PCR-based amplification of the target nucleic acid sequences followed by in situ detection of target and amplicons. Prior to in situ PCR, cells or tissue samples generally are fixed and permeabilized to preserve morphology and permit access of the PCR reagents to the intracellular sequences to be amplified; optionally, an intracellular reverse transcription step is introduced to generate cDNA from RNA templates, which enables detection of low copy RNA sequences. PCR amplification of target sequences is next performed; then, intracellular PCR products are visualized by ISH or immunohistochemistry.

Quantitative Nuclease Protection Assay (qNPA)

In particular embodiments of the disclosed methods, nucleic acids are detected in the sample utilizing a quantitative nuclease protection assay and array (such as an array described below). The quantitative nuclease protection assay is described in International Patent Publications WO 99/032663; WO 00/037683; WO 00/037684; WO 00/079008; WO 03/002750; and WO 08/121927; and U.S. Pat. Nos. 6,238,869; 6,458,533; and 7,659,063, each of which is incorporated herein by reference in their entirety. See also, Martel et al, *Assay and Drug Development Technologies.* 2002, 1 (1-1):61-71; Martel et al, *Progress in Biomedical Optics and Imaging,* 2002, 3:35-43; Martel et al, *Gene Cloning and Expression Technologies*, Q. Lu and M. Weiner, Eds., Eaton Publishing, Natick (2002); Seligmann, B. *PharmacoGenomics,* 2003, 3:36-43; Martel et al, "Array Formats" in "Microarray Technologies and Applications," U. R. Muller and D. Nicolau, Eds, Springer-Verlag, Heidelberg; Sawada et al, *Toxicology in Vitro,* 20:1506-1513; Bakir et al., *Biorg. & Med. Chem Lett,* 17: 3473-3479; Kris, et al, *Plant Physiol.* 144: 1256-1266; Roberts et al., *Laboratory Investigation,* 87: 979-997; Rimsza et al., *Blood,* 2008 Oct. 15, 112 (8): 3425-3433; Pechhold et al., *Nature Biotechnology,* 27, 1038-1042. All of these are fully incorporated by reference herein.

Using qNPA methods, a nuclease protection probe (NPP) is allowed to hybridize to the target sequence, which is followed by incubation of the sample with a nuclease that digests single stranded nucleic acid molecules. Thus, if the probe is detected, (e.g. it is not digested by the nuclease) then the target of the probe, for example a target nucleic acid shown in Table(s) 3, 4, 11 and/or 13, is present in the sample, and this presence can be detected (e.g., quantified). NPPs can be designed for individual targets and added to an assay as a cocktail for identification on an array; thus, multiple genes targets can be measured within the same assay and/or array.

In some examples, cells in the melanocyte-containing sample are used directly, or are first lysed or permeabilized in an aqueous solution (for example using a lysis buffer). The aqueous solution or lysis buffer may include detergent (such as sodium dodecyl sulfate) and/or one or more chaotropic agents (such as formamide, guanidinium HCl, guanidinium isothiocyanate, or urea). The solution may also contain a buffer (for example SSC). In some examples, the lysis buffer includes about 15% to 25% formamide (v/v), about 0.01% to 0.1% SDS, and about 0.5-6×SSC. The buffer may optionally include tRNA (for example, about 0.001 to about 2.0 mg/ml) or a ribonuclease. The lysis buffer may also include a pH indicator, such as Phenol Red. In a particular example, the lysis buffer includes 20% formamide, 3×SSC (79.5%), 0.05% DSD, 1 μg/ml tRNA, and 1 mg/ml Phenol Red. Cells are incubated in the aqueous solution for a sufficient period of time (such as about 1 minute to about 60 minutes, for example about 5 minutes to about 20 minutes, or about 10 minutes) and at a sufficient temperature (such as about 22° C. to about 115° C., for example, about 37° C. to about 105° C., or about 90° C. to about 110° C.) to lyse or permeabilize the cell. In some examples, lysis is performed at about 95° C., if the nucleic acid to be detected is RNA. In other examples, lysis is performed at about 105° C., if the nucleic acid to be detected is DNA.

In some examples, a nucleic acid protection probe (NPP) (such as those shown in SEQ ID NOS: 1-36 and 123-164) complementary to the target can be added to a sample at a concentration ranging from about 10 pM to about 10 nM (such as about 30 pM to 5 nM, about 100 pM to about 1 nM), in a buffer such as, for example, 6×SSPE-T (0.9 M NaCl, 60 mM $NaH_2PO_4$, 6 mM EDTA, and 0.05% Triton X-100) or lysis buffer (described above). In one example, the probe is added to the sample at a final concentration of about 30 pM. In another example, the probe is added to the sample at a final concentration of about 167 pM. In a further example, the probe is added to the sample at a final concentration of about 1 nM. In such examples, NPPs not digested by a nuclease, such as S1, if the NPP is hybridized to (forms a duplex with) a complementary sequence, such as a target sequence.

One of skill in the art can identify conditions sufficient for an NPP to specifically hybridize to its target present in the test sample. For example, one of skill in the art can determine experimentally the features (such as length, base composition, and degree of complementarity) that will enable a nucleic acid (e.g., NPP) to hybridize to another nucleic acid (e.g., a target nucleic acid in Table(s) 3, 4, 11 and/or 13) under conditions of selected stringency, while minimizing non-specific hybridization to other substances or molecules. Typically, the nucleic acid sequence of an NPP will have sufficient complementarity to the corresponding target sequence to enable it to hybridize under selected stringent hybridization conditions, for example hybridization at about 37° C. or higher (such as about 37° C., 42° C., 50° C., 55° C., 60° C., 65° C., 70° C., 75° C., or higher). Among the hybridization reaction parameters which can be varied are salt concentration, buffer, pH, temperature, time of incubation, amount and type of denaturant such as formamide.

The nucleic acids in the sample are denatured (for example at about 95° C. to about 105° C. for about 5-15 minutes) and hybridized to a NPP for between about 10 minutes and about 24 hours (for example, at least about 1 hour to 20 hours, or about 6 hours to 16 hours) at a temperature ranging from about 4° C. to about 70° C. (for example, about 37° C. to about 65° C., about 45° C. to about 60° C., or about 50° C. to about 60° C.). In some examples, the probes are incubated with the sample at a temperature of at least about 40° C., at least about 45° C., at least about 50° C., at least about 55° C., at least about 60° C., at least about 65° C., or at least about 70° C. In one example, the probes are incubated with the sample at about 60° C. In another example, the NPPs are incubated with the sample at about 50° C. These hybridization temperatures are exemplary, and one of skill in the art can select appropriate hybridization temperature depending on factors such as the length and nucleotide composition of the NPPs.

In some embodiments, the methods do not include nucleic acid purification (for example, nucleic acid purification is not performed prior to contacting the sample with the probes and/or nucleic acid purification is not performed following contacting the sample with the probes). In some examples, no pre-processing of the sample is required except for cell lysis. In some examples, cell lysis and contacting the sample with the NPPs occur sequentially, in some non-limiting examples without any intervening steps. In other examples, cell lysis and contacting the sample with the NPPs occur concurrently.

Following hybridization of the one or more NPPs and nucleic acids in the sample, the sample is subjected to a nuclease protection procedure. NPPs which have hybridized to a full-length nucleic acid are not hydrolyzed by the nuclease and can be subsequently detected.

Treatment with one or more nucleases will destroy nucleic acid molecules other than the probes which have hybridized to nucleic acid molecules present in the sample. For example, if the sample includes a cellular extract or lysate, unwanted nucleic acids, such as genomic DNA, cDNA, tRNA, rRNA and mRNAs other than the gene of interest, can be substantially destroyed in this step. One of skill in the art can select an appropriate nuclease, for example based on whether DNA or RNA is to be detected. Any of a variety of nucleases can be used, including, pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the undesirable nucleic acids present in the sample. In a particular example, the nuclease is specific for single-stranded nucleic acids, for example S1 nuclease. An advantage of using a nuclease specific for single-stranded nucleic acids in some method embodiments disclosed here is to remove such single-stranded ("sticky") molecules from subsequent reaction steps where they may lead to unnecessary background or cross-reactivity. S1 nuclease is commercially available from, for example, Promega, Madison, Wis. (cat. no. M5761); Life Technologies/Invitrogen, Carlsbad, Calif. (cat. no. 18001-016); Fermentas, Glen Burnie, Md. (cat. no. EN0321), and others. Reaction conditions for these enzymes are well-known in the art and can be optimized empirically.

In some examples, S1 nuclease diluted in an appropriate buffer (such as a buffer including sodium acetate, sodium chloride, zinc sulfate, and detergent, for example, 0.25 M sodium acetate, pH 4.5, 1.4 M NaCl, 0.0225 M $ZnSO_4$, 0.05% KATHON) is added to the hybridized probe mixture and incubated at about 50° C. for about 30-120 minutes (for example, about 60-90 minutes) to digest non-hybridized nucleic acid and unbound NPP.

The samples optionally are treated to otherwise remove non-hybridized material and/or to inactivate or remove residual enzymes (e.g., by phenol extraction, precipitation, column filtration, etc.). In some examples, the samples are optionally treated to dissociate the target nucleic acid from the probe (e.g., using base hydrolysis and heat). After hybridization, the hybridized target can be degraded, e.g., by nucleases or by chemical treatments, leaving the NPPs in direct proportion to how much NPP had been hybridized to target. Alternatively, the sample can be treated so as to leave the (single strand) hybridized portion of the target, or the duplex formed by the hybridized target and the probe, to be further analyzed.

The presence of the NPPs (or the remaining target or target:NPP complex) is then detected. Any suitable method can be used to detect the probes (or the remaining target or target:NPP complex). In some examples, the NPPs include a detectable label and detecting the presence of the NPP(s) includes detecting the detectable label. In some examples, the NPPs are labeled with the same detectable label. In other examples, the NPPs are labeled with different detectable labels (such as a different label for each target). In other examples, the NPPs are detected indirectly, for example by hybridization with a labeled nucleic acid. In some examples, the NPPs are detected using a microarray, for example, a microarray including detectably labeled nucleic acids (for example labeled with biotin or horseradish peroxidase) that are complementary to the NPPs. In other examples, the NPPs are detected using a microarray including capture probes and programming linkers, wherein a portion of the programming linker is complementary to a portion of the NPPs and subsequently incubating with detection linkers, a portion of which is complementary to a separate portion of the NPPs. The detection linkers can be detectably labeled, or a separate portion of the detection linkers are complementary to additional nucleic acids including a detectable label (such as biotin or horseradish peroxidase). In some examples, the NPPs are detected on a microarray, for example, as described in International Patent Publications WO 99/032663; WO 00/037683; WO 00/037684; WO 00/079008; WO 03/002750; and WO 08/121927; and U.S. Pat. Nos. 6,238,869; 6,458,533; and 7,659,063, incorporated herein by reference in their entirety.

Briefly, in one non-limiting example, following hybridization and nuclease treatment, the solution is neutralized and transferred onto a programmed ARRAYPLATE (HTG Molecular Diagnostics, Tucson, Ariz.; each element of the ARRAYPLATE is programmed to capture a specific probe, for example utilizing an anchor attached to the plate and a programming linker associated with the anchor), and the NPPs are captured during an incubation (for example, overnight at about 50° C.). The probes can instead be captured on X-MAP beads (Luminex, Austin, Tex.), an assay referred to as the QBEAD assay, or processed further, including as desired PCR amplification or ligation reactions, and for instance then measured by sequencing). The media is removed and a cocktail of probe-specific detection linkers are added, in the case of the ARRAYPLATE and QBEAD assays, which hybridize to their respective (captured) probes during an incubation (for example, 1 hour at about 50° C.). Specific for the ARRAYPLATE and QBEAD assays, the array or beads are washed and then a triple biotin linker (an oligonucleotide that hybridizes to a common sequence on every detection linker, with three biotins incorporated into it) is added and incubated (for example, 1 hour at about 50° C.). For the ARRAYPLATE (mRNA assay), HRP-labeled avidin (avidin-HRP) or streptavidin poly-HRP is added and incubated (for example at about 37° C. for 1 hour), then washed to remove unbound avidin-HRP or streptavidin poly-HRP. Substrate is added and the plate is imaged to measure the intensity of every element within the plate. In the case of QBEAD Avidin-PE is added, the beads are washed, and then measured by flow cytometry using the Luminex 200, FLEXMAP 3D, or other appropriate instrument. One of skill in the art can design suitable capture probes, programming linkers, detection linkers, and other reagents for use in a quantitative nuclease protection assay based upon the NPPs utilized in the methods disclosed herein.

In some examples, instead of using a detection linker, NPPs are directly biotinylated.

Nucleic Acid Amplification

In some method examples, nucleic acid molecules (such as nucleic acid gene products (e.g., mRNA, miRNA or lncRNA) or nuclease protection probes) are amplified prior to or as a means to their detection. In some examples, nucleic acid expression levels are determined during amplification, for example by using real time RT-PCR.

In one example, a nucleic acid sample can be amplified prior to hybridization, for example hybridization to complementary oligonucleotides present on an array. If a quantitative result is desired, a method is utilized that maintains or controls for the relative frequencies of the amplified nucleic acids. Methods of "quantitative" amplification are well known. For example, quantitative PCR involves simultaneously co-amplifying a known quantity of a control sequence using the same primers. This provides an internal standard that can be used to calibrate the PCR reaction. The array can then include probes specific to the internal standard for quantification of the amplified nucleic acid.

In some examples, the primers used for the amplification are selected so as to amplify a unique segment of the gene product of interest (such as RNA of a gene shown in any of Table(s) 3, 4, 11, and/or 13). In other embodiments, the primers used for the amplification are selected so as to amplify a NPP specific for a gene product of interest (such as RNA of a gene shown in any of Table(s) 3, 4, 11, and/or 13). Primers that can be used to amplify variable gene products (e.g., shown in any of Table(s) 4, 11, and/or 13), as well as normalization gene products (e.g., see Table 3), are commercially available or can be designed and synthesized according to well-known methods.

In one example, RT-PCR can be used to detect RNA (e.g., mRNA, miRNA or lncRNA) levels in melanocyte-containing tissue samples (e.g., skin biopsy). Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling.

Although PCR can use a variety of thermostable DNA-dependent DNA polymerases, it typically employs the Taq DNA polymerase. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendable by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments dissociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

A variation of RT-PCR is real time quantitative RT-PCR, which measures PCR product accumulation through a dual-labeled fluorogenic probe (e.g., Taqman® probe). Real time PCR is compatible both with quantitative competitive PCR, where internal competitor for each target sequence is used for normalization, and with quantitative comparative PCR using a normalization gene contained within the sample, or a normalization gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available, e.g., from PE Applied Biosystems (Foster City, Calif.).

An alternative quantitative nucleic acid amplification procedure is described in U.S. Pat. No. 5,219,727. In this method, the amount of a target sequence (e.g., the expression product of a gene listed in any of Table(s) 4, 11 and/or 13) in a sample is determined by simultaneously amplifying the target sequence and an internal standard nucleic acid segment. The amount of amplified nucleic acid from each segment is determined and compared to a standard curve to determine the amount of the target nucleic acid segment that was present in the sample prior to amplification.

RNA Sequencing

RNA sequencing provides another way to obtain multiplexed and, in some embodiments, high-throughput gene expression information. Numerous specific methods of RNA sequencing are known and/or being developed in the art (for one review, see Chu and Corey, *Nuc. Acid Therapeutics,* 22:271 (2012)). Whole-transcriptome sequencing and targeted RNA sequencing techniques each are available and are useful in the disclosed methods. Representative methods for sequencing-based gene expression analysis include serial analysis of gene expression (SAGE), gene expression analysis by massively parallel signature sequencing (MPSS), whole transcriptome shotgun sequencing (aka, WTSS or RNA-Seq), or nuclease-protection sequencing (aka, qNPS or NPSeq; see PCT Pub. No. WO2012/151111).

Proteins for Detecting Gene Expression

In some embodiments of the disclosed methods, determining the level of gene expression in a melanocyte-containing sample (e.g., skin biopsy) includes detecting one or more proteins (for example by determining the relative or actual amounts of such proteins) in the sample. Routine methods of detecting proteins are known in the art, and the disclosure is not limited to particular methods of protein detection.

Protein gene products (e.g., those in any of Table(s) 4 and/or 11) or normalization proteins (e.g., those in Table 3) can be detected and the level of protein expression in the sample can be determined through novel epitopes recognized by protein-specific binding agents (such as antibodies or aptamers) specific for the target protein (such as those in any of Table(s) 3, 4, and/or 11) used in immunoassays, such as ELISA assays, immunoblot assays, flow cytometric assays, immunohistochemical assays, an enzyme immunoassay, radioimmuno assays, Western blot assays, immunofluorescent assays, chemiluminescent assays and other peptide detection strategies (Wong et al., *Cancer Res.,* 46: 6029-6033, 1986; Luwor et al., *Cancer Res.,* 61: 5355-5361, 2001; Mishima et al., *Cancer Res.,* 61: 5349-5354, 2001; Ijaz et al., *J. Med. Virol.,* 63: 210-216, 2001). Generally these methods utilize monoclonal or polyclonal antibodies.

Thus, in some embodiments, the level of target protein expression (such as those in any of Table(s) 3, 4, and/or 11) present in the biological sample and thus the amount of protein expressed is detected using a target protein specific binding agent, such as an antibody of fragment thereof, or an aptamer, which can be detectably labeled. In some embodiments, the specific binding agent is an antibody, such as a polyclonal or monoclonal antibody, that specifically binds to the target protein (such as those in any of Table(s) 3, 4, and/or 11). Thus in certain embodiments, determining the level or amount of protein in a biological sample includes contacting a sample from the subject with a protein specific binding agent (such as an antibody that specifically binds a protein shown in any of Table(s) 3, 4, and/or 11), detecting whether the binding agent is bound by the sample, and thereby measuring the amount of protein present in the sample. In one embodiment, the specific binding agent is a monoclonal or polyclonal antibody that specifically binds to the target protein (such as those in any of Table(s) 3, 4, and/or 11). One skilled in the art will appreciate that there are commercial sources for antibodies to target proteins, such as those in any of Table(s) 3, 4, and/or 11.

The presence of a target protein (such as those in any of Table(s) 3, 4, and/or 11) can be detected with multiple specific binding agents, such as one, two, three, or more specific binding agents. Thus, the methods can utilize more than one antibody. In some embodiments, one of the antibodies is attached to a solid support, such as a multiwell plate (such as, a microtiter plate), bead, membrane or the like. In practice, microtiter plates may conveniently be utilized as the solid phase. However, antibody reactions also can be conducted in a liquid phase.

In some examples, the method can include contacting the sample with a second antibody that specifically binds to the first antibody that specifically binds to the target protein (such as those in any of Table(s) 3, 4, and/or 11). In some examples, the second antibody is detectably labeled, for example with a fluorophore (such as FITC, PE, a fluorescent protein, and the like), an enzyme (such as HRP), a radiolabel, or a nanoparticle (such as a gold particle or a semiconductor nanocrystal, such as a quantum dot (QDOT®)). In this method, an enzyme which is bound to the antibody will react with an appropriate substrate, such as a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme.

Detection can also be accomplished by visual comparison of the extent of enzymatic reaction of a substrate in comparison with similarly prepared standards. It is also possible to label the antibody with a fluorescent compound. Exemplary fluorescent labeling compounds include fluorescein isothiocyanate, rhodamine, phycoerythrin, phycocyanin, allophycocyanin, o-phthaldehyde, Cy3, Cy5, Cy7, tetramethylrhodamine isothiocyanate, phycoerythrin, allophycocyanins, Texas Red and fluorescamine. The antibody can also be detectably labeled using fluorescence emitting metals such as $^{152}$Eu, or others of the lanthanide series. Other metal compounds that can be conjugated to the antibodies include, but are not limited to, ferritin, colloidal gold, such as colloidal superparamagnetic beads. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. Examples of chemiluminescent labeling compounds are luminol, isoluminol, theromatic acridinium ester, imidazole, acridinium salt and oxalate ester. Likewise, a bioluminescent compound can be used to label the antibody. In one example, the antibody is labeled with a bioluminescence compound, such as luciferin, luciferase or aequorin. Haptens that can be conjugated to the antibodies include, but are not limited to, biotin, digoxigenin, oxazalone, and nitrophenol. Radioactive compounds that can be conjugated or incorporated into the antibodies include but are not limited to technetium 99m ($^{99}$Tc), $^{125}$I and amino acids including any radionucleotides, including but not limited to, $^{14}$C, $^{3}$H and $^{35}$S.

Generally, immunoassays for proteins (such as those in any of Table(s) 3, 4, and/or 11) typically include incubating a biological sample in the presence of antibody, and detecting the bound antibody by any of a number of techniques well known in the art. In one example, the biological sample (such as one containing melanocytes) can be brought in contact with, and immobilized onto, a solid phase support or carrier such as nitrocellulose or a multiwell plate, or other solid support which is capable of immobilizing cells, cell particles or soluble proteins. The support may then be washed with suitable buffers followed by treatment with the antibody that specifically binds to the target protein (such as those in any of Table(s) 3, 4, and/or 11). The solid phase support can then be washed with the buffer a second time to remove unbound antibody. If the antibody is directly labeled, the amount of bound label on solid support can then be detected by conventional means. If the antibody is unlabeled, a labeled second antibody, which detects that antibody that specifically binds to the target protein (such as those in any of Table(s) 3, 4, and/or 11) can be used.

Alternatively, antibodies are immobilized to a solid support, and then contacted with proteins isolated from a biological sample, such as a tissue biopsy from the skin or eye, under conditions that allow the antibody and the protein to bind specifically to one another. The resulting antibody: protein complex can then be detected, for example by adding another antibody specific for the protein (thus forming an antibody:protein:antibody sandwich). If the second antibody added is labeled, the complex can be detected, or alternatively, a labeled secondary antigay can be used that is specific for the second antibody added.

A solid phase support or carrier includes materials capable of binding a sample, antigen or an antibody. Exemplary supports include glass, polystyrene, polypropylene, polyethylene, dextran, nylon, amylases, natural and modified celluloses, polyacrylamides, gabbros and magnetite. The nature of the carrier can be either soluble to some extent or insoluble. The support material may have virtually any possible structural configuration so long as the coupled molecule is capable of binding to its target (such as an antibody or protein). Thus, the support configuration may be spherical, as in a bead, or cylindrical, as in the inside surface of a test tube, or the external surface of a rod. Alternatively, the surface may be flat such as a sheet or test strip.

In one embodiment, an enzyme linked immunosorbent assay (ELISA) is utilized to detect the target protein(s) (e.g., see Voller, "The Enzyme Linked Immunosorbent Assay (ELISA)," *Diagnostic Horizons* 2:1-7, 1978). ELISA can be used to detect the presence of a protein in a sample, for example by use of an antibody that specifically binds to a target protein (such as those in any of Table(s) 3, 4, and/or 11). In some examples, the antibody can be linked to an enzyme, for example directly conjugated or through a secondary antibody, and a substance is added that the enzyme can convert to a detectable signal.

Detection can also be accomplished using any of a variety of other immunoassays; for example, by radioactively labeling the antibodies or antibody fragments. In another example, a sensitive and specific tandem immunoradiometric assay may be used (see Shen and Tai, *J. Biol. Chem.,* 261:25, 11585-11591, 1986). The radioactive isotope can be detected by such means as the use of a gamma counter or a scintillation counter or by autoradiography.

In one example, a spectrometric method is utilized to detect or quantify an expression level of a target protein (such as those in any of Table(s) 3, 4, and/or 11). Exemplary spectrometric methods include mass spectrometry, nuclear magnetic resonance spectrometry, and combinations thereof. In one example, mass spectrometry is used to detect the presence of a target protein (such as those in any of Table(s) 3, 4, and/or 11) in a melanocyte-containing sample, such as a skin biopsy (see for example, Stemmann et al., *Cell* 107(6):715-26, 2001).

A target protein (such as those in any of Table(s) 3, 4, and/or 11) also can be detected by mass spectrometry assays coupled to immunaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of proteins separated by two-dimensional polyacrylamide gel electrophoresis (2D-PAGE) (Kiernan et al., *Anal. Biochem.,* 301: 49-56, 2002).

Quantitative mass spectroscopic methods, such as SELDI, can be used to analyze protein expression in a melanocyte-containing sample, such as a skin biopsy. In one example, surface-enhanced laser desorption-ionization time-of-flight (SELDI-TOF) mass spectrometry is used to detect protein expression, for example by using the ProteinChip (Ciphergen Biosystems, Palo Alto, Calif.). Such methods are well known in the art (e.g., see U.S. Pat. Nos. 5,719,060; 6,897,072; and 6,881,586). Briefly, one version of SELDI uses a chromatographic surface with a chemistry that selectively captures analytes of interest, such as those in any of Table(s) 3, 4, and/or 11.

Optional Assay Control Measures

Optionally, assays used to detect gene expression products (e.g., nucleic acids (such as mRNA, miRNA, lncRNA) or protein) will have both positive and negative process control elements used to assess assay performance.

A positive control can be any known element, preferably of a similar nature to the target (e.g., RNA target, then RNA (or cDNA) positive control), that can be included in an assay (or sample) and detected in parallel with the target(s) and that does not interfere (e.g., crossreact) with such target(s) detection. In one example, the positive control is an in vitro transcript (IVT) that is run in parallel as a separate sample or is "spiked" into each sample at a known amount. IVT-specific binding agents (e.g., oligonucleotide probes, such as a nuclease protection probe)) and, if applicable, IVT-specific detection agents also are included in each assay to ensure a positive result for such in vitro transcript. In another example, an IVT transcript can be designed from non-crossreacting regions of the *Methanobacterium* sp. AL-21 chromosome (NC_015216).

Negative process control elements can include analyte-specific binding agents (e.g., oligonucleotides or antibodies) designed or selected to detect a gene product that is not expected to be expressed in the applicable test sample. For example, an analyte-specific binding agent that does recognize any gene expression product in the human transcriptome or proteome may be included in a multiplexed assay (such as an oligonucleotide probe or antibody specific for a plant or insect or nematode RNA or protein, respectively, where human gene expression products are the desired targets). This negative control element should not generate signal in the applicable assay. Any above-background signal for such negative process control element is an indicator of assay failure. In one example, the negative control is ANT.

Gene expression can vary across sample types or subjects due to the biology and/or due to variability related to specimen stability, integrity or input level as well as the assay process and system. In order to minimize non-biological related sources of variability (especially in multiplexed assays), gene expression products that do not or are found by bioinformatic methods not to significantly vary (e.g., "housekeepers" or normalizers) among samples of interest are measured in particular embodiments. In some such embodiments, expression levels for candidate normalization gene products will demonstrate adequate (e.g., above-background) and/or non-saturated intensity values. Further discussion of normalizer gene expression products is found elsewhere in this disclosure.

In some situations, anomalous signals may result from unexpected process-related issues that are not otherwise controlled, e.g., by analysis of normalizers; thus, in some embodiments, it is useful to include a sample-independent process control element(s) to indicate a successful or failed assay on any specimen, irrespective of the specimen stability, integrity, or input level. Method embodiments in which nucleic acid gene expression products are detected may include a known concentration of a RNA sample (e.g., in vitro transcript RNA or IVT) in every assay. Such a control element (e.g., IVT) will be measured in each assay and act as an assay process quality control.

The MAQC (Microarray Array Quality Control) project proposed that a "Universal Human Reference RNA" could be a useful external-control standard for microarray gene expression assays. Accordingly, some disclosed method embodiments involving RNA gene expression products may, but need not, include a parallel-processed sample containing Universal Human Reference RNA. If such universal RNA sample includes all or some of the RNAs targeted for detection by the applicable assay, a positive signal can be expected for such included RNAs, which may serve as an (or another) assay process quality control.

Gene Expression Data

It is well accepted that gene expression data "contain the keys to address fundamental problems relating to the prevention and cure of diseases, biological evolution mechanisms and drug discovery" (Lu and Han, *Information Systems,* 28:243-268 (2003)). In some examples, distilling the information from such data is as simple as making a qualitative determination from the presence, absence or qualitative amount (e.g., high, medium, low) of one or more gene products detected. In other examples, raw gene expression data may be pre-processed (e.g., background subtracted, log transformed, and/or corrected), normalized, and/or applied in classification algorithms. These aspects are described in more detail below.

Data Pre-Processing

Background Subtraction

In some method embodiments, raw gene expression data is background subtracted. This correction may be used, for example, where data has been collected using multiplexed methods, such as microarrays. One aim of such transformation is to correct for local effects, e.g., where one portion of a microarray surface may look "brighter" than another portion of the surface without any biological reason. Methods of background subtraction are well known in the art and include, e.g., (i) local background subtraction (e.g., consider all pixels that are outside the spot mask but within the bounding box centered at the spot center), (ii) morphological opening background estimation (relies on non-linear morphological filters, such as opening, erosion, dilation and rank filters (see, Soille, Morphological Image Analysis: Principles and Applications, Berlin: Springer-Verlag (1999), to create a background image for subtraction from the original image), (iii) constant background (subtracts a constant background for all spots), Normexp background correction (a convolution of normal and exponential, distributions is fitted to the foreground intensities, using the background intensities as a covariate, and the expected signal given the observed foreground becomes the corrected intensity).

Data Transformation

Many biological variables (e.g., gene expression data) do not meet the assumptions of parametric statistical tests, e.g., such variables are not normally distributed, the variances are not homogeneous, or both (Durbin et al., *Bioinformatics,* 18:S105 (2002)). In some cases, transforming the data will make it fit the statistical assumptions better. In some method embodiments, useful data transformation can include (i) log transformation, which consists of taking the log of each observation, e.g., base-10 logs, base-2 logs, base-e logs (also known as natural logs); the log selection makes no difference because such logs differ by a constant factor; or variance-stabilizing transformation, e.g., as described by Durbin (supra). In specific examples, raw expression values for each biomarker detected in such method (e.g., at least two Table 4, 11 and/or 13 biomarkers and/or at least one normalization biomarker) are log (e.g., log 2 or log 10) transformed. In other embodiments, the normalizing step can include dividing each of the at least two Table 4, 11 and/or 13 biomarkers log (e.g., log 2 or log 10) transformed raw expression values by the log (e.g., log 2 or log 10) transformed raw expression value(s) of the at least one normalization biomarker.

Data Filters

Gene expression data may be filtered in some method embodiments to remove data that may be considered unreliable. It is understood that there are many methods known in the art for assessing the reliability of gene expression data and the following non-limiting examples are merely representative.

Gene expression data may be excluded from a disclosed method, in some cases, if it is not expressed or is expressed at an undetectable level (not above background). Oppositely, gene expression data may be excluded from analysis, in some cases, if the expression of a negative control (e.g., ANT) gene is greater than an standard cut off (e.g., more than 100, 200, 250, or 300 relative light units, or more than 1%, 2%, 3%, 4%, 5%, 6%, 7%, 8%, 9%, or 10% above background).

For embodiments involving probe-sets or genes, there are a number of specific data filters that may be useful, including:

(i) Data arising from unreliable probe sets may be selected for exclusion from analysis by ranking probe-set reliability against a series of reference datasets. For example, RefSeq and Ensembl (EMBL) are considered very high quality reference datasets. Data from probe sets matching RefSeq or Ensembl sequences may in some cases be specifically included in microarray analysis experiments due to their expected high reliability. Similarly data from probe-sets matching less reliable reference datasets may be excluded from further analysis, or considered on a case by case basis for inclusion; or (ii) Probe-sets that exhibit no, or low variance may be excluded from further analysis. Low-variance probe-sets may be excluded from the analysis via a Chi-Square test. A probe-set is considered to be low-variance if its transformed variance is to the left of the 99 percent confidence interval of the Chi-Squared distribution with (N−1) degrees of freedom; or (iii) Probe-sets for a given gene or transcript cluster may be excluded from further analysis if they contain less than a minimum number of probes, e.g., following other data pre-processing steps. For example in some embodiments, probe-sets for a given gene or transcript cluster may be excluded from further analysis if they contain less than 1, 2, 3, 4, or 5 probes.

Optionally, a statistical outlier program can be used that determines whether one of several replicates is statistically an outlier compared to the others, such as judged by being "x" standard deviations (SD) (e.g. at least 2-SD or at least 3-SD) away from the average, or CV % of replicates greater than a specified amount (e.g., at least 8% in log-transformed space). In an array-based assay, an outlier could result from there being a problem with one of the array spots, or due to an imaging artifact. Outlier removal is typically performed on a gene-by-gene basis, and if most of the genes in one replicate are outliers, one can apply a pre-established rule that eliminates the entire replicate. For instance, a pipetting error resulting in the improper addition of a critical reagent could cause the entire replicate to be an outlier.

In some examples where gene expression is measured in sample replicates (e.g., triplicates), reproducibility can be measured by pairwise correlation and by pairwise sample linear regression, and a correlation r>=0.95 used as acceptance of replicate (e.g., triplicate) reproducibility. In more specific examples, replicates with pairwise correlation r=>0.90 can be further reviewed by a simple regression model; in which case, if the intercept of the linear regression is statistically significantly different from zero, the replicate removed from further consideration. Any sample with more than 25% (e.g., 1 out of 4) or more, 33% (e.g., 1 out of 3) or more, 50% (e.g., 2 out of 4) or more, or 67% (e.g., 2 out of 3) or more failed replicates may be considered a "failed sample" and removed from further analysis.

Normalization

The objective of normalization is to remove variability due to experimental error (for example due to be due to pipetting, plate position, image artifacts, different amounts of total RNA, etc.) so that variation due to biological effects can be observed and quantified. This process helps ensure the differences observed between different sample types is due truly to difference in sample biology and not due to some technical artifact. There are several points during experimentation at which errors can be introduced and which can be eliminated by normalization. Methods for normalization of gene expression data are well established in the art (e.g., *Methods in Microarray Normalization*, ed. by Phillip Stafford, Baton Rouge, Fla.: CRC Press an imprint of Taylor & Francis Group, 2008).

Normalization typically involves comparing an experimental value, such as the expression value of one or more Table 4, 11 and/or 13 biomarkers, to one or more normalizing value(s) or factor(s) (e.g., by dividing (or subtracting, typically, after log transformation). A normalizing value can be the raw (or log transformed) expression value of a single normalizer biomarker or can be calculated, e.g., from the expression values of a plurality of normalizers or using methods and calculations known in the art. In some examples, normalizing uses a mean value of the expression of a plurality of normalization biomarkers to generate normalized expression values for each Table 4, 11 and/or 13 biomarker tested. In some examples, normalizing uses raw expression values for each of the Table 4, 11 and/or 13 biomarkers tested, and raw expression values for at least one normalization marker in Table 3, to generate normalized expression values for each Table 4, 11 and/or 13 biomarker tested.

In some embodiments, the expression of one or more "normalization biomarkers" can be determined or measured, such as one or more those in Table 3. For example, expression of 1, 2, 3, 4, 5, 6, 7, 8 or all of BMP-1, MFI2, NCOR2, RAP2b, RPS6KB2, SDHA, RPL19, RPLP0, and ALDOA can be detected in the test sample.

Alternatively, one or more normalization biomarkers useful in a disclosed method can be identified using the methods provided herein. For example, a normalization biomarker is any constitutively expressed gene (or protein) against whose expression another expressed gene (or protein) can be compared (e.g., by dividing (or subtracting, typically, after log transformation) the expression of one by the other). In other examples, a normalization biomarker can be any gene expression product (e.g., mRNA, miRNA, or protein) the expression of which does not significantly differ across a representative plurality of samples, such as nevi and melanoma samples. Accordingly, in some methods, a normalization biomarker can be any gene expression product not listed in Table(s) 4, 11, and/or 13, the expression of which does not significantly differ between melanocyte-containing samples (e.g., a representative population of nevi and melanoma samples). In other examples, the at least one normalization biomarker(s) can include a plurality of normalization biomarkers, none of whose expression is statistically significant difference between nevi and primary melanoma samples.

Another way to identify normalization biomarkers useful in disclosed methods is to determine if, when comparing raw data, the expression of putative normalizers track with one another (i.e., if one normalization biomarker goes up, the other normalization biomarkers should as well). Useful normalizers will track one another across multiple samples of interest. The ratio between putative normalization biomarkers also can be determined and normalizers identified if the ratio between them remains constant across a plurality of samples of interest (e.g., melanocyte-containing samples).

Having identified normalization biomarkers, e.g., as described in this disclosure, some method embodiments include normalizing raw (or log transformed) expression values for each of the at least two biomarkers in Table(s) 4, 11 and/or 13 to raw (or log transformed expression values for at least one normalization biomarker(s).

Alternatively, a normalization value can be determined and such value used to normalize the experimental values (e.g., the gene expression values of at least two different biomarkers from Table(s) 4, 11 and/or 13). For example, a population CT (e.g., mean (such as, arithmetic or geometric mean), median, mode, or average) of a plurality of biomarkers whose range and distribution of expression values is representative of the range and distribution of expression of the gene population in the transcriptome of the sample(s) of interest (e.g., melanocyte-containing samples, such as nevi and/or melanoma samples) may serve as a normalization value in some disclosed methods. In other examples, the expression values of outliers (e.g., +/−one or two standard deviations from the population CT) in the plurality of biomarkers are removed from the original calculation of biomarker plurality's population CT and an outlier-free population CT is determined for the plurality of biomarkers and serves as the normalization value for experimental variables (e.g., gene expression values for at least two genes in Table(s) 4, 11, and/or 13).

In other specific examples, the robust multi-array average (RMA) method may be used to normalize the raw data. The RMA method begins by computing background-corrected intensities for each matched cell on a number of microarrays. The background corrected values are restricted to positive values as described by Irizarry et al. (*Biostatistics,* 4:249 (2003)). After background correction, the base-2 logarithm of each background-corrected matched-cell intensity is then obtained. The background-corrected, log-transformed, matched intensity on each microarray is then normalized using the quantile normalization method in which for each input array and each probe expression value, the array percentile probe value is replaced with the average of all array percentile points, this method is more completely described by Bolstad et al. (*Bioinformatics,* 19(2):185 (2003)). Following quantile normalization, the normalized data may then be fit to a linear model to obtain an expression measure for each probe on each microarray.

In some examples, a first normalization can be across the replicates within a treatment or within technical replicates. This is a normalization to all the tested biomarkers (such as two or more of those in Table(s) 4, 11 and/or 13) weighted to a constant level of the total signal for that set of replicates. In this step, the total signal intensity for each assay (such as a well or bead or lane) in a set of replicates is adjusted so that all are equal. The average total signal is calculated for all the replicates, and then a normalization factor is calculated for each sample which adjusts the total signal form that replicate to the total average signal for all replicates. This normalization factor is use then to normalize the signal for each biomarker in that replicate.

Feature Selection (FS)

Classification algorithms typically perform suboptimally with thousands of features (genes/proteins). Thus, feature selection methods are used to identify features that are most predictive of a phenotype. The selected genes/proteins are presented to a classifier or a prediction model. The following benefits result from reducing the dimensionality of the feature space: (i) improve classification accuracy, (ii) provide a better understanding of the underlying concepts that generated the data, and (iii) overcome the risk of data overfitting, which arises when the number of features is large and the number of training patterns is comparatively small. Feature selection was used to determine the disclosed gene sets; therefore the corresponding classifiers have the foregoing advantages built in.

Feature selection techniques including filter techniques (which assess the relevance of features by looking at the intrinsic properties of the data), wrapper methods (which embed the model hypothesis within a feature subset search), and embedded techniques (in which the search for an optimal set of features is built into a classifier algorithm). Filter FS techniques useful in disclosed methods include: (i) parametric methods such as the use of two sample t-tests or moderated t-tests (e.g., LIMMA), ANOVA analyses, Bayesian frameworks, and Gamma distribution models, (ii) model free methods such as the use of Wilcoxon rank sum tests, between-within class sum of squares tests, rank products methods, random permutation methods, or total number of misclassifications (TNoM) which involves setting a threshold point for fold-change differences in expression between two datasets and then detecting the threshold point in each gene that minimizes the number of missclassifications, and (iii) multivariate methods such as bivariate methods, correlation based feature selection methods (CFS), minimum redundancy maximum relevance methods (MRMR), Markov blanket filter methods, tree-based methods, and uncorrelated shrunken centroid methods. Wrapper methods useful in disclosed methods include sequential search methods, genetic algorithms, and estimation of distribution algorithms. Embedded methods useful in the methods of the present disclosure include random forest (RF) algorithms, weight vector of support vector machine algorithms, and weights of logistic regression algorithms. Saeys et al. describe the relative merits of the filter techniques provided above for feature selection in gene expression analysis. In some embodiments, feature selection is provided by use of the LIMMA software package (Smyth, LIMMA: Linear Models for Microarray Data, In: Bioinformatics and Computational Biology Solutions, ed. by Gentleman et al., New York: Springer, pages 397-420 (2005)).

Classifier Algorithms

In some methods, gene expression information (e.g., for the biomarkers described in Table(s) 3, 4, 11 and/or 13) is applied to an algorithm in order to classify the expression profile (e.g., whether a melanocyte-containing sample (such as a skin biopsy) is a benign nevus or a primary melanoma or neither (such as, indeterminate)). The methods disclosed herein can include gene expression-based classifiers for characterizing melanocyte-containing samples as nevi or melanoma. Specific classifier embodiments are described and, based on the provided gene sets and classification methods, others now are enabled.

A classifier is a predictive model (e.g., algorithm or set of rules) that can be used to classify test samples (e.g., melanocyte-containing samples) into classes (or groups) (e.g., nevus or melanoma) based on the expression of genes in such samples (such as the genes in Table(s) 4, 11 and/or 13). Unlike cluster analysis for which the number of clusters is unknown in advance, a classifier is trained on one or more sets of samples for which the desired class value(s) (e.g., nevus or melanoma) is (are) known. Once trained, the classifier is used to assign class value(s) to future observations.

Illustrative algorithms useful in disclosed methods include, but are not limited to, methods that reduce the number of variables such as principal component analysis algorithms, partial least squares methods, and independent component analysis algorithms. Illustrative algorithms further include, but are not limited to, methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis. Machine learning techniques include bagging procedures, boosting procedures, random forest algorithms, and combinations thereof. Boulesteix et al. (*Cancer Inform.*, 6:77 (2008)) provide an overview of the classification techniques provided above for the analysis of multiplexed gene expression data.

Machine learning is where a computer uses adaptive technology to recognize patterns and anticipate actions; thereby sorting through vast amounts of data and analyzing and identifying patterns. Machine learning algorithms (e.g., Logistic Regression (LR), Random Forest (RF), Support Vector Machine (SVM), K-nearest neighbor (KNN)) can be useful for developing software in applications too complex for people to manually design the algorithm.

In some embodiments, test samples are classified using a trained algorithm. Trained algorithms of the present disclosure include algorithms that have been developed using a reference set of known nevi and melanoma samples. Algorithms suitable for categorization of samples include, but are not limited to, k-nearest neighbor algorithms, concept vector algorithms, naive bayesian algorithms, neural network algorithms, hidden markov model algorithms, genetic algorithms, and mutual information feature selection algorithms or any combination thereof. In some cases, trained algorithms of the present disclosure may incorporate data other than gene expression data such as but not limited to scoring or diagnosis by cytologists or pathologists of the present disclosure, information provided by a disclosed pre-classifier algorithm or gene set, or information about the medical history of a subject from whom a tested sample is taken.

In some specific embodiments, a support vector machine (SVM) algorithm, a random forest algorithm, or a combination thereof provides classification of samples (e.g., melanocyte-containing samples) into nevus or melanoma (e.g., primary melanoma) and, optionally, indeterminate classes. In some embodiments, identified markers that distinguish samples (e.g., nevi vs. melanoma) are selected based on statistical significance. In some cases, the statistical significance selection is performed after applying a Benjamini Hochberg correction for false discovery rate (FDR) (see, *J. Royal Statistical Society*, Series B (Methodological) 57:289 (1995)).

In some cases, a disclosed classifier algorithm may be supplemented with a meta-analysis approach such as that described by Fishel et al. (*Bioinformatics,* 23:1599 (2007)). In some cases, the classifier algorithm may be supplemented with a meta-analysis approach such as a repeatability analysis. In some cases, the repeatability analysis selects markers that appear in at least one predictive expression product marker set.

Exemplary Decision Tree Models

A decision tree algorithm is a flow-chart-like tree structure where each internal node denotes a test on an attribute, and a branch represents an outcome of the test. Leaf nodes represent class labels or class distribution. To generate a decision tree, all the training examples are used at the root, the logical test at the root of the tree is applied and training data then is partitioned into sub-groups based on the values of the logical test. This process is recursively applied (i.e., select attribute and split) and terminated when all the data elements in one branch are of the same class. To classify an unknown sample, its attribute values are tested against the decision tree.

As one example of machine learning, Random Forests are ensemble learning methods for classification (and regression) that operate by constructing a multitude of decision trees at training time and outputting the class that is the mode of the classes output by individual trees. In one particular Random Forest algorithm (Breiman, *Machine Learning,* 45:5-32 (2001)), each tree is constructed as follows:

1. Let the number of training cases be "N," and the number of variables in the classifier be "M"
2. "m" is the number of input variables to be used to determine the decision at a node of the tree; m should be less than M.
3. Choose a training set for this tree by choosing n times with replacement from all N available training cases (i.e., take a bootstrap sample). Use the rest of the cases to estimate the error of the tree, by predicting their classes.
4. For each node of the tree, randomly choose m variables on which to base the decision at that node. Calculate the best split based on these m variables in the training set.
5. Each tree is fully grown and not pruned (as may be done in constructing a normal tree classifier).

For prediction, a new sample is pushed down the tree. It is assigned the label of the training sample in the terminal node it ends up in. This procedure is iterated over all trees in the ensemble, and the mode vote of all trees is reported as the random forest class prediction.

Exemplary Logistic Regression Models

One representative method for developing statistical predictive models using the genes in Table(s) 4, 11 and/or 13 is logistic regression with a binary distribution and a logit link function. Estimation for such models can be performed using Fischer Scoring. However, models estimated with exact logistic regression, Empirical Sandwich Estimators or other bias corrected, variance stabilized or otherwise corrective estimation techniques will also, under many circumstances, provide similar models which while yielding slightly different parameter estimates will yield qualitatively consistent patterns of results. Similarly, other link functions, including but not limited to a cumulative logit, complementary log-log, probit or cumulative probit may be expected to yield predictive models that give the same qualitative pattern of results.

One representative form of a predictive model (algorithm) is:

$$\text{Logit}(Yi)=\beta0+\beta1X1+\beta2X2+\beta3X3 \ldots \beta nXn$$

where βo is an intercept term, βn is a coefficient estimate and Xn is the log expression value for a given gene (e.g., any log, such as log base 2 or log base 10). Typically, the value for all β will be greater than −1,000 and less than 1,000. Often, the β0 intercept term will be greater than −200 and less than 200 with cases in which it is greater than −100 and less than 100. The additional βn, where n>0, can be greater than −100 and less than 100.

In particular method embodiments, the Logit(Yi) output is referred to as a consolidated expression value (CEV) for the at least two Table(s) 4, 11 and/or 13 biomarkers. The CEV is determined by (a) weighting the expression level of the at least two Table(s) 4, 11 and/or 13 biomarkers with a constant predetermined for each of the at least two Table(s) 4, 11 and/or 13 biomarkers, and (b) combining the weighted expression levels of the at least two Table(s) 4, 11 and/or 13 biomarkers to produce the CEV. Such a method can also include comparing the CEV to a reference value that distinguishes known melanoma (e.g., primary melanoma) samples from known benign nevus samples. In one example, the method further includes characterizing the sample as malignant (e.g., primary melanoma) if the CEV falls on the same side of the reference value as do the known melanoma samples. In another example, the method further includes characterizing the sample as benign (e.g., nevus) if the CEV falls on the same side of the reference value as do known benign nevi samples.

Performance of any predictive model contemplated herein may be validated with a number of tests known in the art, including, but not limited to, Wald Chi-Square test (overall model fit), and Hosmer and Lemeshow lack fit test (no statistically detectable lack of fit for the model). Predictors for each gene in the model should be stastically significant (e.g., $p<0.05$).

A number of cross validation methods are available to ensure reproducibility of the results. An exemplary method is a one-step maximum likelihood estimate approximation implemented as part of the SAS Proc Logistic classification table procedure. In some examples, ten (10)-fold cross validation and 66-33% split validation in the open source package Weka can be used for confirmation of results. In other examples, n-fold, including leave-one-out (LOO), cross validation and split sample training/testing provides useful confirmation of results.

In some method embodiments, algorithms (aka, fitted model) provide a predicted event probability, which, for example, is the probability of a melanocyte-containing sample (e.g., skin biopsy) sample being a melanoma (e.g., primary melanoma), being malignant, being a nevus, or being benign. In some instances, a SAS computation method known to those of ordinary skill in the art can be used to compute a reduced-bias estimate of the predicted probability (see, support.sas.com/documentation/cdl/en/statug/63347/HTML/default/viewer.htm#statug_logistic_sec t044.htm (as of Mar. 15, 2013)). In other examples, a series of threshold values, z, where z is between 0 and 1 are set, as typically determined by the ordinarily skilled artisan based on the desired clinical utility of a model or application requirement. If the predicted probability calculated for a particular sample exceeds or equals the pre-set threshold value, z, the sample is assigned to the nevus group; otherwise, it was assigned to the melanoma group or vice versa. In other examples, two threshold values can be set where sample values falling between the two thresholds are assigned an "indeterminate" or "not otherwise assigned" or the like label.

Based on the algorithm output, a determination is made as to whether a tested sample (e.g., a skin sample) is malignant or benign, for example, by comparing the output to a reference standard (e.g., a cutoff determined from known malignant and benign melanocyte-containing samples). In some examples, the steps of calculating the output from the algorithm and/or determining from the algorithm output that the sample is or is not malignant by comparing the output to a reference standard, are performed by a suitably programmed computer. In some examples, the method can also include providing to a user a report comprising the algorithm output or the determination that the sample is or is not malignant or is "consistent with melanoma," or "consistent with nevus" or "indeterminate" or the like. In some examples the report includes a CEV for the at least two biomarkers from Table(s) 4, 11 and/or 13 analyzed.

The resulting output value is compared to a cut-off value. The cut-off value can be determined by a machine learning or logistic regression analysis of normalized expression values for the at least two biomarkers from Table(s) 4, 11 and/or 13 in a plurality of melanocyte-containing samples known in advance to be benign or malignant. Cut-off values may be determined by individual users on a case-by-case basis, for example, by selecting particular sensitivity and specificity values and/or AUC value for the nevi-melanoma classifier being used. Other methods for determine cut-off values are provided in WO 02/103320 and U.S. Pat. Nos. 7,171,311; 7,514,209; 7,863,001; and 8,019,552 (all herein incorporated by reference to the extent describing methods for determining useful cut-off values in diagnostic testing).

In some examples, a tested sample (e.g., a skin biopsy) is characterized as benign if the algorithm output value is on the same side of the cut-off value as the plurality of known benign samples, or characterized as malignant if the output value is on the same side of the cut-off value as the plurality of known malignant samples. In one example, the sample is characterized as benign if the output value is below the cut-off value or as malignant if the output value is above the cut-off value. In another example, the sample is characterized as benign if the output value is above the cut-off value or as malignant if the output value is below the cut-off value.

Molecular Profiling and Classifier Outputs

There typically are four possible outcomes when classifying a biological sample, such as a melanocyte-containing sample, with a disclosed method that includes a binary classifier. If the outcome from a prediction is p and the actual value is also p, then it is called a true positive (TP); however if the actual value is n then it is said to be a false positive (FP). Conversely, a true negative has occurred when both the prediction outcome and the actual value are n, and false negative is when the prediction outcome is n while the actual value is p. Consider an embodiment that seeks to determine whether a sample is a melanoma (e.g., a primary melanoma). A false positive in this case occurs when a sample tests positive, but is not actually a melanoma (e.g., a primary melanoma). A false negative, on the other hand, occurs when the sample tests negative (i.e., not melanoma), when it actually is a melanoma (e.g., a primary melanoma). In some embodiments, ROC curve assuming real-world prevalence of subtypes can be generated by re-sampling errors achieved on available samples in relevant proportions.

The positive predictive value (PPV), or precision rate, or post-test probability of melanoma (e.g., a primary melanoma), is the proportion of samples with positive test results that correctly are melanoma (e.g., a primary melanoma). PPV reflects the probability that a positive test reflects the underlying hypothesis being tested (e.g., a sample is a melanoma (such as, a primary melanoma)). In one example:

False positive rate ($\alpha$)=FP/(FP+TN)−specificity

False negative rate ($\beta$)=FN/(TP+FN)−sensitivity

Power=sensitivity=1−$\beta$

Likelihood-ratio positive=sensitivity/(1−specificity)

Likelihood-ratio negative=(1−sensitivity)/specificity where TN is true negative, FN is false negative and TP and FP are as defined above.

Negative predictive value (NPV) is the proportion of subjects or samples with a negative test result (e.g., nevus or indeterminate) who are correctly diagnosed or subtyped. A high NPV for a given test means that when the test yields a negative result, it is most likely correct in its assessment.

In some embodiments, the results of the gene expression analysis of the disclosed methods provide a statistical confidence level that a given diagnosis (e.g., nevus or melanoma or indeterminate) is correct. In some embodiments, such statistical confidence level is above 85%, 90%, 91%, 92%, 93%, 94%, 95%, 96%, 97%, 98%, 99% or 99.5%.

In one aspect of the present disclosure, samples that have been processed by another method (e.g., histopathology and/or immunocytochemistry) and diagnosed are, then, subjected to disclosed molecular profiling as a second diagnostic screen. This second diagnostic screen enables, at least: 1) a significant reduction of false positives and false negatives, 2) a determination of the underlying genetic, metabolic, or signaling pathways responsible for the resulting pathology, 3) the ability to assign a statistical probability to the accuracy of the diagnosis, 4) the ability to resolve ambiguous results, and 5) the ability to properly characterize a previously ambiguous sample.

In some embodiments, the biological sample is classified as nevus or melanoma (e.g., primary melanoma) with an accuracy of greater than 75%, 80%, 85%, 86%, 87%, 88%, 89%, 90%, 91%, 92%, 93%, 94%, 95%, 96%, 97%, 98%, 99%, or 99.5%. The term accuracy as used in the foregoing sentence includes specificity, sensitivity, positive predictive value, negative predictive value, and/or false discovery rate.

In other cases, receiver operator characteristic (ROC) analysis may be used to determine the optimal assay parameters to achieve a specific level of accuracy, specificity, positive predictive value, negative predictive value, and/or false discovery rate. A ROC curve is a graphical plot that illustrates the performance of a binary classifier system as its discrimination threshold is varied. It is created by plotting the fraction of true positives out of the positives (TPR=true positive rate) vs. the fraction of false positives out of the negatives (FPR=false positive rate) at various threshold settings.

Method Implementation

The methods, such as those involving classifiers, described herein can be implemented in numerous ways. Several representative non-limiting embodiments are described below.

In some method embodiments, gene expression data is input (e.g., manually or automatically) into a computer or other device, machine or apparatus for application of the various algorithms described herein, which is particularly advantageous where a large number of gene expression data points are collected and processed. Other embodiments involve use of a communications infrastructure, for example the internet. Various forms of hardware, software, firmware, processors, or a combination thereof are useful to implement specific classifier and method embodiments. Software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment. The score can be a numerical score (representative of a numerical value) or a non-numerical score representative of a numerical value or range of numerical values (e.g., "A" representative of a 90-95% likelihood of an outcome).

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a response gene, level of a reference gene product(s); normalized level of a response gene; and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, using devices such as fax back). Exemplary output receiving devices can include a display element, a printer, a facsimile device and the like. Electronic forms of transmission and/or display can include email, interactive television, and the like. In one embodiment, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility. In some examples, the method includes generating a report. In some examples the report includes an icon indicating the classification of a sample, such as a "+" or "M" for melanoma or a "−" or "N" for nevi.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present disclosure.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The present disclosure also contemplates a computer-readable storage medium (e.g. CDROM, memory key, flash memory card, diskette, etc.) having stored thereon a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.), the program provides for transmission of data input by the user (e.g., via the internet, via an intranet, etc.) to a computing environment at a remote site. Processing or completion of processing of the data can be carried out at the remote site to generate a report. After review of the report, and completion of any needed manual intervention, to provide a complete report, the complete report can be then transmitted back to the user as an electronic document or printed document (e.g., fax or mailed paper report). The storage medium containing a program as described herein can be packaged with instructions (e.g., for program installation, use, etc.) recorded on a suitable substrate or a web address where such instructions may be obtained. The computer-readable storage medium can also be provided in combination with one or more reagents for carrying out response likelihood assessment (e.g., primers, probes, arrays, or other such kit components).

Output

In some embodiments, once a score for a particular sample (patient) is determined, an indication of that score can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, or other diagram), or an audible output. Thus, the output can include a report that is generated.

For example, the output can be textual (optionally, with a corresponding) score. For example, textual outputs may be "consistent with nevus" or the like, or "consistent with melanoma" or the like (such as, "consistent with primary melanoma"), or "indeterminate" (e.g., not consistent with either nevus or melanoma) or the like. Such textual output can be used, for example, to provide a diagnosis of benign sample (e.g., nevus) or malignant sample (e.g., primary melanoma), or can simply be used to assist a clinician in distinguishing a nevus from a melanoma (e.g., a primary melanoma).

In other examples, the output is a numerical value (e.g., quantitative output), such as an amount of gene or protein expression (such as those in any of Table(s) 3, 4, 11 and/or 13) in the sample or a relative amount of gene or protein expression (such as those in any of 4, 11 and/or 13) in the sample as compared to a control. In additional examples, the output is a graphical representation, for example, a graph that indicates the value (such as amount or relative amount) of gene or protein expression (such as those in any of Table(s) 3, 4, 11 and/or 13) in the sample from the subject on a standard curve. In a particular example, the output (such as a graphical output) shows or provides a cut-off value or level that characterizes the sample tested as nevus or melanoma (e.g., primary melanoma). In other examples, the output is an icon, such as a "N" or "−" if the sample is classified as a nevus, "M" or "+ "if the sample is classified as a melanoma", or "I" or "?" if the sample is classified as a indeterminate (e.g., not consistent with either nevus or melanoma). In some examples, the output is communicated to the user, for example by providing an output via physical, audible, or electronic means (for example by mail, telephone, facsimile transmission, email, or communication to an electronic medical record).

In additional examples, the output can provide qualitative information regarding the relative amount of gene or protein expression (such as those in any of Table(s) 3, 4, 11 and/or 13) in the sample, such as identifying presence of an increase in gene or protein expression (such as those in any of any of Table(s) 4, 11 and/or 13) relative to a control, a decrease in gene or protein expression (such as those in any of Table(s) 4, 11 and/or 13) relative to a control, or no change in gene or protein expression (such as those in any of Table(s) 4, 11 and/or 13) relative to a control.

In some examples, the output is accompanied by guidelines for interpreting the data, for example, numerical or other limits that indicate the presence or absence of primary melanoma. The guidelines need not specify whether a nevus or melanoma (e.g., primary melanoma), is present or absent, although it may include such a diagnosis. The indicia in the output can, for example, include normal or abnormal ranges or a cutoff, which the recipient of the output may then use to interpret the results, for example, to arrive at a diagnosis or treatment plan. In other examples, the output can provide a recommended therapeutic regimen. In some examples, the test may include determination of other clinical information (such as determining the amount of one or more additional melanoma biomarkers in the sample).

Clinical Use Steps

Disclosed methods may result in a melanocyte-containing sample (e.g., skin biopsy) being characterized as benign (e.g., nevus) or malignant (e.g., melanoma, such as primary melanoma) or indeterminate or suspicious (e.g., suggestive of a cancer, disease, or condition), or non-diagnostic (e.g., providing inadequate information concerning the presence or absence of a cancer, disease, or condition). Each of these (and other possible) results is useful to the trained clinical professional. Some method embodiments include clinically relevant steps as described in more detail below.

Diagnosis Indications

A diagnosis informs a subject (e.g., patient) what disease or condition s/he has or may have. As more particularly described throughout this disclosure, any result of any disclosed method that characterizes a melanocyte-containing sample can be provided, e.g., to a subject or health professional, as a diagnosis. Accordingly, some method embodiments contemplated providing a diagnosis (such as, benign (e.g., nevus) or malignant (e.g., melanoma, such as primary melanoma) or indeterminate or suspicious (e.g., suggestive of a cancer, disease, or condition), or non-diagnostic (e.g., providing inadequate information concerning the presence or absence of a cancer, disease, or condition) to a subject or health professional.

Prognostic Indications

Prognosis is the likely health outcome for a subject whose sample received a particular test result (e.g., nevus versus melanoma). A poor prognosis means the long-term outlook for the subject is not good, e.g., the 1-, 2-, 3- or 5-year survival is 50% or less (e.g., 40%, 30%, 25%, 20%, 15%, 10%, 5%, 2% or 1% or less). On the other hand, a good prognosis means the long-term outlook for the subject is fair to good, e.g., the 1-, 2-, 3- or 5-year survival is greater than 30%, 40%, 50%, 60%, 70%, 75%, 80% or 90%.

A subject whose melanocyte-containing sample is characterized as malignant (e.g., melanoma) is likely to have a poorer prognosis (with respect to that disease or condition) than a subject whose melanocyte-containing sample is characterized as benign (e.g., nevus). Accordingly, particular method embodiments include prognosing a comparatively poor outcome (see above) for a subject from whom a test sample characterized as malignant (e.g., melanoma, such as primary melanoma, or the like) is taken. Conversely, other exemplary methods include prognosing a comparatively good outcome (see above) for a subject from whom a test sample characterized as benign (e.g., nevus or the like) is taken.

Therapeutic (Predictive) Indications

The disclosed methods can further include selecting subjects for treatment for melanoma (e.g., primary melanoma), if the sample is diagnosed as a melanoma (e.g., primary melanoma). Alternatively, the disclosed methods can further include selecting subjects for no treatment, if the sample is diagnosed as a benign nevus.

In some embodiments, the disclosed methods of diagnosis include one or more of the following depending on the patient's diagnosis: a) prescribing a treatment regimen for the subject if the subject's determined diagnosis is positive for a primary melanoma (such as treatment with one or more chemotherapeutic agents, additional surgery to remove more tissue, or combinations thereof); b) not prescribing a treatment regimen for the subject if the subject's determined diagnosis is negative for primary melanoma or is positive for a benign nevus; c) administering a treatment (such as treatment with one or more chemotherapeutic agents, additional surgery to remove more tissue, or combinations thereof) to the subject if the subject's determined diagnosis is positive for primary melanoma; and d) not administering a treatment regimen to the subject if the subject's determined diagnosis is primary melanoma or is positive for a benign nevus. In an alternative embodiment, the method can include recommending one or more of (a)-(d). Thus, the disclosed methods can further include treating a subject for primary melanoma, if the sample from the subject is characterized as being a primary melanoma.

In some examples, chemotherapy is used to treat a subject diagnosed with melanoma using a disclosed method. In cancer treatment, chemotherapy refers to the administration of one or more agents (chemotherapeutic agents) to kill or slow the reproduction of rapidly multiplying cells, such as tumor or cancer cells. In a particular example, chemotherapy refers to the administration of one or more agents to significantly reduce the number of tumor cells in the subject, such as by at least about 50%. "Chemotherapeutic agents" include any chemical agent with therapeutic usefulness in the treatment of cancer. Examples of chemotherapeutic agents can be found for example in Fischer et al. (eds), *The Cancer Chemotherapy Handbook,* 6th ed., Philadelphia: Mosby 2003, and/or Skeel and Khleif (eds), *Handbook of Cancer Chemotherapy,* 8th ed., Philadelphia: Lippincott, Williams & Wilkins (2011)).

Chemotherapies, typically used to treat melanoma include interleukin 2 (IL2), dacarbazine, interferon, ipilimumab, carboplatin with taxol, granulocyte macrophage colony stimulating factor (GMCSF), and/or vemurafenib. Use of chemotherapeutic agent in a subject can decrease a sign or a symptom of a cancer, such as melanoma, or can reduce, stop or reverse the progression, metastasis and/or growth of a cancer, such as inhibiting metastasis.

Arrays

Disclosed herein are arrays that can be used to detect expression (such as expression of two or more of the sample-type-specific biomarkers in Table(s) 4, 11 and/or 13), for example, for use in characterizing a melanocyte-containing sample as a benign nevus or a primary melanoma as discussed above. In some embodiments, the disclosed arrays can also be used to detect expression of one or more normalization biomarkers (e.g., those in Table 3). In other embodiments, the disclosed arrays can also be used to detect expression of sets of genes described throughout this disclosure, such as in Table 6, 8 or 14. In particular examples, the array surface comprises a plate, a bead (or plurality of beads), or flow cell (e.g., with multiple channels).

In some embodiments an array can include a solid surface including specifically discrete regions or addressable locations, each region having at least one immobilized oligonucleotide capable of directly hybridizing to biomarkers in Table(s) 4, 11 and/or 13, and in some examples to a normalization gene shown in Table 3. In some examples, the array includes immobilized capture probes capable of directly or indirectly specifically hybridizing with all 32 biomarkers listed in Table 4, and all normalization biomarkers in Table 3, or all of the biomarkers listed in Table 11, and all normalization biomarkers in Table 3. The oligonucleotide probes are identifiable by position on the array. In another example, an array can include specifically discrete regions, each region having at least one or at least two immobilized capture probes. The immobilized capture probes are capable of directly or indirectly specifically hybridizing with at least two different biomarkers in Table(s) 4, 11 and/or 13, and in some examples to a normalization gene shown in Table 3. The capture probes are identifiable by position on the array. The probes on the array can be attached to the surface in an addressable manner. For example, each addressable location can be a separately identifiable bead or a channel in a flow cell.

For example, the array can include at least three addressable locations, each location having immobilized capture probes with the same specificity, and each location having capture probes having a specificity that differs from capture probes at each other location. The capture probes at two of the at least three locations are capable of directly or indirectly specifically hybridizing a biomarker listed in Table(s) 4, 11 and/or 13, and the capture probes at one of the at least three locations is capable of directly or indirectly specifically hybridizing a normalization biomarker listed in Table 3. In addition, the specificity of each capture probe is identifiable by the addressable location the array. In some examples the array further includes at least two discrete regions (such wells on a multi-well surface, or channels in a flow cell), each region having the at least three addressable locations. In some example, such an array includes immobilized capture probes capable of directly or indirectly specifically hybridizing with all biomarkers listed in Table 4, 6, 8, 11, 13, or 14 and at least two normalizers (e.g., RPS6KB2 and SDHA) in Table 3. In some examples, the capture probe(s) indirectly hybridize with the at least two biomarkers listed in Table(s) 4, 11 and/or 13 and the at least one normalization biomarker in Table 3 through a nucleic acid programming linker, wherein the programming linker is a hetero-bifunctional linker which has a first portion complementary to the capture probe(s) and a second portion complementary to a nuclease protection probe (NPP), wherein the NPP is complementary to one of the at least two biomarkers listed in Table(s) 4, 11 and/or 13 or the at least one normalization biomarker in Table 3. Thus, in some examples the array also includes the nucleic acid programming linkers.

In some embodiments the array includes oligonucleotides that include or consist essentially of oligonucleotides that are complementary to at least 2 at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or, as applicable, at least 21, at least 22, at least 23, at least 24, at least 25, at least 26, at least 27, at least 28, at least 29, at least 30, at least 31, or all of the biomarkers in Table(s) 4, 11 and/or 13 (such as 2, 3, 4, 5, 6, 7, 8, 9, 10, 11, 12, 13, 14, 15, 16, 17, 18, 19, or, as applicable, 20, 21, 22, 23, 24, 25, 26, 27, 28, 29, 30, 31, or all of the biomarkers in Table(s) 4, 11 and/or 13). In some examples, the array further includes oligonucleotides that are complementary to normalization biomarkers, such as at least 1, at least 2 at least 3, at least 4, at least 5, at least 6, at least 7, at least 8, or all of the biomarkers in Table 3 (such as 1, 2, 3, 4, 5, 6, 7, 8 or 9 of the normalization biomarkers in Table 3, or RPS6KB2 and SDHA). In some examples, the array further includes one or more control oligonucleotides (such as 1, 2, 3, 4, 5, 6, 7, 8, 9, 10, or more control oligonucleotides), for example, one or more positive and/or negative controls. In some examples, the control oligonucleotides are complementary to one or more of DEAD box polypeptide 5 (DDX5), glyceraldehyde-3-phosphate dehydrogenase (GAPDH), fibrillin 1 (FBN1), or *Arabidopsis thaliana* AP2-like ethylene-responsive transcription factor (ANT).

In some embodiments, the array can include a surface having spatially discrete regions (such as wells on a multi-well surface, or channels in a flow cell), each region including an anchor stably (e.g., covalently) attached to the surface and nucleic acid programming linker, wherein the programming linker is a hetero-bifunctional linker which has a first portion complementary to the capture probe(s) and a second portion complementary to a nuclease protection probe (NPP), wherein the NPP is complementary to a target nucleic acid (such as those in Table(s) 4, 11, and/or 13). In some embodiments the array includes or consists essentially of bifunctional linkers in which the first portion is complementary to an anchor and the second portion is complementary to an NPP, wherein the NPP is complementary to one of the at least 2 at least 3, at least 4, at least 5, at least 6, at least 7, at least 8, at least 9, at least 10, at least 11, at least 12, at least 13, at least 14, at least 15, at least 16, at least 17, at least 18, at least 19, or, as applicable, at least 20, at least 21, at least 22, at least 23, at least 24, at least 25, at least 26, at least 27, at least 28, at least 29, at least 30, at least 31, or all 32 of the biomarkers in Table(s) 4, 11, and/or 13 (such as 2, 3, 4, 5, 6, 7, 8, 9, 10, 11, 12, 13, 14, 15, 16, 17, 18, 19, or, as applicable, 20, 21, 22, 23, 24, 25, 26, 27, 28, 29, 30, 31, or 32 of the biomarkers in Table(s) 4, 11, and/or 13). In some examples, the array further includes bifunctional linkers in which the first portion is complementary to an anchor and the second portion is complementary to an NPP complementary to a normalization biomarker, such as at least 1, at least 2 at least 3, at least 4, at least 5, at least 6, at least 7, at least 8, or all of the biomarkers in Tables 3 (such as 1, 2, 3, 4, 5, 6, 7, 8 or 9 of the biomarkers in Table 3). Such arrays have attached thereto the anchor hybridized to at least a segment of the bifunctional linker that is not complementary to the NPP. In another example, the array further includes bifunctional linkers in which the second portion of the bifunctional linker is complementary to an NPP complementary to a control gene (such as DDX5, GAPDH, FBN1, or ANT). Such arrays can further include (1) the anchor probe hybridized to the first portion of the programming linker, (2) NPPs hybridized to the second portion of the programming linker (which in some examples are biotinylated), (3) bifunctional detection linkers having a first portion hybridized to the NPPs and a second portion hybridized to a detection probe, (4) a detection probe; (5) a label (such as avidin HRP), or combinations thereof.

In some examples, a collection of up to 47 different capture (i.e., anchor) oligonucleotides can be spotted onto the surface at spatially distinct locations and stably associated with (e.g., covalently attached to) the derivatized surface. For any particular assay, a given set of capture probes can be used to program the surface of each well to be specific for as many as 47 different targets or assay types of interest, and different test samples can be applied to each of the 96 wells in each plate. The same set of capture probes can be used multiple times to re-program the surface of the wells for other targets and assays of interest.

Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluoride, polyfluoroethylene-propylene, polyethylenevinyl alcohol, polymethylpentene, polychlorotrifluoroethylene, polysulfones, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567). Other examples of suitable substrates for the arrays disclosed herein include glass (such as functionalized glass), Si, Ge, GaAs, GaP, $SiO_2$, $SiN_4$, modified silicon nitrocellulose, polystyrene, polycarbonate, nylon, fiber, or combinations thereof. Array substrates can be stiff and relatively inflexible (for example glass or a supported membrane) or flexible (such as a polymer membrane).

In general, suitable characteristics of the material that can be used to form the solid support surface include: being amenable to surface activation such that upon activation, the surface of the support is capable of stably (e.g., covalently, electrostatically, reversibly, irreversibly, or permanently) attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In another example, a surface activated organic polymer is used as the solid support surface. One example of a surface activated organic polymer is a polypropylene material aminated via radio frequency plasma discharge. Other reactive groups can also be used, such as carboxylated, hydroxylated, thiolated, or active ester groups.

Array Formats

Within an array, each arrayed sample is addressable, in that its location can be reliably and consistently determined within dimensions (e.g., at least two dimensions) of the array. The feature application location on an array can assume different shapes. For example, the array can be regular (such as arranged in uniform rows and columns, or be set forth in a plurality of individually identifiable beads) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

One example includes a linear array of oligonucleotide bands, generally referred to in the art as a dipstick. Another suitable format includes a two-dimensional pattern of discrete cells (such as 4096 squares in a 64 by 64 array). In one example, the array includes up to 47 (e.g., 5, between 5 and 16, between 5 and 47, 16, between 16 and 47) addressable locations per reaction chamber; thus, in a 96-well array, there may be 96×5, 96×16, 96×47 addressable locations with the addressable locations within each reaction chamber (e.g., well) being the same or different (e.g., using programmable array technologies); provided, however, it is understood in that art that universally programmable arrays may be flexibly programmed to capture any number of analytes up to the number of addressable locations that can physically be printed on the array surface of interest. Other embodiments include arrays comprising physically separate surfaces combined together into a set of surfaces that when combined create an addressable array; for example, a set of individually identifiable (e.g., addressable) beads, each programmed or printed to capture a specific analyte. As is appreciated by those skilled in the art, other array formats including, but not limited to slot (rectangular) and circular arrays are equally suitable for use (see U.S. Pat. No. 5,981,185). In some examples, the array is a multi-well plate (such as a 96-well plate). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, beads, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for coupling oligonucleotides to a solid support and for directly synthesizing the oligonucleotides onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (such as PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second set of rows that are now perpendicular to the first set. This process creates a multiple-channel array whose intersection generates a plurality of discrete cells.

The oligonucleotides can be bound to the support by either the 3'-end of the oligonucleotide or by the 5' end of the oligonucleotide. In one example, the oligonucleotides are bound to the solid support by the 3'-end. However, one of skill in the art can determine whether the use of the 3'-end or the 5'-end of the oligonucleotide is suitable for bonding to the solid support. In general, the internal complementarity of an oligonucleotide probe in the region of the 3'-end and the 5'-end determines binding to the support.

Kits

Also disclosed herein are kits that can be used to detect expression (such as expression of two or more of the biomarkers in Table(s) 4, 11 and/or 13), for example for use in characterizing a sample as a benign nevus or a primary melanoma as discussed above. In some embodiments, the disclosed kits can also be used to detect expression of one or more normalization biomarkers (e.g., those in Table 3). In particular examples, the kit includes one or more of the arrays provided herein.

In some examples the kits include probes and/or primers for the detection of nucleic acid or protein expression, such as two or more of the biomarkers in Table(s) 4, 11 and/or 13, and in some examples, one or more normalization biomarkers in Table 3. In some examples, the kits include antibodies that specifically bind to biomarkers listed in Table(s) 4, 11 and/or 13. For example, the kits can include one or more nucleic acid probes needed to construct an array for detecting the biomarkers disclosed herein.

In some examples, the kit includes nucleic acid programming linkers. The programming linkers are hetero-bifunctional having a first portion complementary to the capture probe(s) on the array and a second portion complementary to a nuclease protection probe (NPP), wherein the NPP is complementary to one of the at least two biomarkers listed in Table(s) 4, 11 and/or 13 or to at least one normalization biomarker in Table 3. In one example, the programming linkers are pre-hybridized to the capture probes, such that they are not covalently attached so that the surface includes the addressable immobilized capture probes and the nucleic acid programming linkers. In such an example, the kit does not have a separate container with programming linkers In some examples, the kit includes NPPs. The NPPs are complementary to the second portion of the programming linker. Exemplary NPPs are shown in SEQ ID NOS: 1-36, and 123-164.

In some examples, the kit includes bifunctional detection linkers. Such linkers can be labeled with a detection probe and are capable of specifically hybridizing to the NPPs or to the target (such as those in Table(s) 4, 11 and/or 13).

In some examples, the kit includes an array disclosed herein, and one or more of a container containing a buffer (such as a lysis buffer); a container containing a nuclease specific for single-stranded nucleic acids; a container containing nucleic acid programming linkers; a container containing NPPs; a container containing a plurality of bifunctional detection linkers; a container containing a detection probe (such as one that is triple biotinylated); and a container containing a detection reagent (such as avidin HRP).

In one example, the kit includes a graph or table showing expected values or ranges of values of the biomarkers in Table(s) 4, 11 and/or 13 expected in a normal skin cell (e.g., benign nevus) or a primary melanoma, or clinically useful cutoffs. In some examples, kits further include control samples, such as particular quantities of nucleic acids or proteins for those biomarkers in Table(s) 4, 11 and/or 13.

The kits may further include additional components such as instructional materials and additional reagents, for example detection reagents, such as an enzyme-based detection system (for example, detection reagents including horseradish peroxidase or alkaline phosphatase and appropriate substrate), secondary antibodies (for example antibodies that specifically bind the primary antibodies that specifically bind the targets (e.g., proteins) in Table(s) 3, 4, 11, and/or 13), or a means for labeling antibodies. The kits may also include additional components to facilitate the particular application for which the kit is designed (for example microtiter plates). In one example, the kit of further includes control nucleic acids. Such kits and appropriate contents are well known to those of ordinary skill in the art. The instructional materials may be written, in an electronic form (such as a computer diskette or compact disk) or may be visual (such as video files).

The following examples are provided to illustrate certain particular features and/or embodiments. These examples should not be construed to limit the invention to the particular features or embodiments described.

EXAMPLES

Example 1

Gene Selection Using a Discovery Set of Clinically Characterized Skin Samples Nevi and melanoma cells, like all cells, express a vast number of genes, most of which are not relevant to distinguishing between such groups. Thus, in order to extract useful gene information and reduce dimensionality, this Example describes the initial screening of the expression of greater than 2600 mRNA targets to identify significantly differentially expressed mRNAs in formalin-fixed, paraffin-embedded ("FFPE") skin samples biopsied from human subjects. Further described are methodological details used throughout the Examples.

A discovery set of 39 FFPE tissue sections, each approximately 5 um thick and mounted on a microscope slide, was provided by the John Wayne Cancer Institute (JWCI) tissue bank. The set included 14 normal skin samples, 10 nevi samples, 5 primary melanoma samples, and 10 samples of melanoma metastases.

Sample Preparation and Lysis

Briefly, each FFPE tissue section was measured to determine its approximate area (in $cm^2$). The tissue section then was scraped into a labeled eppendorf tube using a razor blade and avoiding any excess paraffin on the slide. The sample was suspended in 25 ul pre-warmed (50° C.) SSC buffer including formamide and SDS per each 0.3 $cm^2$ of the applicable tissue section. Five-hundred (500) ul of mineral oil containing a surfactant (e.g., Brij-97) ("Non-aqueous Layer") then was overlaid on the tissue suspension, and this lysis reaction was incubated at 95° C. for 10-15 minutes.

After briefly cooling the reaction mixture, proteinase K was added to a final concentration of 1 mg/ml and the incubation continued at 50 C for 30-60 minutes. A portion of the lysis reaction was used immediately in a nuclease protection assay (see below), or the lysis reaction (or remaining portion thereof) was frozen and stored at −80° C. Frozen lysis reactions were thawed at 50° C. for 10-15 minutes before a subsequent use.

Nuclease Protection Assay ("NPA")

Twenty-five (25) ul of each lysed reaction mixture was placed in a well of a 96-well plate and overlaid with 70 ul Non-aqueous Layer. To each well was added 5 ul of nuclease protection probe (NPP) mix. One (1) nM (an excess of) NPP complementary to each of the plurality of mRNA targets to be detected was present in the NPP mix. NPPs for ArrayPlate detection were (i) 50-base pairs in length with each half of the NPP having a Tm in the range of 40° C.-75° C. (and full length Tms in the range of 60° C.-85° C.) and (ii) tested in silico (using NCBI BLAST) and with in vitro transcripts for specificity to the respective mRNA target (and substantially no cross-reactivity with other NPPs, other targets, or other analytes in the NPA reaction). NPPs for ArraySlide detection differ only in that they contain an internal biotinylated base (T) biased toward the 3' end of the NPP. NPPs are further described in connection with genes specifically identified in other Examples.

The 96-well NPA plate was heated at 95° C. for 10-15 minutes to denature nucleic acids and, then, allowed to incubate at 60° C. for 6-16 hours to permit hybridization of the NPPs to their respective mRNA targets.

Following the hybridization step, 20 ul of excess S1 nuclease (2.5 U/ul) in sodium acetate buffer was added to the aqueous phase of each well. The S1 reaction proceeded at 50° C. for 90-120 minutes to digest unbound mRNA and unbound NPPs. In some sets of reactions, BSA in molecular-biology-grade water was added to a final concentration of 40 mg/ml.

During the S1 digestion step, a 96-well "Stop" plate was prepared by adding 10 ul of solution contain 0.1 M EDTA and 1.6 N NaOH to each well corresponding to the reactions in the 96-well NPA plate. The entire volume (approx. 120 ul) of each reaction in the 96-well NPA plate was transferred to a corresponding well in the second 96-well Stop plate. The Stop plate was incubated at 95° C. for 15-20 minutes and, then, cooled for 5-10 minutes at room temperature prior to the addition of 10 ul 1.6 N HCl to neutralize the NaOH previously added to each reaction.

The nuclease protection assay reactions in this Example were interrogated directly (e.g., without purification or reverse transcription of target mRNA analytes) using (i) a first, 96-well-plate-based array (ArrayPlate No. 1) custom designed to detect in each well the expression of 34 human putative melanoma-related mRNAs (or controls), (ii) a second ArrayPlate (i.e., No. 2) custom designed to detect 33 human putative melanoma-related mRNAs (or controls), (iii) a first, glass-slide-based, 21-well (ArraySlide No. 1) custom "cancer transcriptome" array capable of detecting 1829 human putative cancer-related mRNAs (or controls) in each well, and (iv) a second ArraySlide (i.e., No. 2) "whole transcriptome" custom array capable of detecting in each 2600 mRNAs putatively representative of the human transcriptome. The targets to be interrogated by each of the foregoing arrays was determined, e.g., on the basis of literature searches and public knowledge.

ArrayPlate Capture and Detection

ArrayPlate Nos. 1 and 2 were programmed with 40 ul 50-base pair programming linkers ("PL") at 5 nM in SSC buffer containing SDS ("SSC-S"). The PLs were artificial, 25-base pair, bi-functional synthetic oligonucleotide constructs (adaptors) complementary in part to a universal anchor sequence affixed to the array surface and complementary in the other part to the particular NPP addressed to the particular array location. Following the programming step, the entire aqueous phase (60-65 ul) of each reaction from the Stop plate was added to a corresponding well of the programmed ArrayPlate and incubated at 50° C. for 16-24 hour to capture undigested NPPs (which were bound to target during the nuclease step and, therefore, are quantifiable surrogates for targets present in the sample). Thereafter, 5 nM bi-functional detection linker ("DL") in SSC-S including 1% nonfat dry milk was added to each reaction followed by 1 hour incubation at 60° C. The DLs were artificial 25-base pair, bi-functional synthetic oligonucleotide constructs complementary in part to its respective NPP and complementary in the other part to one or more (e.g., two or three) copies of a biotin-labeled detection probe ("DP"), which DP was capable of specifically binding the detection-region designed into all DLs. To complete the detection "sandwich," 40 ul of 3 nM DP was added to the reactions followed by 50° C. incubation for 45-60 min. Next, 40 ul avidin peroxidase (1:600) in SSC-S including 1% nonfat dry milk was added followed by incubation at 37° C. for 30-45 minute. Finally, a chemiluminescent substrate mix was added that, in the presence of peroxidase enzyme, generated light that was captured using a HTG OMIX™ imager. Gene expression is directly related to the intensity of light emitted at each addressable position of the ArrayPlate.

ArraySlide Capture and Detection

The entire aqueous phase of each nuclease protection assay reaction (60-65 ul) was then hybridized to ArraySlide No. 1 or No. 2 for 16-24 hour at 50° C. for capture of the NPPs. After capture of the biotinylated NPPs, the respective ArraySlide was washed rigorously with 1×SSC containing 1% Tween ("Wash Buffer"). Fifty (50) ul of avidin-peroxidase (1:600) in detection enzyme buffer (1×SSC-S, 0.05% Tween and non-fat, dry milk) was added for 45 minutes at 37° C. ArraySlides were washed followed by addition of TSA-Plus Cy3 reagent in amplification diluent (Perkin Elmer) for detection. After a 3-minute room temperature incubation, TSA-Plus Cy3 reactions were stopped by washing the ArraySlides in Wash Buffer. Finally, the ArraySlides were spun dry and scanned at 5 um resolution using a GenePix 4200AL microarray slide scanner (Molecular Devices, Sunnyvale, Calif.). Probe intensities were extracted from TIFF images using NimbleScan 2.5 software (Roche NimbleGen, Madison, Wis.) for analysis as described below.

Data Analysis

Raw data from each of the arrays in this Example were processed using BRB array tools (freely available for research use, as of Jun. 4, 2012, on the internet at linus.nci.nih.gov/~brb/download_full_v4_2_1_stable.html). Briefly, data was subjected to minimum intensity thresholding, quantile normalization and certain data filters were applied to remove non-differential data points from further analysis. Data was log 2 transformed and analyzed to find statistically significant differential genes among the group arrays based on p-values and log fold change values.

Seventy-eight (78) genes were selected for further study based on (a) significant ($p \leq 0.05$) differential expression in nevi versus primary melanoma samples and, in some cases, (b) mRNA expression that exceeded 3000 raw signal intensity in each sample population in which such expression was measured. An additional four (4) genes (SDHA, RPS6KB2, RPL37A, and TFRC) originally included as putative controls also were carried forward for further study.

Example 2

Genes Significantly Differentially Expressed in a Second Set of Clinically Characterized Skin Samples—Normalization to Four This Example describes the identification of a set of 32 genes, the mRNA expression of which is significantly different between human skin biopsies characterized by the JWCI tissue bank as either nevi or primary melanomas.

Two custom ArrayPlates (referred to as ArrayPlates No. 3 and 4) were constructed to measure the expression of the 82 mRNA targets identified in or carried forward from Example 1 plus 6 additional targets identified by pathway analysis or used as negative controls. The gene lists for ArrayPlates No. 3 and 4 are shown in Table 1 below:

TABLE 1

| ArrayPlate Gene Lists | | | |
|---|---|---|---|
| ArrayPlate No. 3 | | ArrayPlate No. 4 | |
| Symbol | GenBank Accession No. | Symbol | GenBank Accession No. |
| SDHA | NM_004168 | SDHA | NM_004168 |
| RPS6KB2 | NM_003952 | RPS6KB2 | NM_003952 |
| RPL37A | NM_000998 | RPL37A | NM_000998 |
| TFRC | NM_003234 | TFRC | NM_003234 |
| ANT | NM_119937 | ANT | NM_119937 |
| MAGEA2 | NM_005361 | BIRC7 | NM_139317 |
| PAX3 | NM_181457 | BIRC5 | NM_001168 |
| CDK2 | NM_001798 | MET | NM_001127500 |
| PRAME | NM_206953 | HIF1A | NM_001530 |
| MFI2 | NM_005929 | ALK | NM_004304 |
| MCM6 | NM_005915 | DAZAP2 | NM_014764 |
| S100B | NM_006272 | EVI2B | NM_006495 |
| PDIA4 | NM_004911 | LDHA | NM_005566 |
| SOX4 | NM_003107 | ERCC1 | NM_001983 |
| BRAF | NM_004333 | ESR1 | NM_000125 |
| PPIA | NM_021130 | ALDOA | NM_000034 |
| MAGED2 | NM_014599 | CTNNB1 | NM_001904 |
| GALNTL1 | NM_001168368 | ARID1A | NM_139135 |
| PTEN | NM_000314 | NPHP1 | NM_001128179 |
| HRAS | NM_005343 | AF090940 | AF090940 |
| TP53 | NM_000546 | DUX4 | NM_033178 |

TABLE 1-continued

| ArrayPlate Gene Lists | | | |
|---|---|---|---|
| ArrayPlate No. 3 | | ArrayPlate No. 4 | |
| Symbol | GenBank Accession No. | Symbol | GenBank Accession No. |
| CTNNB1 | NM_001904 | POLR2J3 | NM_001097615 |
| TYR | NM_000372 | HADHA | NM_000182 |
| TEX13A | NM_031274 | AK027225 | AK027225 |
| BMP1 | NM_001199 | IGFBP5 | NM_000599 |
| TGFB1 | NM_000660 | BC017937 | BC017937 |
| NR4A1 | NM_002135 | OAZ1 | NM_004152 |
| PIP4K2A | NM_005028 | TACSTD2 | NM_002353 |
| PDLIM7 | NM_213636 | ATXN2L | NM_148416 |
| TADA3L | NM_006354 | PLIN2 | NM_001122 |
| B4GALT1 | NM_001497 | PFDN6 | NM_014260 |
| RAP2B | NM_002886 | HMGA1 | NM_002131 |
| B2M | NM_004048 | ZFYVE16 | NM_014733 |
| NCOR2 | NM_001077261 | AF168811 | AF168811 |
| SP100 | NM_003113 | BAX | NM_004324 |
| SAT1 | NM_002970 | AU159040 | AU159040 |
| STAT2 | NM_005419 | BRD7P3 | NR_002730 |
| RUNX1 | NM_001001890 | RNF126 | NM_194460 |
| GNAS | NM_016592 | ETV2 | NM_014209 |
| SOCS3 | NM_003955 | TPSAB1 | NM_003294 |
| BAX | NM_004324 | ZFPL1 | NM_006782 |
| CREBBP | NM_001079846 | COX16 | NM_016468 |
| HIST1H2BN | NM_003520 | AK023563 | AK023563 |
| HP1BP3 | NM_016287 | BEST1 | NM_004183 |
| LZTS1 | NM_021020 | PICALM | NM_001008660 |
| SQSTM1 | NM_003900 | NOP56 | NM_006392 |
| TPSAB1 | NM_003294 | PTMS | NM_002824 |

mRNA expression was measured in 100 FFPE tissue sections, consisting of 39 nevus samples (from melanoma-naive patients) and 61 primary melanoma samples.

Sample preparation and lysis, nuclease protection assay, and array capture and detection were performed substantially as described for ArrayPlates Nos. 1 and 2 in Example 1.

Table 2 shows NPP sequences for (i) targets found in this Example to be significantly differentially expressed between nevi and melanoma samples and (ii) targets whose expression was used for normalization. Other NPP sequences useful in a disclosed invention are describe elsewhere or can be determined by one of ordinary skill in the art using guidance provided in this disclosure and publicly available sequences of the disclosed targets (e.g., SEQ ID NOs. shown in Tables 11 and 13).

TABLE 2

| Exemplary Nuclease Protection Probe Sequences | | | |
|---|---|---|---|
| Gene Name | Accession No. | NPP Sequence (5'-3'; wrapped at line break) | SEQ ID NO. |
| B2M | NM_004048 | CTGCTGGATGACGTGAGTAAACCTGAA TCTTTGGAGTACGCTGGATAGCC | 1 |
| B4GALT1 | NM_001497 | GTCTTGGAACCTGAGCCCAGGCTGGAC CTGGCAAAGGCGCTCAGTGGTAG | 2 |
| BMP1 | NM_001199 | CCGCAAGGTCGATAGGTGAACACAATA TAGCTGTCCTCGTCAGTGCGCTC | 3 |
| BRAF | NM_004333 | GTAAGTGGAACATTCTCCAACACTTCC ACATGCAATTCTTCTCCAGTAAG | 4 |
| CDK2 | NM_001798 | CAAGTTCAGAGGGCCCACCTGAGTCCA AATAGCCCAAGGCCAAGCCTGGT | 5 |
| CREBBP | NM_001079846 | CCTGGGTTGATACTAGAGCCGCTGCCT CCTCGTAGAAGCTCCGACAGTTG | 6 |

TABLE 2-continued

Exemplary Nuclease Protection Probe Sequences

| Gene Name | Accession No. | NPP Sequence (5'-3'; wrapped at line break) | SEQ ID NO. |
|---|---|---|---|
| CTNNB1 | NM_001904 | CAGCATCTGTGATGGTTCAGCCAAACG CTGGACATTAGTGGGATGAGCAG | 7 |
| GALNTL1 | NM_001168368 | GGGCTCAGCTTGTCACTCTCCAGCTGGT TGAAGGCGTGCTGTCTGTAGGG | 8 |
| GNAS | NM_016592 | CTCGCTGAGTCTTAGATTCCGCAGCCTA AGACTCGAGAGAGGTGCCTCCG | 9 |
| MAGEA2 | NM_005361 | CTCAGGCTCTCCACCTGGATGCTTGGCA GATCCTAGAACCACTGCATCTG | 10 |
| MAGED2 | NM_014599 | CTTCACCTTTCGGGCTTTCTTGGCTTTG ACCTTGGGCCGAGTATCCTGAT | 11 |
| MCM6 | NM_005915 | TCCTGGTGTGCTAAGCTTGGAGACGTC AGGCACAACAATCAGTGTCCCTG | 12 |
| MFI2 | NM_005929 | GCTGGCATTGAAGAACTCGCTCACTGC TGTGAGGACGTCACAGTCCTTGG | 13 |
| NCOR2 | NM_001077261 | CCCGGTACAGCAGCGGGTACACAGCAC TCCGGGAGTGCCCTGGCTCCGTC | 14 |
| NR4A1 | NM_002135 | CGCCACAGCTGCCACGTGCTCCTTCAG GCAGCTGGCGATGCGGTTCTGCA | 15 |
| PDIA4 | NM_004911 | CACATCAAACCTGCTGGCCAGCACAGA CGCTGAGGTTGCATCGATCTTGG | 16 |
| PDLIM7 | NM_213636 | CTTCGATGTGTGTGAGGCTACCCGCATT CTCGCCATCGATGCTCAGCACC | 17 |
| PIP4K2A | NM_005028 | ATTCACTCACTCACTCACTCACTCATTC ATTCGGCCATAGCTGGAATCAA | 18 |
| PPIA | NM_021130 | TGGTATCACCCAGGGAATACGTAACCA GACAACACACAAGACTGAGATGC | 19 |
| PRAME | NM_206953 | GTCTGGCTGTGTCTCCCGTCAAAGGCTG CCATGAAGAGTGGCGGGAAGAG | 20 |
| PTEN | NM_000314 | CTTCACCTTTAGCTGGCAGACCACAAA CTGAGGATTGCAAGTTCCGCCAC | 21 |
| RAP2B | NM_002886 | CCTCTCCTCCTGCTCCTTCATATGGTTC TCCCGGACTTCCTTCCATGTAT | 22 |
| RPL37A | NM_000998 | CTGATGGCGGACTTTACCGTGACAGCG GAAGTGGTATTGTACGTCCAGGC | 23 |
| RPS6KB2 | NM_003952 | GCTTCACATACGTGGCGCCGTCTGTCCT GGACAGCATCAAGGAGGGCTTC | 124 |
| RUNX1 | NM_001001890 | GCAGAGTCACACACATGCAAACACGCA CTCTTCGGAAGGCAGCCACTGTC | 24 |
| SAT1 | NM_002970 | ATTTCAAACATGCAACAACGCCACTGG TAATAAAGCTTTGGAATGGGTGC | 25 |
| SDHA | NM_004168 | GAAGAAGCCCTTTGAGGAGCACTGGAG GAAGCACACCCTGTCCTATGTGG | 123 |
| SOCS3 | NM_003955 | GTCTTCTCTACCAGGAGCCTGAGGTGA AAGATGTCCCGTCTCCTCCATCC | 26 |
| SOX4 | NM_003107 | CTCCGCCTCTCGAATGAAAGGGATCTT GTCGCTGTCTTTGAGCAGCTTCC | 27 |
| SP100 | NM_003113 | CCATGGTTGTGTAGCTCTGCCTCTGGGC TTTCTTCATCACAGGGCAACGG | 28 |
| SQSTM1 | NM_003900 | CCCAGGAAACATCAGCACACACACACA CAGGGACCCTCCCTTCATGTCAC | 29 |

TABLE 2-continued

| Exemplary Nuclease Protection Probe Sequences | | | |
|---|---|---|---|
| Gene Name | Accession No. | NPP Sequence (5'-3'; wrapped at line break) | SEQ ID NO. |
| STAT2 | NM_005419 | CGGGATTCAATCTCATGTTGCTGGCTCT CCACAGGTGTTTCGAGAACTGG | 30 |
| TADA3 | NM_006354 | CTACCCATCCAGCAGCTTCAGGATGCT CTCACGCTCCTTCAGAGTCTTCC | 31 |
| TEX13A | NM_031274 | AGTATGAGTATGAGGCAGGGAGCTGGA CAGGAAGAGGTTCTGATGAGGCT | 32 |
| TFRC | NM_003234 | GACGTGCTGCAGGGAAGTCCTCTCCTG GCTCCTCCCTCACTGGAGACTCG | 33 |
| TGFB1 | NM_000660 | GGTAGTGAACCCGTTGATGTCCACTTG CAGTGTGTTATCCCTGCTGTCAC | 34 |
| TP53 | NM_000546 | CCCGGGACAAAGCAAATGGAAGTCCTG GGTGCTTCTGACGCACACCTATT | 35 |
| TPSAB1 | NM_003294 | CGCCAGCAGCAGCAGATTCAGCATCCT GGCCGCTCCCTGTTCCTTCTACC | 36 |

Data Analysis

All analysis in Examples 2 and 3 was performed in SAS version 9.3 unless otherwise specified.

A. Transformation and Quality Control

The data was processed using a HTG OMIX™ imaging device and a 16 bit image was extracted. As is standard practice in genomic research, the raw intensity values were log base 2 transformed in order to make the scale of the data more linear. Each gene had three independent observations and all three observations were averaged with a geometric mean (although an arithmetic mean would serve equally well) to create a composite average log base 2 expression value for each gene. The plant gene ANT (AP2-like ethylene-responsive transcription factor; GenBank mRNA RefSeq No. NM_119937; SEQ ID NO. 122) was used as a negative control on each array. Samples for which ANT was detectable above background was used to screen and remove assay failures. Descriptive statistical analyses were also conducted to screen for errors in the data file.

B. Selection of Genes for Normalization

The scientific dogma that any gene remains constant in its expression across all sample types or subjects (i.e., universal "housekeeper" gene) is losing favor (e.g., Avison, Measuring Gene Expression, Psychology Press, 2007, p. 128). Thus, other alternatives for selecting genes suitable for normalization, especially, of microarray data have been developed. Some suitable methods are described herein and others are known to those of ordinary skill in the art.

Expression of "normalization" genes were used to normalize the data to uncontrollable process variables such as cellular content in sample loads. The first step in screening candidate normalization genes for this Example was to run a Satterthwaite T-Test to determine that there was no statistically significant difference in expression of such candidate normalization genes between the samples in the populations of interest, i.e., nevi and primary melanoma samples. Initially, this analysis was performed using an average of triplicate raw expression values and later confirmed with normalized expression values. A p-value exceeding 0.05 was set as a lower bound for determining a lack of significance.

Expression levels for candidate normalization genes were then inspected to ensure adequate and non-saturated intensity values. Adequate and non-saturated intensity values were defined as 1.5 expression units above background and below saturation.

Candidate normalization genes were also selected on the basis of minimal standard deviations. An upper bound of 2.0 expression units was set as a cutoff. Candidate normalization genes with standard deviations larger than this cutoff were removed from consideration. The goal was to select among remaining candidate normalization genes those which had the lowest standard errors between the sample populations of interest (i.e., nevi and primary melanoma samples).

It is noted that a coefficient of variation (CV) can also be used in place of a standard deviation in this and other applicable analyses. A CV is a statistical method for describing the dispersion of data or a variable irrespective of the unit of measurement. Since a CV is calculated by dividing the standard deviation (or in some SAS procedures the root mean square error) by the mean and the unit of expression measurement for genes across an array is very similar, using a CV or a standard deviation rarely, if ever, results in qualitatively different patterns of results in which one would be led to draw different conclusions as to the validity of a housekeeper.

Figure 2B:
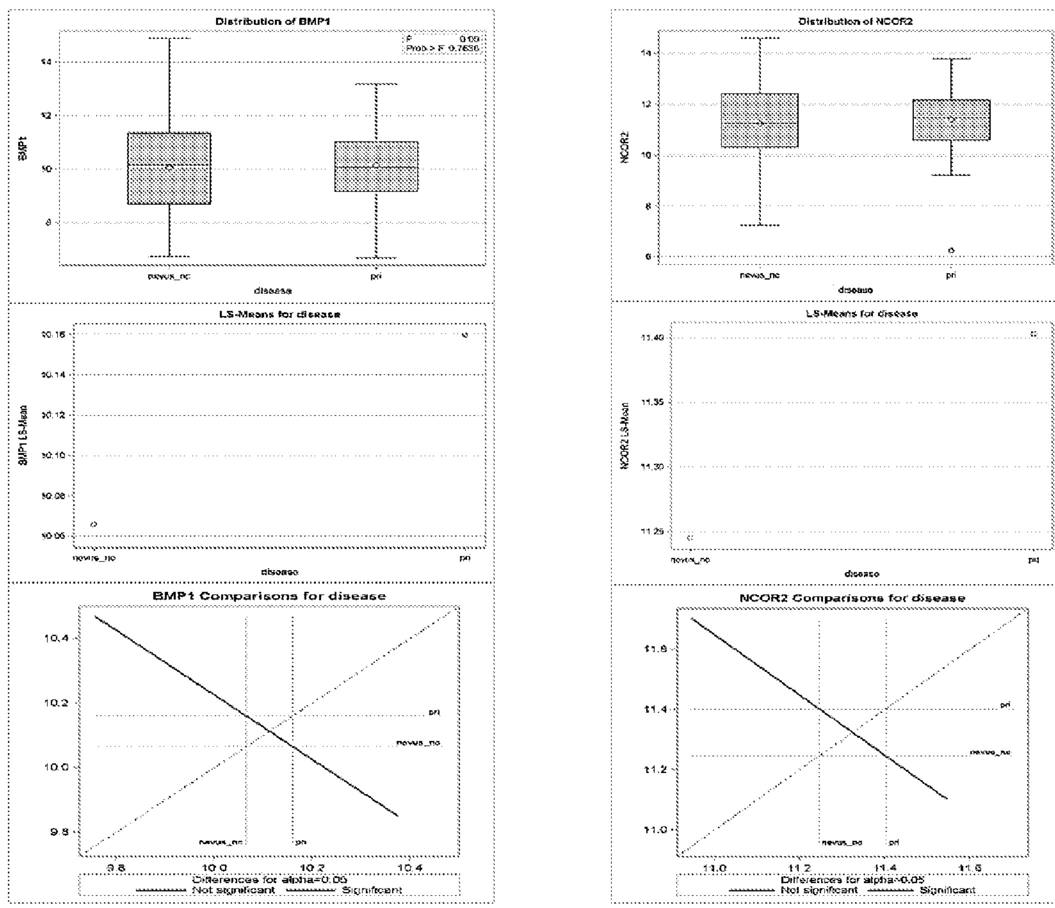
Figure 4:
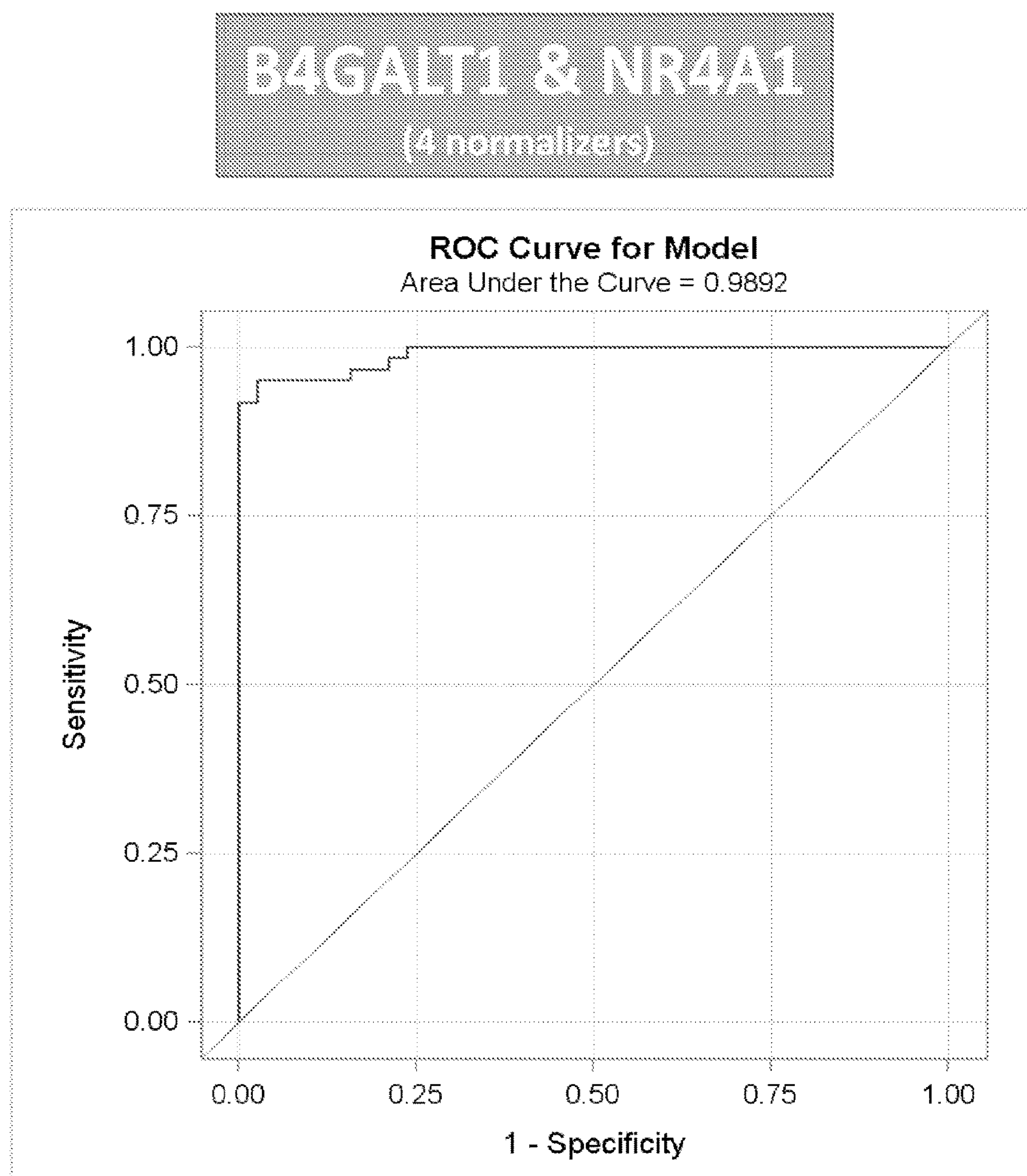
FIG. 4 shows the ROC curve for the representative B4GALT1 and NR4A1 (4-normalizer) model. The ROC curve illustrates the very high sensitivity and specificity for the model. Sensitivity represents the true positive rate (i.e., if a person has a disease, how often will the test be positive; or, sensitivity=(true positives/(true positive+false negative)). Specificity represents the true negative rate (i.e., if a person does not have the disease how often will the test be negative; or, specificity=(true negatives/(true negative+false positives). The area under the curve (AUC=0.9892) illustrates the ability of the model to differentiate between the two populations, i.e., nevi and primary melanoma, with very high accuracy.

An exemplary normalization genes (also referred to as "normalizers") selected throughout these Examples as representative for human nevi and primary melanoma skin biopsies are shown in Table 3. The box plots, means plots and SAS diffograms for the representative normalizers BMP-1, MF12, NCOR2 and RAP2b are shown in FIGS. 2A and 2B. In the SAS diffograms, for example, the dashed diagonal line (from bottom left to top right; colored blue) represents p=0.5; the x and y axes plot the normalized average log 2 intensity value; and lines on each axis denote the mean normalized average log 2 intensity value for each group as indicated. The solid diagonal line (from top left to bottom right; colored red), crosses the dashed p=0.5 reference line, which illustrates no statistically significant difference between nevi and primary samples with p>0.05.

TABLE 3

| Representative Normalization Genes Identified for Nevi and Primary Melanoma Samples | | | |
|---|---|---|---|
| Symbol | Name | GenBank Ref. No. | SEQ ID NO(s). |
| BMP-1 | *Homo sapiens* bone morphogenetic protein 1, variant 1 | NM_001199 (var 1) NR_033404 (var 5/nc); NR_033403 (var 4/nc); NM_006129 (var 3) | 40-43 |
| MFI2 | *Homo sapiens* antigen p97 (melanoma associated) identified by monoclonal antibodies 133.2 and 96.5 (MFI2) | NM_005929 (var 1) NM_033316 (var 2) | 37, 38 |
| NCOR2 | *Homo sapiens* nuclear receptor corepressor 2 | NM_001077261 (var 2) NM_001206654 (var 3); NM_006312 (var 1) | 44-46 |
| RAP2b | *Homo sapiens* RAP2B, member of RAS oncogene family | NM_002886 | 39 |
| RPS6KB2 | *Homo sapiens* ribosomal protein S6 kinase, 70 kDa, polypeptide 2 | NM_003952 | 120 |
| SDHA | *Homo sapiens* succinate dehydrogenase complex, subunit A, flavoprotein (Fp) (SDHA), nuclear gene encoding mitochondrial protein | NM_004168 | 121 |
| RPL19 | Ribosomal Protein L19 | NM_000981 | |
| RPLP0 | Large Ribosomal Phosphoprotein P0 | NM_001002 (var 1); NM_053275 (var 2) | |
| ALDOA | Fructose-bisphosphate Aldolase A (aka, Fructose-1,6-Bisphosphate Aldolase A; ALDA; Aldolase 1; Fructoaldolase A | NM_000034 (var 1); NM_184041 (var 2); NM_184043 (var 3); NM_001127617 (var 4) NM_001243177 (var 6) | |

C. Univariate Screening of Genes

To normalize the data with the foregoing normalizers, the average log 2 expression value for all replicates for each gene was divided by the geometric mean of the BMP-1, MF12, NCOR2 and RAP2b normalizers (this is also known to some in the art as "normalization to some" and may be referred to as "normalization to four" herein). As previously mentioned, an arithmetic mean also would suffice for the foregoing purposes. The resulting value was multiplied by a constant of 10.

Following normalization, each other (non-normalizer) gene was screened to determine if there was a statistically significant difference in expression of that gene between nevi and primary melanoma samples. A statistically significant difference indicates that the gene has some ability to differentiate between the two groups. A Bonferroni correction was used to select a nominal level of alpha (p-value cutoff for significance) in order to protect against alpha inflation and multiple testing. A Satterthwaite T-Test was used to screen each gene in a univariate fashion. A Satterthwaite corrected T-Test was used to ensure accurate estimates in the case of unequal variances between groups.

Table 4 shows the list of genes that were found to have statistically significant differences in mRNA expression between nevi and primary melanoma samples.

TABLE 4

| Genes Differentiating Between Nevi and Primary Melanoma Samples | | | | |
|---|---|---|---|---|
| Symbol | Name | GenBank Ref. No(s). | P-value | SEQ ID NO(s). |
| B2M | *Homo sapiens* beta-2-microglobulin | NM_004048 | <0.01 | 119 |
| B4GALT1 | *Homo sapiens* UDP-Gal: betaGlcNAc beta 1,4-galactosyltransferase, polypeptide 1 | NM_001497 | <0.01 | 50 |
| BRAF | *Homo sapiens* v-raf murine sarcoma viral oncogene homolog B1 | NM_004333 | <0.01 | 63 |
| CDK2 | *Homo sapiens* cyclin-dependent kinase 2 | NM_001798 (var 1); NM_052827 (var 2) | <0.01 | 112, 113 |
| CREBBP | *Homo sapiens* CREB binding protein | NM_004380 (var 1); NM_001079846 (var 2) | <0.01 | 109, 110 |
| CTNNB1 | *Homo sapiens* catenin (cadherin-associated protein), beta 1 | NM_001904 | <0.01 | 83 |
| GALNTL1 | *Homo sapiens* UDP-N-acetyl-alpha-D- | NM_001168368 (var 1); NM_020692 (var 2) | <0.01 | 103, 104 |

TABLE 4-continued

Genes Differentiating Between Nevi and Primary Melanoma Samples

| Symbol | Name | GenBank Ref. No(s). | P-value | SEQ ID NO(s). |
|---|---|---|---|---|
| | galactosamine: polypeptide N-acetyl-galactosaminyltransferase-like 1 | | | |
| GNAS | *Homo sapiens* GNAS complex locus | NM_000516 (var 1); NM_080425 (var 2); NM_080426 (var 3); NM_016592 (var 4); NM_001077488 (var 6) NM_001077489 (var 7); NR_003259 (var 8/nc) | <0.01 | 85-91 |
| MAGEA2 | *Homo sapiens* melanoma antigen family A, 2 | NM_005361 (var 1); NM_175742 (var 2); NM_175743 (var 3) | <0.01 | 105-107 |
| MAGED2 | *Homo sapiens* melanoma antigen family D, 2 | NM_014599 (var 1); NM_177433 (var 2); NM_201222 (var 3) | <0.01 | 95-97 |
| MCM6 | *Homo sapiens* minichromosome maintenance complex component 6 | NM_005915 | <0.01 | 82 |
| NR4A1 | *Homo sapiens* nuclear receptor subfamily 4, group A, member 1 | NM_002135 (var 1); NM_173157 (var 2); NM_001202233 (var 3) | <0.01 | 47-49 |
| PDIA4 | *Homo sapiens* protein disulfide isomerase family A, member 4 | NM_004911 | <0.01 | 81 |
| PDLIM7 | *Homo sapiens* PDZ and LIM domain 7 (enigma) | NM_005451 (var 1); NM_203352 (var 2); NM_213636 (var 4) | <0.01 | 70-72 |
| PIP4K2A | *Homo sapiens* phosphatidylinositol-5-phosphate 4-kinase, type II, alpha | NM_005028 | <0.01 | 79 |
| PPIA | *Homo sapiens* peptidylprolyl isomerase A (cyclophilin A) | NM_021130 | <0.01 | 93 |
| PRAME | *Homo sapiens* preferentially expressed antigen in melanoma | NM_006115 (var 1); NM_206953 (var 2); NM_206954 (var 3); NM_206955 (var 4); NM_206956 (var 5) | <0.01 | 98-102 |
| PTEN | *Homo sapiens* phosphatase and tensin homolog | NM_000314 | <0.01 | 94 |
| RPL37A | *Homo sapiens* ribosomal protein L37a (RPL37A) | NM_000998 | <0.01 | 84 |
| RUNX1 | *Homo sapiens* runt-related transcription factor 1 | NM_001754 (var 1); NM_001001890 (var 2); NM_001122607 (var 3) | <0.01 | 66-68 |
| SAT1 | *Homo sapiens* spermidine/spermine N1-acetyltransferase 1 | NM_002970 (var 1) NR_027783 (var 2/nc) | <0.01 | 51, 52 |
| SOCS3 | *Homo sapiens* suppressor of cytokine signaling 3 | NM_003955 | <0.01 | 69 |
| SOX4 | *Homo sapiens* SRY (sex determining region Y)-box 4 | NM_003107 | <0.01 | 80 |
| SP100 | *Homo sapiens* SP100 nuclear antigen | NM_001080391 (var 1); NM_003113 (var 2); NM_001206701 (var 3); NM_001206702 (var 4); NM_001206703 (var 5); NM_001206704 (var 6) | <0.01 | 73-78 |
| SQSTM1 | *Homo sapiens* sequestosome 1 | NM_003900 (var 1); NM_001142298 (var 2); NM_001142299 (var 3) | <0.01 | 116-118 |
| STAT2 | *Homo sapiens* signal transducer and activator of transcription 2 | NM_005419 (var 1); NM_198332 (var 2) | <0.01 | 114, 115 |
| TADA3 | *Homo sapiens* transcriptional adaptor 3 | NM_006354 (var 1); NM_133480 (var 2) | <0.01 | 61, 62 |
| TEX13A | *Homo sapiens* testis expressed 13A | NM_031274 | <0.01 | 108 |
| TFRC | *Homo sapiens* transferrin receptor (p90, CD71) | NM_003234 (var 1); NM_001128148 (var 2) | <0.01 | 64, 65 |

TABLE 4-continued

| Genes Differentiating Between Nevi and Primary Melanoma Samples | | | | |
|---|---|---|---|---|
| Symbol | Name | GenBank Ref. No(s). | P-value | SEQ ID NO(s). |
| TGFB1 | *Homo sapiens* transforming growth factor, beta 1 | NM_000660 | <0.01 | 92 |
| TP53 | *Homo sapiens* tumor protein p53 | NM_000546 (var 1); NM_001126112 (var 2); NM_001126114 (var 3); NM_001126113 (var 4); NM_001126115 (var 5); NM_001126116 (var 6); NM_001126117 (var 7); NM_001126118 (var 8) | <0.01 | 53-60 |
| TPSAB1 | *Homo sapiens* tryptase alpha/beta 1 | NM_003294 | <0.01 | 111 |

A covariance matrix for the normalized data with the disease variable being a binary-coded dummy variable, where "0" represented nevi and "1" represented primary melanoma, was created. Table 5 shows how the expression of each indicated gene covaries with the disease variable:

TABLE 5

| Disease Covariance | |
|---|---|
| Symbol | Covariance v. Disease Variable |
| B2M | 0.1253 |
| B4GALT1 | 0.2552 |
| BRAF | 0.3014 |
| CDK2 | 0.146 |
| CREBBP | 0.086 |
| CTNNB1 | 0.205 |
| GALNTL1 | 0.1324 |
| GNAS | 0.205 |
| MAGEA2 | 0.3195 |
| MAGED2 | 0.129 |
| MCM6 | 0.2381 |
| NR4A1 | 0.766 |
| PDIA4 | 0.165 |
| PDLIM7 | 0.1693 |
| PIP4K2A | 0.4079 |
| PPIA | 0.1539 |
| PRAME | 0.3603 |
| PTEN | 0.164 |
| RPL37A | −0.409 |
| RUNX1 | 0.2568 |
| SAT1 | 0.4122 |
| SOCS3 | 0.4256 |
| SOX4 | 0.1853 |
| SP100 | 0.203 |
| SQSTM1 | −0.092 |
| STAT2 | 0.0731 |
| TADA3 | 0.184 |
| TEX13A | 0.2098 |
| TFRC | 0.2609 |
| TGFB1 | 0.1114 |
| TP53 | 0.265 |
| TPSAB1 | 0.188 |

As shown in Table 5, the mean expression value for each gene in Table 4 is higher (positive value) in primary melanoma than in nevi except for RPL37A and SQSTM1 (negative value) where the means are higher in nevi as compared to primary melanoma. In other words, except as noted, the genes in Table 4 tend to be upregulated in primary melanoma as compared to their expression in nevi.

Using these genes individually or in combinations will yield predictive models (e.g., regression models or, in more specific examples, linear regression models) capable of characterizing (e.g., diagnosing) test samples as benign nevi or primary melanoma. Illustrative, non-limiting gene combinations for use in disclosed methods, arrays or kits are at least 2, 3, 4, 5, 6, 7, 8, or all 9 of MAGEA2, PRAME, PDIA4, NR4A1, PDLIM7, B4GALT1, SAT1, RUNX1, and/or SOCS3.

In addition to overall significance, when selecting model combinations among the set of 32 genes, a number of measures were used to help determine which genes paired or combined well together to form a predictive model. One specific method was to minimize multicollinearity between predictors (i.e., the Xn variables; see below) in the model as measured by the variance inflation factor (VIF) of each Xn variable gene in a model. Any combinations of the genes (e.g., mRNA or miRNA) in Table(s) 4, 11 and/or 13 in which all predictor Xn variables have a variance inflation factor (VIF) less than 10 is likely to have useful predictive value for differentiating between samples from benign nevi versus those from primary melanoma and, accordingly, are contemplated by this disclosure.

D. Logistic Regression Models

The basis used for developing statistical predictive models using the genes in Table 4 was logistic regression with a binary distribution and a logit link function. Estimation for the models was performed using Fischer Scoring. However, models estimated with exact logistic regression, Empirical Sandwich Estimators or other bias corrected, variance stabilized or otherwise corrective estimation techniques will also, under many circumstances, provide similar models which while yielding slightly different parameter estimates will yield qualitatively consistent patterns of results. Similarly, other link functions, including but not limited to a cumulative logit, complementary log-log, probit or cumulative probit may be expected to yield predictive models that give the same qualitative pattern of results.

The primary form of the model (algorithm) in this Example is:

$$\mathrm{Logit}(Yi)=\beta 0+\beta 1X1+\beta 2X2+\beta 3X3 \ldots \beta nXn$$

where βo is an intercept term, βn is a coefficient estimate and Xn is the log base 2 expression value for a given gene. Typically, the value for all β will be greater than −1,000 and less than 1,000. Often, the β0 intercept term will be greater than −200 and less than 200 with cases in which it is greater than −100 and less than 100. The additional βn, where n>0, will likely be greater than −100 and less than 100.

To validate model performance a number of tests were conducted. A Wald Chi-Square test was used and the test needed to show a statistically significant result for overall model fit. A Hosmer and Lemeshow lack fit test needed to indicate not statistically detectable lack of fit for the model. Predictors for each gene in the model needed to be significant $p<0.05$.

A number of cross validation methods were used to ensure reproducibility of the results. The primary method was a one-step maximum likelihood estimate approximation implemented as part of the SAS Proc Logistic classification table procedure. Ten (10)-fold cross validation and 66-33% split validation was also performed in the open source package Weka for additional confirmation of results. While logistic regression is the mathematical underpinning in this Example, other statistical, mathematical and data mining procedures (such as probit regression, support vector machines or clustering algorithms) can produce models which give the same qualitative pattern of results.

Applying logistic regression modeling to the data in the present Example, the following Table 6 shows non-limiting combinations of genes that accurately differentiate between nevi and primary melanoma samples and the values for the corresponding predictive algorithm.

TABLE 6

Exemplary Predictive Combinations (Normalized to Four) with Algorithm Values

| Embodiment | Gene Combination (From left to right, each gene represents X1, X2 . . . Xn, as applicable, in the algorithm: Output = β0 + β1X1 + β2X2 . . . βnXn) | Regression Coefficients and Intercept (β0) |
|---|---|---|
| B1 | N4RA1, B4GALT1<br>As an example:<br>Output = −59.0958 + 1.5998(NR4A1) + 4.2115(B4GALT1) | β0 = −59.0958<br>β1 = 1.5998<br>β2 = 4.2115 |
| B2 | NR4A1, SOX4 | β0 = −39.1063<br>β1 = 2.0554<br>β2 = 1.8234 |
| B3 | NR4A1, SOX4, B4GALT1 | β0 = −75.3582<br>β1 = 1.9674<br>β2 = 1.5141<br>β3 = 4.0622 |
| B4 | NR4A1, SOX4, SQSTM1, B2M | β0 = −34.8327<br>β1 = 2.2925<br>β2 = 2.2998<br>β3 = −3.2193<br>β4 = 2.1559 |
| B5 | MAGED2, SAT1, SOX4 | β0 = −49.3358<br>β1 = 0.2919<br>β2 = 3.0513<br>β3 = 2.3171 |
| B6 | N4RA1, BRAF | β0 = −43.4593<br>β1 = 2.1785<br>β2 = 2.3159 |
| B7 | NR4A1, RPL37A | β0 = −9.6524<br>β1 = 3.2965<br>β2 = −2.1656 |
| B8 | NR4A1, SQSTM1, TPSAB1 | β0 = −7.6589<br>β1 = 2.7873<br>β2 = −3.6387<br>β3 = 1.6122 |
| B9 | NR4A1, TFRC, SAT1 | β0 = −43.3177<br>β1 = 1.5862<br>β2 = 0.111<br>β3 = 2.354 |
| B10 | TFRC, SAT1 | β0 = −40.4475<br>β1 = 1.3975<br>β2 = 2.5618 |

TABLE 6-continued

Exemplary Predictive Combinations (Normalized to Four) with Algorithm Values

| Embodiment | Gene Combination (From left to right, each gene represents X1, X2 . . . Xn, as applicable, in the algorithm: Output = β0 + β1X1 + β2X2 . . . βnXn) | Regression Coefficients and Intercept (β0) |
|---|---|---|
| B11 | SOCS3, TFRC, BRAF | β0 = −42.6409<br>β1 = 1.7603<br>β2 = −0.032<br>β3 = 3.048 |
| B12 | SOCS3, TFRC | β0 = −34.9546<br>β1 = 1.1505<br>β2 = 2.4557 |
| B13 | SOCS3, SOX4, SAT1, BRAF | β0 = −93.1404<br>β1 = 2.3007<br>β2 = 0.9978<br>β3 = 4.3683<br>β4 = 1.8052 |

FIGS. 3-7 show particular results of the model using the combination of N4RA1 and B4GALT1 as described in this Example to accurately determine whether a sample is properly characterized (e.g., diagnosed) as a nevus or a primary melanoma.

The algorithms disclosed in Table 6 were used to characterize test FFPE skin biopsies as primary melanoma or nevi. The algorithms (aka, fitted model) provide a predicted event probability, which, in this Example, was the probably of a sample being a primary melanoma. A SAS computation method known to those of ordinary skill in the art was used to compute a reduced-bias estimate of the predicted probability (see, support.sas.com/documentation/cdl/en/statug/63347/HTML/default/viewer.htm#statug_logistic_sect044.htm (as of Jun. 22, 2012)).

A series of threshold values, z, where z was between 0 and 1 were set. If the predicted probability calculated for a particular sample exceeded or equaled the pre-set threshold value, z, the sample was assigned to the primary melanoma group; otherwise, it was assigned to the nevi group. The respective group assignments were then cross-checked against the known clinical data to determine, among other things, true positives, true negatives, false positives, and false negative. These results are shown, for example, in Classification Tables such as those set forth in FIGS. 5 and 6.

Figure 5:
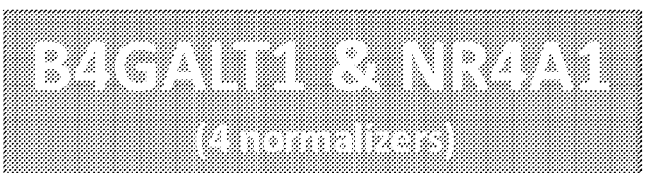
FIG. 5 shows the classification results after SAS cross validation for the representative B4GALT1 and NR4A1 (4-normalizer) model at different thresholds. The probability level is the probability of calling a test sample a primary melanoma. By raising the threshold (cut-off value) for calling a sample a primary melanoma the model obtained very high specificity and good sensitivity. These results further demonstrated that very high specificity and good sensitivity was obtained using this model over a wide range of threshold values.

Threshold values can be determined by the ordinarily skilled artisan based on the desired clinical utility of the model. FIGS. 5 and 6 demonstrate this point using a representative NR4A1 and B4GALT1 (normalized to four) model. A higher threshold can be set for making a primary melanoma call; for example, see the region highlighted in FIG. 5 (probability level 0.700-0.780). In this case, the false positive rate was relatively low or, stated otherwise, there was a higher specificity than sensitivity. Conversely, the threshold for calling a sample a primary melanoma can be lowered; for example see the region highlighted in FIG. 6 (probability level 0.240-0.620). At which threshold levels, the model would provide fewer false negatives or a higher sensitivity but a somewhat lower specificity.

It is noted that the "Output" from the model equations provided in Tables 6 and 8 is a logit. The logit is the log of the odds ratio for a sample being a primary melanoma. As an alternative, an ordinarily skilled artisan could use a logit as a threshold value for calling a sample primary melanoma or nevi. Equivalent results will be obtained under either method. For example, choosing a predicted probability of 0.5 will give the same results as using a logit of 0. This can be understood because an odds ratio of 1 is interpreted as there being an equal probability of a sample being primary melanoma or nevi. The logarithm of 1 is equal to zero and thus the logit of zero is equal to an odds ratio of 1. Given that an odds ratio of 1 or a logit of zero is a 50/50 probability of a sample being primary melanoma or nevi, a predicted probability of 0.5 is an equivalent result; and thus using either the predicted probability from a fitted model or a logit output will lead to the same results.

Example 3

Analysis with Two Alternative Normalizers Demonstrates the Robustness of Models for Predicting Nevi Versus Primary Melanoma The robustness of the predictive (e.g., diagnostic) gene combinations described in Example 2 was further shown by using an alternate set of normalization genes to normalize the data. Among other things shown in this Example, such analysis had no meaningful impact on the [N4RA1, B4GALT1] predictive model, which outcome is believed to be representative of all predictive models described in Example 2.

RPL37A, RPS6KB2, SDHA, and TFRC were included on arrays described in Examples 1 and 2 as putative "housekeeper" genes. As discussed above, the concept of a "housekeeper" gene (e.g., a gene whose expression is invariant across sample types) is losing favor and so should be (and was) tested in fact.

The composite average log base 2 expression value (see Example 2) for each of these candidate "housekeeper" genes was normalized to such value for each of the other candidate "housekeeper" genes. Coefficients of variation (CV) and standard deviations (SD) for each normalized "housekeeper" were calculated and are as shown in Table 7.

TABLE 7

Coefficients of variation (CV) and standard deviations for each normalized "housekeeper".

| Candidate "Housekeeper" | CV | SD |
|---|---|---|
| RPL37A | 0.101384 | 0.894 |
| RPS6KB2 | 0.023556 | 0.365 |
| SDHA | 0.022369 | 0.339 |
| TFRC | 0.070521 | 0.719 |

A candidate "housekeeper" was discarded as a legitimate normalizer if its CV was more than two-fold greater than the CV of the lowest CV of the other candidates. Accordingly, only RPS6KB2 and SDHA were selected as normalizers in this Example.

General information regarding this representative set of two normalization genes for human nevi and primary melanoma skin biopsies is described above in Table 3.

The composite average log base 2 expression values for each of the genes in Table 4 were normalized to the composite average log base 2 expression values for RPS6KB2 and SDHA, and the logistic regression analysis described in Example 2 repeated for each of the predictive gene combinations shown in Table 6.

The corresponding intercepts and coefficients for each predictive algorithm where gene (Xn) was normalized to two (i.e., RPS6KB2 and SDHA) is shown in following Table 8.

TABLE 8

Exemplary Predictive Combinations (Normalized to Two) with Algorithm Values

| Embodiment | Gene Combination (From left to right, each gene represents X1, X2 . . . Xn, as applicable, in the algorithm: Output = β0 + β1X1 + β2X2 . . . βnXn) | Regression Coefficients and Intercept (β0) |
|---|---|---|
| B1 | NR4A1, B4GALT1 | β0 = −39.9861<br>β1 = 1.9964<br>β2 = 2.1807 |
| B2 | NR4A1, SOX4 | β0 = −25.7153<br>β1 = 2.1472<br>β2 = 0.4994 |
| B3 | NR4A1, SOX4, B4GALT1 | β0 = −39.4785<br>β1 = 1.9795<br>β2 = −0.4937<br>β3 = 2.5948 |
| B4 | NR4A1, SOX4, SQSTM1, B2M | β0 = −12.6489<br>β1 = 2.5444<br>β2 = 0.6808<br>β3 = −3.7649<br>β4 = 1.9304 |
| B5 | MAGED2, SAT1, SOX4 | β0 = −26.6321<br>β1 = −2.5752<br>β2 = 4.2547<br>β3 = 1.3862 |
| B6 | N4RA1, BRAF | β0 = −38.9049<br>β1 = 2.2051<br>β2 = 2.1615 |
| B7 | NR4A1, RPL37A | β0 = −2.9081<br>β1 = 3.0926<br>β2 = −2.4906 |
| B8 | NR4A1, SQSTM1, TPSAB1 | β0 = −13.1057<br>β1 = 3.004<br>β2 = −3.7264<br>β3 = 2.0336 |
| B9 | NR4A1, TFRC, SAT1 | β0 = −62.1051<br>β1 = 1.6769<br>β2 = 2.2591<br>β3 = 2.6097 |
| B10 | TFRC, SAT1 | β0 = −69.1937<br>β1 = 3.8901<br>β2 = 3.6063 |
| B11 | SOCS3, TFRC, BRAF | β0 = −59.3456<br>β1 = 1.4668<br>β2 = 2.4699<br>β3 = 3.1692 |
| B12 | SOCS3, TFRC | β0 = −35.5872<br>β1 = 0.9893<br>β2 = 3.0369 |
| B13 | SOCS3, SOX4, SAT1, BRAF | β0 = −108.5<br>β1 = 4.1954<br>β2 = −7.3183<br>β3 = 6.3842<br>β4 = 8.8727 |

The algorithms disclosed in Table 8 were determined and tested as described in Example 2.

Figure 9:
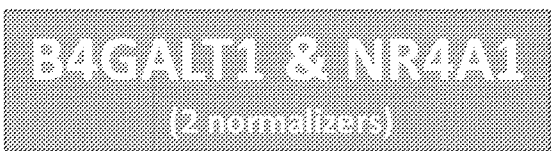
FIG. 9 shows a probability classification table for the B4GALT1 and NR4A1 (2-normalizer) model. These results demonstrate that the model maintained very high sensitivity and specificity. Compared to the B4GALT1 and NR4A1 (4-normalizer) model, the overall specificity of the 2-normalizer model was somewhat attenuated across the range of the model; however, there is always a tradeoff between sensitivity and specificity. The overall sensitivity for thresholds of 0.34 and below showed that the model provided moderately higher sensitivity while maintaining good specificity. Given that the clinical implications are far worse for misdiagnosing a sample, trading some specificity for sensitivity is an acceptable outcome. The B4GALT1 and NR4A1 (2-normalizer) model had overall correct classification of 88.9% or better for approximately 50% of the thresholds.

FIGS. 8 and 9 show (i) the overall B4GALT1 and NR4A1 (2-normalizer) model fit remains highly significant; (ii) the AUC is 97.67 (indicating, e.g., a 97.67% probability that B4GALT1 and NR4A1 (2-normalizer) predictive model will rank a randomly chosen positive instance higher than a randomly chosen negative instance); (iii) 90% plus correct classification over ~50% of possible thresholds after SAS cross validation; (iv) attenuated specificity across the range of possible thresholds after SAS cross validation; and (v) moderate increase in maximum sensitivity after SAS cross validation as compared to the Example 2 model for this same molecular signature.

In summary, this Example demonstrates that the B4GALT1 and NR4A1 model for characterizing samples as nevi or primary melanoma on a molecular level is repeatable across normalization methods. A similar outcome is expected for the other predictive signatures described in Examples 2 and 3 (and elsewhere herein) using analogous computations. The robustness and utility of these representative and other disclosed models for characterizing a test sample as a nevus or primary melanoma, thus, are clearly demonstrated.

Example 4

Classification of Melanoma and Nevi Using Machine Learning Methods

In this Example, mRNA and miRNA expression in a third set of FFPE skin samples biopsied from human subjects was determined using a set of four ArrayPlates, including ArrayPlates Nos. 3 and 4 (see Examples 2 and 3). Such data was used to successfully identify sets of mRNAs and miRNAs significantly differentially expressed in melanoma and nevi samples and to train machine learning (e.g., Random Forest (Breiman, *Machine Learning,* 45 (1): 5-32 (2001)) melanoma-nevi classifiers.

A set of 115 FFPE tissue sections, each approximately 5 um thick and mounted on a microscope slide, was provided by the John Wayne Cancer Institute (JWCI) tissue bank. The set included 56 nevi samples and 59 primary melanoma samples.

The samples were analyzed for expression of 181 (including controls) mRNAs or miRNAs on a set of four ArrayPlates. Assay and detection methods for ArrayPlates Nos. 3-5 (mRNA only) were substantially as described in Example 1. Assay and detection methods for ArrayPlate No. 6 (miRNA and mRNA codetection) were substantially as described in PCT Publication No. WO2013/049231. NPPs for ArrayPlate No. 6 normalizer and negative control (ANT) mRNAs were 25 mers corresponding to the 3'-most 25 nucleotides of the respective control NPPs described elsewhere in these Examples. The set of ArrayPlates included ArrayPlates Nos. 3 and 4 (see Table 1), "ArrayPlate No. 5" specific for mRNA targets, and "ArrayPlate No. 6" specific for miRNA targets (plus mRNA controls). The target listings for ArrayPlates Nos. 5 and 6 are shown in Table 9. There were some common mRNA targets on ArrayPlate Nos. 3-6; thus, data was gathered for 101 different mRNAs (including controls) and 42 different miRNAs.

TABLE 9

ArrayPlate Target List

| ArrayPlate No. 5 | | ArrayPlate No. 6 | |
|---|---|---|---|
| Identifier | GenBank Accesssion No. | Identifier | GenBank or miRBase* Identifier (as applicable) |
| MAGEA2 | NM_005361 | SDHA | NM_004168 |
| PAX3 | NM_181457 | RPS6KB2 | NM_003952 |
| GALNTL1 | NM_001168368 | RPL37A | NM_000998 |
| MAGEA1 | NM_004988 | TFRC | NM_003234 |
| PanMAGEA3-12 | | ANT | NM_119937 |
| BIRC7 | NM_139317 | 23b | hsa-miR-23b |
| BIRC5 | NM_001168 | 211 | hsa-miR-211 |
| XIAP | NM_001167 (v1); | 1224-3p | hsa-miR-1224-3p |
| | NM_001204401 (v2); | 193A-5P | hsa-miR-193a-5p |
| | NR_037916.1 | 146A | hsa-miR-146a |
| | (noncoding v3) | 513b | hsa-miR-513b |
| PRAME | NM_206953 | 133A | hsa-miR-133a |
| MET | NM_001127500 | 182 | hsa-miR-182 |
| MFI2 | NM_005929 | 205 | hsa-miR-205 |

TABLE 9-continued

ArrayPlate Target List

| ArrayPlate No. 5 | | ArrayPlate No. 6 | |
|---|---|---|---|
| Identifier | GenBank Accesssion No. | Identifier | GenBank or miRBase* Identifier (as applicable) |
| MCAM | NM_006500 | 665 | hsa-miR-665 |
| | (GI: 71274106) | 1254 | hsa-miR-1254 |
| BAD | NM_004322 (v1); | 200C | hsa-miR-200c |
| | NM_032989 (v2) | 292 | mmu-miR-292-3p |
| BCL2 | NM_000633 (alpha); | 200A | hsa-miR-200a |
| | NM_000657 (beta) | 21 | hsa-miR-21 |
| HIF1A | NM_001530 | 140-3p | has-miR-140-3p |
| MIB1 | NM_020774 | 140-5p | has-miR-140-5p |
| TOP2A | NM_001067 | 29C | hsa-miR-29c |
| WT1 | e.g., NM_000378 | 142-5P | hsa-miR-142-5p |
| | (variant A) or also | 595 | hsa-miR-595 |
| | other variants (e.g., | 207 | mmu-miR-207 |
| | B-F) | 106a | hsa-miR-106a |
| MCM2 | NM_004526 | 122 | hsa-miR-122 |
| MCM6 | NM_005915 | 1304 | hsa-miR-1304 |
| ALK | NM_004304 | 155 | hsa-miR-155 |
| S100B | NM_006272 | 191 | hsa-miR-191 |
| PDIA4 | NM_004911 | 375 | hsa-miR-375 |
| SOX4 | NM_003107 | 612 | hsa-miR-612 |
| XRCC5 | NM_021141 | 650 | hsa-miR-650 |
| DAZAP2 | NM_014764 | 1180 | hsa-miR-1180 |
| EVI2B | NM_006495 | 183 | hsa-miR-183 |
| LDHA | NM_005566 | 203 | hsa-miR-203 |
| BRAF | NM_004333 | 1293 | hsa-miR-1293 |
| ERCC1 | NM_001983 | 342-3p | hsa-miR-342-3p |
| ESR1 | NM_000125 | 1294 | hsa-miR-1294 |
| RPL19 | NM_000981 | 19b | hsa-miR-19b |
| SDHA | NM_004168 | 557 | hsa-miR-557 |
| ALDOA | NM_000034 | 1198-5p | mmu-miR-1198-5p |
| RPLP0 | NM_001002; | let-7a | hsa-let-7a |
| | NM_053275 | 1291 | hsa-miR-1291 |
| PPIA | NM_021130 | 29b | hsa-miR-29b |
| ANT | See other Examples | 150 | hsa-miR-150 |
| MAGEB1 | NM_002363 (v1); | | |
| | NM_177404 (v2); | | |
| | NM_177415 (v3); | | |
| MAGEC2 | NM_016249 | | |
| MAGED2 | NM_014599 | | |

*Kozomara and Griffiths-Jones, Nuc. Acids Res., 39 (Database Issue): D152 (2011)

Normalizing genes were SDHA and RPS6KB2 on ArrayPlate Nos. 3, 4 and 6, and SDHA, RPL19, RPLP0 and ALDOA on ArrayPlate No. 5 (see, also, Table 3). None of these normalizers showed any significant difference across sample types as described elsewhere in these Examples.

Due to limited sample availability, not all samples were run on each array and all raw data was subject to rigorous quality control (i.e., pre-processing), as follows: Raw data was background subtracted and log 2 transformed. Any samples for which greater than 200 RLU was measured for the negative control gene, ANT, were deemed to have failed, and all data from those particular wells were removed from further consideration. A coefficient of variance (CV) was determined for replicate expression values for each gene. If the CV for sample replicates exceeded 8%, the replicate farthest from the average was removed as an outlier. Replicate reproducibility was measured by pairwise correlation and by pairwise simple linear regression. If the correlation had r>=0.90 and the intercept of the linear regression was not statistically significantly different from zero, such replicate was accepted; otherwise, it was deemed failed. Any sample with more than two failed replicates was defined as a failed sample. Data failing to meet quality standards were removed from the analysis. A summary is provided in Table 10:

TABLE 10

| Summary of Samples and Genes Analyzed | | | | |
|---|---|---|---|---|
| ArrayPlate No. | # Targets | Sample Class | # Samples Run | # Samples after Data QC |
| 3 | 47 | Melanoma | 59 | 57 |
| | | Nevus | 56 | 54 |
| 4 | 47 | Melanoma | 59 | 53 |
| | | Nevus | 40 | 34 |
| 5 | 40 | Melanoma | 58 | 46 |
| | | Nevus | 35 | 32 |
| 6 | 47 | Melanoma | 59 | 59 |
| | | Nevus | 50 | 50 |

Univariate Analysis

Several univariant analyses of the processed data (e.g., log-fold change, two sample t-test (False Discovery Rate (FDR) adjusted p-value), and AUC logistic regression analysis) were performed to evaluate whether a particular gene was significantly differentially expressed between sample types in each data set.

Figure 10A:
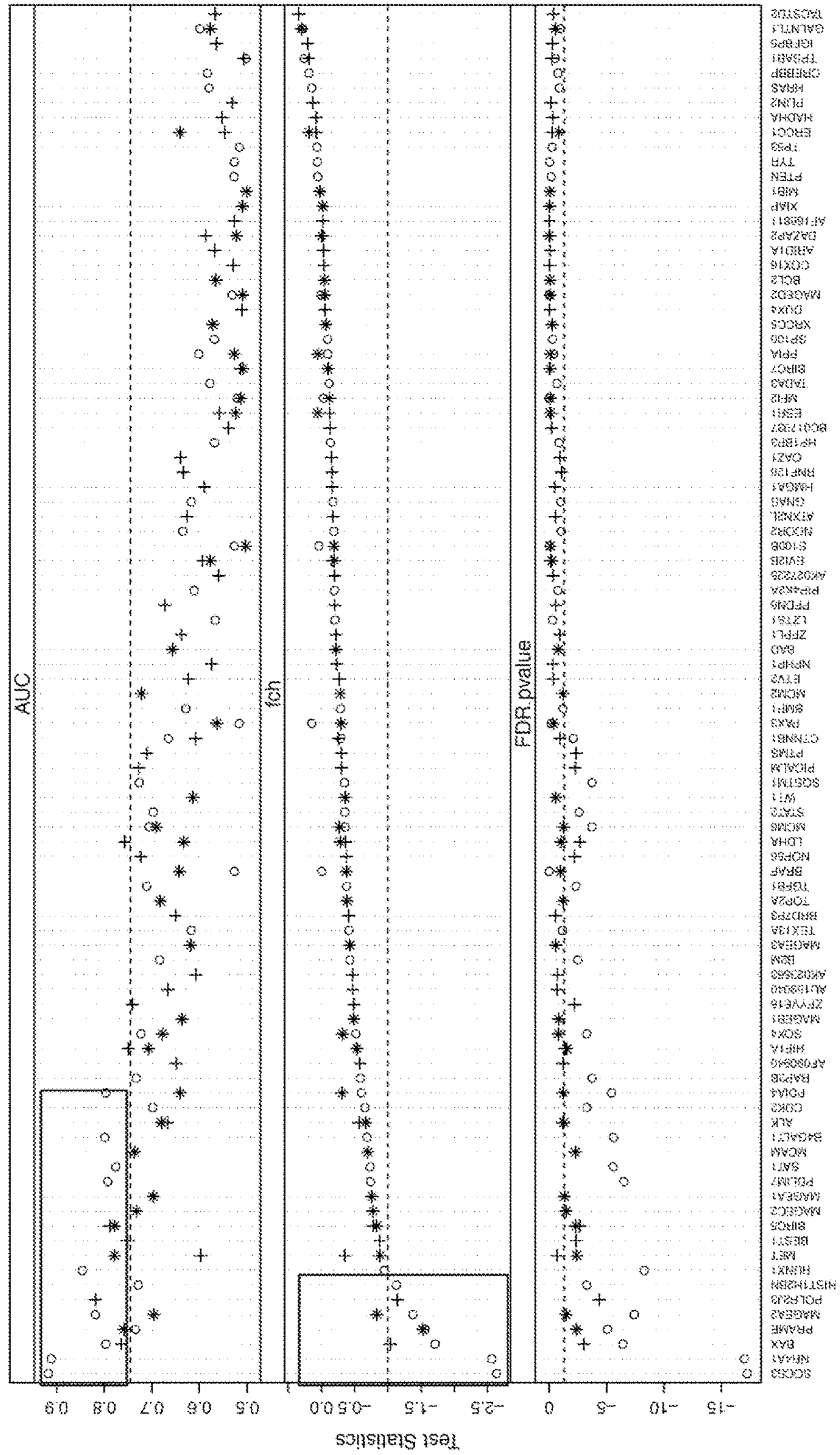
FIG. 10A shows three scatter plots, each showing the result of a univariate statistical test (AUC (top), fold change (fch; middle), and FDR-adjusted p-value (bottom)) for each gene (as measured by mRNA expression) listed on the x-axis. The dotted line in each scatterplot shows the selected cut off for statistical significance. The result is considered significant if above the AUC cut off (also boxed), below the fold change cut off (also boxed), or below the FDR-adjusted p-value cut off. The symbol representing each gene represents on which ArrayPlate (AP) the expression data was measured.

The results of univariate analyses for the three mRNA arrays (i.e., ArrayPlates 3-5) are shown in FIG. 10A. The values for each of three tests performed ((i) Area under the Receiver Operating Characteristic (ROC) curve (AUC), (ii) log-fold change (fch), and (iii) two sample t-test (FDR adjusted p-value; FDR.pvalue)) are shown. Genes for which expression data was gathered are shown on the x-axis, and the value of the respective univariate statistic is shown on the y-axis. For the AUC analysis, a higher value is desirable. In this case, 0.75 (at dotted line) was assigned as the cut off of statistical significance. Genes with AUCs above that line are candidates for distinguishing nevi from melanoma. For the log-fold change analysis, negative 1 and positive 1 (each of which equals a two-fold difference in expression between nevi and melanoma) were assigned as the cut offs for statistical significance. Genes with log-fold change greater than positive 1 and less than negative 1 are candidates for distinguishing nevi from melanoma. For FDR adjusted p-values, a lower value is desirable, and 0.05 (at dotted line) was assigned as the cut off of statistical significance. Genes with expression below that line are candidates for distinguishing nevi from melanoma.

Figure 10B:
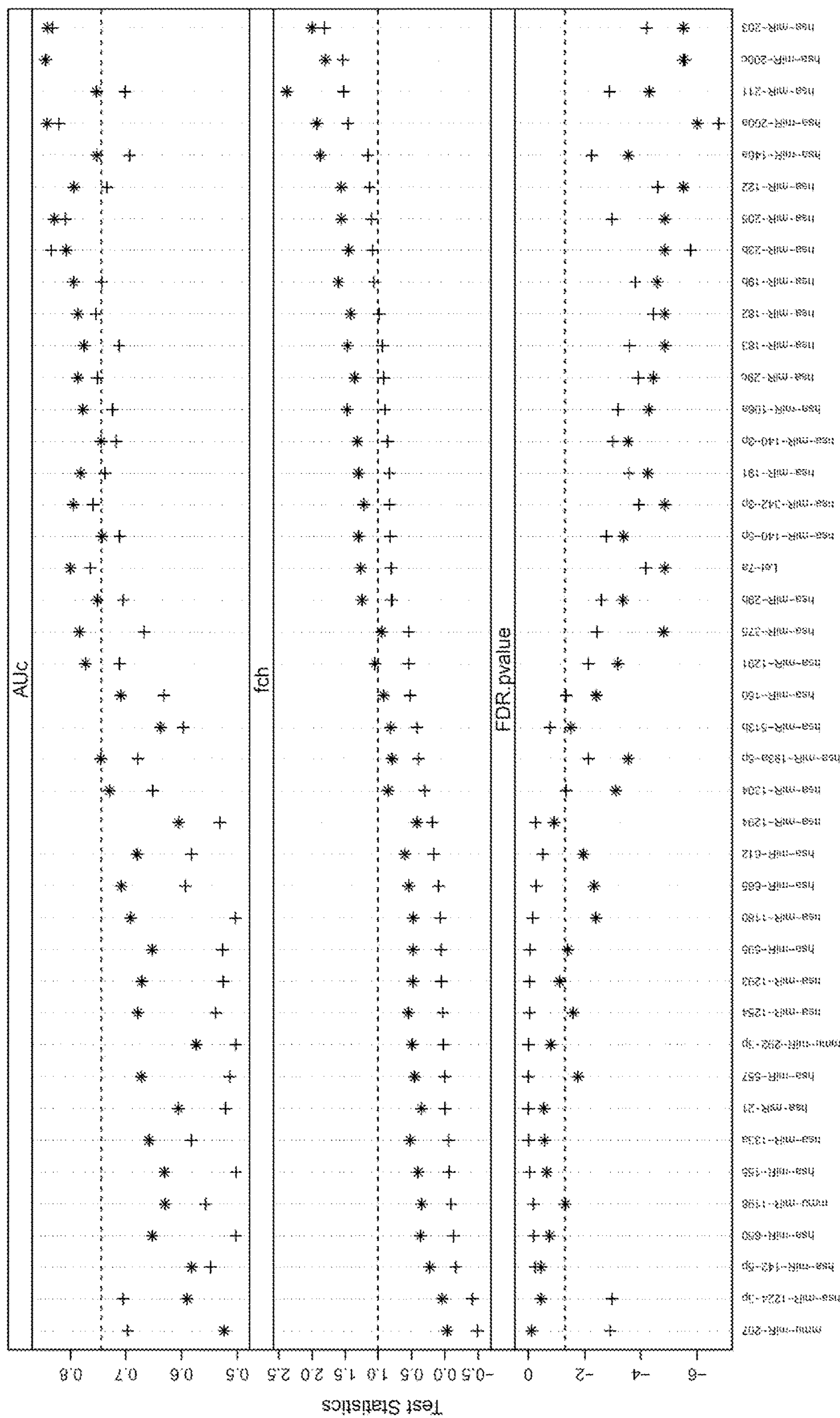
FIG. 10B shows similar results as FIG. 10A for each indicated miRNA (x-axis), except that the cut off for fold change is positive 1 (vs. negative 1) and the fold change result is considered significant if above the line. The expression value for each miRNA was (+) or was not (*) normalized.

The results of univariate analysis for the miRNA array are shown in FIG. 10B. As above, AUC under a ROC curve, log-fold change and two sample t-test (FDR adjusted p-value) were determined for each of the miRNAs listed on the x-axis. The value of the respective univariate statistic is on the y-axis. The data labeled “HK” show miRNA expression data normalized to the “housekeepers” on ArrayPlate No. 6 and “NO.HK” show unnormalized miRNA expression data. Normalized and unnormalized data generally provide similar results. Statistical cut offs for AUC, fold-change and two sample t-test (FDR adjusted p-value) were the same as for the mRNA analysis above. miRNAs with AUC greater than 0.75, fold-change greater than positive 1, and FDR adjusted p-value below the cut off line are candidates for distinguishing nevi from melanoma.

The positive outcome of the univariate analyses (i.e., identification of mRNA and miRNA significantly differentially expressed between melanoma and nevi) supported the decision to proceed with more resource-consuming multivariate analyses and further melanoma-nevi classifier development.

Multivariate Analysis

A multivariant analysis then was performed to determine which subsets of the detected targets most powerfully (from a statistical perspective) distinguished between melanoma and nevi sample types. Multiple feature selection methods (RF, LIMMA, t-test, AUC) were used to evaluate whether a particular gene was significantly differentially expressed between sample types in each data set. Machine learning algorithms (e.g., Logistic Regression (LR), Random Forest (RF), Support Vector Machine (SVM), K-nearest neighbor (KNN)) were used to develop an initial classifier. Both feature selection and classification performance were evaluated in a leave one out cross-validated fashion. Error rate as a function of gene number and Receiver Operating Characteristic (ROC) curve were used to evaluate the performance of the classifier.

Figure 11:
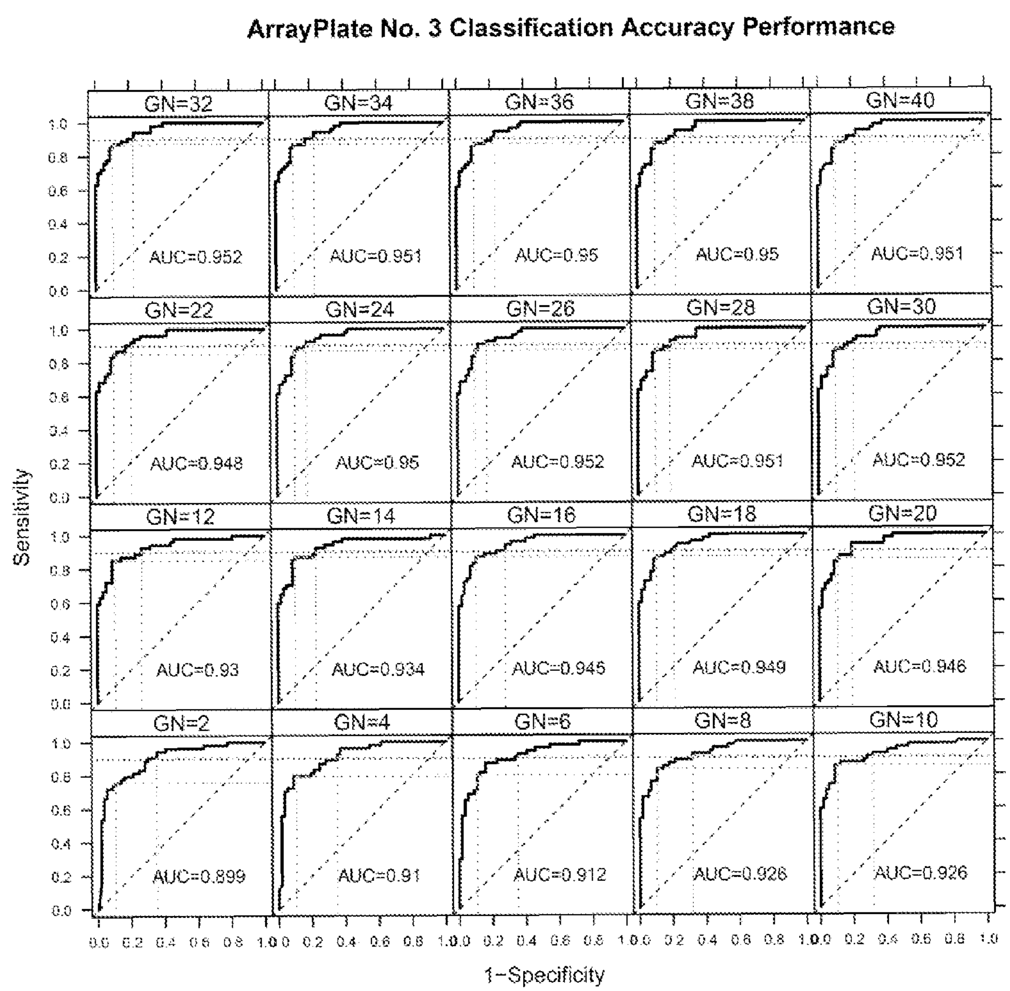
FIG. 11 shows the classification accuracy (based on AUC) of exemplary two (bottom left) to 40 (top right) gene nevus/melanoma classifiers built on the expression data from ArrayPlate No. 3. In each case, the AUC equals or exceed 0.9 indicating good accuracy regardless of the number of genes in the classifier and increasing classifier accuracy until approximately 18-gene classifiers whereafter the AUC is relatively stable at approximately 0.95.

For the genes detected in ArrayPlate No. 3, FIG. 11 shows the AUC performance of classifiers based on the top 2 (GN=2) through the top 40 (GN=40) genes on that array. For this type of analysis, AUC increases with higher sensitivity (i.e., true positive rate shown on the y-axis) and lower false positive rate (i.e., “1-Specificity” shown on the x-axis) of the tested classifier. This figure demonstrates that AUC exceeded 0.93 (1.00 is “perfect”) with all ArrayPlate No. 3 classifiers greater than 12 genes. One of ordinary skill in the art will appreciate that this result does not mean one could not select a classifier with fewer than 12 genes based on the information disclosed herein; however, such classifier may not have as high sensitivity and specificity. In some settings, high sensitivity or high specificity may not be the greatest priority and classifiers may be accordingly selected. For example, it may be considered worse outcome for a melanoma-nevi classifier to misidentify a melanoma as a nevus rather than to misidentify a nevus as a melanoma; in that case, a classifier may be selected to minimize false negatives while being a bit more lax on false positives (when null hypothesis=melanoma or not).

Figure 12:
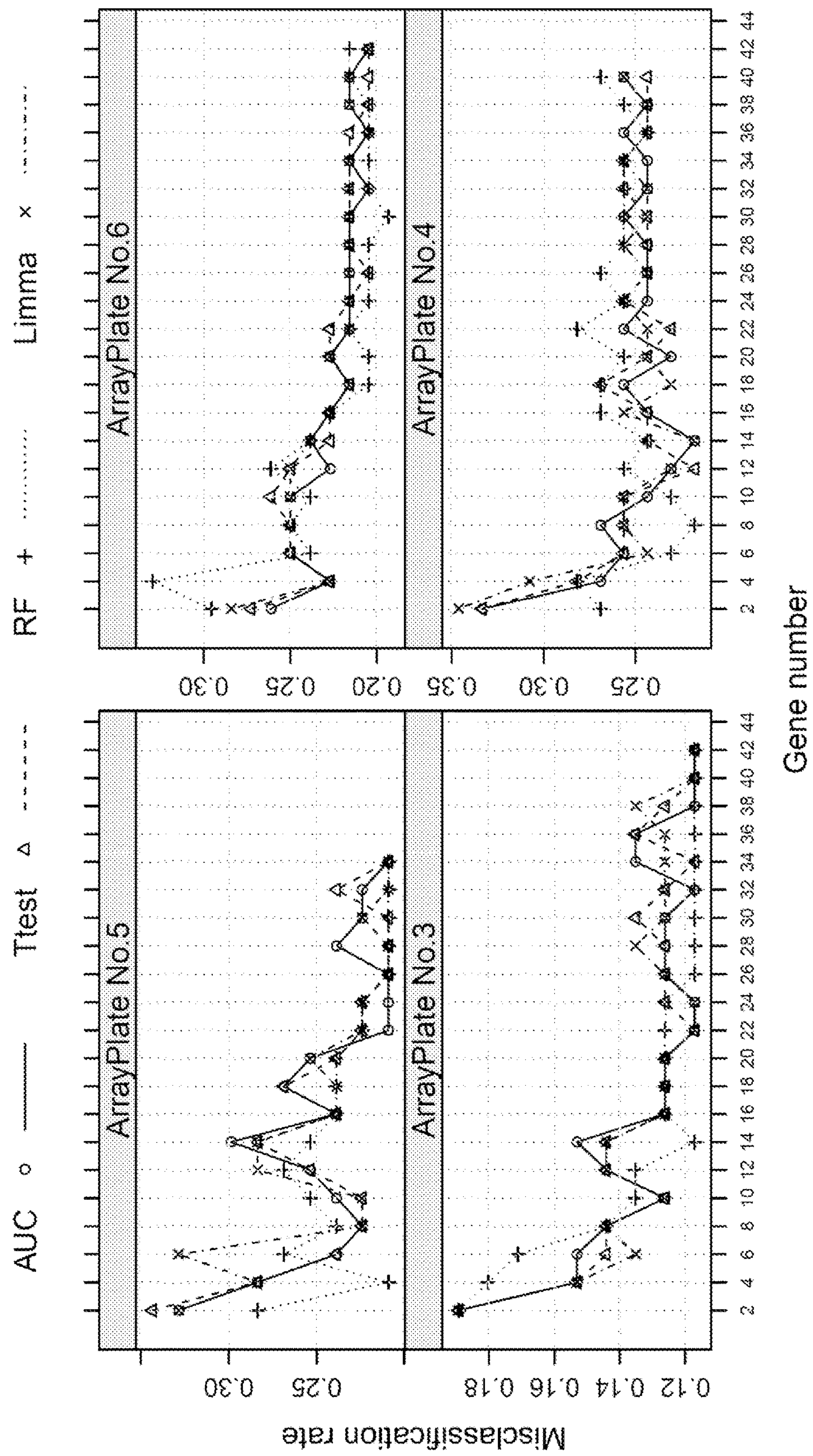
FIG. 12 is a composite of four line graphs, each showing the misclassification rate (y-axis) of two to 40 gene (x-axis) AUC, T-test, Random Forest, or LIMMA classification models based on expression data collected from ArrayPlate Nos. 3-6, as indicated.

For the genes in each of ArrayPlate Nos. 3-6, FIG. 12 shows the error rate of classifiers determined by the various statistical methods (i.e., AUC, t-test, Random Forest, LIMMA) as a function of the number of genes in the classifier. This figure indicates that the misclassification error of a melanoma-nevi classifier is minimized when such a classifier has about 10 or more genes. As above, this result does not mean one could not select a classifier with fewer than about 10 genes based on the information disclosed herein; however, such classifier is likely to be more error prone.

For each of ArrayPlate Nos. 3-5, the genes with the highest occurrence frequency in leave-one-out cross validation (LOOCV) of Random Forest algorithms and the best performance as measured by AUC were selected and consolidated into the gene list shown in Table 11. A similar approach was used to select miRNAs shown in Table 13, and exemplary combinations of genes shown in Table 14.

Based on the above analysis, the mRNAs and miRNAs shown in Tables 11, 13 and 14, as applicable, were selected as useful (in combinations of at least 2, 3, 4, 5, 6, 7, 8, or, as applicable, 9, 10, 11, 12, 13, 14, 15 or more) to accurately classify a test sample as a nevus or melanoma. In particular examples, such classifier utilizes a machine learning (e.g., Random Forest or support vector machine) algorithm. Representative nuclease protection probes used to detect the respective expression product in this Example are also shown in Tables 11 and 13. In some examples, the expression levels of these genes are normalized to one or more housekeepers, such as SDHA, RPS6KB2, RPL37A, and/or TFRC (such as, SDHA and RPS6KB2).

TABLE 11

| Genes (mRNAs) For Nevus-Melanoma Classification | | |
|---|---|---|
| Symbol | Representative NPP (5' to 3') | SEQ ID NO. |
| B4GALT1 | GTCTTGGAACCTGAGCCCAGGCTGGACCTGGCA AAGGCGCTCAGTGGTAG | 125 |
| BAX | CGATGCGCTTGAGACACTCGCTCAGCTTCTTGG TGGACGCATCCTGAGGC | 126 |
| MAGEA2 | CTCAGGCTCTCCACCTGGATGCTTGGCAGATCC TAGAACCACTGCATCTG | 127 |
| NR4A1 | CGCCACAGCTGCCACGTGCTCCTTCAGGCAGCT GGCGATGCGGTTCTGCA | 128 |
| PDIA4 | CACATCAAACCTGCTGGCCAGCACAGACGCTGA GGTTGCATCGATCTTGG | 129 |
| PRAME | GTCTGGCTGTGTCTCCCGTCAAAGGCTGCCATG AAGAGTGGCGGGAAGAG | 130 |
| RUNX1 | GCAGAGTCACACACATGCAAACACGCACTCTTC GGAAGGCAGCCACTGTC | 131 |
| SOCS3 | GTCTTCTCTACCAGGAGCCTGAGGTGAAAGATG TCCCGTCTCCTCCATCC | 132 |
| SAT1 | ATTTCAAACATGCAACAACGCCACTGGTAATAA AGCTTTGGAATGGGTGC | 133 |
| PDLIM7 | CTTCGATGTGTGTGAGGCTACCCGCATTCTCGC CATCGATGCTCAGCACC | 134 |
| BIRC5 | GCACAGGCTCACAGAAGCCGAGATCCACATCA CCGCCTGGCATGCAAAGG | 135 |
| HIF1A | GGCCATTTCTGTGTGTAAGCATTTCTCTCATTTC CTCATGGTCACATGGA | 136 |
| MET | CAAAGAAGTTGATGAACCGGTCCTTTACAGATG AAAGGACTTTGGCTCCC | 137 |
| MAGEC2 | GGACTACTGGGAATGCTCTCGGTAAGATTTGGT ATCACACCAGAGGGCAC | 138 |
| ERCC1 | AGTGGGAAGGCTCTGTGTAGATCGGAATAAGG GCTTGGCCACTCCAGGAG | 139 |
| POLR2J3 | GAGGTTGCAGTGAGCCAAGATCGCGCCAGCCTG GCGACAGAGTGAGACTC | 140 |
| LDHA | TCCATCATCTCTCCCTTCAATTTGTCTTCGATGA CATCAACAAGAGCAAG | 141 |
| PICALM | GACAGGCTGGCTGTATATTAAGGTTGGTTGCGT CATTACAGGAACACTTC | 142 |
| ZFYVE16 | GAAGTTCGCTGTGAGGAAGCCAACTCTGAAGA AACTGAGCAGTGGTTAGA | 143 |
| BEST1 | GTTTCTCCAACTGCTTGTGTTCTGCCGGAGTCAT AAAGCCTGCTTGCACC | 144 |

Additional detail on several of the above-listed genes may be found in Table 4; similar detail for the remaining genes is provided in Table 12 below:

TABLE 12

| Supplement to Table 4 | | |
|---|---|---|
| Symbol | Name | GenBank Ref. No(s). |
| BAX | BCL2-Associated X Protein | NM_138761 (GI: 163659848) (alpha); NM_004324.3 (GI: 34335114) (beta); NM_138763 (GI: |

TABLE 12-continued

| Supplement to Table 4 | | |
|---|---|---|
| Symbol | Name | GenBank Ref. No(s). |
| | | 163659849) (delta); NM_138764 (GI: 242117892) (sigma); NR_027882 (GI: 242117894) (epsilon, non-coding) |
| BIRC5 | Baculoviral IAP Repeat-Containing Protein 5 (aka, Apoptosis Inhibitor 4; API4 Survivin) | NM_001168 (GI: 59859877) (v1); NM_001012270 (GI: 59859879) (v2); NM_001012271 (GI: 59859881) (v3) |
| HIF1A | Hypoxia-Inducible Factor 1, Alpha Subunit (aka, Hif1-Alpha; Member of PAS Superfamily 1; MOP1) | NM_001530 (GI: 194473733) (v1); NM_181054 (GI: 194473734) (v2); NM_001243084 (GI: 340545530) (v3) |
| MET | MET PROTOONCOGENE (aka, Hepatocyte Growth Factor Receptor; HGFR) | NM_001127500 (GI: 188595715) (v1); NM_000245 (GI: 42741654) (v2) |
| MAGEC2 | Melanoma Antigen, Family C, 2 (aka, Cancer-Testis Antigen 10; CT10; HCA587; Melanoma Antigen, Family E, 1; MAGEE1 | NM_016249 (GI: 262050676) |
| ERCC1 | Excision-Repair, Complementing Defective, in Chinese Hamster, 1 (aka, Complementation of DNA Repair Defect UV-20 of Chinese Hamster Ovary Cells; UV20 | NM_202001 (GI: 260593723) (v1); NM_001983 (GI: 260593722) (v2); NM_001166049 (GI: 260593724) (v3) |
| POLR2J3 | *Homo sapiens* polymerase (RNA) II (DNA directed) polypeptide J3 (aka, POLR2J2, RPB11b1, RPB11b2) | NM_001097615 (GI: 332634983) |
| LDHA | Lactate Dehydrogenase A (aka, LDH, Subunit M) | NM_005566 (GI: 207028465) (v1); NM_001135239 (GI: 207028493) (v2); NM_001165414 (GI: 260099722) (v3); NM_001165415 (GI: 260099724) (v4); NM_001165416 (GI: 260099726) (v5); NR_028500 (GI: 260099728) (v6, noncoding) |
| PICALM | Phosphatidylinositol-Binding Clathrin Assembly Protein (aka, Clathrin Assembly Lymphoid-Myeloid Leukemia Gene; CALM; CLTH; LAP, Homolog of *Drosophila* LAP | NM_007166 (GI: 332688229) (v1); NM_001008660 (GI: 332688228) (v2); NM_001206946 (GI: 332688230) (v3); NM_001206947 (GI: 332635086) (v4) |
| ZFYVE16 | Zinc Finger FYVE Domain-Containing Protein 16 (aka, Endosome-Associated FYVE Domain Protein; ENDOFIN; KIAA0305) | NM_014733 (GI: 157426863) (v1); NM_001105251 (GI: 157426865) |
| BEST1 | Bestrophin 1 (aka, VMD2 Gene, TU15B) | NM_004183 (GI: 212720874) (v1); NM_001139443 (GI: 212720888) (v2) |

TABLE 13

| miRNAs For Nevus-Melanoma Classification | | | |
|---|---|---|---|
| Identifier | Representative NPP (5' to 3') | SEQ ID NO | miRBase Accession No. |
| hsa.miR.122 | CAAACACCATTGTCACACTCCA | 145 | MI0000442 |
| hsa.miR.1291 | ACTGCTGGTCTTCAGTCAGGGCCA | 146 | MI0006353 |
| hsa.miR.191 | CAGCTGCTTTTGGGATTCCGTTG | 147 | MI0004941 |
| hsa.miR.19b | TCAGTTTTGCATGGATTTGCACA | 148 | MI0000074 |
| hsa.miR.200a | ACATCGTTACCAGACAGTGTTA | 149 | MI0000737 |
| hsa.miR.200c | TCCATCATTACCCGGCAGTATTA | 150 | MI0000650 |

TABLE 13-continued

| miRNAs For Nevus-Melanoma Classification | | | |
|---|---|---|---|
| Identifier | Representative NPP (5' to 3') | SEQ ID NO | miRBase Accession No. |
| hsa.miR.203 | CTAGTGGTCCTAAACATTTCAC | 151 | MI0000283 |
| hsa.miR.205 | CAGACTCCGGTGGAATGAAGGA | 152 | MI0000285 |
| hsa.miR.21 | TCAACATCAGTCTGATAAGCTA | 153 | MI0000077 |
| hsa.miR.23b | GGTAATCCCTGGCAATGTGAT | 154 | MI0000439 |
| hsa.miR.29c | TAACCGATTTCAAATGGTGCTA | 155 | MI0000735 |
| hsa.miR.342.3p | ACGGGTGCGATTTCTGTGTGAGA | 156 | MI0000805 |
| hsa.miR.375 | TCACGCGAGCCGAACGAACAAA | 157 | MI0000783 |
| hsa.miR.665 | AGGGGCCTCAGCCTCCTGGT | 158 | MI0005563 |
| hsa.miR.1304 | CACATCTCACTGTAGCCTCAAA | 159 | MI0006371 |
| hsa.miR.142.5p | AGTAGTGCTTTCTACTTTATG | 160 | MI0000458 |
| hsa.miR.1254 | ACTGCAGGCTCCAGCTTCCAGGCT | 161 | MI0006388 |
| hsa.let.7a | AACTATACAACCTACTACCTCA | 162 | MI0000060 |
| hsa.miR.140.5p | CTACCATAGGGTAAAACCACTG | 163 | MI0000456 |
| hsa.miR.183 | AGTGAATTCTACCAGTGCCATA | 164 | MI0000273 |

TABLE 14

| Exemplary Gene Combinations | |
|---|---|
| Embodiment | Gene Combination |
| C1 | B4GALT1, BAX, MAGEA2, NR4A1, PDIA4, PRAME, RUNX1, SOCS3, SAT1, PDLIM7, BIRC5, MET, MAGEC2, POLR2J3, ZFYVE16, BEST1 |
| C2 | NR4A1, SOCS3, PRAME, POLR2J3, BEST1, RUNX1, BIRC5, MET, PDLIM7, ZFYVE16, HIF1A, PICALM |
| C3* | MAGEA2, PRAME, PDIA4, NR4A1, PDLIM7, B4GALT1, SAT1, RUNX1, SOCS3 |
| C4 | hsa.miRNA.342.3p, hsa.miRNA.191, hsa.miRNA.29c, hsa.miRNA.183, hsa.miRNA.182, hsa.miRNA.19b, hsa.miRNA.23b, hsa.miRNA.205, hsa.miRNA.122, hsa.miRNA.200a, hsa.miRNA.200c, hsa.miRNA.203 |

*Combination found in each of Table 4 and Table 11

In summary, this Example demonstrates the utility of specified mRNA and miRNA, for example, as used in machine learning (e.g., Random Forest or support vector machine) models, to characterizing samples as nevi or melanoma (e.g., primary melanoma).

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

The invention claimed is:

1. A method of treating an indeterminant or atypical nevi in a subject, comprising:

measuring nucleic acid expression of (i) biomarkers MAGEA2, PRAME, PDIA4, NR4A1, PDLIM7, B4GALT1, SAT1, RUNX1, and SOCS3, and (ii) at least one normalization biomarker(s), in a nevi biopsy sample obtained from a subject, thereby generating raw expression values for each of the biomarkers and the at least one normalization biomarker(s);

normalizing the raw expression values for each of the biomarkers to the raw expression values for the at least one normalization biomarker(s) to generate normalized expression values for each of the biomarkers;

using the normalized expression values in a regression or machine learning algorithm to generate an output value;

measuring an output value on a same side of a cut-off value as a plurality of known malignant melanoma samples; and administering one or more chemotherapeutic agents, immunotherapy, or radiation therapy, performing additional surgery to remove lymph nodes or more tissue, or combinations thereof, thereby treating the indeterminant or atypical nevi in the subject.

2. The method of claim 1, wherein the at least one normalization biomarker(s) has no statistically significant difference in expression between nevi and primary melanoma samples.

3. The method of claim 1, wherein the at least one normalization biomarker comprises 1, 2, 3, 4, 5, 6, 7, 8 or all 9 of the biomarkers in Table 3.

4. The method of claim 1, further comprising:

measuring gene expression values for a plurality of biomarkers in the nevi biopsy sample; wherein the range of expression for the plurality of biomarkers is representative of the full range of biomarker expression in the sample transcriptome;

calculating a central tendency expression value for such plurality of biomarkers;

optionally, removing outliers and calculating a recalculated plurality central tendency expression value without the outlier expression values; and using the central tendency expression value or, optionally, the recalculated plurality central tendency expression value, to normalize the raw expression values for each of the biomarkers.

5. The method of claim 1, wherein the biomarkers further comprise at least two of the biomarkers in Table 4, and wherein the output value was generated by a logistic regression algorithm.

6. The method of claim 1, wherein the algorithm is $$\text{Output Value} = \beta 0 + \beta 1X1 + \beta 2X2 + \ldots \beta nXn$$

wherein Xn are log expression value for the biomarkers MAGEA2, PRAME, PDIA4, NR4A1, PDLIM7, B4GALT1, SAT1, RUNX1, and SOCS3, wherein β0 is greater than −200 and less than 200, wherein all β for n>0 are greater than −1,000 and less than 1,000.

7. The method of claim 1, wherein the biomarkers further comprise at least two of the biomarkers in Tables 11 and 13, and wherein the output value was generated by a machine learning algorithm.

8. The method of claim 7, wherein the biomarkers further comprise at least two of the biomarkers in Table 11 or at least two of the biomarkers in Table 13.

9. The method of claim 1, wherein the biomarkers further comprise:

at least two of BAX, BIRC5, MET, MAGEC2, POLR2J3, ZFYVE16, and BEST1 or at least two of POLR2J3, BEST1, BIRC5, MET, ZFYVE16, HIF1A, and PICALM, and wherein the output value was generated by a machine learning algorithm.

10. The method of claim 1, wherein the biomarkers further comprise at least 50%, at least 75%, at least 80%, at least 90%, at least 95% or at least 98% of the genes in Table 4, Table 11, Table 13, or both Table 4 and Table 11.

11. The method of claim 1, wherein measuring nucleic acid expression comprises contacting the nevi biopsy sample with a plurality of nucleic acid probes or paired amplification primers, wherein each probe or paired primers is/are specific and complementary to one of the least two biomarkers, under conditions that permit the plurality of nucleic acid probes or paired primers to hybridize to its/their complementary biomarkers.

12. The method of claim 11, further comprising, after contacting the sample with the plurality of nucleic acid probes, contacting the sample with a nuclease that digests single-stranded nucleic acid molecules.

13. The method of claim 1, wherein the one or more chemotherapeutic agents comprise dacarbazine, interferon, ipilimumab, carboplatin with taxol, granulocyte macrophage colony stimulating factor (GMCSF), and/or vemurafenib.

* * * * *

UNITED STATES PATENT AND TRADEMARK OFFICE

CERTIFICATE OF CORRECTION

PATENT NO. : 9,758,829 B2
APPLICATION NO. : 14/405739
DATED : September 12, 2017
INVENTOR(S) : Wang et al.

It is certified that error appears in the above-identified patent and that said Letters Patent is hereby corrected as shown below:

In the Claims

Claim 1, Column 357, Lines 37 and 62-63, "indeterminant" should be --indeterminate--.

Signed and Sealed this
Seventh Day of November, 2017

Joseph Matal

Joseph Matal
*Performing the Functions and Duties of the*
*Under Secretary of Commerce for Intellectual Property and*
*Director of the United States Patent and Trademark Office*